(12) United States Patent
Mortarino

(10) Patent No.: US 9,326,840 B2
(45) Date of Patent: May 3, 2016

(54) PROSTHETIC DEVICE AND METHOD OF MANUFACTURING THE SAME

(75) Inventor: Enrico Mortarino, Hickory, NC (US)

(73) Assignee: ALLERGAN, INC., Irvine, CA (US)

( * ) Notice: Subject to any disclaimer, the term of this patent is extended or adjusted under 35 U.S.C. 154(b) by 247 days.

(21) Appl. No.: 13/088,706

(22) Filed: Apr. 18, 2011

(65) Prior Publication Data

US 2011/0257665 A1  Oct. 20, 2011

Related U.S. Application Data

(63) Continuation-in-part of application No. 12/680,404, filed as application No. PCT/US2009/063717 on Nov. 9, 2009, now abandoned.

(60) Provisional application No. 61/122,520, filed on Dec. 15, 2008.

(51) Int. Cl.
*A61F 2/00* (2006.01)
*A61F 2/12* (2006.01)
*A61L 27/36* (2006.01)
(Continued)

(52) U.S. Cl.
CPC .............. *A61F 2/0063* (2013.01); *A61F 2/12* (2013.01); *A61L 27/3604* (2013.01); *D04B 1/22* (2013.01); *D04B 21/08* (2013.01); *D04B 21/12* (2013.01); *A61F 2002/0068* (2013.01); *D10B 2509/08* (2013.01)

(58) Field of Classification Search
CPC .......... D04B 1/22; A04B 21/00; A04B 21/12; A04B 21/14; A04B 21/145; A04B 21/16; A04B 21/165; A04B 21/18; A04B 21/08; A61F 28/0063; A61F 28/12; A61F 28/90; A61F 28/0077

USPC ........ 606/151; 623/23.72, 23.74; 66/191–195
See application file for complete search history.

(56) References Cited

U.S. PATENT DOCUMENTS 848,605 A    3/1907  Schmic
955,541 A *  4/1910  Peterson ................... 139/387 R
(Continued)

FOREIGN PATENT DOCUMENTS

DE    3917174    12/1990
DE    19928635   10/2000
(Continued)

OTHER PUBLICATIONS

Altman et al., Silk based biomaterials, *Biomaterials* (2003) 24:401-416.
(Continued)

*Primary Examiner* — Dianne Dornbusch
(74) *Attorney, Agent, or Firm* — Linda Allyson Nassif

(57) ABSTRACT

A biocompatible surgical silk mesh prosthetic device employs a knit pattern that substantially prevents unraveling and preserves the stability of the mesh device, especially when the mesh device is cut. An example prosthetic device employs a knitted mesh including at least two yarns laid in a knit direction and engaging each other to define a plurality of nodes. The at least two yarns include a first yarn and a second yarn extending between and forming loops about two nodes. The second yarn has a higher tension at the two nodes than the first yarn. the second yarn substantially prevents the first yarn from moving at the two nodes and substantially prevents the knitted mesh from unraveling at the nodes.

11 Claims, 131 Drawing Sheets

(51) Int. Cl.
   *D04B 1/22*    (2006.01)
   *D04B 21/08*   (2006.01)
   *D04B 21/12*   (2006.01)

(56) References Cited

U.S. PATENT DOCUMENTS

| | | | |
|---|---|---|---|
| 1,300,696 A * | 4/1919 | Branson | 66/193 |
| 1,709,662 A | 4/1929 | Ellis | |
| 1,815,279 A | 7/1931 | Takamine, Jr. | |
| 1,828,736 A | 10/1931 | Harvey, Jr. | |
| 1,896,494 A | 2/1933 | Myers et al. | |
| 1,921,022 A | 9/1933 | Fink et al. | |
| 1,990,588 A | 2/1935 | Bueno | |
| 2,040,949 A | 5/1936 | Olpin et al. | |
| 3,124,136 A | 3/1964 | Usher | |
| 3,314,123 A * | 4/1967 | Groebli | 28/165 |
| 3,552,154 A * | 1/1971 | Lesley | 6/192 |
| 3,595,276 A | 7/1971 | Wrzesieo | |
| 3,672,187 A * | 6/1972 | Simpson | 66/192 |
| 3,922,888 A * | 12/1975 | Patterson | 66/192 |
| 3,931,721 A * | 1/1976 | Adamson | 66/195 |
| 3,952,555 A * | 4/1976 | Lesley | 66/195 |
| 3,999,407 A * | 12/1976 | Odham | 66/193 |
| 4,089,071 A * | 5/1978 | Kalnberz et al. | 623/23.61 |
| 4,118,842 A | 10/1978 | Norris et al. | |
| 4,141,207 A | 2/1979 | Mizushima et al. | |
| 4,248,064 A * | 2/1981 | Odham | 66/192 |
| 4,340,091 A * | 7/1982 | Skelton et al. | 139/383 R |
| 4,388,364 A * | 6/1983 | Sanders | 442/313 |
| 4,518,640 A * | 5/1985 | Wilkens | 428/102 |
| 4,530,113 A * | 7/1985 | Matterson | 623/1.51 |
| 4,792,336 A | 12/1988 | Hlavacek et al. | |
| 4,816,028 A * | 3/1989 | Kapadia et al. | 623/1.52 |
| 4,942,875 A | 7/1990 | Hlavacek et al. | |
| 4,984,570 A * | 1/1991 | Langen et al. | 602/44 |
| 4,987,665 A | 1/1991 | Dumican | |
| 5,120,829 A | 6/1992 | Pierschbacher et al. | |
| 5,134,006 A * | 7/1992 | Irvin | 428/68 |
| 5,171,505 A | 12/1992 | Lock | |
| 5,178,630 A * | 1/1993 | Schmitt | 623/1.52 |
| 5,191,777 A * | 3/1993 | Schnegg | 66/195 |
| 5,250,077 A | 10/1993 | Fuse et al. | |
| 5,252,285 A | 10/1993 | Lock | |
| 5,353,486 A | 10/1994 | Schmidt et al. | |
| 5,366,504 A * | 11/1994 | Andersen et al. | 623/1.5 |
| 5,385,836 A | 1/1995 | Kimura et al. | |
| 5,456,697 A | 10/1995 | Chesterfield et al. | |
| 5,456,711 A | 10/1995 | Hudson | |
| 5,490,602 A * | 2/1996 | Wilson et al. | 216/56 |
| 5,509,931 A * | 4/1996 | Schmitt | 623/1.52 |
| 5,569,273 A | 10/1996 | Titone et al. | |
| 5,587,456 A | 12/1996 | Pierschbacher et al. | |
| 5,591,822 A | 1/1997 | Pierschbacher et al. | |
| 5,598,615 A | 2/1997 | Takada | |
| 5,606,019 A | 2/1997 | Cappello | |
| 5,674,276 A * | 10/1997 | Andersen et al. | 623/1.5 |
| 5,760,176 A | 6/1998 | Pierschbacher et al. | |
| 5,771,716 A | 6/1998 | Schlussel | |
| 5,795,835 A * | 8/1998 | Bruner et al. | 442/310 |
| 5,849,040 A | 12/1998 | Kanehisa | |
| 5,919,232 A | 7/1999 | Chaffringeon et al. | |
| 5,951,506 A | 9/1999 | Tsubouchi | |
| 5,990,378 A | 11/1999 | Ellis | |
| 6,004,888 A * | 12/1999 | Sugimoto et al. | 442/60 |
| 6,006,552 A * | 12/1999 | Matsuda et al. | 66/193 |
| 6,042,592 A | 3/2000 | Schmitt | 606/151 |
| 6,074,722 A * | 6/2000 | Cuccias | 428/107 |
| 6,076,448 A * | 6/2000 | Rexroad | 87/12 |
| 6,090,116 A | 7/2000 | D'Aversa et al. | |
| 6,110,590 A | 8/2000 | Zarkoob et al. | |
| 6,113,623 A | 9/2000 | Sgro | |
| 6,136,022 A * | 10/2000 | Nunez et al. | 623/1.1 |
| 6,146,418 A | 11/2000 | Berman | |
| 6,159,877 A | 12/2000 | Scholz et al. | |
| 6,164,339 A * | 12/2000 | Greenhalgh | 139/1 R |
| 6,171,984 B1 * | 1/2001 | Paulson et al. | 442/331 |
| 6,175,053 B1 | 1/2001 | Tsubouchi | |
| 6,175,533 B1 | 1/2001 | Lee | |
| 6,228,132 B1 | 5/2001 | Prince et al. | |
| 6,233,978 B1 * | 5/2001 | Gehring et al. | 66/195 |
| 6,287,316 B1 * | 9/2001 | Agarwal et al. | 606/151 |
| 6,287,340 B1 | 9/2001 | Altman et al. | |
| 6,302,922 B1 | 10/2001 | Kanehisa | |
| 6,303,136 B1 | 10/2001 | Li et al. | |
| 6,389,851 B1 * | 5/2002 | Groshens | 66/192 |
| 6,408,656 B1 | 6/2002 | Ory et al. | |
| 6,440,740 B1 | 8/2002 | Tsubouchi et al. | |
| 6,443,964 B1 | 9/2002 | Ory et al. | |
| 6,540,773 B2 * | 4/2003 | Dong | 623/1.13 |
| 6,592,617 B2 * | 7/2003 | Thompson | 623/1.53 |
| 6,630,414 B1 | 10/2003 | Matsumoto | |
| 6,638,284 B1 | 10/2003 | Rousseau et al. | |
| 6,729,356 B1 | 5/2004 | Baker et al. | |
| 6,737,371 B1 | 5/2004 | Planck et al. | |
| 6,773,459 B2 | 8/2004 | Dauner et al. | |
| 6,783,554 B2 | 8/2004 | Amara et al. | |
| 6,827,743 B2 * | 12/2004 | Eisermann et al. | 623/23.54 |
| 6,848,281 B2 | 2/2005 | Ishihara et al. | |
| 6,856,715 B1 * | 2/2005 | Ebbesen et al. | 385/14 |
| 6,866,681 B2 | 3/2005 | Laboureau et al. | |
| 6,902,932 B2 | 6/2005 | Altman et al. | |
| 6,912,877 B2 | 7/2005 | Yokoyama et al. | |
| 6,946,003 B1 * | 9/2005 | Wolowacz et al. | 623/23.72 |
| 6,966,918 B1 | 11/2005 | Schuldt-Hempe et al. | |
| 6,971,252 B2 | 12/2005 | Therin et al. | |
| 7,021,086 B2 | 4/2006 | Ory et al. | |
| 7,025,063 B2 * | 4/2006 | Snitkin et al. | 128/885 |
| 7,115,388 B2 | 10/2006 | Tsubouchi | |
| 7,156,858 B2 | 1/2007 | Schuldt-Hempe et al. | |
| 7,166,570 B2 | 1/2007 | Hunter et al. | |
| 7,285,637 B2 | 10/2007 | Armato et al. | |
| 7,293,433 B1 | 11/2007 | McMurray | |
| 7,331,199 B2 | 2/2008 | Ory et al. | |
| 7,338,531 B2 | 3/2008 | Ellis et al. | |
| 7,341,601 B2 | 3/2008 | Eisermann et al. | |
| 7,476,249 B2 | 1/2009 | Frank | |
| 7,614,258 B2 * | 11/2009 | Cherok et al. | 66/192 |
| 7,824,701 B2 | 11/2010 | Binette et al. | |
| 7,828,855 B2 | 11/2010 | Ellis et al. | |
| 7,842,780 B2 | 11/2010 | Kaplan et al. | |
| 7,875,074 B2 | 1/2011 | Chen et al. | |
| 7,900,484 B2 | 3/2011 | Cherok et al. | |
| 8,007,531 B2 | 8/2011 | Frank | |
| 8,157,822 B2 | 4/2012 | Browning | |
| 8,177,834 B2 * | 5/2012 | Carlson et al. | 623/1.51 |
| 8,197,542 B2 | 6/2012 | Becker | |
| 8,202,317 B2 | 6/2012 | Becker | |
| 8,226,715 B2 * | 7/2012 | Hwang et al. | 623/13.14 |
| 8,323,675 B2 | 12/2012 | Greenawalt | |
| 8,418,508 B2 | 4/2013 | Lecuivre et al. | |
| 8,689,362 B2 | 4/2014 | Lavin | |
| 8,726,700 B2 | 5/2014 | Waldman et al. | |
| 8,746,014 B2 | 6/2014 | Mortarino | |
| 2002/0156437 A1 | 10/2002 | McDevitt et al. | |
| 2003/0044155 A1 * | 3/2003 | Maiden | 385/137 |
| 2003/0061839 A1 * | 4/2003 | Kost | 66/192 |
| 2003/0087433 A1 | 5/2003 | Tsubouchi et al. | |
| 2003/0106346 A1 * | 6/2003 | Matsumoto | 66/195 |
| 2003/0106347 A1 * | 6/2003 | Kost | 66/195 |
| 2003/0165548 A1 | 9/2003 | Tsubouchi et al. | |
| 2003/0183978 A1 | 10/2003 | Asakura | |
| 2003/0228815 A1 * | 12/2003 | Bhatnagar et al. | 442/164 |
| 2004/0005363 A1 | 1/2004 | Tsukada et al. | |
| 2004/0029478 A1 | 2/2004 | Planck et al. | |
| 2004/0093069 A1 | 5/2004 | Priewe et al. | |
| 2004/0170827 A1 | 9/2004 | Crighton | |
| 2004/0176658 A1 | 9/2004 | McMurray | |
| 2004/0211225 A1 * | 10/2004 | Dickerson | 66/142 |
| 2004/0219630 A1 | 11/2004 | Tsubouchi | |
| 2004/0224406 A1 | 11/2004 | Altman et al. | |
| 2005/0089552 A1 | 4/2005 | Altman et al. | |
| 2005/0228408 A1 | 10/2005 | Fricke et al. | |
| 2005/0240261 A1 * | 10/2005 | Rakos et al. | 623/1.51 |
| 2005/0260706 A1 | 11/2005 | Kaplan et al. | |

(56) References Cited

U.S. PATENT DOCUMENTS

| | | |
|---|---|---|
| 2005/0288797 A1* | 12/2005 | Howland .................. 623/23.74 |
| 2006/0009835 A1* | 1/2006 | Osborne et al. ............. 623/1.13 |
| 2006/0013950 A1* | 1/2006 | Porter et al. .................. 427/171 |
| 2006/0015184 A1* | 1/2006 | Winterbottom et al. ... 623/18.11 |
| 2007/0041952 A1 | 2/2007 | Guilak et al. |
| 2007/0088434 A1 | 4/2007 | Frank et al. |
| 2007/0207186 A1* | 9/2007 | Scanlon et al. ............... 424/424 |
| 2008/0038236 A1 | 2/2008 | Gimble et al. |
| 2008/0097601 A1 | 4/2008 | Codori-Hurff et al. |
| 2008/0131509 A1 | 6/2008 | Hossainy et al. |
| 2008/0176960 A1 | 7/2008 | Tsukada et al. |
| 2008/0200086 A1* | 8/2008 | Porter et al. .................. 442/189 |
| 2008/0206302 A1 | 8/2008 | Sittinger et al. |
| 2008/0228028 A1* | 9/2008 | Carlson et al. ................. 600/36 |
| 2008/0300683 A1 | 12/2008 | Altman et al. |
| 2009/0024162 A1 | 1/2009 | Shalaby et al. |
| 2009/0030454 A1 | 1/2009 | Knight et al. |
| 2009/0214649 A1 | 8/2009 | Gazit et al. |
| 2010/0023029 A1 | 1/2010 | Young |
| 2010/0145367 A1 | 6/2010 | Ratcliffe |
| 2010/0209405 A1 | 8/2010 | Altman et al. |
| 2010/0249924 A1 | 9/2010 | Powell et al. |
| 2010/0256756 A1 | 10/2010 | Altman et al. |
| 2011/0009960 A1 | 1/2011 | Altman |
| 2011/0022171 A1 | 1/2011 | Richter et al. |
| 2011/0054604 A1 | 3/2011 | Becker et al. |
| 2011/0054605 A1 | 3/2011 | Becker et al. |
| 2011/0106249 A1 | 5/2011 | Becker et al. |
| 2011/0167602 A1 | 7/2011 | Altman et al. |
| 2011/0171453 A1 | 7/2011 | Altman et al. |
| 2011/0184227 A1 | 7/2011 | Altman et al. |
| 2011/0189773 A1 | 8/2011 | Altman et al. |
| 2011/0190795 A1 | 8/2011 | Hotter et al. |
| 2011/0224703 A1 | 9/2011 | Mortarino et al. |
| 2011/0257665 A1 | 10/2011 | Mortarino et al. |
| 2011/0257761 A1 | 10/2011 | Mortarino |
| 2011/0282365 A1 | 11/2011 | Hadba et al. |
| 2011/0301717 A1 | 12/2011 | Becker |
| 2012/0053690 A1 | 3/2012 | Frank |
| 2012/0150204 A1 | 6/2012 | Mortarino et al. |
| 2012/0165957 A1 | 6/2012 | Everland et al. |
| 2012/0184974 A1 | 7/2012 | Becker |
| 2012/0185041 A1 | 7/2012 | Mortarino et al. |
| 2012/0226352 A1 | 9/2012 | Becker |
| 2012/0244143 A1 | 9/2012 | Lo et al. |
| 2013/0317526 A1 | 11/2013 | Mortarino |
| 2015/0148823 A1 | 5/2015 | Mortarino et al. |

FOREIGN PATENT DOCUMENTS

| | | |
|---|---|---|
| EP | 0677297 | 10/1995 |
| EP | 0889156 A1 | 12/1996 |
| EP | 1241178 | 9/2002 |
| EP | 1506789 A1 | 2/2005 |
| EP | 2016956 | 1/2009 |
| EP | 2068766 | 10/2011 |
| GB | 545153 | 5/1942 |
| JP | H06-245989 | 9/1994 |
| WO | 95-25550 | 9/1995 |
| WO | 00-57812 | 10/2000 |
| WO | WO 00/72782 | 12/2000 |
| WO | WO 02/29141 | 4/2002 |
| WO | WO 2004/062697 | 7/2004 |
| WO | 2004080346 A2 | 9/2004 |
| WO | WO 2005/123114 | 12/2005 |
| WO | 2006102477 | 9/2006 |
| WO | WO 2009/023615 | 2/2009 |
| WO | WO 2010/074827 | 7/2010 |
| WO | WO 2010/141133 | 12/2010 |
| WO | 2011031854 A1 | 3/2011 |
| WO | 2012145311 A1 | 10/2012 |
| WO | 2015027144 A1 | 2/2015 |

OTHER PUBLICATIONS

Cappello et al., In-situ self-assembling protein polymer gel systems for administration, delivery, and release of drugs, *USA Journal of controlled release: official journal of the Controlled Release Society* (Apr. 30, 1998), 53(1-3):105-17, San Diego, CA 92121.

Horan et al., In vitro degradation of silk fibroin, *USA Biomaterials* (Jun. 2005), 26(17):3385-93.

Horan, et al., Biological and biomechanical assessment of a long-term bioresorbable silk-derived surgical mesh in an abdominal body wall defect model, *Hernia* (2009) 13(2):189-99.

Kardestuncer et al., RGD-tethered silk substrate stimulates the differentiation of human tendon cells, *Clinical Orthopaedics and Related Research* (2006), No. 448:pp. 234-239.

Kundu et al., Natural protective glue protein, sericin bioengineered by silkworms: Potential for biomedical and biotechnological applications, *Progress in Polymer Science* (2008) 33:998-1012.

Panilaitis et al., Macrophage responses to silk, *Biomaterials* (2003) 24(18):3079-3085.

Tamada, Y., Symposium Preprints, *The Society of Fiber Science and Technology* (1998) p. S-51.

Tsukada, Preparation and application of porous silk fibroin materials, *Journal of Applied Polymer Science* (1994).

Yanagisawa et al., Improving cell-adhesive properties of recombinant *Bombyx mori* silk by incorporation of collagen or fibronectin derived peptides produced by transgenic silkworms, *Biomacromolecules* (2007), 8 (11):3487-3492.

Zhu et al., Preparation and Characterization of Regenerated *Bombyx mori* silk fibroin fiber containing recombinant cell-adhesive proteins; nonwoven fiber and monofilament, *Journal of Applied Polymer Science* (2008), vol. 109:2956-2963.

* cited by examiner

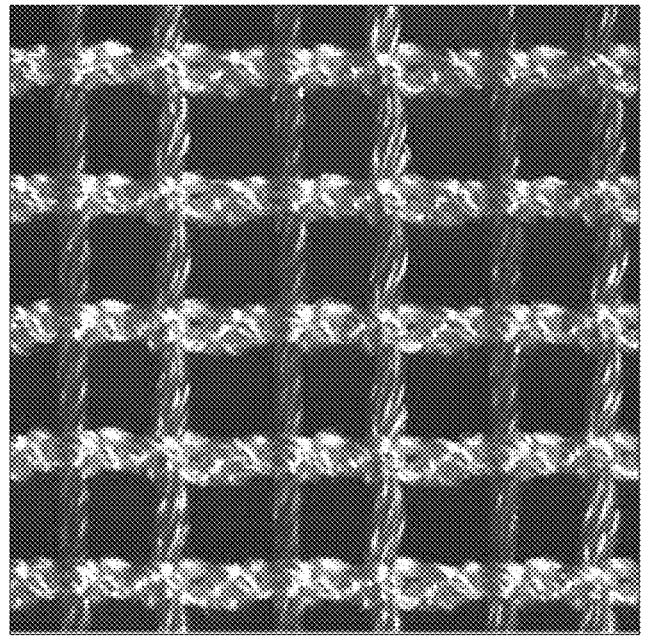

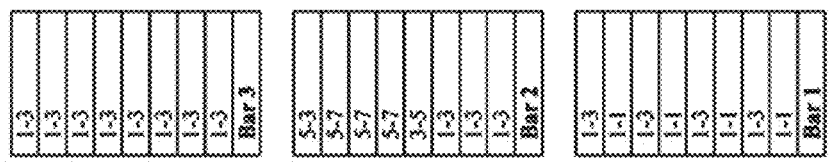
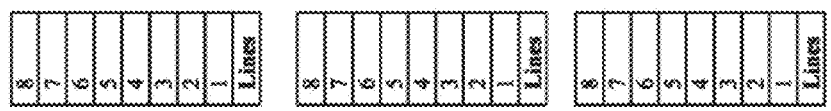
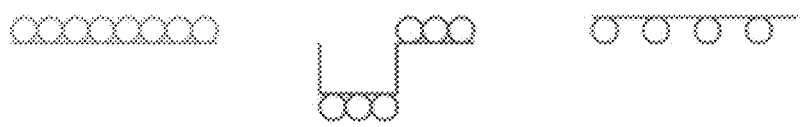
FIG. 25

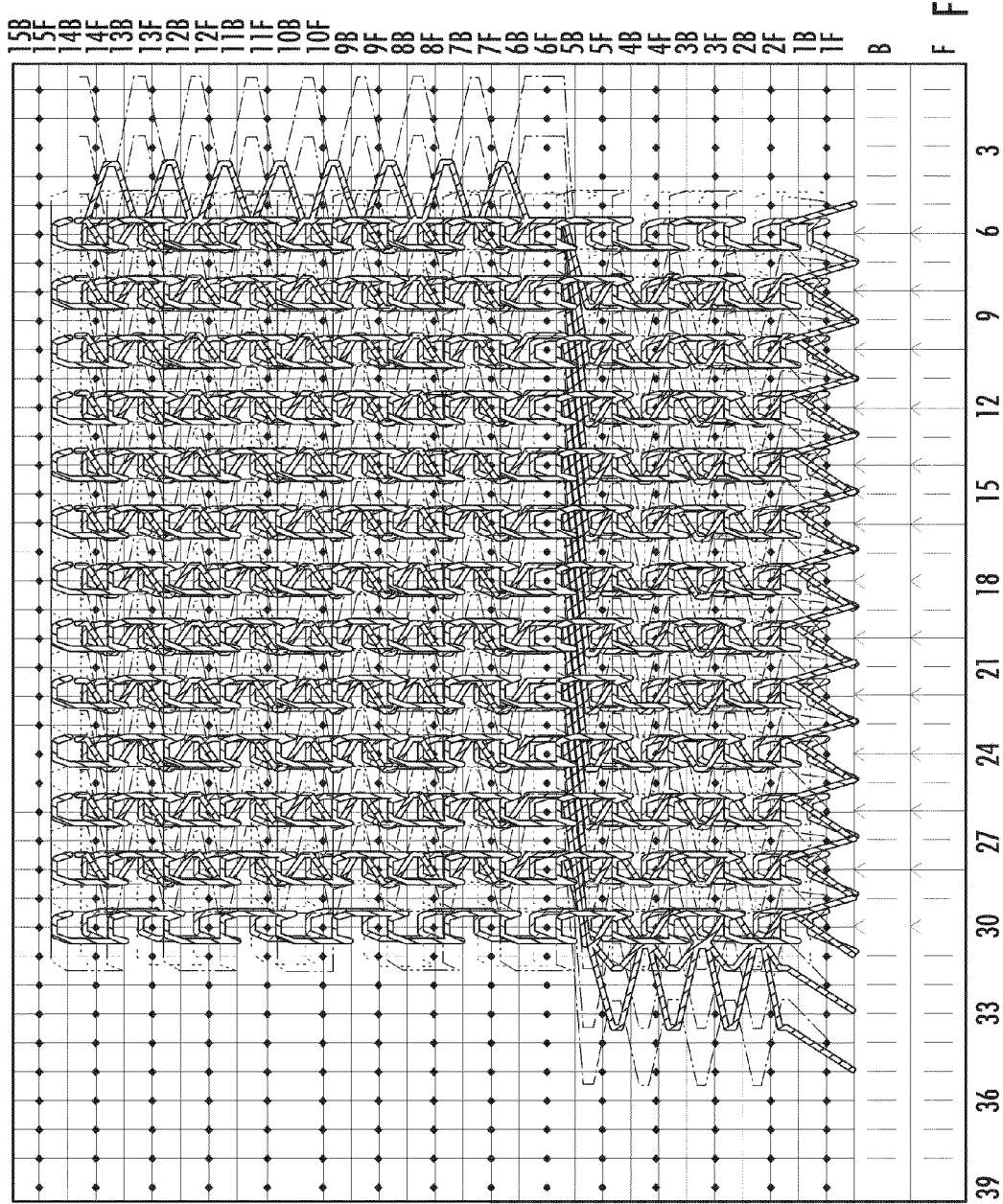

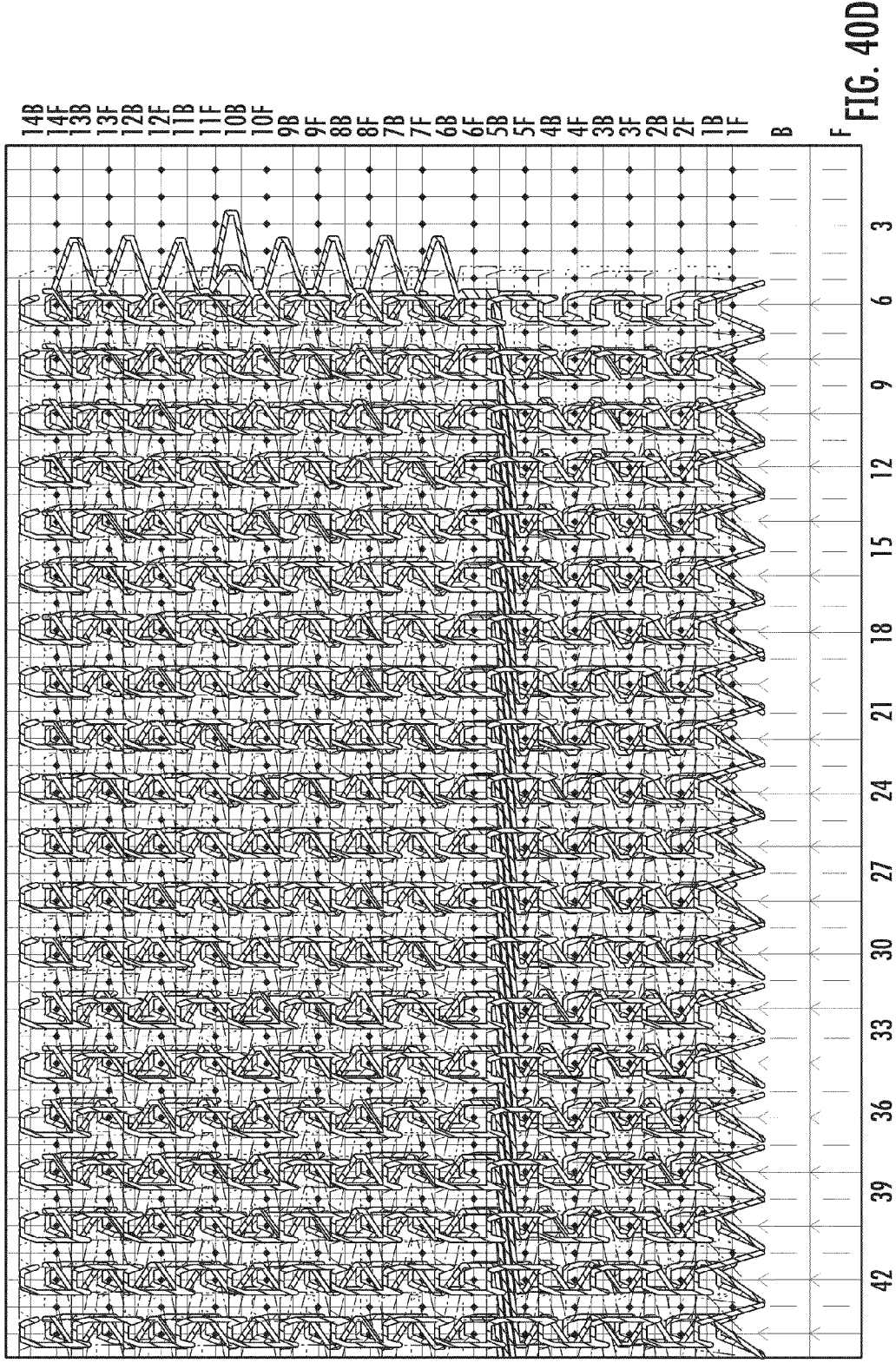

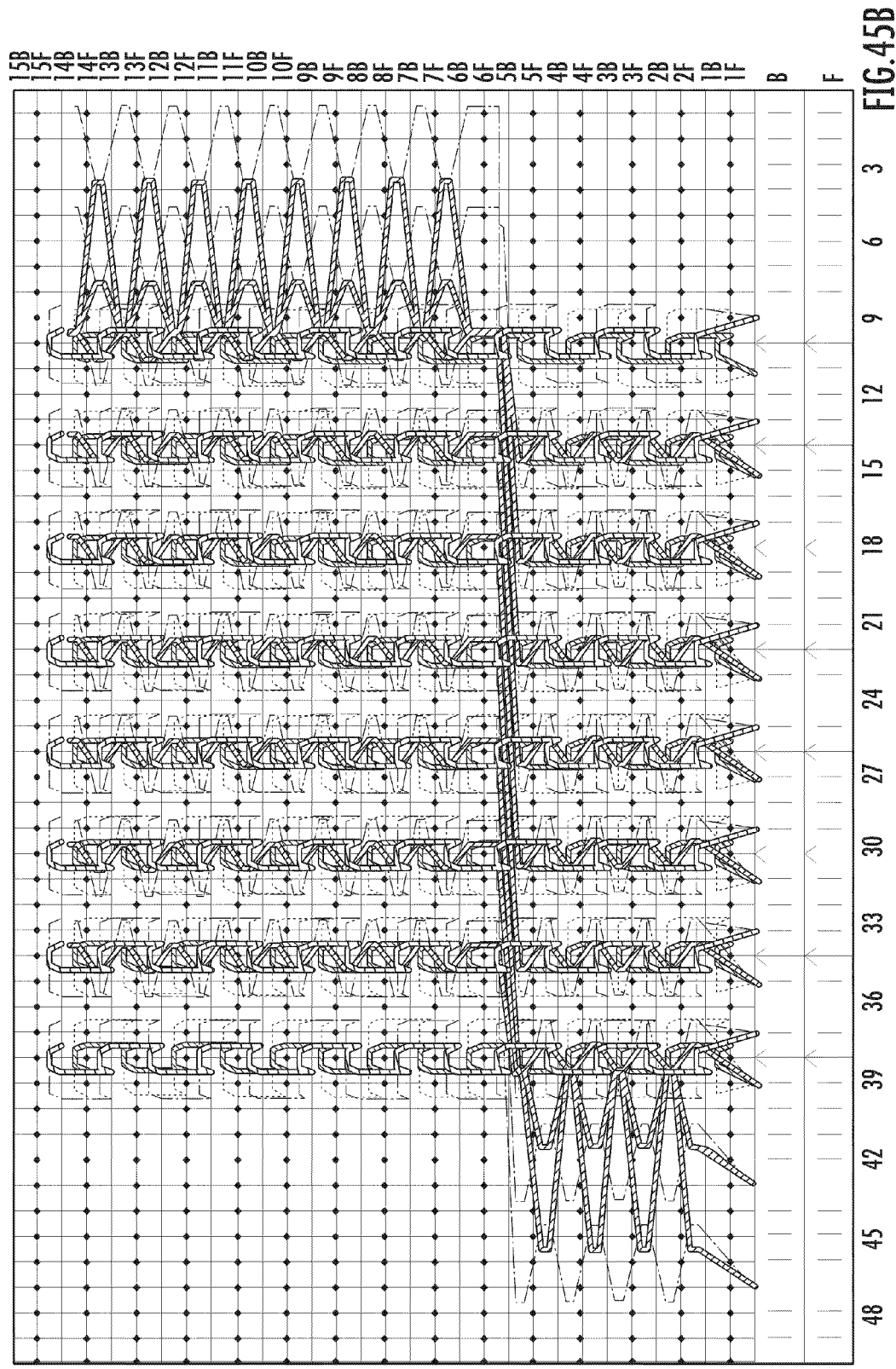

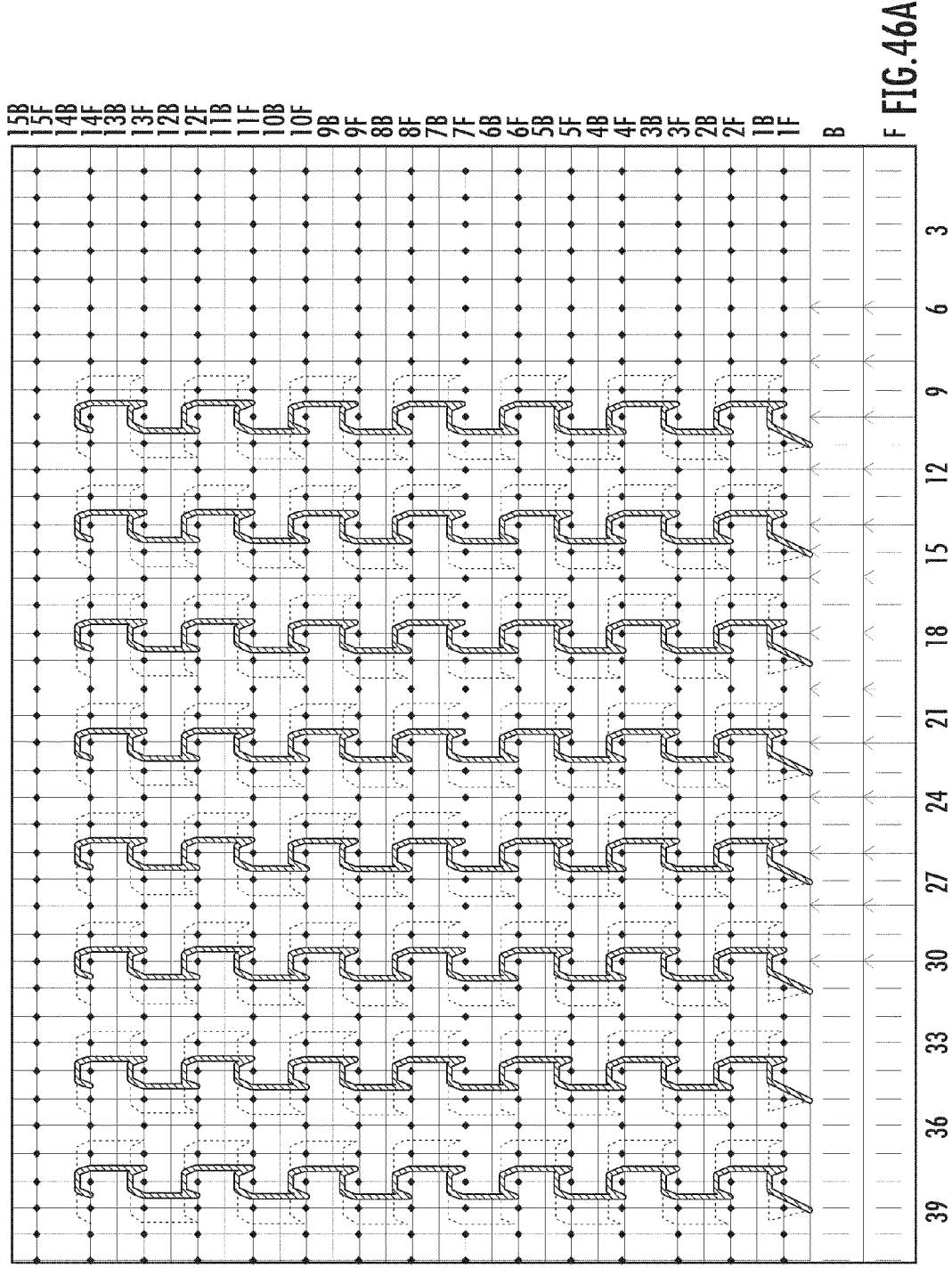

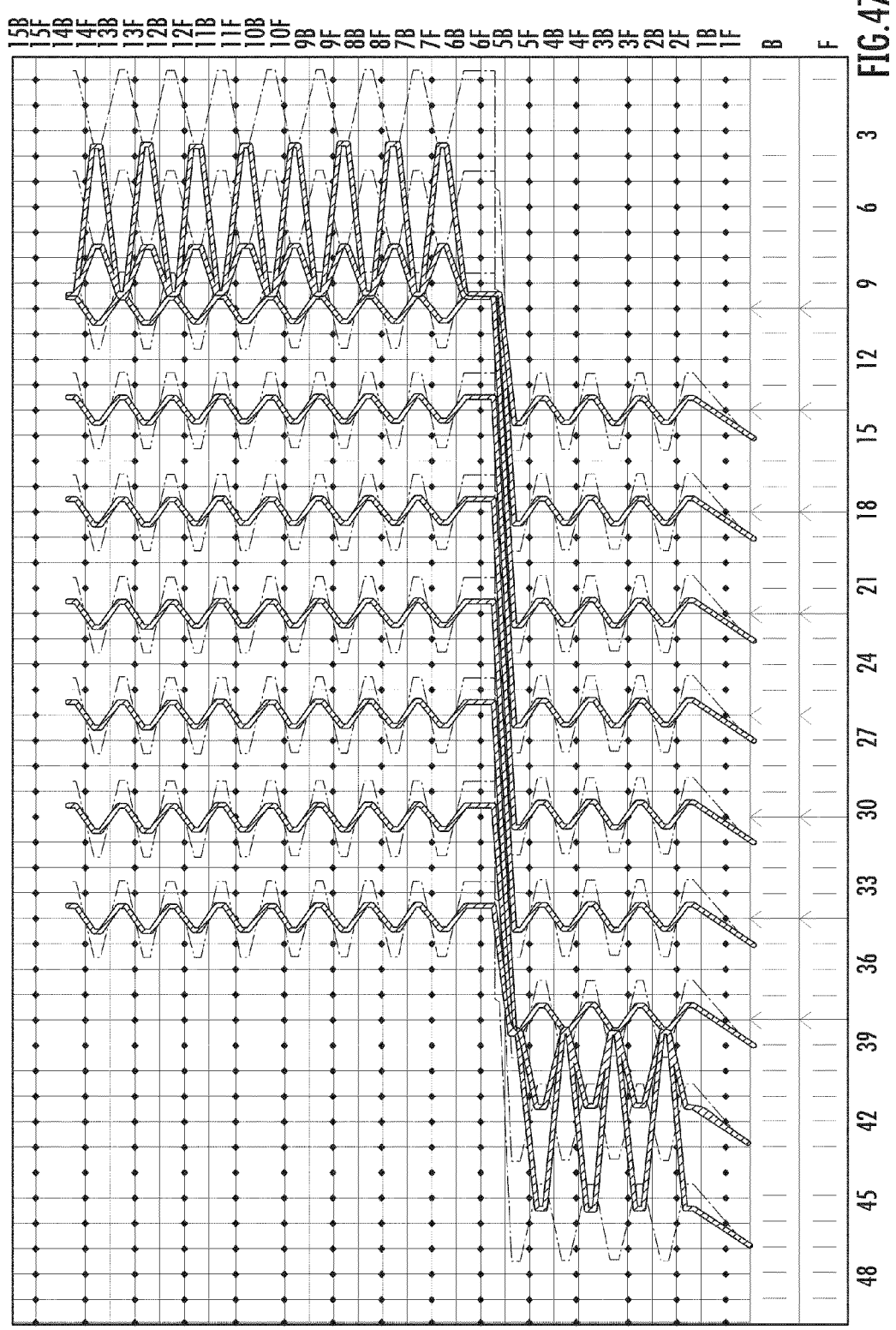

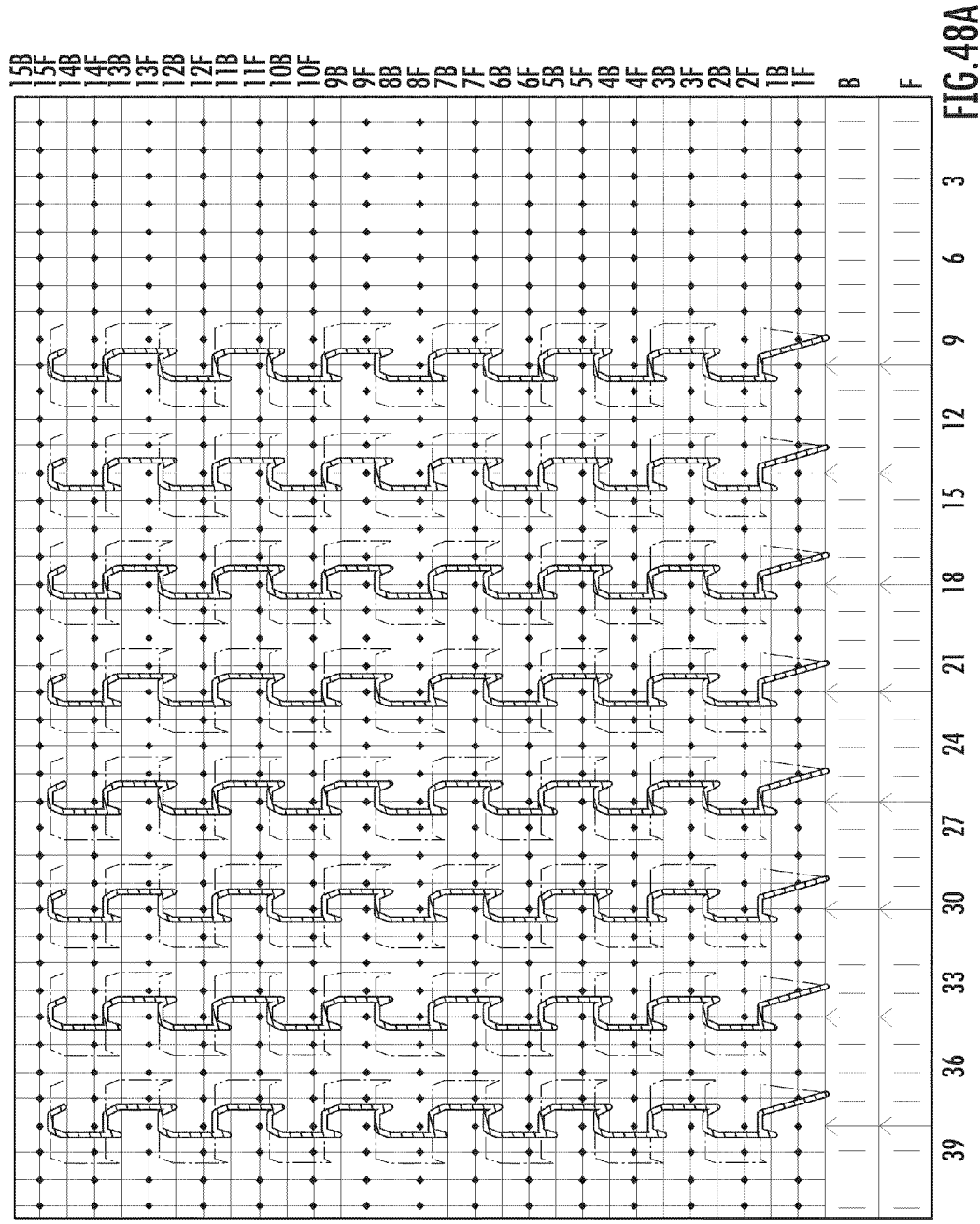

PROSTHETIC DEVICE AND METHOD OF MANUFACTURING THE SAME

CROSS-REFERENCE TO RELATED APPLICATIONS

This application is a continuation-in-part application which claims priority to U.S. utility patent application Ser. No. 12/680,404, filed Mar. 26, 2010, which is a national stage entry of PCT/US09/63717, filed Nov. 9, 2009, which claims priority to and the benefit of U.S. provisional patent application No. 61/122,520, filed Dec. 15, 2008, all of which applications are hereby expressly incorporated by reference herein in their entireties.

FIELD OF THE INVENTION

The present invention generally relates to a prosthetic device for tissue repair, and, more particularly, to a surgical silk mesh device employing a stable knit structure.

BACKGROUND OF THE INVENTION

Surgical mesh initially used for hernia and abdominal wall defects are now being used for other types of tissue repair, such as rotator cuff repair, pelvic floor dysfunction, and reconstructive or cosmetic surgeries. It is projected that in 2010, there will be more than 8 million hernia procedures, 800,000 rotator cuff repairs, 3 million pelvic prolapse repairs, 600,000 urinary incontinence repairs, and 1.5 million reconstructive or aesthetic plastic surgeries. Most of these procedures will likely employ implantable surgical mesh devices currently on the market, including: Bard Mesh (polypropylene) by C. R. Bard; Dexon (polyglycolic acid) by Synecture/US Surgical; Gore-Tex (polytetrafluoroethylene) by W. L. Gore; Prolene (polypropylene), Prolene Soft (polypropylene), Mersilene Mesh (polyester), Gynemesh (polypropylene), Vicryl Knitted Mesh (polyglactin 910), TVT (polypropylene) by Ethicon; Sparc tape (polypropylene) by American Medical Systems; and IVS tape (polypropylene) by TYCO Healthcare International.

Surgical mesh devices are typically biocompatible and may be formed from bioresorbable materials and/or non-bioresorbable materials. For example, polypropylene, polyester, and polytetrafluoroethylene (PTFE) are biocompatible and non-bioresorbable, while polyglactin 910 and polyglycolic acid are biocompatible and bioresorbable.

Though current surgical mesh devices may be formed from different materials, they have various similar physical and mechanical characteristics beneficial for tissue repair. However, despite the benefits provided by current surgical mesh devices, their use may be accompanied by a variety of complications. Such complications, for example, may include scar encapsulation and tissue erosion, persistent infection, pain, and difficulties associated with revision surgery. In addition, the use of an absorbable material may result in reoccurrence due to rapid resorption of the implant material and loss of strength.

Although polypropylene monofilament may be a highly regarded material for surgical mesh devices, polypropylene mesh devices can induce intense scar formations and create a chronic foreign body reaction with the formation of a fibrous capsule, even years after implantation. Minor complaints of seromas, discomfort, and decreased wall mobility are frequent and observed in about half of the patients implanted with polypropylene mesh devices. Moreover, polypropylene generally cannot be placed next to the bowel due to the propensity of adhesion formation.

Although the use of multifilament polyester may improve conformity with the abdominal wall, it is also associated with a variety of disadvantages. For example, higher incidences of infection, enterocutaneous fistula formation, and small bowel obstruction have been reported with the use of multifilament polyester compared to other materials. Indeed, the small interstices of the multifilament yarn make it more susceptible to the occurrence of infection, and thus multifilament polyester is not commonly used within the United States.

The use polytetrafluoroethylene (PTFE) may be advantageous in minimizing adhesions to the bowel. However, the host tissue encapsulates the PTFE mesh, resulting in weak in-growth in the abdominal wall and weaker hernia repair. This material, though not a good mesh material on its own, has found its place as an adhesion barrier.

Absorbable materials, such as Vicryl and Dexon, used for hernia repair have the advantage of being placed in direct contact with the bowel without adhesion or fistula formation. A study has observed that Vicryl has comparable burst strength to nonabsorbable mesh at three weeks but is significantly weaker at twelve weeks due to a quick absorption rate. Meanwhile, the same study observed that Dexon has more in-growth at twelve weeks with less absorption of the mesh. The concern with absorbable meshes is that the rate of absorption is variable, possibly leading to hernia recurrence if the proper amount of new tissue is not there to withstand the physiologic stresses placed on the hernia defect.

A significant characteristic of a biomaterial is its porosity, because porosity is the main determinant for tissue reaction. Pore sizes of >500-600 µm permit in-growth of soft tissue; pore sizes of >200-300 µm favor neo-vascularisation and allow mono-morphological restitution of bony defects; pore sizes of <200 µm are considered to be almost watertight, hindering liquid circulation at physiological pressures; and pores of <100 µm only lead to in-growth of single cell types instead of building new tissues. Finally, a pore size of <10 µm hinders any in-growth and increases the chance of infection, sinus tract formation, and encapsulation of the mesh. Bacteria averaging 1 µm in size can hide in the small interstices of the mesh and proliferate while protected from neutrophilic granulocytes averaging 10-15 µm.

Other important physical characteristics for surgical mesh devices include thickness, burst strength, and material stiffness. The thickness of surgical mesh devices vary according to the particular repair procedure. For example, current surgical mesh device hernia, pelvic floor dysfunction, and reconstructive/cosmetic procedures range in thickness from approximately 0.635 mm to 1.1 mm. For rotator cuff repair, a thickness of 0.4 mm to 5 mm is typically employed.

Intra-abdominal pressures of 10-16 N, with a mean distension of 11-32% results in the need for a surgical mesh with a burst strength that can resist the stress of the inner abdomen before healthy tissue comes into being.

Material stiffness is an important mechanical characteristic for surgical mesh, especially when used for pelvic floor dysfunction, because material stiffness has been associated with the likelihood of tissue erosion. Surgical mesh devices formed from TVT, IVS, Mersilene, Prolene, Gynemesh, Sparc tape, for example, currently have an ultimate tensile strength (UTS) that exceeds the forces exerted by intra-abdominal pressures of 10-16 N. With the low force in the abdomen, the initial stiffness of the material is an important consideration. Moreover, the stiffness may exhibit non-linear behavior most likely due to changes in the fabric structure, e.g., unraveling of the knit, weave, etc. A surgical mesh device of lesser stiffness may help reduce tissue erosion and may conform to the contours of the body more effectively.

SUMMARY OF THE INVENTION

In view of the disadvantages of current surgical mesh devices, there continues to be a need for a surgical mesh that is biocompatible and absorbable, has the ability to withstand the physiological stresses placed on the host collagen, and minimizes tissue erosion, fistulas, or adhesions. Thus, embodiments according to aspects of the present invention provide a biocompatible surgical silk mesh prosthetic device for use in soft and hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like. Thus, the mesh device of the present invention is suitable for use in a variety or reconstructive or support applications including, but not limited to, breast reconstruction, breast augmentation revision, breast augmentation support, standard breast augmentation, chest wall repair, organ support, body contouring, abdominoplasty, facial reconstruction, hernia repair, and pelvic floor repair.

Advantageously, the open structure of these embodiments allows tissue in-growth while the mesh device degrades at a rate which allows for a smooth transfer of mechanical properties to the new tissue from the silk scaffold. According to a particular aspect of the present invention, embodiments employ a knit pattern, referred to as a "node-lock" design. The "node-lock" design substantially prevents unraveling and preserves the stability of the mesh device, especially when the mesh device is cut.

In a particular embodiment, a prosthetic device includes a knitted mesh including at least two yarns laid in a knit direction and engaging each other to define a plurality of nodes, the at least two yarns including a first yarn and a second yarn extending between and forming loops about two nodes, the second yarn having a higher tension at the two nodes than the first yarn, the second yarn substantially preventing the first yarn from moving at the two nodes and substantially preventing the knitted mesh from unraveling at the nodes.

In an example of this embodiment, the first yarn and the second yarn are formed from different materials. In another example of this embodiment, the first yarn and the second yarn have different diameters. In further embodiments, wherein the first yarn and the second yarn have different elastic properties. In yet a further example of this embodiment, the at least two yarns are formed from silk.

In another example of this embodiment, a first length of the first yarn extends between the two nodes and a second length of the second yarn extends between the two nodes, the first length being greater than the second length. For instance, the first yarn forms an intermediate loop between the two nodes and the second yarn does not form a corresponding intermediate loop between the two nodes. The first length of the first yarn is greater than the second length of the second yarn.

In yet another example of this embodiment, the first yarn is included in a first set of yarns and the second yarn is included in a second set of yarns, the first set of yarns being applied in a first wale direction, each of the first set of yarns forming a first series of loops at each of a plurality of courses for the knitted mesh, the second set of yarns being applied in a second wale direction, the second wale direction being opposite from the first wale direction, each of the second set of yarns forming a second series of loops at every other of the plurality of courses for the knitted mesh, the first set of yarns interlacing with the second set of yarns at the every other course to define the nodes for the knitted mesh, the second set of yarns having a greater tension than the first set of yarns, the difference in tension substantially preventing the knitted mesh from unraveling at the nodes.

In a further example of this embodiment, the first yarn is included in a first set of yarns and the second yarn is included in a second set of yarns, the first set of yarns and the second set of yarns being alternately applied in a wale direction to form staggered loops, the first set of yarns interlacing with the second set of yarns to define the nodes for the knitted mesh, the alternating application of the first set of yarns and the second set of yarns causing the first set of yarns to have different tensions relative to the second set of yarns at the nodes, the difference in tension substantially preventing the knitted mesh from unraveling at the nodes.

In yet a further example of this embodiment, the first yarn is included in a first set of yarns and the second yarn is included in a second set of yarns, the first set of yarns forming a series of jersey loops along each of a first set of courses for a knitted mesh, the second set of yarns forming a second series of alternating tucked loops and jersey loops along each of a second set of courses for the knitted mesh, the second set of courses alternating with the first set of courses, the second set of yarns having a greater tension than the first set of yarns, the tucked loops of the second set of yarns engaging the jersey loops of the first set of yarns to define nodes for the knitted mesh, the tucked loops substantially preventing the knitted mesh from unraveling at the nodes.

In another particular embodiment, a method for making a knitted mesh for a prosthetic device, includes: applying a first set of yarns in a first wale direction on a single needle bed machine, each of the first set of yarns forming a first series of loops at each of a plurality of courses for a knitted mesh; applying a second set of yarns in a second wale direction on the single needle bed machine, the second wale direction being opposite from the first wale direction, each of the second set of yarns forming a second series of loops at every other of the plurality of courses for the knitted mesh; and applying a third set of yarns in every predetermined number of courses for the knitted mesh, the application of the third set of yarns defining openings in the knitted mesh, wherein the first set of yarns interlaces with the second set of yarns at the every other course to define nodes for the knitted mesh, and the second set of yarns has a greater tension than the first set of yarns, the difference in tension substantially preventing the knitted mesh from unraveling at the nodes.

In yet another embodiment, a method for making a knitted mesh for a prosthetic device, includes: applying a first set of yarns to a first needle bed of a double needle bed machine in a wale direction; applying a second set of yarns to a second needle bed of the double needle bed machine in a wale direction; and applying a third set of yarns in every predetermined number of courses for the knitted mesh, the application of the third set of yarns defining openings in the knitted mesh, wherein the first set of yarns and the second set of yarns are alternately applied to form staggered loops at the first needle bed and the second needle bed, respectively, and the first set of yarns interlaces with the second set of yarns to define nodes for the knitted mesh, the alternating application of the first set of yarns and the second set of yarns causing the first set of yarns to have a different tension relative to the second set of yarns at the nodes, the difference in tension substantially preventing the knitted mesh from unraveling at the nodes.

In a further particular embodiment, a method for making a knitted mesh for a prosthetic device, includes: forming, on a flat needle bed machine, a first series of jersey loops along each of a first set of courses for a knitted mesh; and forming, on the flat needle bed machine, a second series of alternating tucked loops and jersey loops along each of a second set of courses for the knitted mesh, the second set of courses alternating with the first set of courses; wherein the second set of courses has a greater tension than the first set of courses, and the tucked loops along the second set of courses engage the jersey loops of the first set of courses and substantially prevents the knitted mesh from unraveling at the tucked loops. In an example of this embodiment, a continuous yarn forms the first set of courses and the second set of courses. In another example of this embodiment, the first set of courses and the second set of courses are formed by different yarns. In yet another example of this embodiment, the first set of courses and the second set of courses are formed by different yarns having different diameters.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 1A illustrates the technical back of an example mesh produced on a single needle bed warp knitting machine according to aspects of the present invention.

FIG. 1B illustrates the technical front of the example mesh illustrated in FIG. 1A.

FIG. 2 illustrates an example mesh produced on a double needle bed warp knitting machine according to aspects of the present invention. Thus.

FIG. 25 illustrates an example pattern layout for the single needle bed mesh according to aspects of the present invention.

FIGS. 28B and 28C illustrate an example pattern layout for the mesh design of FIG. 28A including all pattern and ground bars according to aspects of the present invention.

FIGS. 36C and 36D are enlarged views of the example pattern layout and ground bars of FIG. 34B.

FIGS. 40B and 40C illustrate an example pattern layout for the silk-based mesh design of FIG. 40A in accordance with the present invention including all pattern and ground bars according to aspects of the present invention.

FIGS. 40D and 40E are enlarged views of the example pattern layout and ground bars of FIG. 40B.

FIGS. 45B and 45C illustrate an example pattern layout for the silk-based mesh design of FIG. 45A in accordance with the present invention including all pattern and ground bars according to aspects of the present invention.

FIGS. 46A and 46B illustrate an example pattern layout for a double needle bed mesh or scaffold according to aspects of the present invention from FIG. 45B for ground bar #4.

FIGS. 47A and 47B illustrate an example pattern layout for a double needle bed mesh or scaffold according to aspects of the present invention from FIG. 45B for pattern bar #5.

FIGS. 48A and 48B illustrate an example pattern layout for a double needle bed mesh according to aspects of the present invention from FIG. 45B for ground bar #7.

DETAILED DESCRIPTION

Figure 2A:
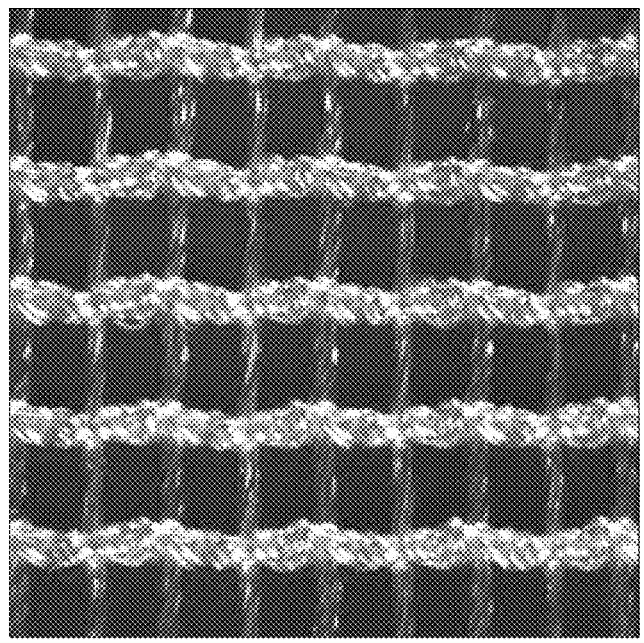
FIG. 2A shows the technical front 200A of the mesh 200 embodiment of the present invention.

Embodiments according to aspects of the present invention provide a biocompatible surgical silk mesh device for use in soft or hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of these embodiments allows tissue in-growth while the mesh bioresorbs at a rate which allows for a smooth transfer of mechanical properties to the new tissue from the silk scaffold. Furthermore, embodiments employ a knit pattern that substantially prevents unraveling, especially when the mesh device is cut. In particular, embodiments may preserve the stability of the mesh device by employing a knit pattern that takes advantage of variations in tension between at least two yarns laid in a knit direction. For example, a first yarn and a second yarn may be laid in a knit direction to form "nodes" for a mesh device. The knit direction for the at least two yarns, for example, may be vertical during warp knitting or horizontal during weft knitting. The nodes of a mesh device, also known as intermesh loops, refer to intersections in the mesh device where the two yarns form a loop around a knitting needle. In some embodiments, the first yarn is applied to include greater slack than the second yarn, so that, when a load is applied to the mesh device, the first yarn is under a lower tension than the second device. A load that places the at least two yarns under tension may result, for example, when the mesh device is sutured or if there is pulling on the mesh device. The slack in the first yarn causes the first yarn to be effectively larger in diameter than the second yarn, so that the first yarn experiences greater frictional contact with the second yarn at a node and cannot move, or is "locked," relative to the second yarn. Accordingly, this particular knit design may be referred to as a "node-lock" design.

In general, node-lock designs according to aspects of the present invention employ at least two yarns under different tensions, where a higher tension yarn restricts a lower tension yarn at the mesh nodes. The at least two yarns thus differentially engage each other in a defined pattern to form a plurality of interconnections at each of which the yarns lockingly engage. To achieve variations in tension between yarns, other node-lock designs may vary the yarn diameter, the yarn materials, the yarn elastic properties, and/or the knit pattern such that the yarns are differentially engaged. For example, the knit pattern described previously applies yarns in varying lengths to create slack in some yarns so that they experience less tension. Because the lower tension yarn is restricted by the higher tension yarn, node-lock designs substantially prevent unraveling of the mesh or disengagement of the yarns from each other when tension is applied to the fabric when the mesh is cut. As such, the embodiments allow the mesh device to be cut to any shape or size while maintaining the stability of the mesh device. In addition, node-lock designs provide a stability that makes it easy to pass the mesh device through a cannula for laparoscopic or arthroscopic surgeries without damaging the material.

Although the node-lock design may employ a variety of polymer materials, a mesh device using silk according to aspects of the present invention can bioresorb at a rate sufficient to allow tissue in-growth while slowly transferring the load-bearing responsibility to the native tissue. Particular embodiments may be formed from *Bombyx mori* silkworm silk fibroin. The raw silk fibers have a natural globular protein coating known as sericin, which may have antigenic properties and must be depleted before implantation. Accordingly, the yarn is taken through a depletion process. The depletion of sericin is further described, for example, by Gregory H. Altman et al., "Silk matrix for tissue engineered anterior cruciate ligaments," Biomaterials 23 (2002), pp. 4131-4141, the contents of which are incorporated herein by reference. As a result, the silk material used in the device embodiments contains substantially no sensitizing agents, in so far as can be measured or predicted with standardized biomaterials test methods.

Figure 22:
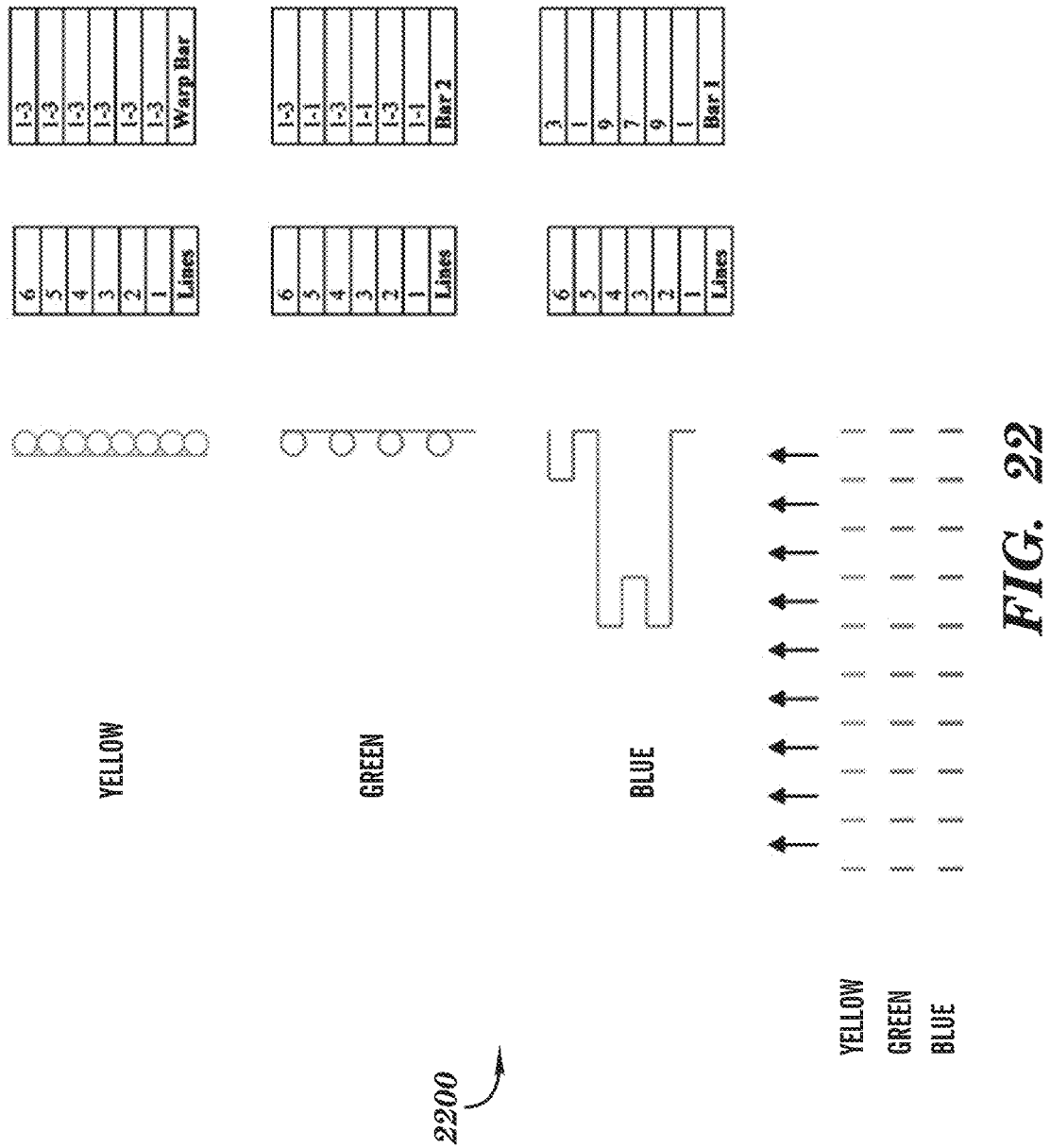
FIG. 22 illustrates an example pattern layout for a single needle bed mesh according to aspects of the present invention.

A surgical mesh device according to aspects of the present invention may be created on a single needle bed Comez Acotronic/600-F or a Comez 410 ACO by the use of three movements as shown in the pattern layout 2200 in FIG. 22: two movements in the wale direction, the vertical direction within the fabric, and one in the course direction, the horizontal direction of the fabric. The movements in the wale direction go in opposing directions; a first yarn moving in one direction loops every course while the second yarn moving in the opposite direction loops every other course. The yarns follow a repeated pattern of 3-1 and 1-1/1-3 on a 20 gauge knitting machine, using only half of the needles available on the needle bed. The interlacing of the loops within the fabric allow for one yarn to become under more tension than the other under stress, locking it around the less tensioned yarn; keeping the fabric from unraveling when cut. The other movement within the fabric occurs in every few courses creating the openings in the mesh. These yarns follow a pattern of 1-9/9-7/7-9/9-1/1-3/3-1. These yarns create tension within the fabric when under stress, locking the yarns in the fabric; preventing the fabric from unraveling.

Figure 26:
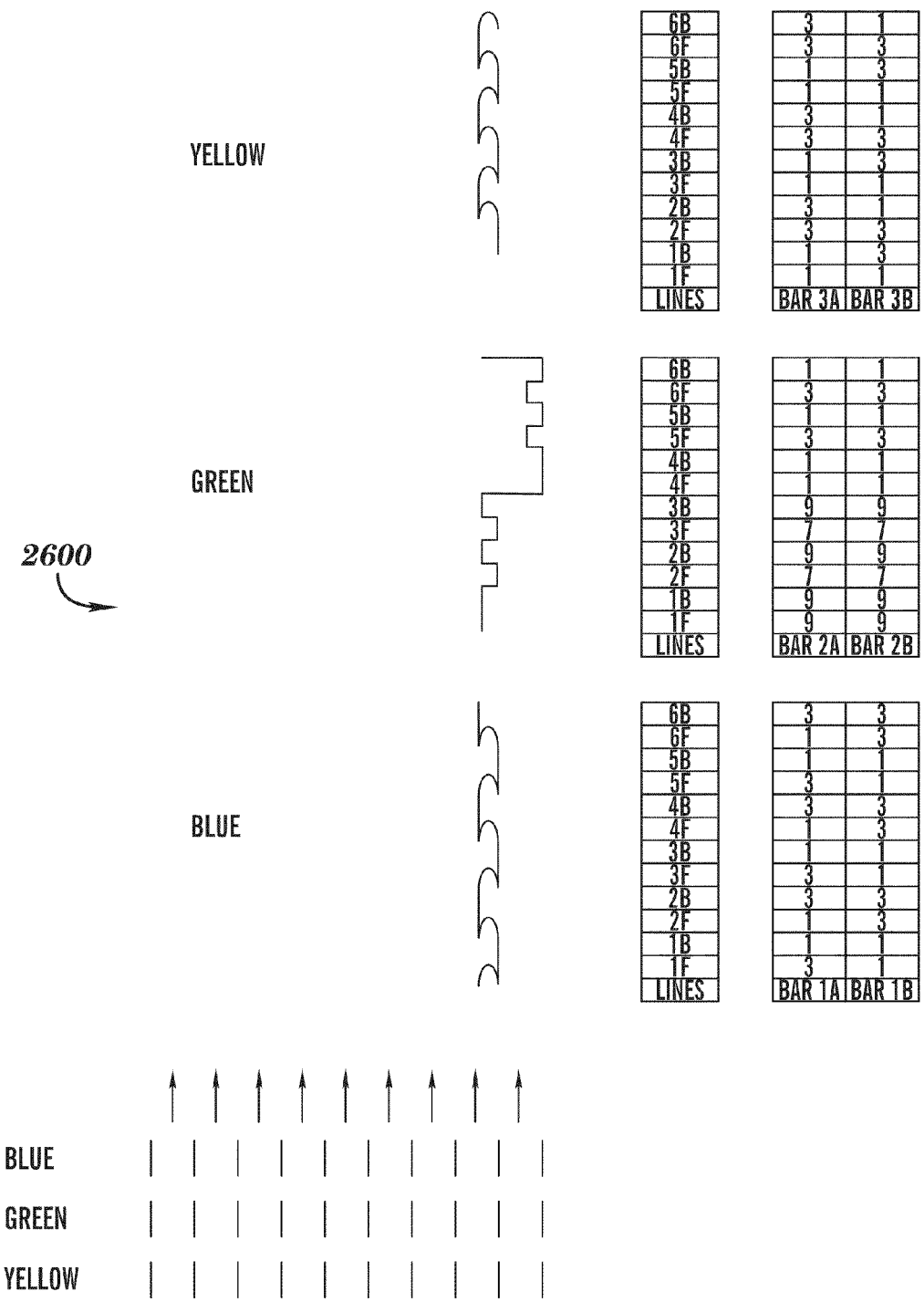
FIG. 26 illustrates an example pattern layout of the double needle bed mesh according to aspects of the present invention.

A surgical mesh device according to aspects of the present invention may be created on a double needle bed Comez DNB/EL-800-8B knitting machine by the use of three movements as shown in the pattern layout 2600 in FIG. 26: two movements in the wale direction and one in the course direction. The two movements in the wale direction occur on separate needle beds with alternate yarns; loops that occur in every course movement are staggered within the repeat. The yarns follow a repeated pattern of 3-1/1-1/1-3/3-3 and 1-1/1-3/3-3/3-1. The third movement happens with the yarn that traverses the width of the fabric. The yarn follows the pattern 9-9/9-9/7-7/9-9/7-7/9-9/1-1/1-1/3-3/1-1/3-3/1-1. This fabric is also made at half gauge on a 20 gauge knitting machine and prevents unraveling due to the tension created between the yarns when stressed. The repeat the yarn follows within the pattern is illustrated in FIG. 26.

Figure 23:
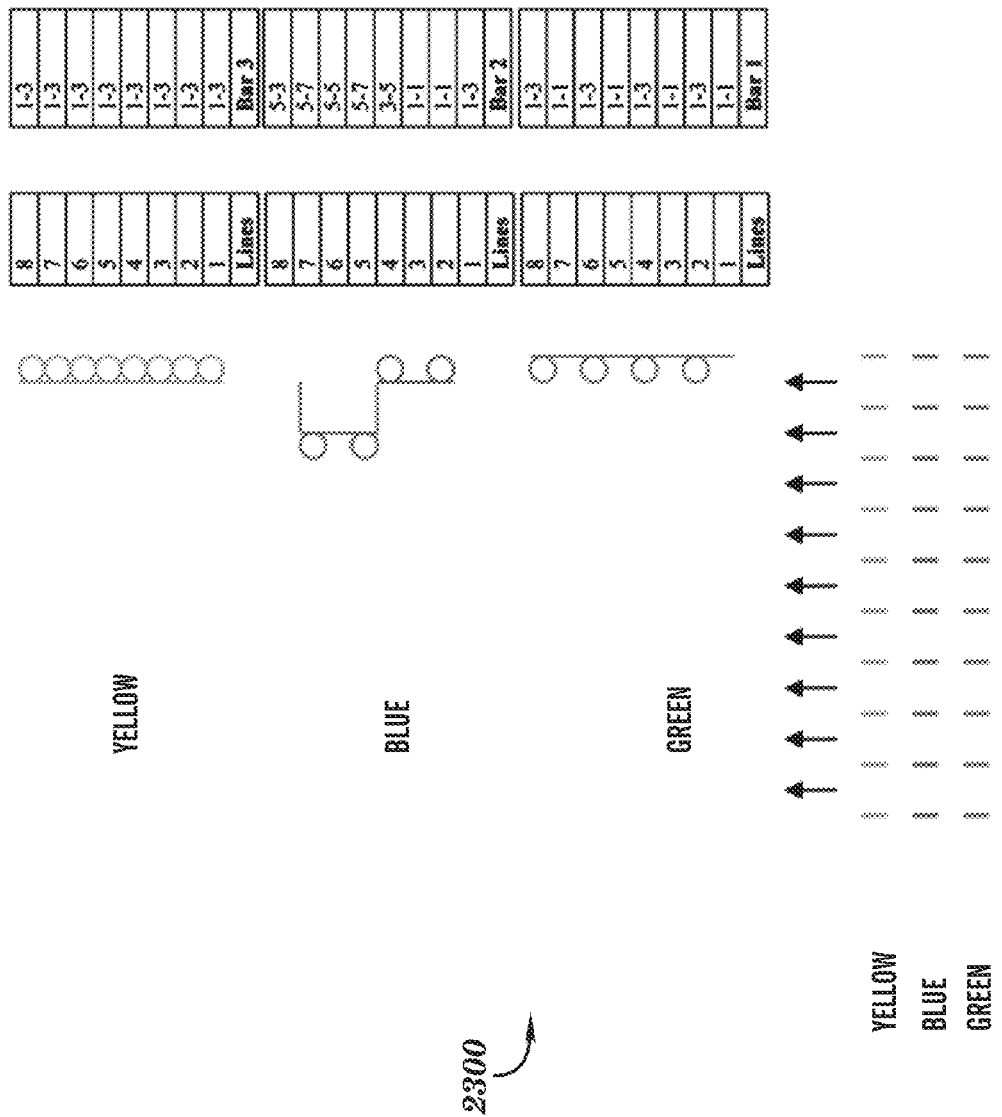
FIG. 23 illustrates an example pattern layout for a single needle bed mesh according to aspects of the present invention.
Figure 24:
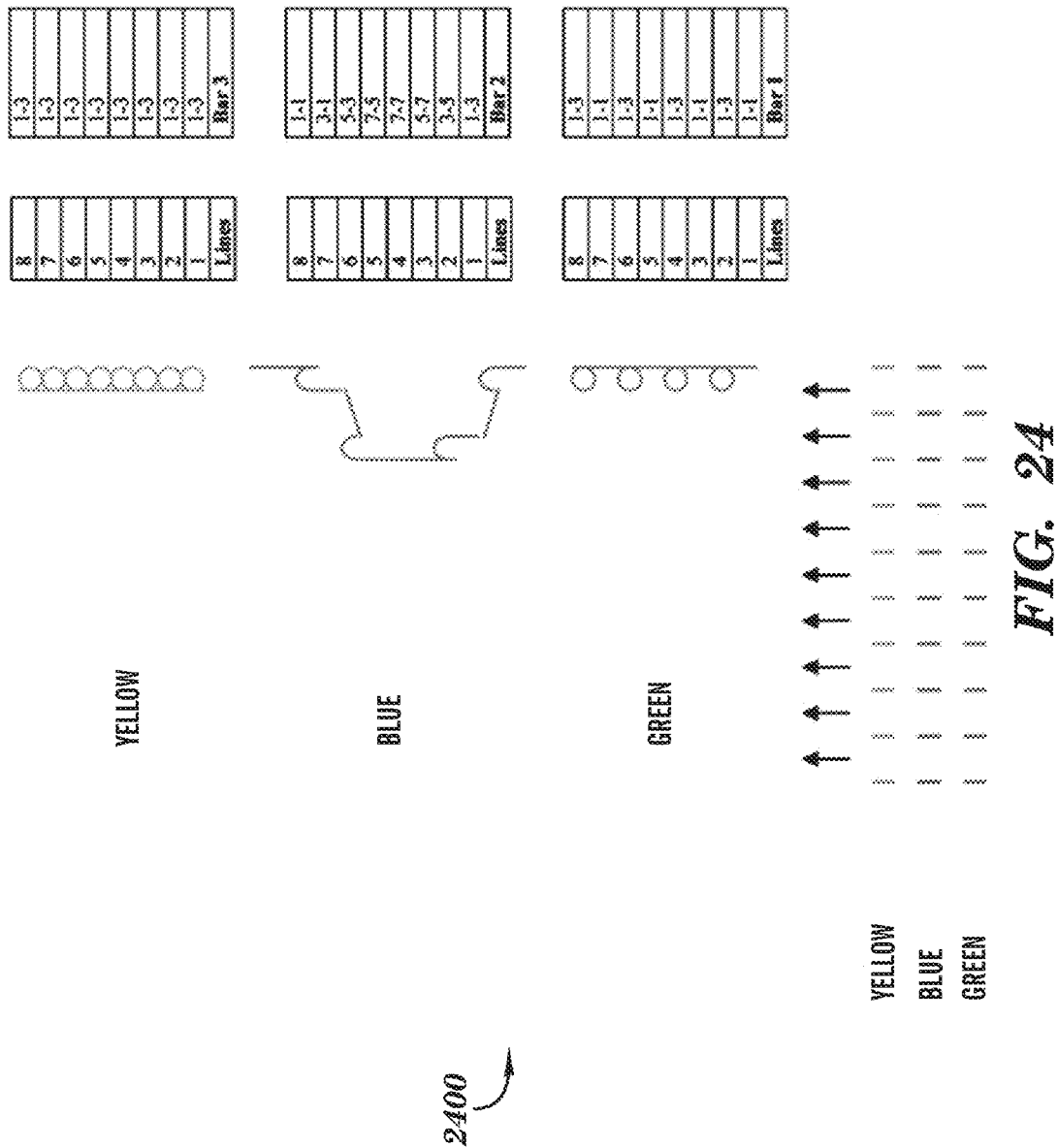
FIG. 24 illustrates an example pattern layout for a single needle bed mesh according to aspects of the present invention.

According to the pattern layouts 2300, 2400, and 2500 illustrated in FIGS. 23, 24 and 25, respectively, variations of the surgical mesh pattern are demonstrated for the Single Needle Bed including knitting with an added warp bar in place of using a weft bar insertion. These variations include knitting with the node lock yarns while moving it perpendicularly to one or more wales. These variations may include, but are not limited to, knitting either an open or closed chain stitch in either all or alternating courses. Utilizing a third warp bar, as opposed to a weft bar insertion can also be applied to the double needle warp knitting machine.

Figure 27:
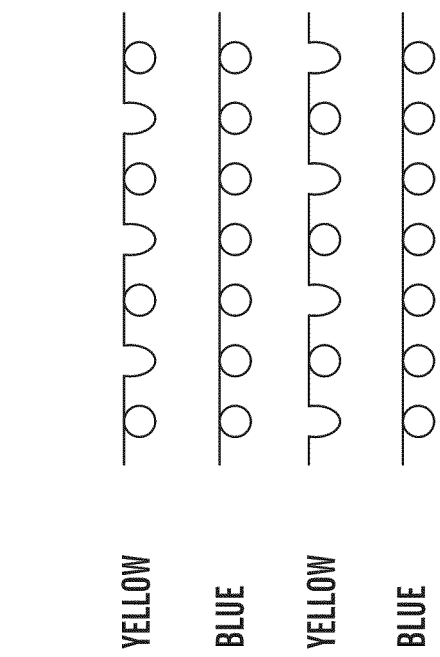
FIG. 27 illustrates an example pattern layout for the double needle bed weft knitting machine according to aspects of the present invention.

A surgical mesh device according to aspects of the present invention may be formed on the Shima Seiki flat needle bed machine as shown in the pattern layout 2700 in FIG. 27. This knit includes a continuous yarn or at least two different yarn sizes, one of which could be, though not limited to a different material. The knitted mesh would be formed by a regular jersey knit on the first row with loops formed by either a continuous yarn or a yarn of a certain yarn size, while the loops in the second row are formed by tucked loops that occur alternately with jersey knit loops of the same continuous yarn or with a yarn of a different size. The mesh would be shaped during knitting by use of increasing or decreasing stitches; a fashioning technique.

In embodiments employing silk yarn, the silk yarn may be twisted from yarn made by 20-22 denier raw silk fibers approximately 40 to 60 μm in diameter. Preferably, raw silk fibers ranging from 10 to 30 denier may be employed; however any fiber diameters that will allow the device to provide sufficient strength to the intended area are acceptable. Advantageously, a constant yarn size may maximize the uniformity of the surgical mesh mechanical properties, e.g. stiffness, elongation, etc., physical and/or biological properties. However, the yarn size may be varied in sections of the surgical mesh in order to achieve different mechanical, physical and/or biological characteristics in the preferred surgical mesh locations. Factors that may influence the size of the yarn include, but are not limited to: ultimate tensile strength (UTS); yield strength, i.e. the point at which yarn is permanently deformed; percent elongation; fatigue and dynamic laxity (creep); bioresorption rate; and transfer of cell/nutrients into and out of the mesh. The knit pattern layouts 2200, 2300, 2400, 2500, and 2600 illustrated in FIGS. 22-26, respectively, may be knitted to any width limited by the knitting machine width and could be knitted with any of the gauges available with the various crochet machine or warp knitting machine. TABLE 2 outlines the fabric widths that may be achieved using different numbers of needles on different gauge machines. It is understood that the dimensions in TABLE 1 are approximate due to the shrink factor which depends on stitch design, stitch density, and yarn size used.

TABLE 1

| Gauge | Needle Count | Knitting Width |
| --- | --- | --- |
| 48 | 2-5,656 | 0.53-2,997.68 mm |
| 24 | 2-2,826 | 1.06-2,995.56 mm |
| 20 | 2-2,358 | 1.27-2,994.66 mm |
| 18 | 2-2,123 | 1.41-2,993.43 mm |
| 16 | 2-1,882 | 1.59-2,992.38 mm |
| 14 | 2-1,653 | 1.81-2,991.93 mm |
| 12 | 2-1,411 | 2.12-2,991.32 mm |
| 10 | 2-1,177 | 2.54-2,989.58 mm |
| 5 | 2-586 | 5.08-2,976.88 mm |

Embodiments of a prosthetic device according to the present invention may be knitted on a fine gauge crochet knitting machine. A non-limiting list of crochet machines capable of manufacturing the surgical mesh according to aspects of the present invention are provided by: Changde Textile Machinery Co., Ltd.; Comez; China Textile Machinery Co., Ltd.; Huibang Machine; Jakob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinery Co., Ltd.; Taiwan Giu Chun Ind. Co., Ltd.; Zhangjiagang Victor Textile; Liba; Lucas; Muller Frick; and Texma.

Embodiments of a prosthetic device according to the present invention may be knitted on a fine gauge warp knitting machine. A non-limiting list of warp knitting machines capable of manufacturing the surgical mesh according to aspects of the present invention are provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of a prosthetic device according to the present invention may be knitted on a fine gauge flat bed knitting machine. A non-limiting list of flat bed machines capable of manufacturing the surgical mesh according to aspects of the present invention are provided by: Around Star; Boosan; Cixing Textile Machine; Fengshen; Flying Tiger Machinery; Fujian Hongqi; G & P Görteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

FIGS. 1-20 illustrate an example meshes produced according to aspects of the present invention. Referring to FIGS. 1A and B, an example mesh 100 is produced on a single needle bed warp knitting machine according to aspects of the present invention. FIG. 1A shows the technical back 100A of the mesh 100, and FIG. 1B shows the technical front 100B of the mesh 100.

Figure 2B:
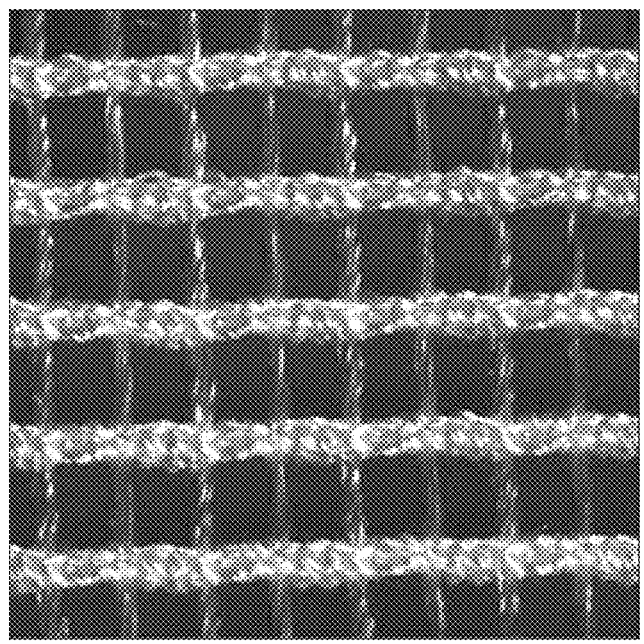
FIG. 2B shows the technical back 200B of the mesh 200 embodiment of the present invention.

Referring to FIGS. 2A and B, an example mesh 200 is produced on a double needle bed warp knitting machine according to aspects of the present invention. FIG. 2A shows the technical front 200A of the mesh 200, and FIG. 2B shows the technical back 200B of the mesh 200.

Figure 3:
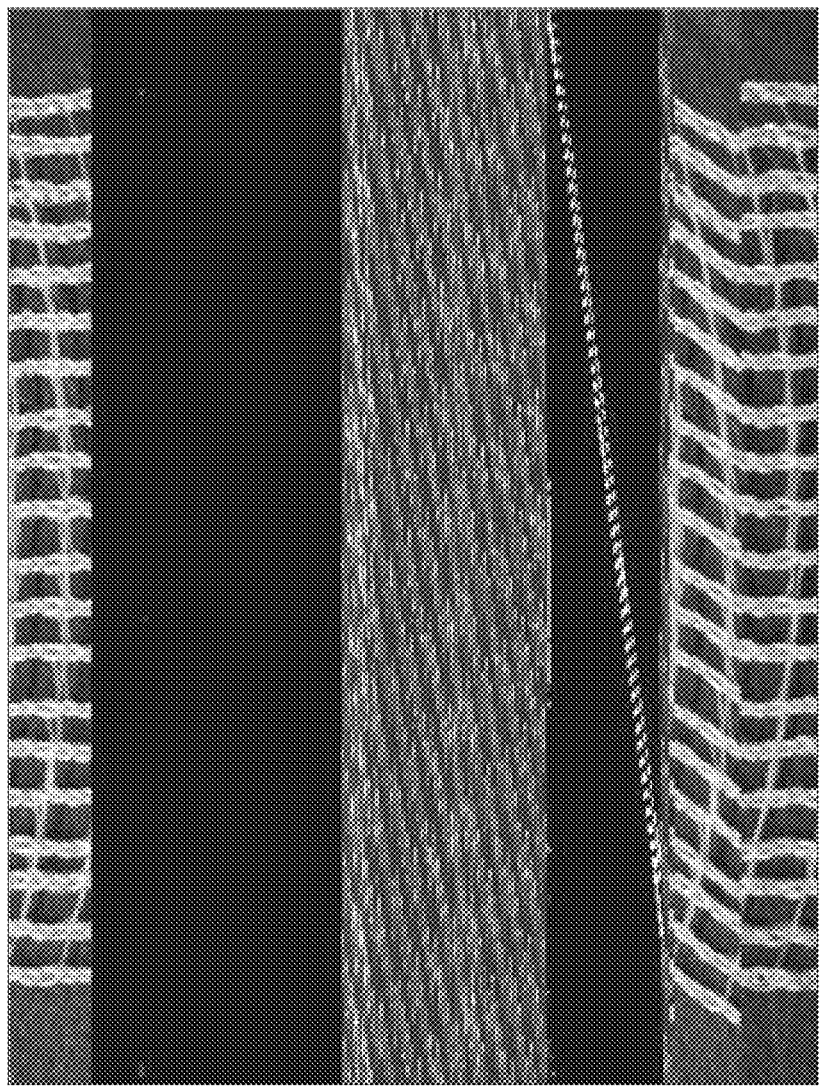
FIG. 3 illustrates an example mesh produced with single filament silk yarn according to aspects of the present invention.

FIG. 3 illustrates an example mesh 300 produced with single filament silk yarn according to aspects of the present invention.

Figure 4:
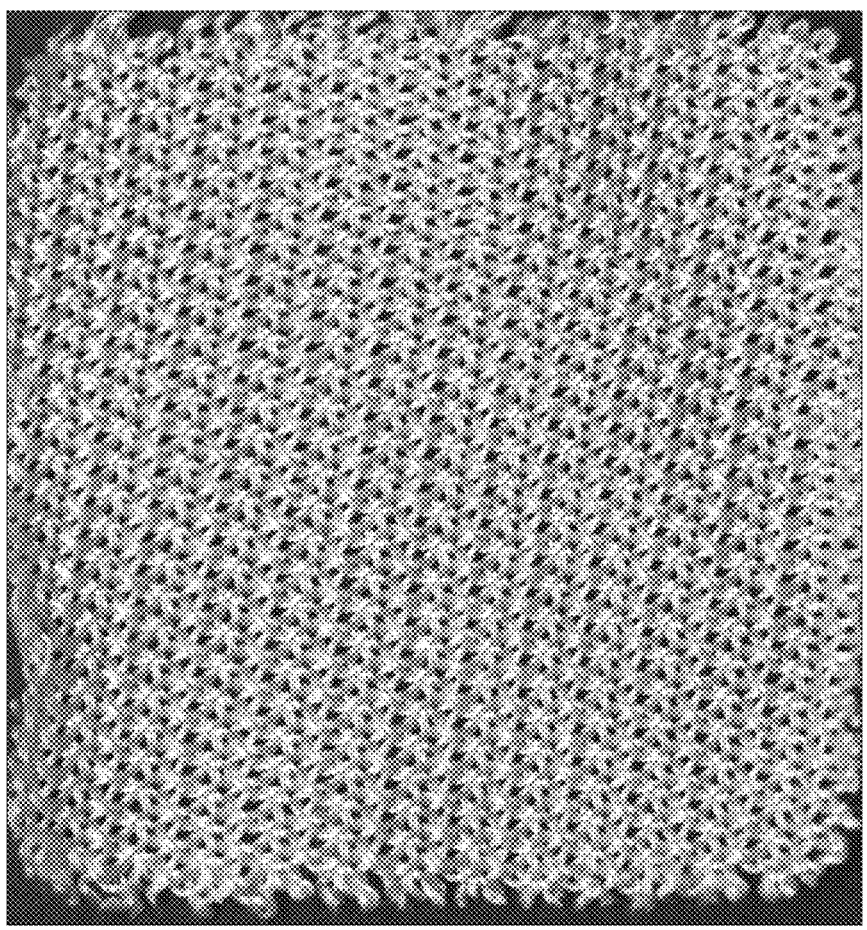
FIG. 4 illustrates an example mesh produced on a single needle bed warp knitting machine according to aspects of the present invention.

FIG. 4 shows an example mesh 400 produced on a single needle bed warp knitting machine according to aspects of the present invention.

Figure 5B:
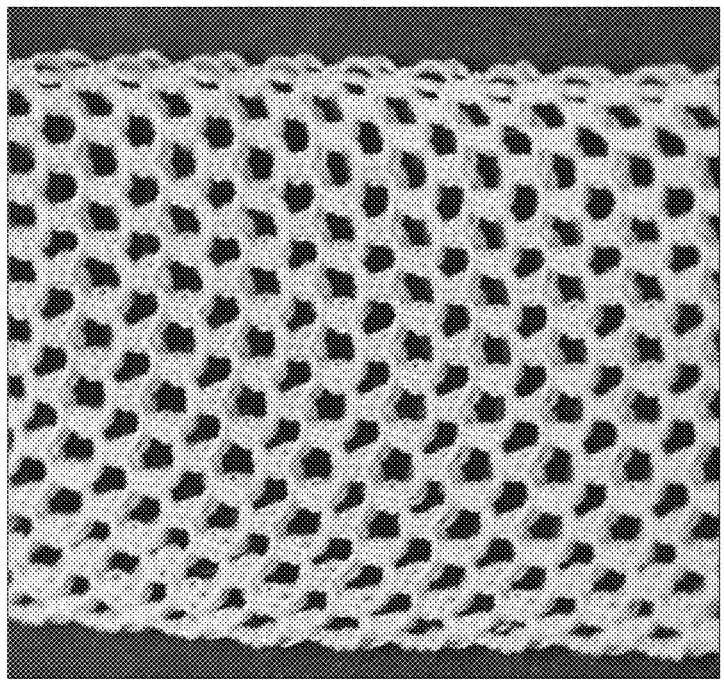
FIG. 5B illustrates an example mesh produced on a double needle bed warp knitting machine, the example mesh having a hexagonal pore according to aspects of the present invention.
Figure 5A:
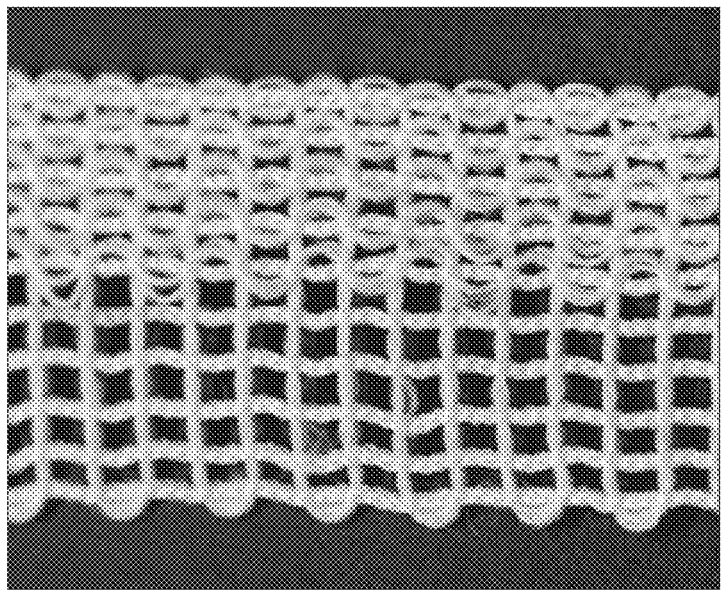
FIG. 5A illustrates an example mesh produced on a double needle bed warp knitting machine, the example mesh having a parallelepiped pore with a section demonstrating a plush design according to aspects of the present invention.

FIG. 5A illustrates an example mesh 500A produced on a double needle bed warp knitting machine. The mesh 500A has a parallelepiped pore with a section demonstrating a plush design according to aspects of the present invention. Meanwhile, FIG. 5B illustrates an example mesh 500B produced on a double needle bed warp knitting machine. The example mesh 500B has a hexagonal pore according to aspects of the present invention.

Figure 6B:
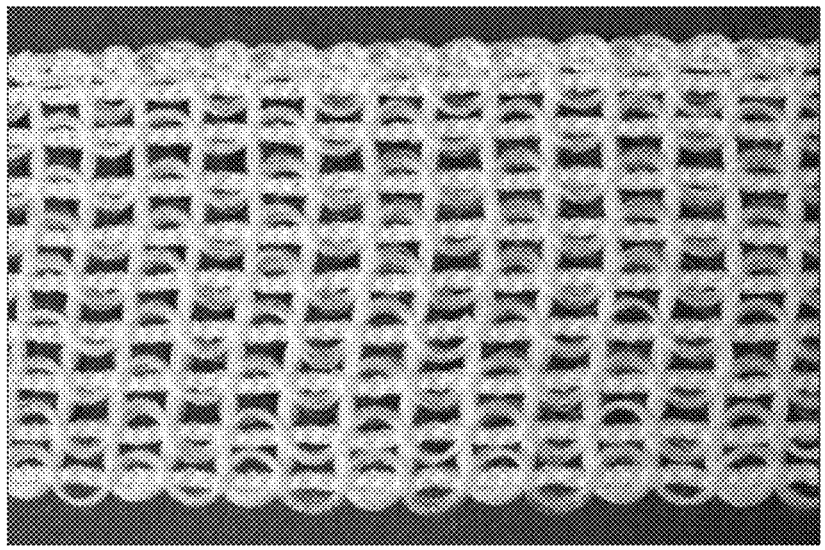
FIG. 6 illustrates an example narrow mesh fabrics of varying stitch densities incorporating a plush variation according to aspects of the present invention. Thus, FIGS. 6A and B illustrate example narrow mesh fabrics 600A and 600B according to aspects of the present invention.
Figure 6A:
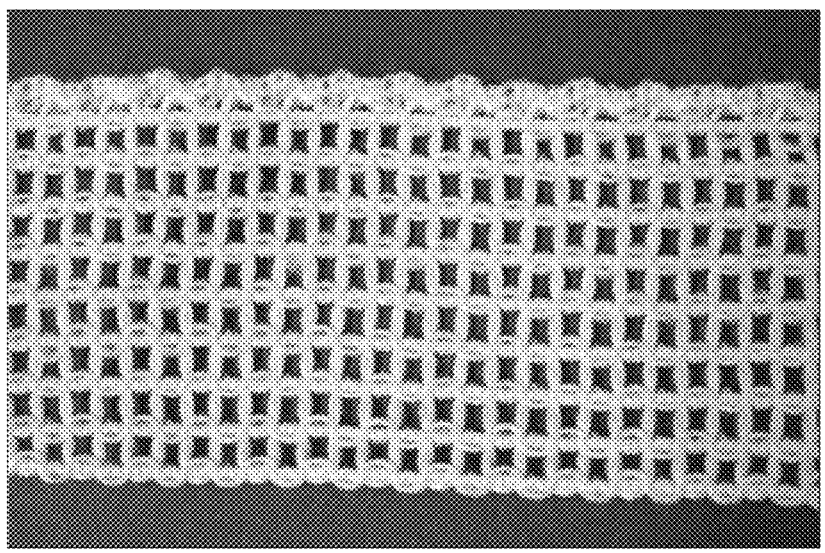

FIGS. 6A and B illustrate an example narrow mesh fabrics 600A and 600B according to aspects of the present invention. The mesh fabrics 600A and 600B have varying stitch densities incorporating a plush variation.

Figure 7:
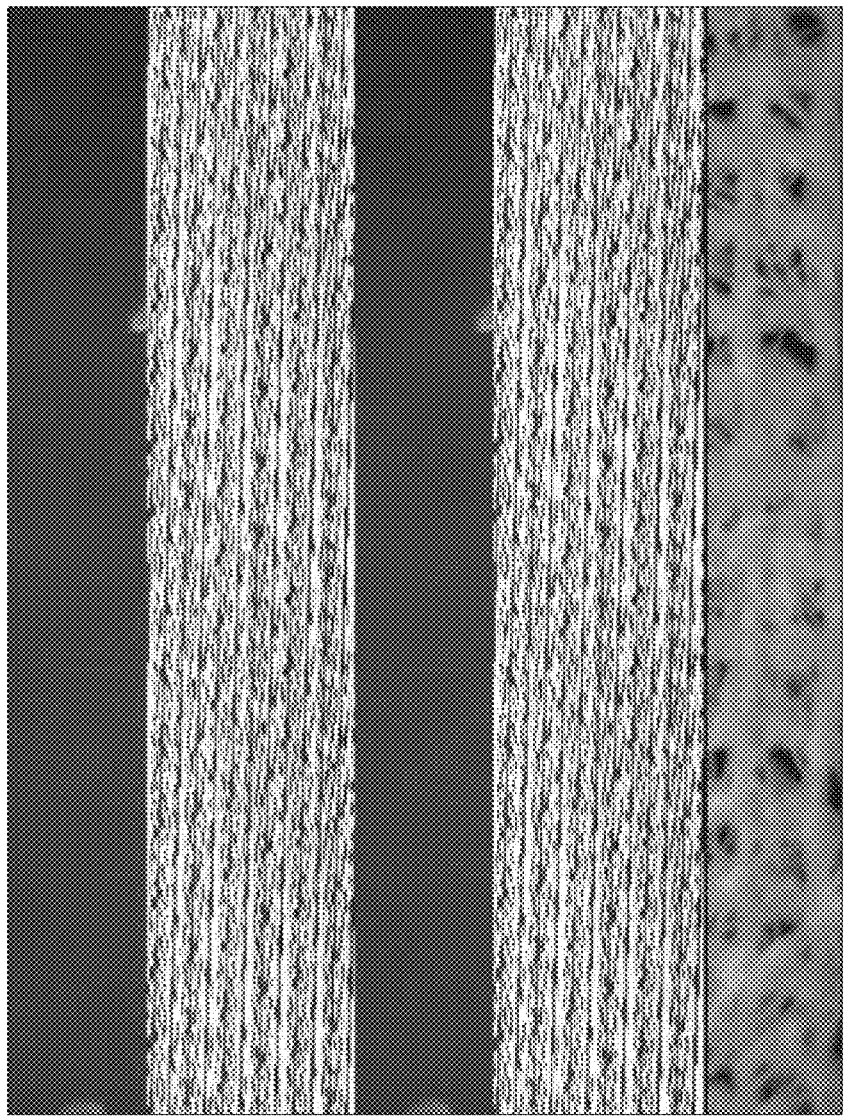
FIG. 7 illustrates an example mesh incorporating loop pile according to aspects of the present invention.
Figure 8:
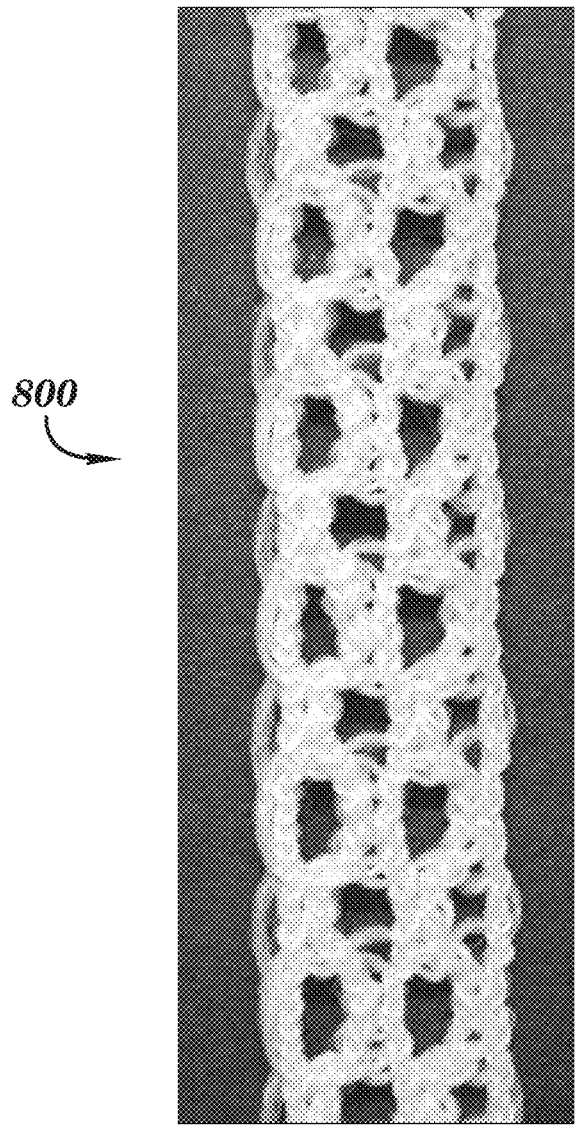
FIG. 8 illustrates an example narrow mesh fabric with pore design achieved through variation in the yarn feed rate according to aspects of the present invention.

Referring to FIG. 7, an example mesh 700 incorporates loop pile according to aspects of the present invention. FIG. 8 illustrates an example narrow mesh fabric 800 with pore design achieved through variation in the yarn feed rate according to aspects of the present invention.

Figure 9B:
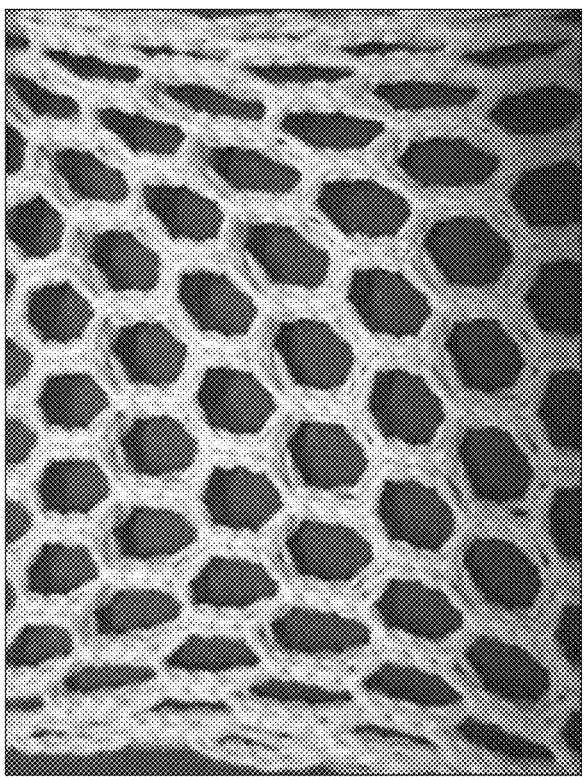
FIG. 9B illustrates an example opened mesh fabric with hexagonal shaped pores according to aspects of the present invention.
Figure 9A:
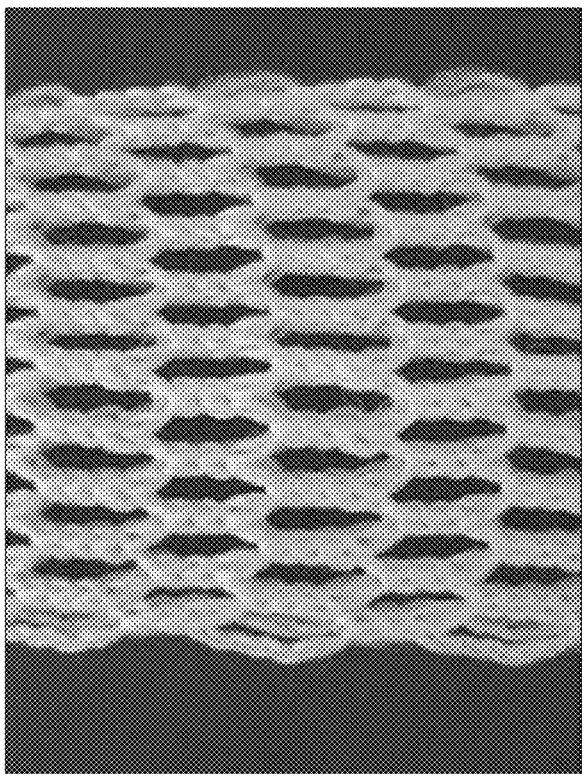
FIG. 9A illustrates an example collapsed mesh fabric with hexagonal shaped pores according to aspects of the present invention.

FIG. 9A illustrates an example collapsed mesh fabric 900A with hexagonal-shaped pores according to aspects of the present invention. Meanwhile, FIG. 9B illustrates an example opened mesh fabric 900B with hexagonal shaped pores according to aspects of the present invention.

Figure 10:
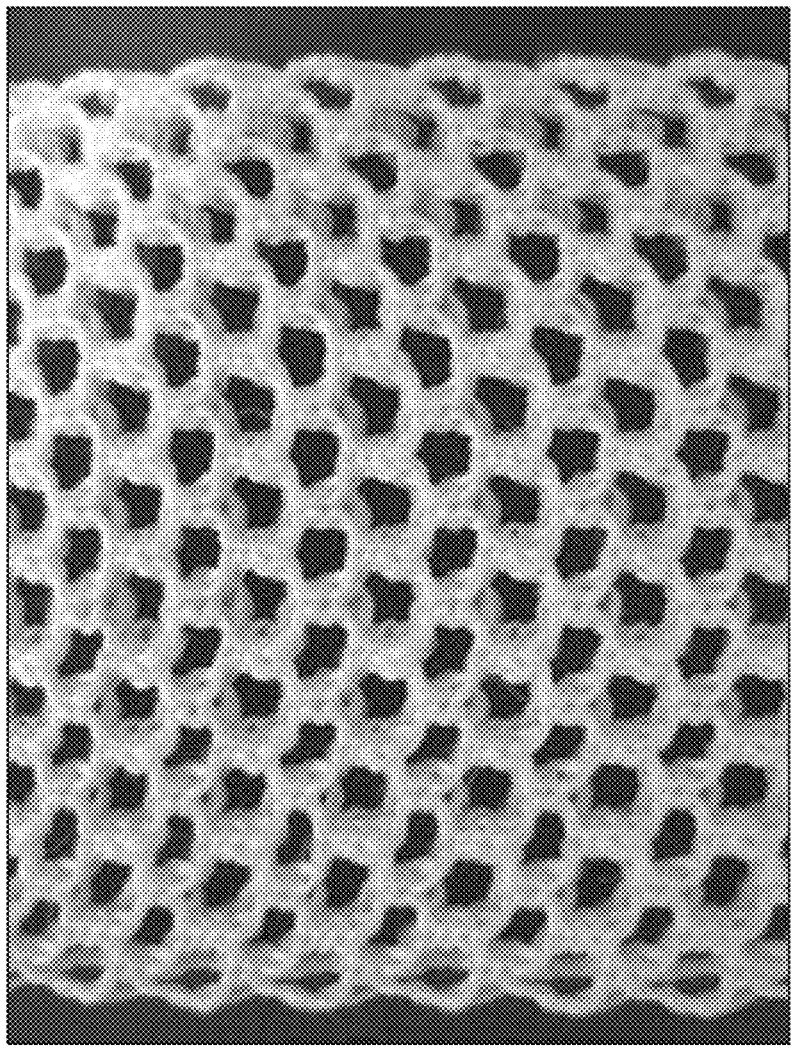
FIG. 10 illustrates an example of a stable, non-collapsible, hexagonal-shaped porous mesh fabric according to aspects of the present invention.

As shown in FIG. 10, an example of a stable, non-collapsible mesh fabric 1000 includes hexagonal-shaped pores according to aspects of the present invention.

Figure 11B:
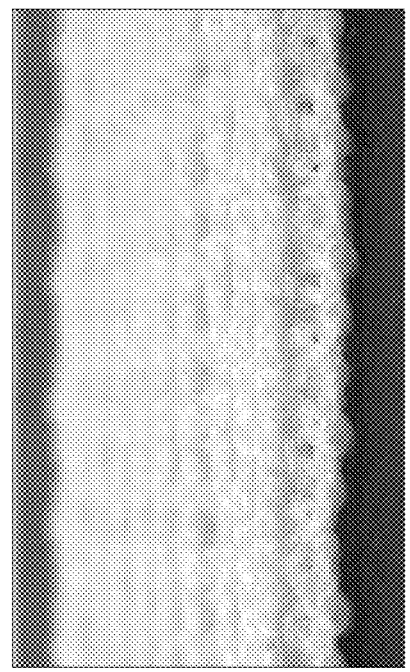
FIG. 11B illustrates the 2.55 mm thickness of the example three-dimensional mesh of FIG. 11A.
Figure 11A:
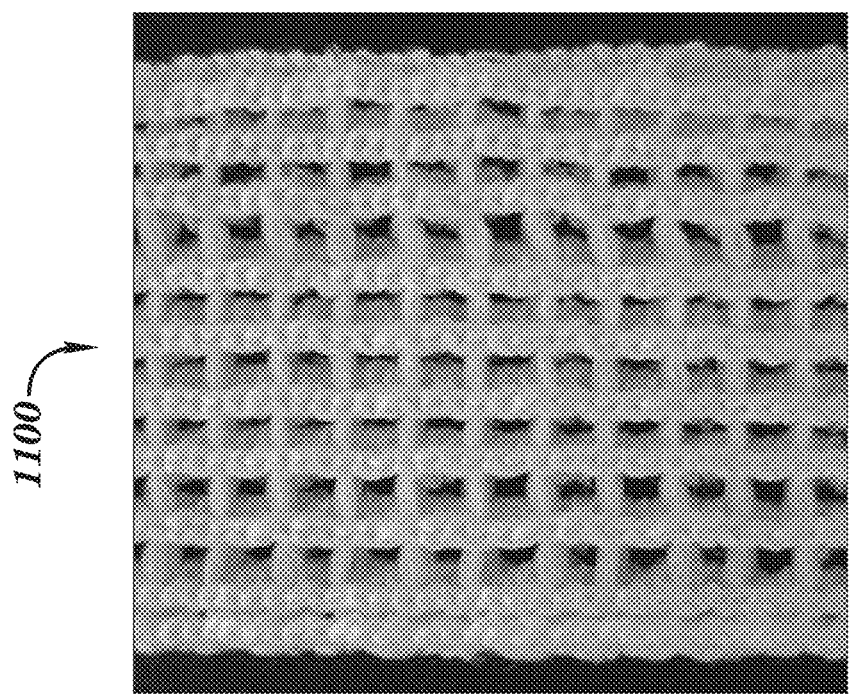
FIG. 11A illustrates an example of a three-dimensional mesh with the same technical front and technical back according to aspects of the present invention.
Figure 12:
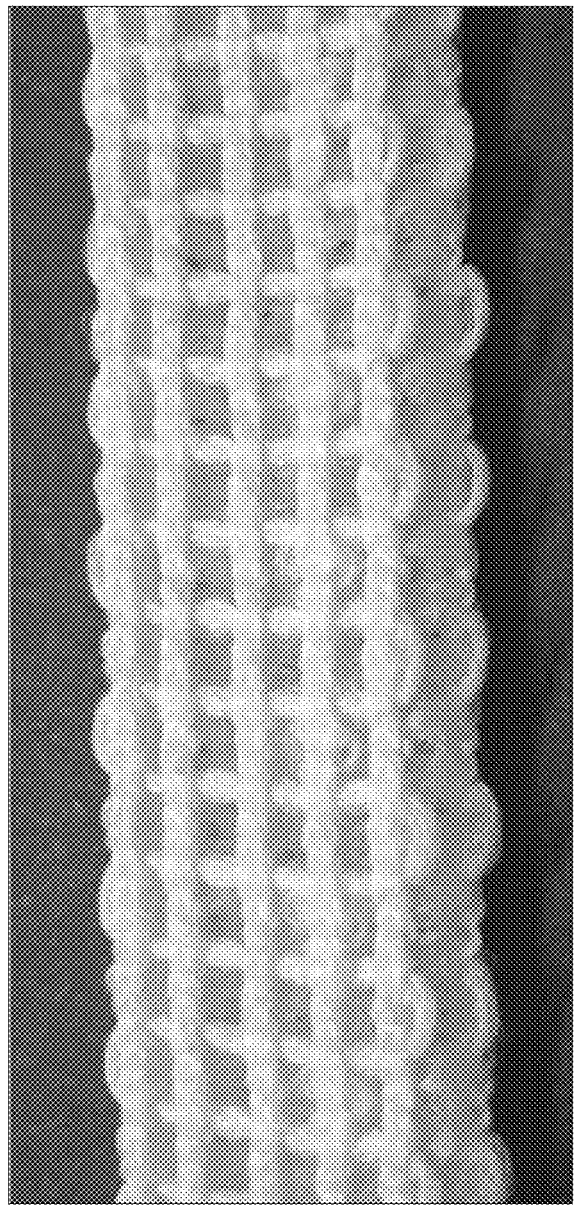
FIG. 12 illustrates an example of a three-dimensional mesh with a thickness of 3.28 mm according to aspects of the present invention.

FIG. 11A illustrate an example three-dimensional mesh 1100 with the same technical front and technical back according to aspects of the present invention. FIG. 11B illustrates the 2.55 mm thickness of the three-dimensional mesh 1100. FIG. 12 illustrates another example three-dimensional mesh 1200 with a thickness of 3.28 mm according to aspects of the present invention.

Figure 13A:
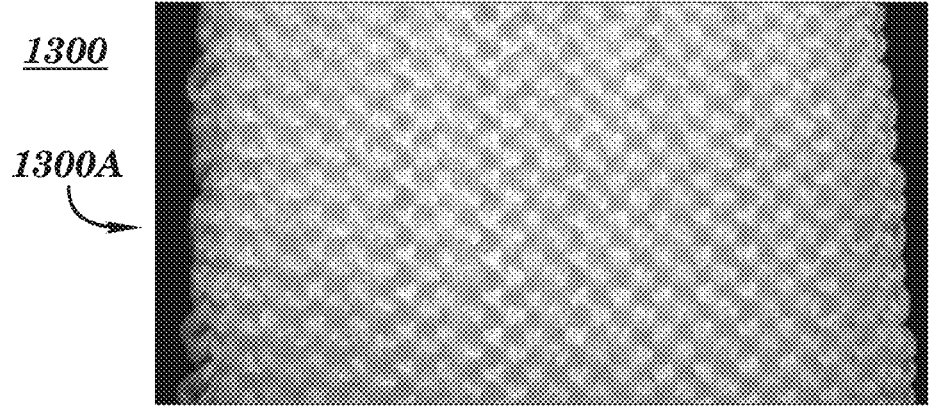
FIG. 13A illustrates the technical front of an example non-porous mesh according to aspects of the present invention.
Figure 13B:
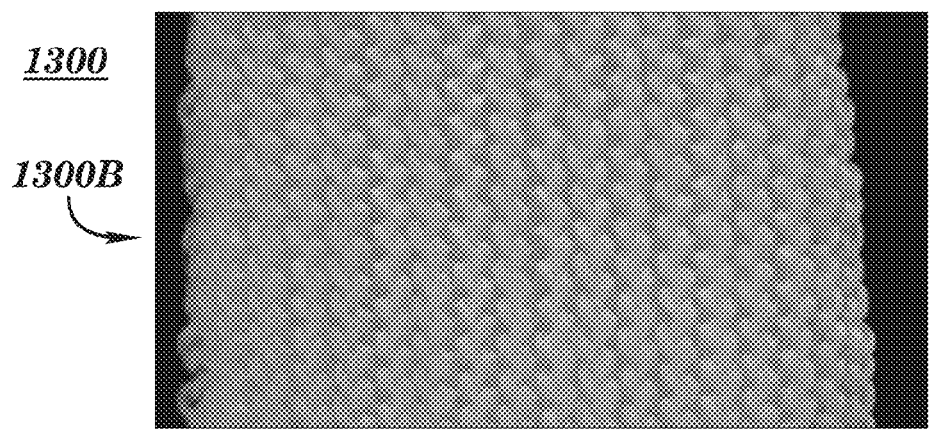
FIG. 13B illustrates the technical back of the example non-porous mesh of FIG. 13A.
Figure 13C:
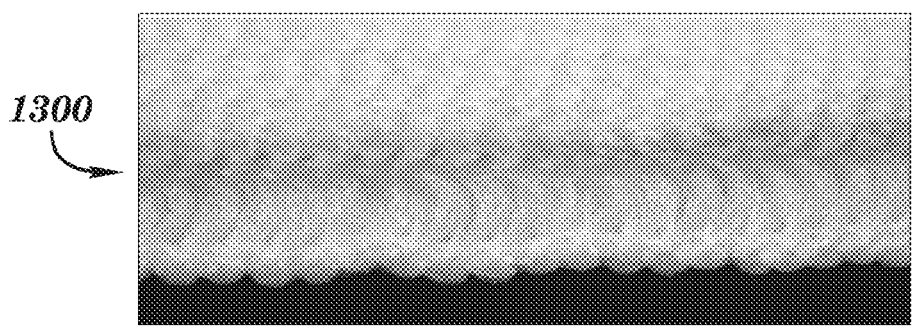
FIG. 13C illustrates the 5.87 mm thickness of the example non-porous mesh of FIG. 13A.

FIGS. 13A-C illustrate an example non-porous mesh 1300 according to aspects of the present invention. FIG. 13A shows the technical front 1300A of the non-porous mesh 1300. FIG. 13B shows the technical back 1300B of the non-porous mesh 1300. FIG. 13C shows that non-porous mesh 1300 has a thickness of 5.87 mm.

Figure 14A:
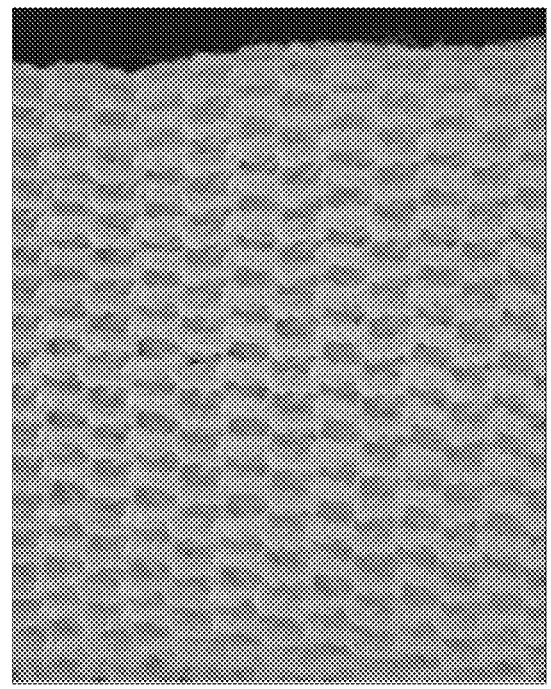
FIG. 14A illustrates an example of a three-dimensional mesh with the same technical front and technical back according to aspects of the present invention.
Figure 14B:
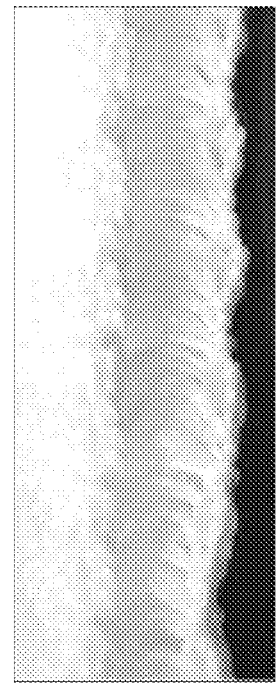
FIG. 14B illustrates the 5.36 mm thickness of the example three-dimensional mesh of FIG. 14A.
Figure 15A:
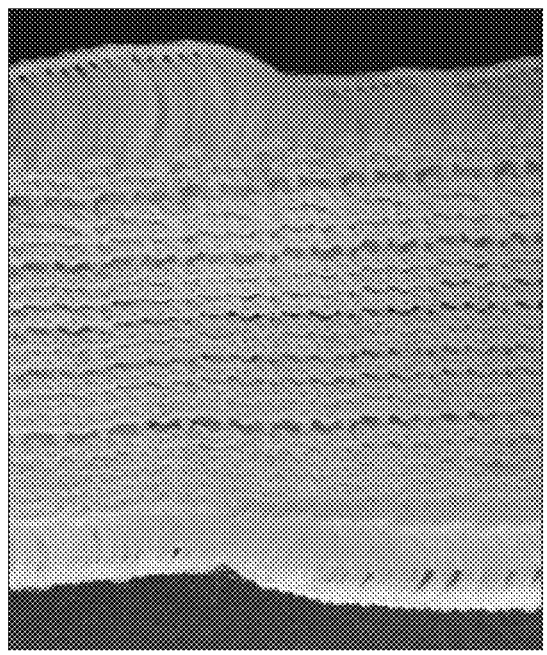
FIG. 15A illustrates the technical front of an example three-dimensional mesh fabric according to aspects of the present invention.
Figure 15B:
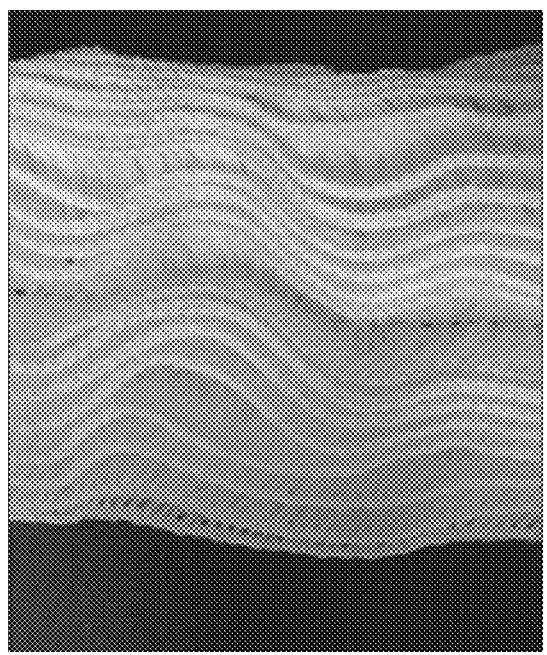
FIG. 15B illustrates the technical back of the example three-dimensional mesh fabric of FIG. 15A.
Figure 16:
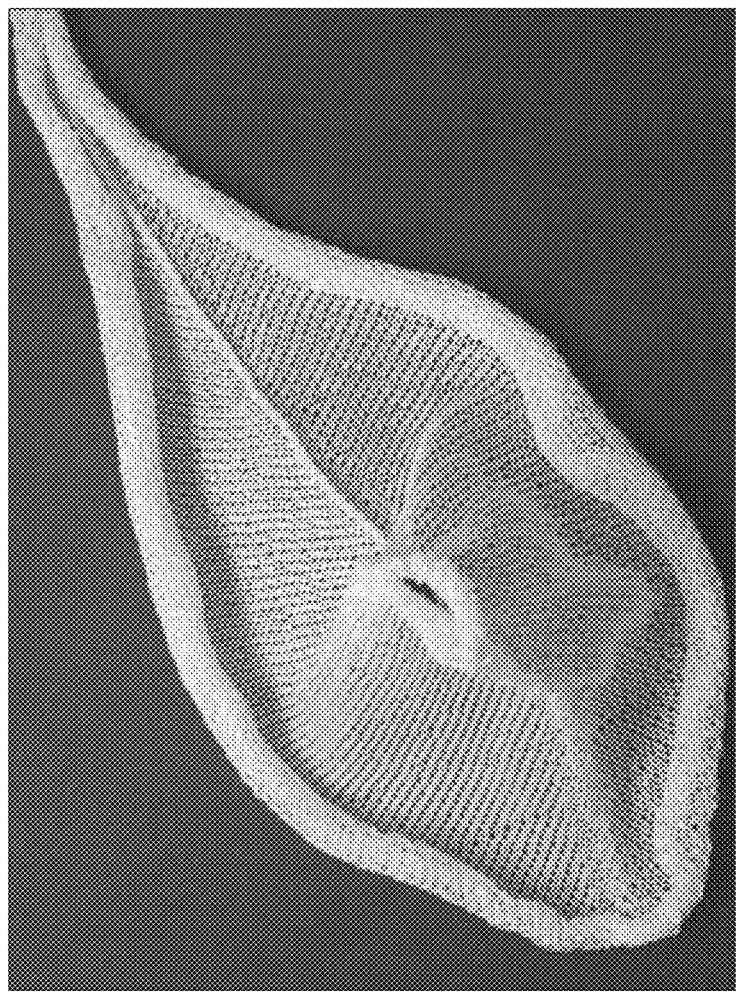
FIG. 16 illustrates an example mesh produced on a double needle bed weft knitting machine demonstrating shaping of the mesh for a breast support application according to aspects of the present invention.
Figure 17:
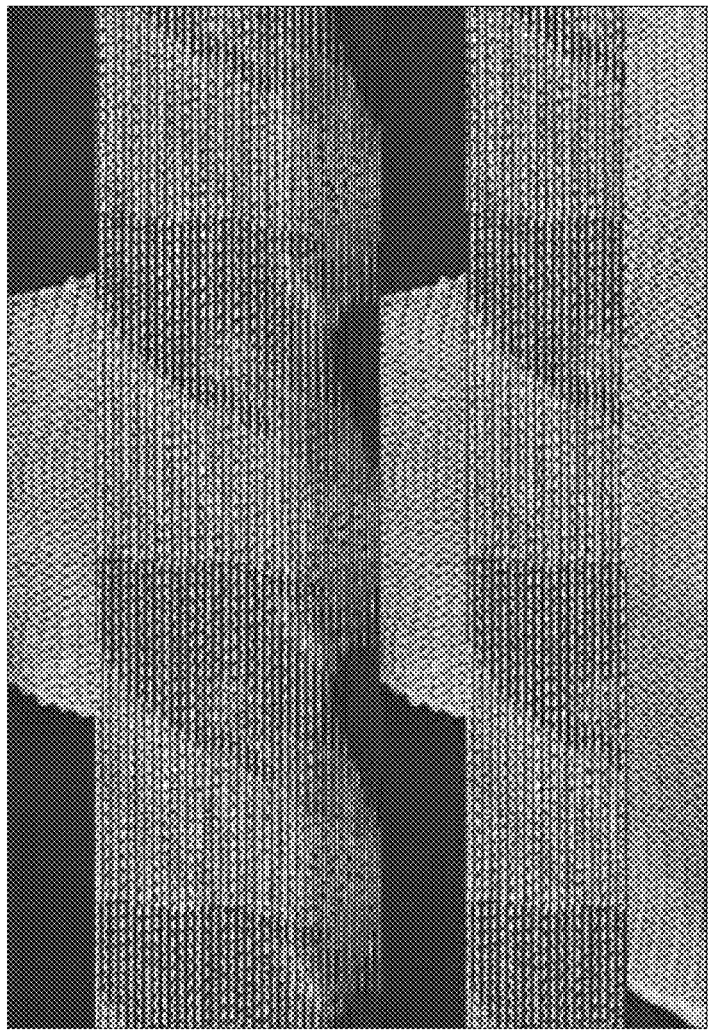
FIG. 17 illustrates another example mesh produced on a double needle bed weft knitting machine demonstrating shaping of the mesh for a breast support application according to aspects of the present invention.
Figure 18:
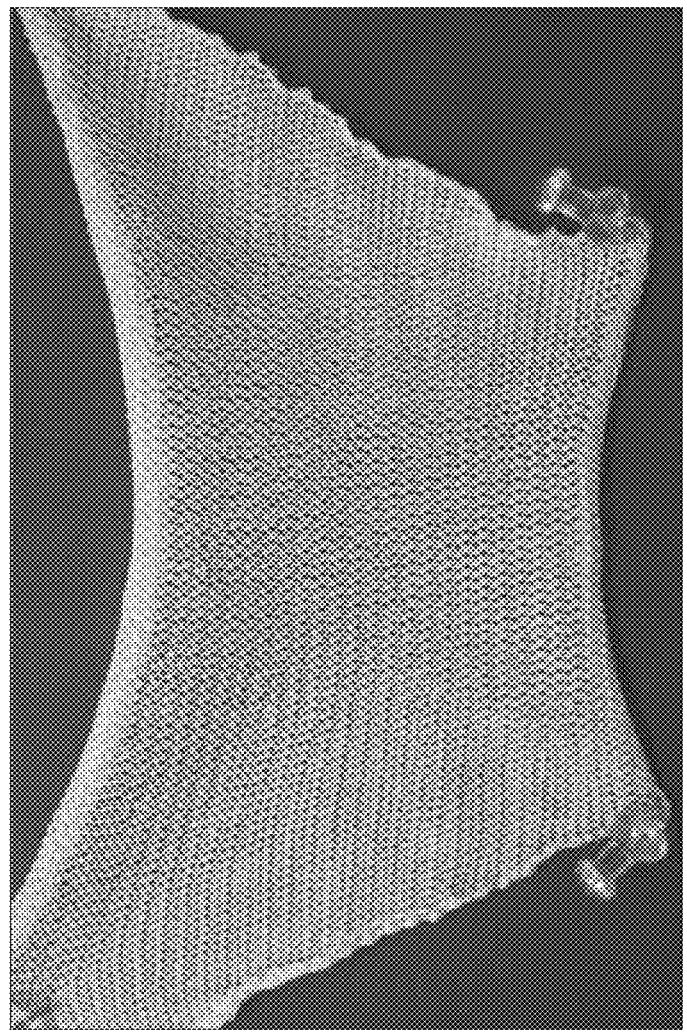
FIG. 18 illustrates yet another example mesh produced on a double needle bed weft knitting machine demonstrating shaping of the mesh for a breast support application according to aspects of the present invention.
Figure 19:
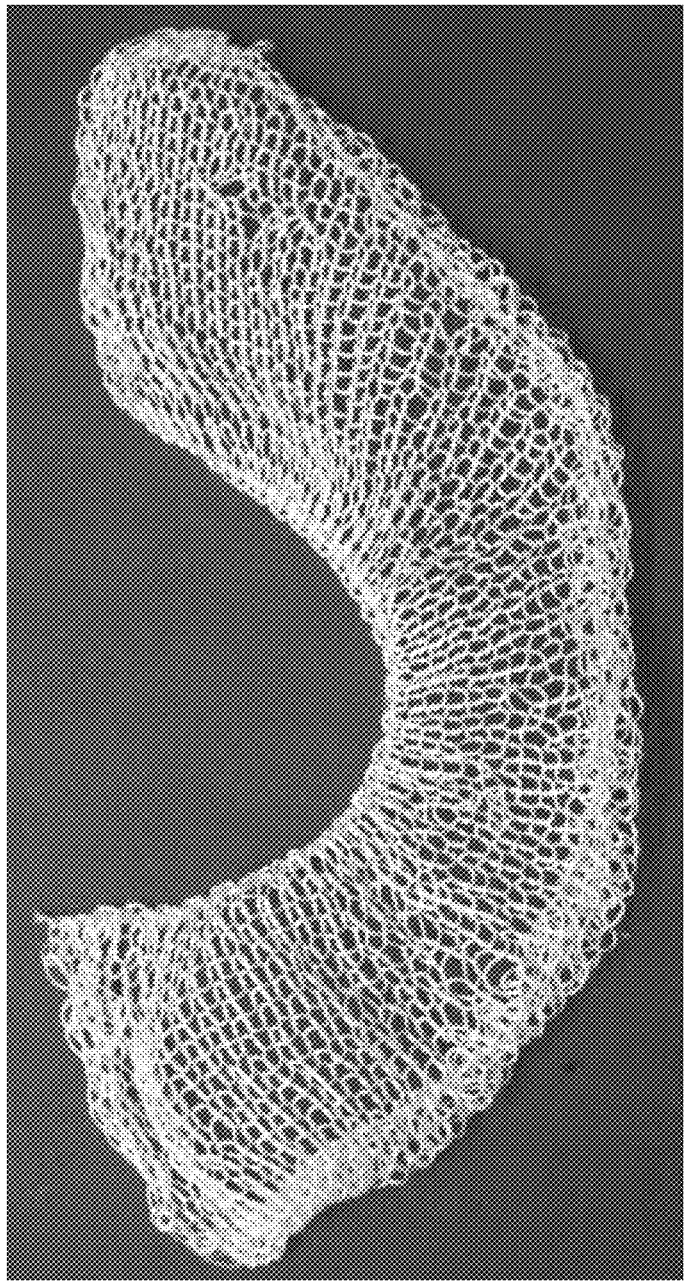
FIG. 19 illustrates a further mesh produced on a double needle bed weft knitting machine demonstrating shaping of the mesh for a breast support application according to aspects of the present invention.
Figure 20:
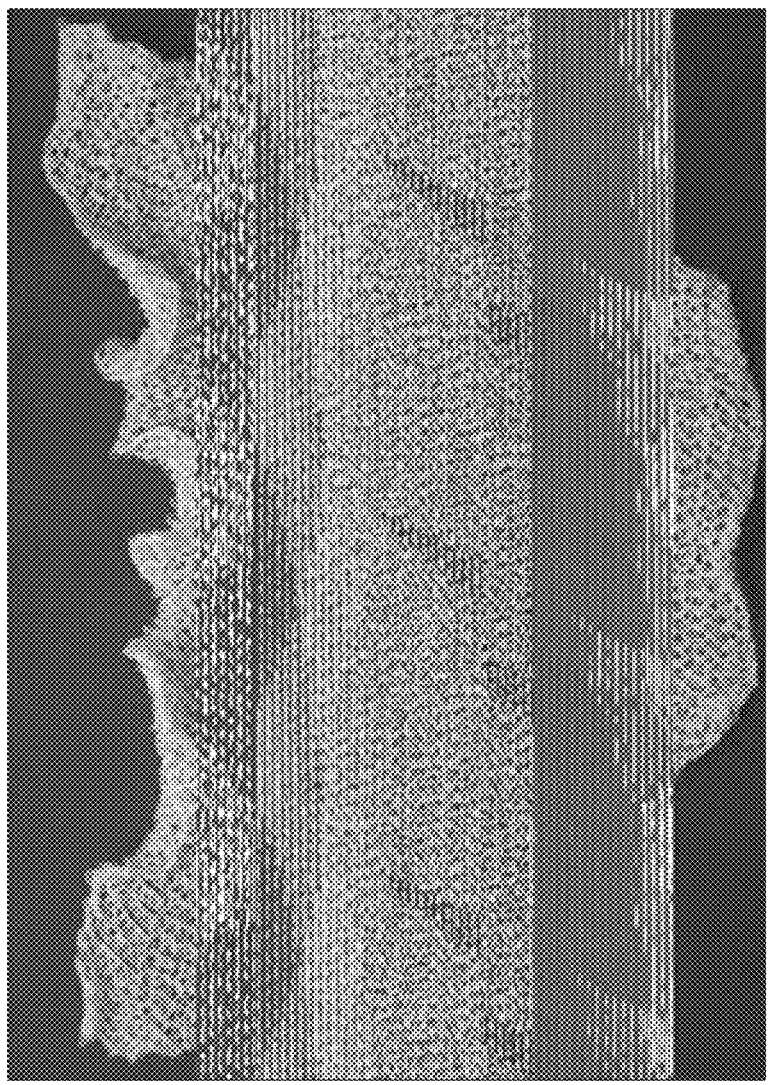
FIG. 20 illustrates another example mesh produced on a double needle bed weft knitting machine demonstrating shaping of the mesh for a breast support application according to aspects of the present invention.

FIG. 14A illustrates an example three-dimensional mesh 1400 with the same technical front and technical back according to aspects of the present invention. FIG. 14B shows that the three-dimensional mesh 1400 has a thickness of approximately 5.36 mm. FIGS. 15A and B illustrate another example three-dimensional mesh fabric 1500 according to aspects of the present invention. FIG. 15A shows the technical front 1500A of the fabric 1500, and FIG. 15B illustrates the technical back 1500B of the fabric 1500.

FIGS. 16-20 illustrate respective example meshes 1600, 1700, 1800, 1900, and 2000 that are produced on a double needle bed weft knitting machine. The meshes 1600, 1700, 1800, 1900, and 2000 demonstrate shaping of a mesh for a breast support application according to aspects of the present invention.

Figure 28A:
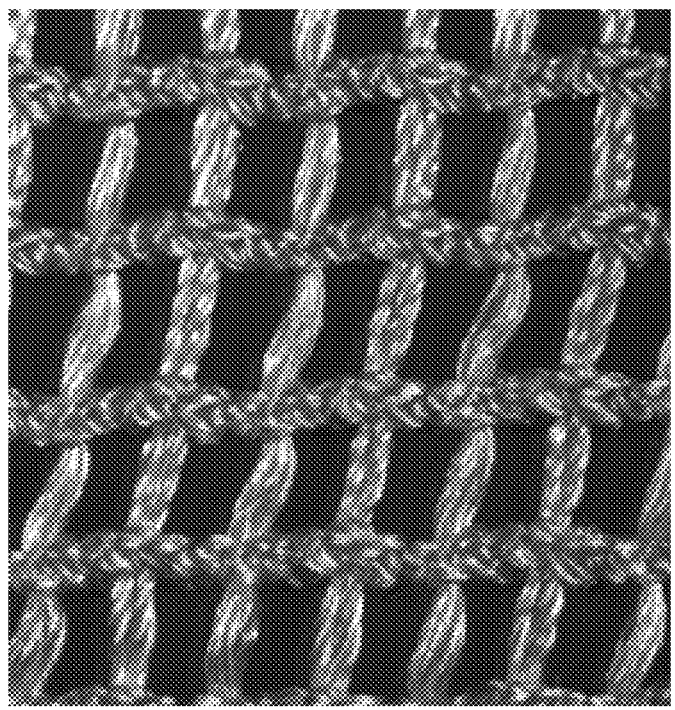
FIG. 28A is a photograph of a pattern layout for a silk-based mesh design in accordance with aspects of the present invention.

FIG. 28A is a photograph of a pattern layout for a silk-based mesh design suitable for use as a mesh in accordance with aspects of the present invention.

Figure 28B:
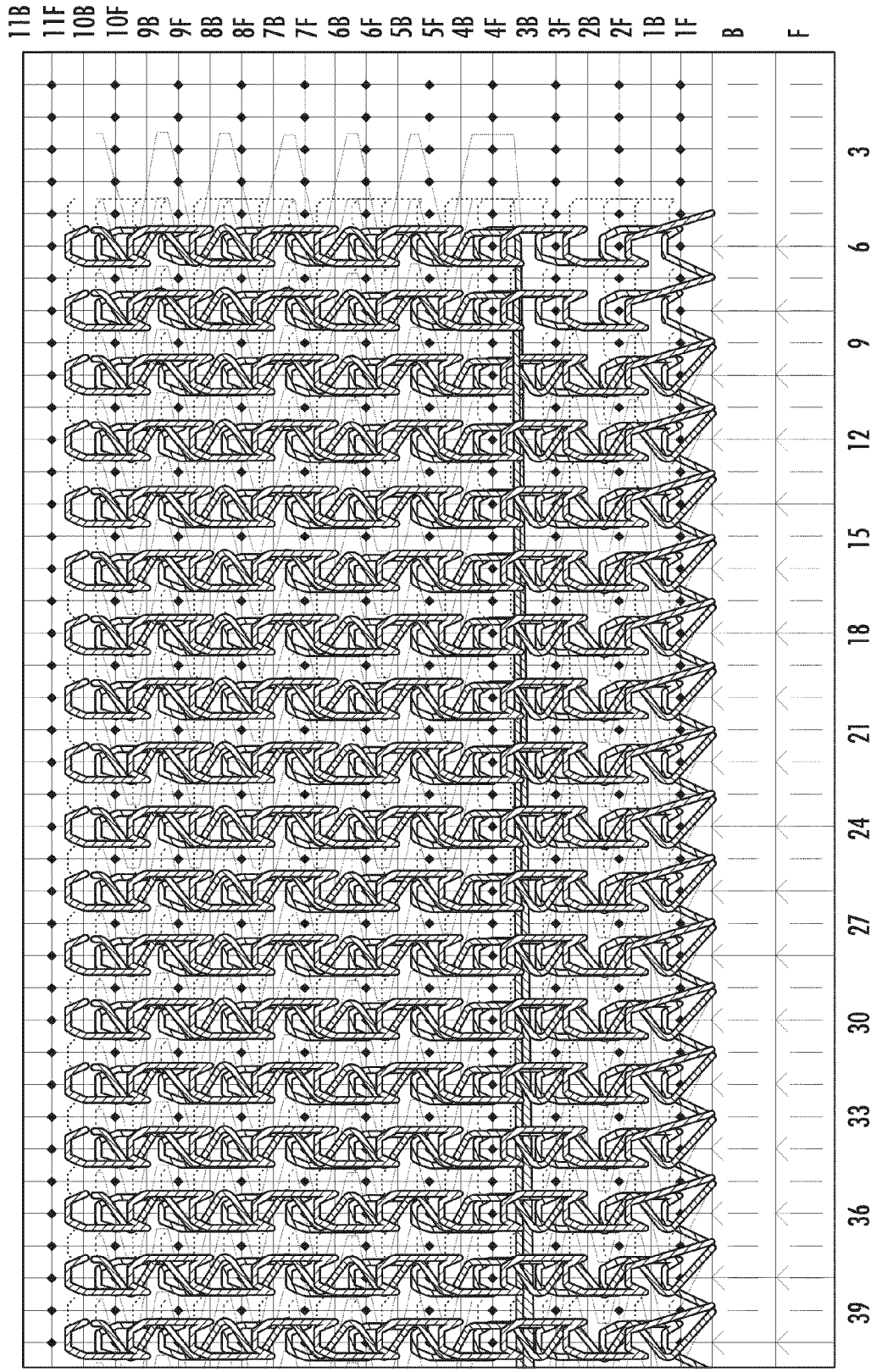
Figure 28C:
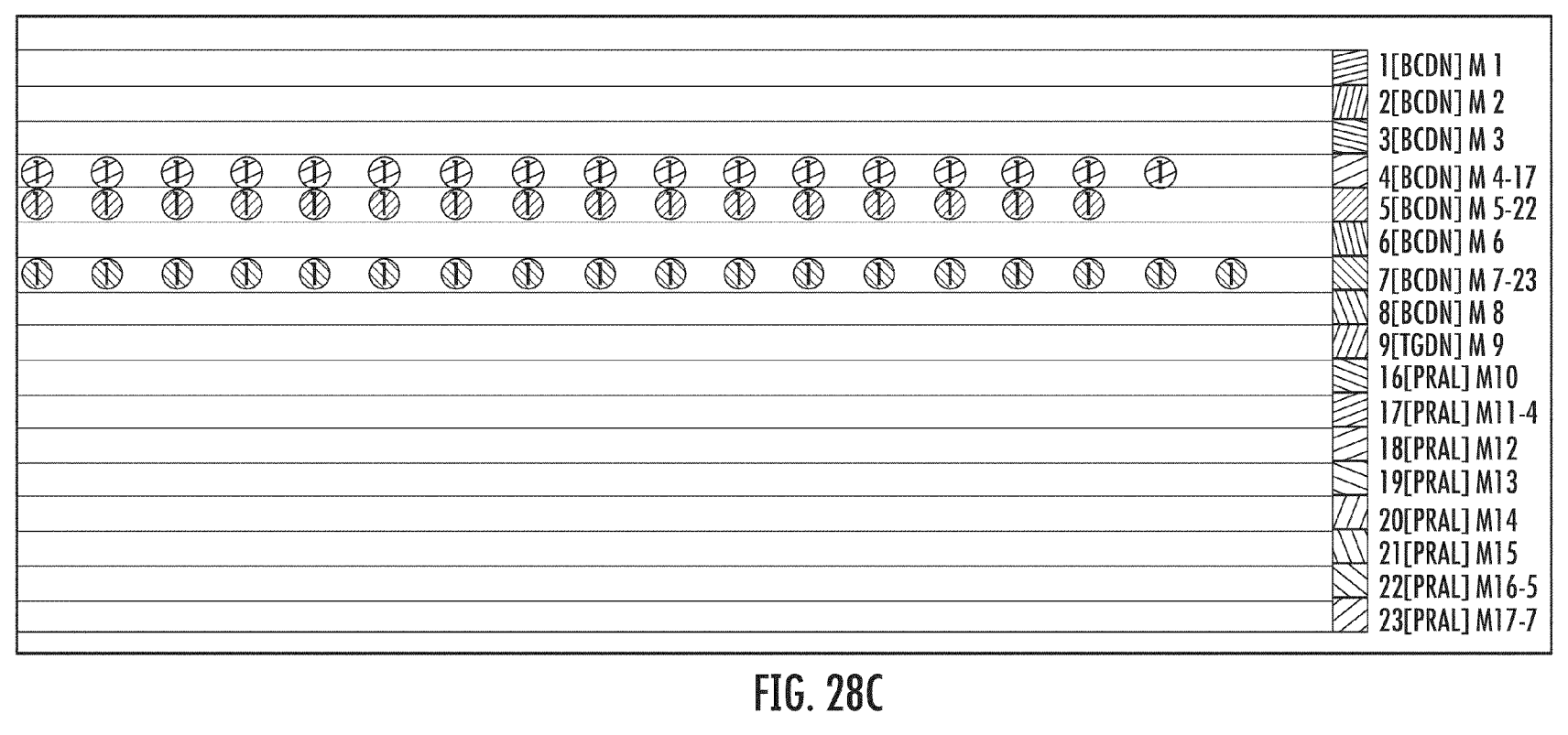
Figure 28D:
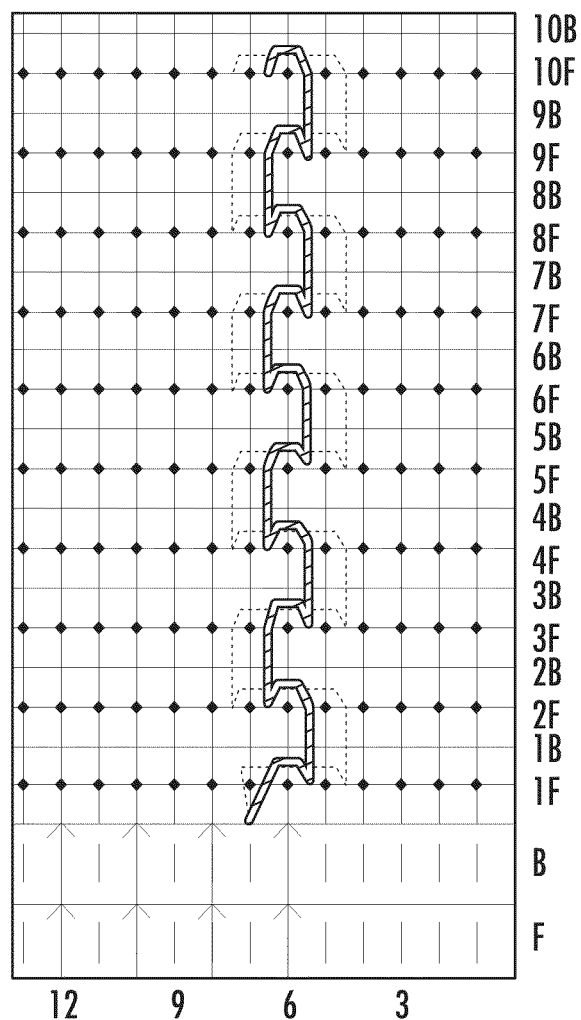
FIGS. 28D and 28E illustrate an example pattern layout for a double needle bed mesh or scaffold according to aspects of the present invention from FIG. 28B for ground bar #4.
Figure 28E:
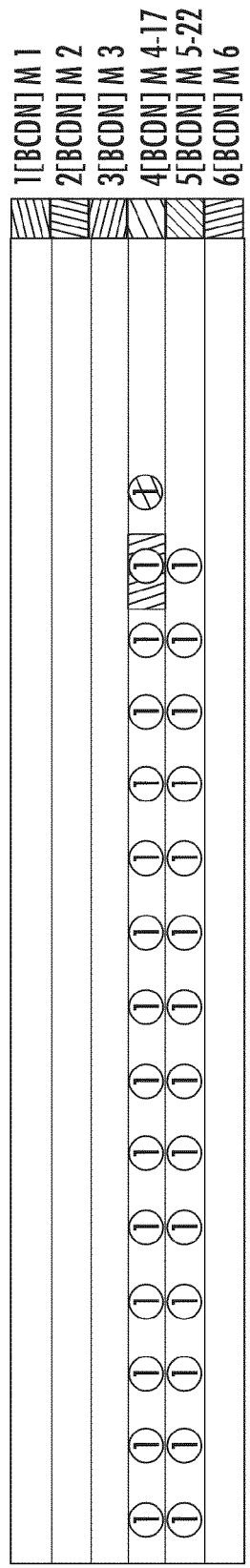
Figure 28F:
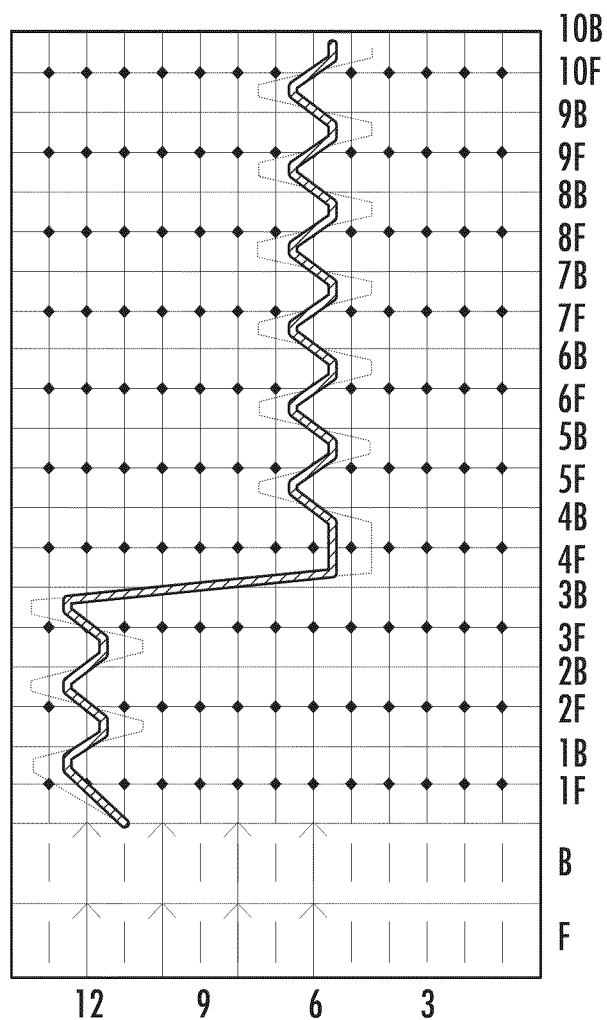
FIGS. 28F and 28G illustrate an example pattern layout for a double needle bed mesh or scaffold according to aspects of the present invention from FIG. 28B for pattern bar #5.
Figure 28G:
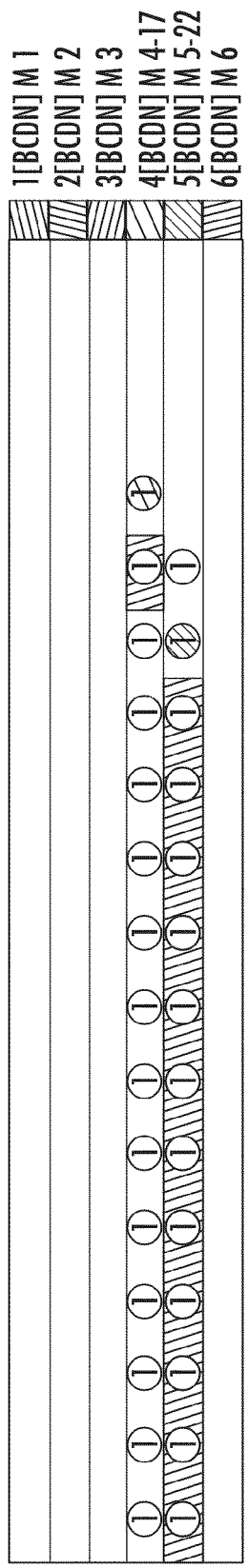
Figure 28H:
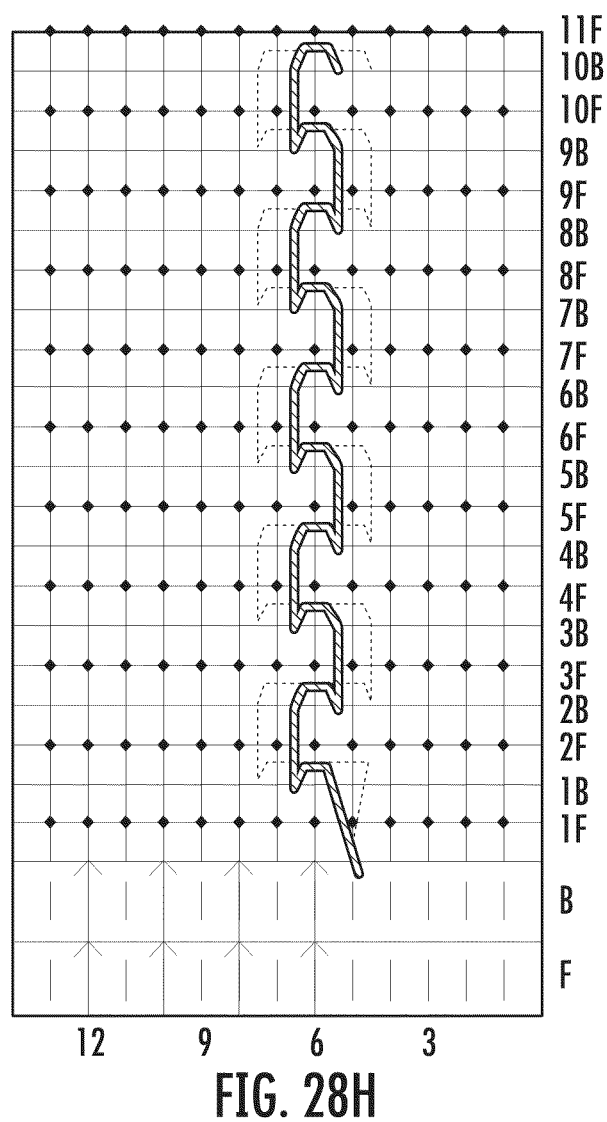
FIGS. 28H and 28I illustrate an example pattern layout for a double needle bed mesh or scaffold according to aspects of the present invention from FIG. 28B for ground bar #7.
Figure 28I:
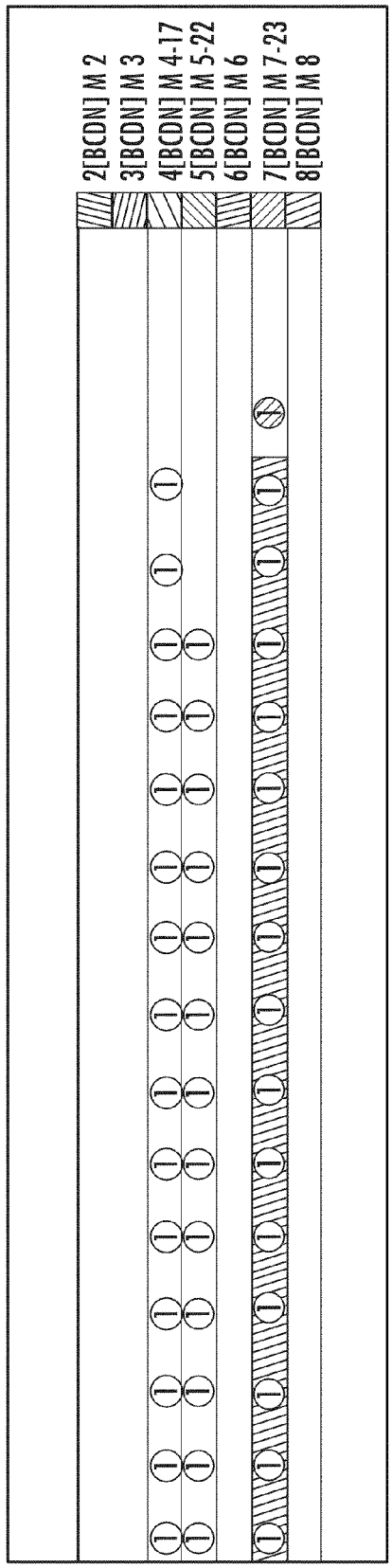
Figure 28J:
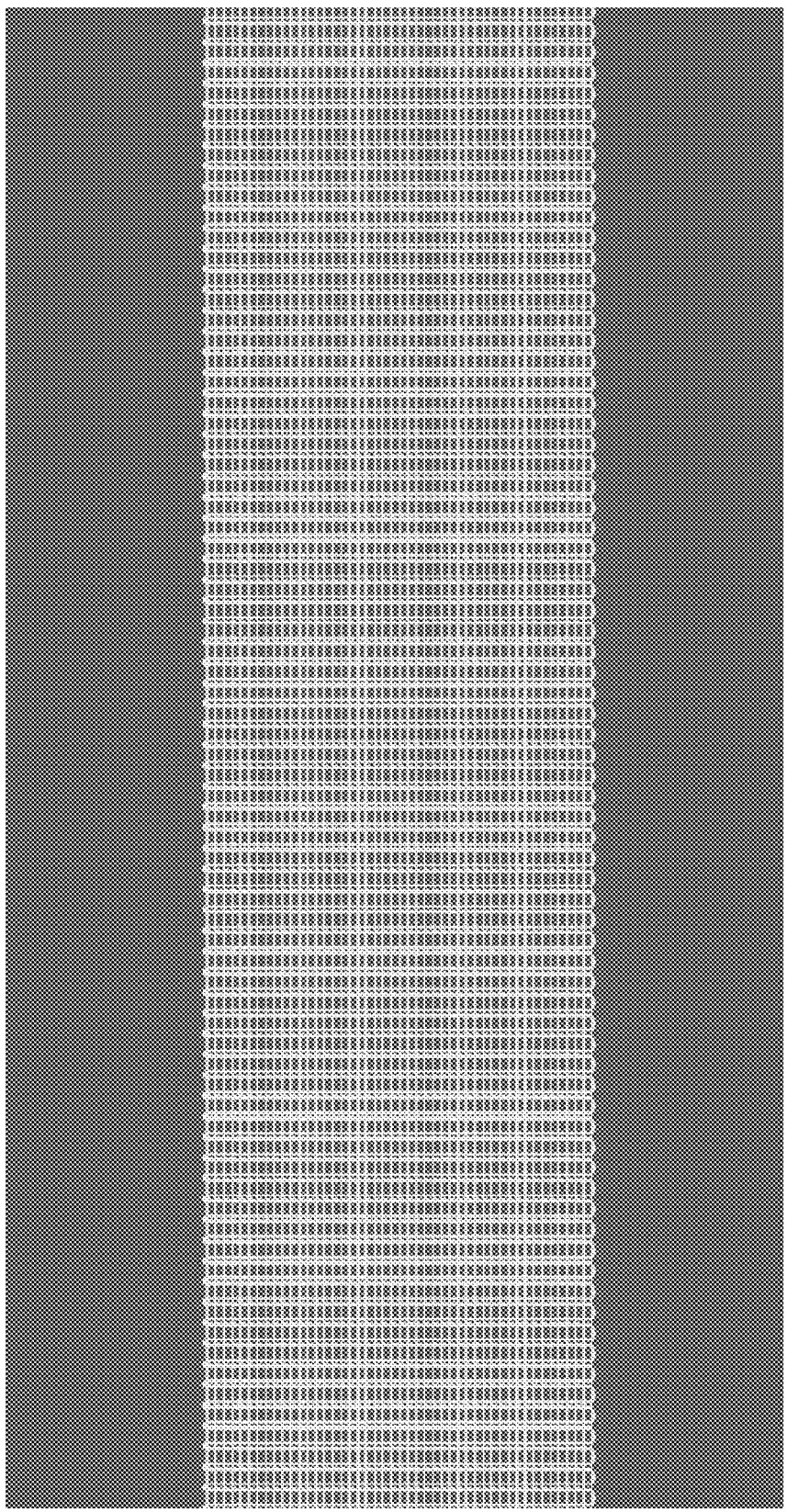
FIG. 28J illustrates an example pattern simulation for a double needle bed mesh demonstrated in FIG. 28B according to aspects of the present invention.

One example mesh in accordance with aspects of the present invention is preferably formed on a raschel knitting machine such as Comez DNB/EL-800-8B set up in 10 gg needle spacing by the use of three movements as shown in pattern layout in FIGS. 28B and C: two movements in the wale direction, the vertical direction within the fabric, and one movement in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3 for one of the wale direction movements as shown in FIGS. 28D and E and 1/1-1/3-3/3-3/1 for the other wale direction movement as shown in FIGS. 28H and I. The interlacing of the loops within the fabric allows for one yarn to become under more tension than the other under stress, locking it around the less tensioned yarn; keeping the fabric from unraveling when cut. The other movement in the course direction as shown in FIGS. 28F and 28G occurs in every few courses creating the porous design of the mesh. These yarns follow a repeat pattern of 9/9-9/9-7/7-9/9-7/7-9/9-7/7-9/9-7/7-9/9/-1/1-1/1-3/3-1/1-3/3-1/1-3/3-1/1-3/3-1/1 for the course direction movement. The pattern simulation layout of this pattern is rendered with ComezDraw 3 software in FIG. 28J considering a yarn design made with 2 ends of Td (denier count) 20/22 raw silk twisted together in the S direction to form a ply with 6 tpi (turns per inch) and further combining three of the resulting ply with 3 tpi. The same yarn design is used for the movements occurring in the wale and course directions. The stitch density or pick count for the mesh in FIG. 28J is 34 picks per centimeter considering the total picks count for the technical front face and the technical back face of the fabric, or 17 picks per cm considering only on the face of the fabric. The operating parameters are not limited to those described in FIGS. 28B-I, but just the optimum values for the specific yarn design used for the pattern simulation layout of FIG. 28J.

Figure 29A:
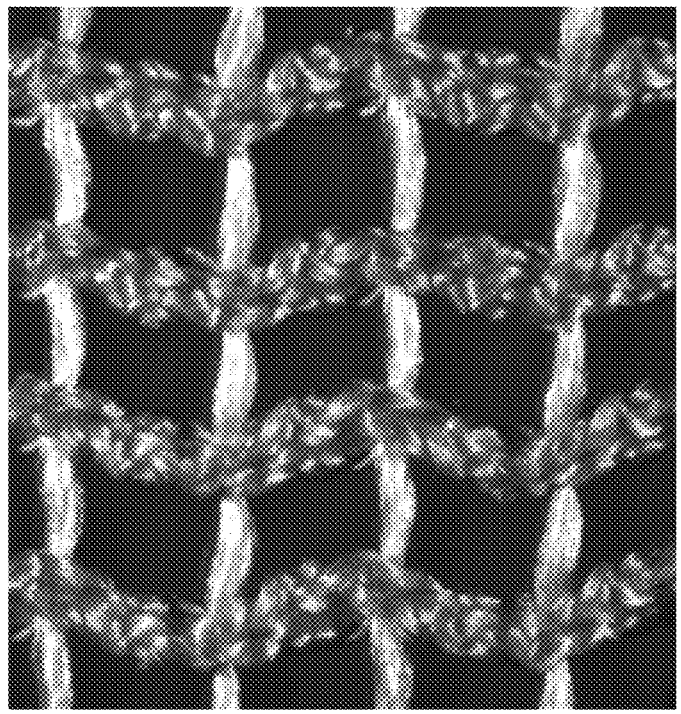
FIG. 29A is a photograph of a pattern layout for a silk-based mesh in accordance with aspects of the present invention.
Figure 29B:
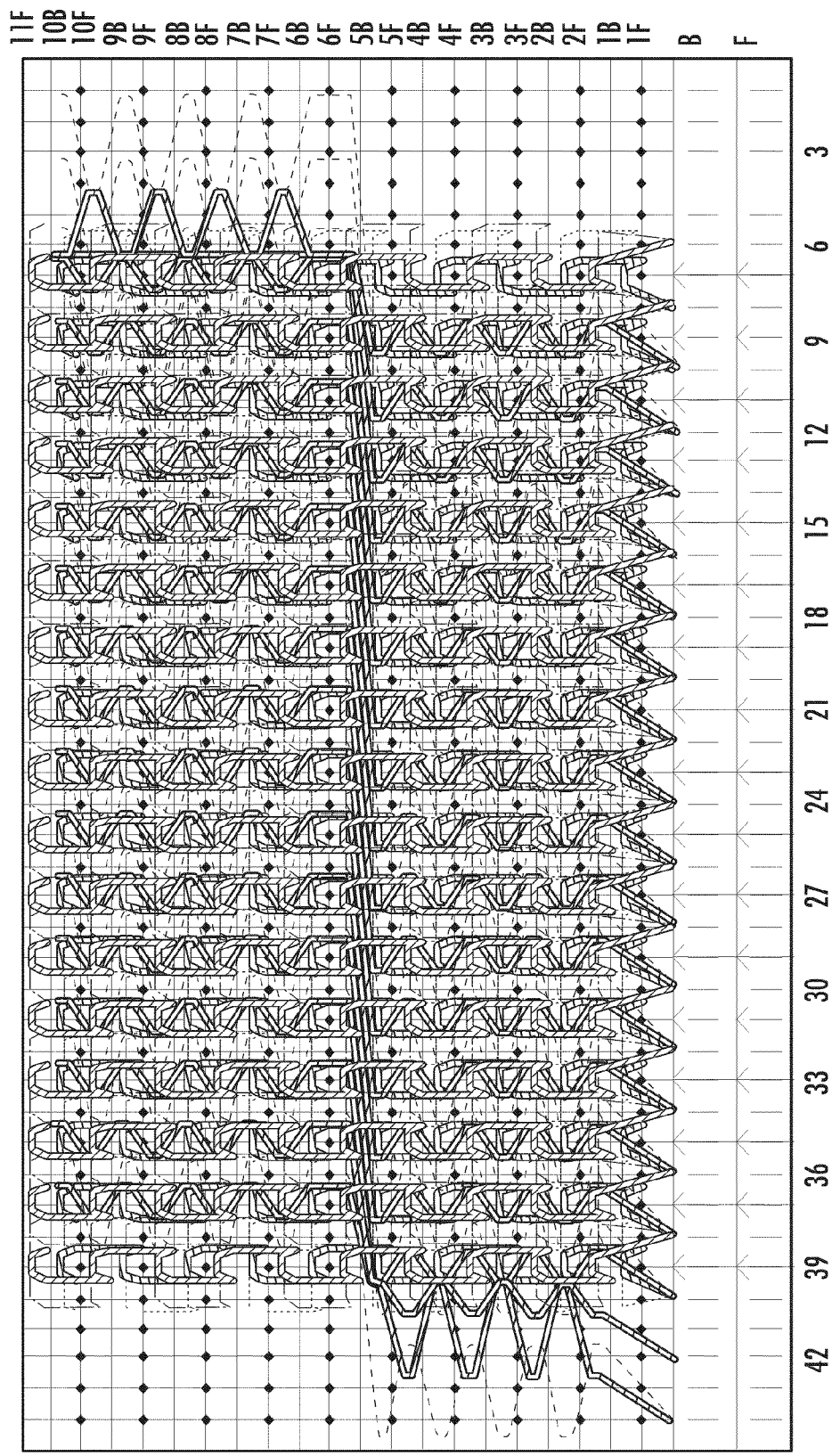
FIGS. 29B and 29C illustrate an example pattern layout for the mesh design of FIG. 29A including all pattern and ground bars according to aspects of the present invention.
Figure 29C:
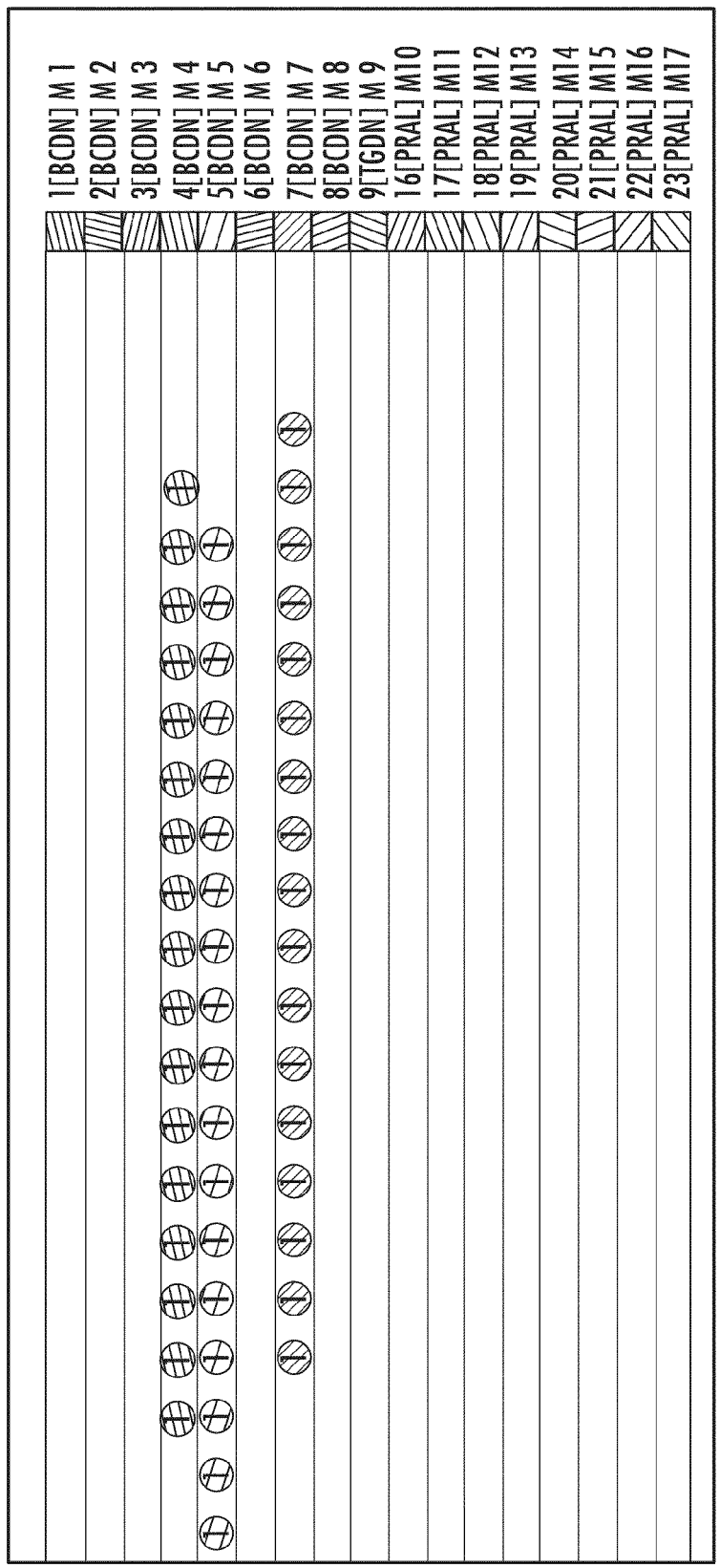
Figure 29D:
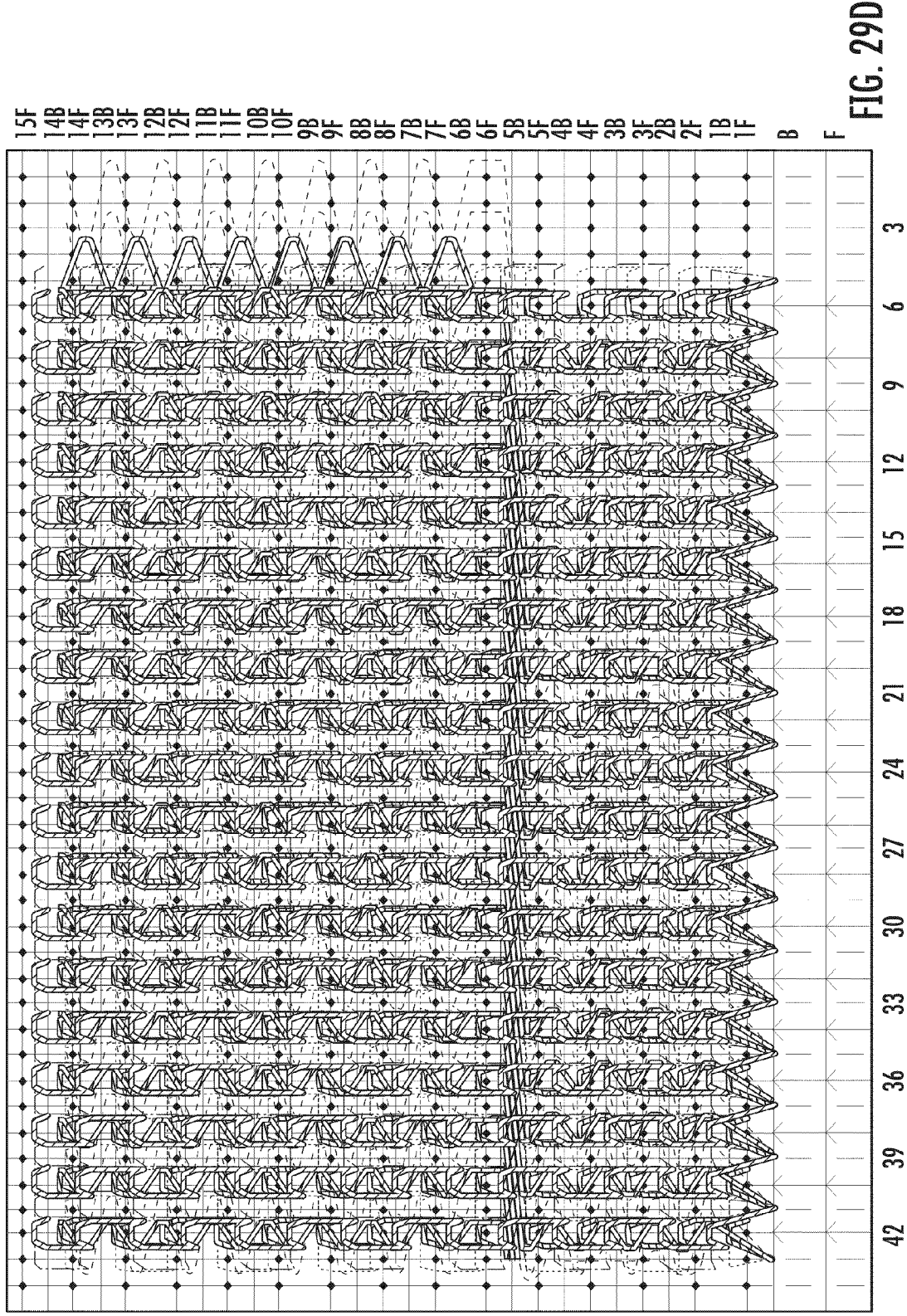
FIGS. 29D and 29E are enlarged views of the example pattern layout and ground bars of FIG. 29B.
Figure 29E:
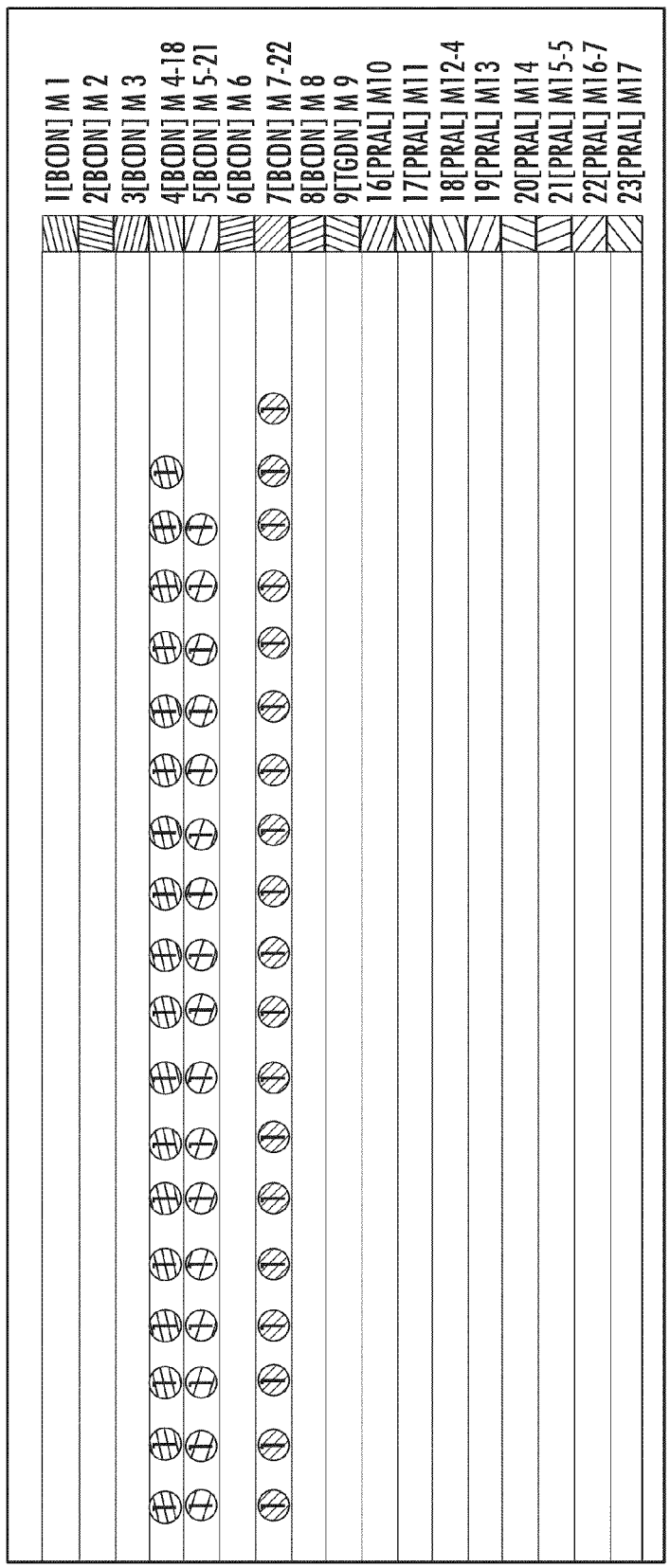

FIG. 29A illustrates a photograph of a pattern layout for a silk-based mesh in accordance with aspects of the present invention.

Figure 30A:
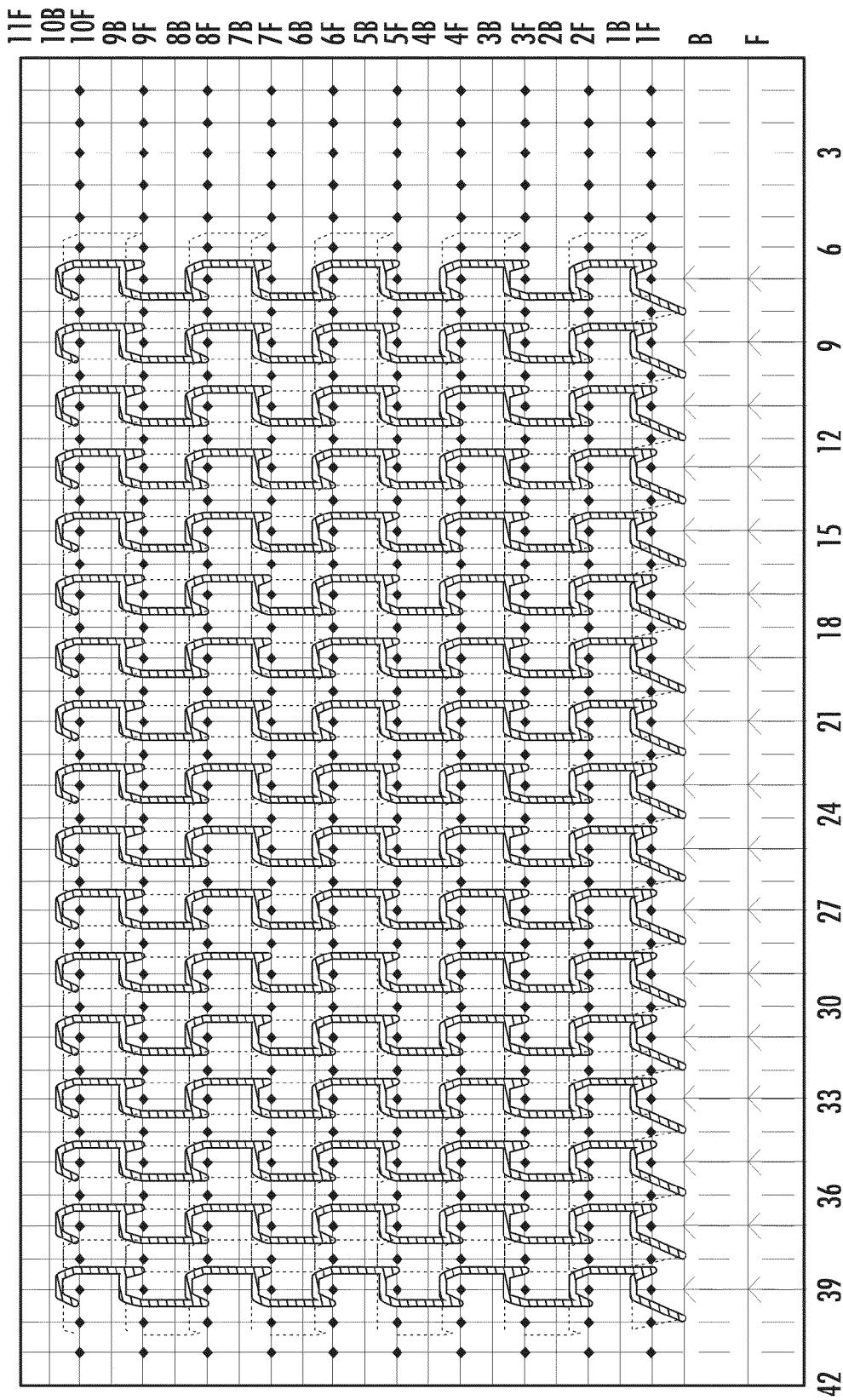
FIGS. 30A and 30B illustrate an example pattern layout for a double needle bed mesh or scaffold according to aspects of the present invention from FIG. 29B for ground bar #4.
Figure 30B:
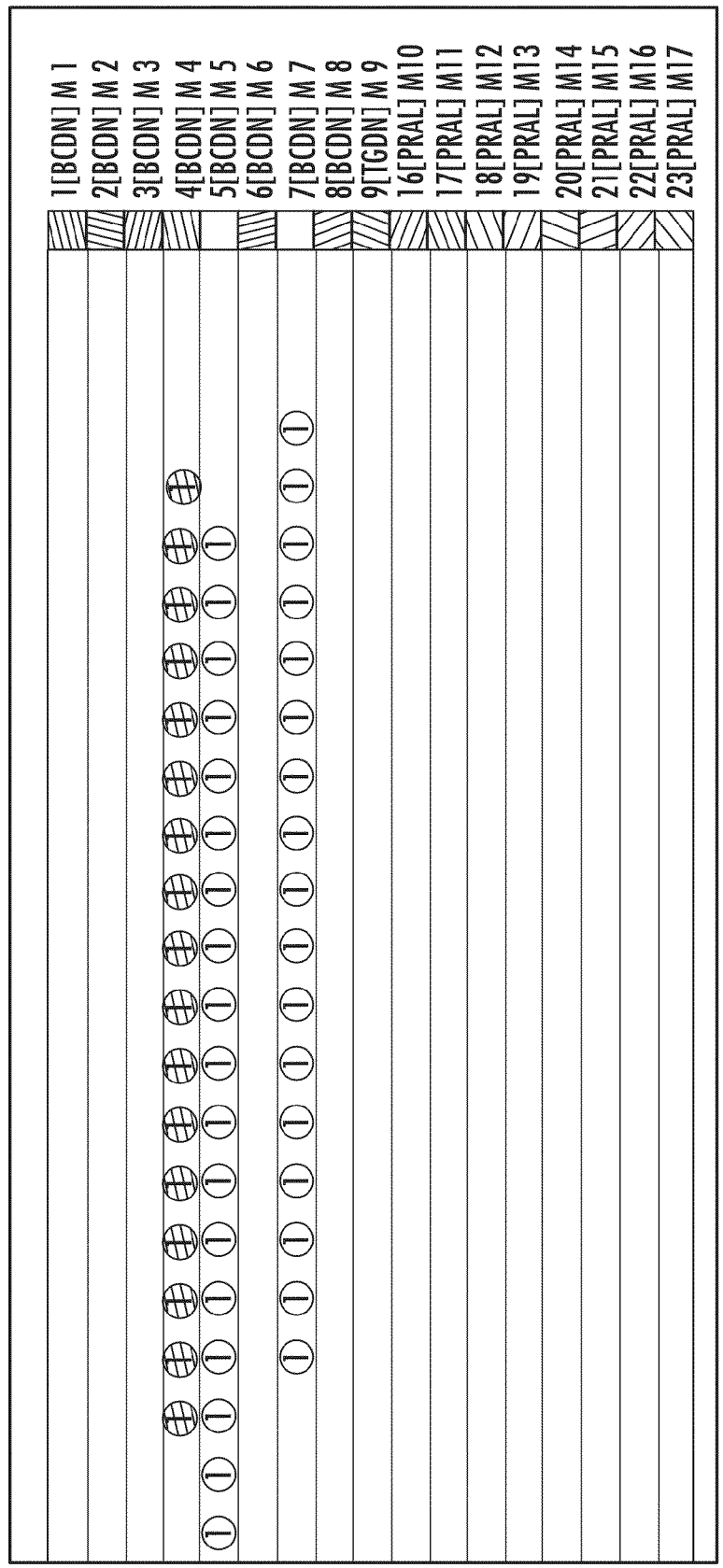
Figure 30C:
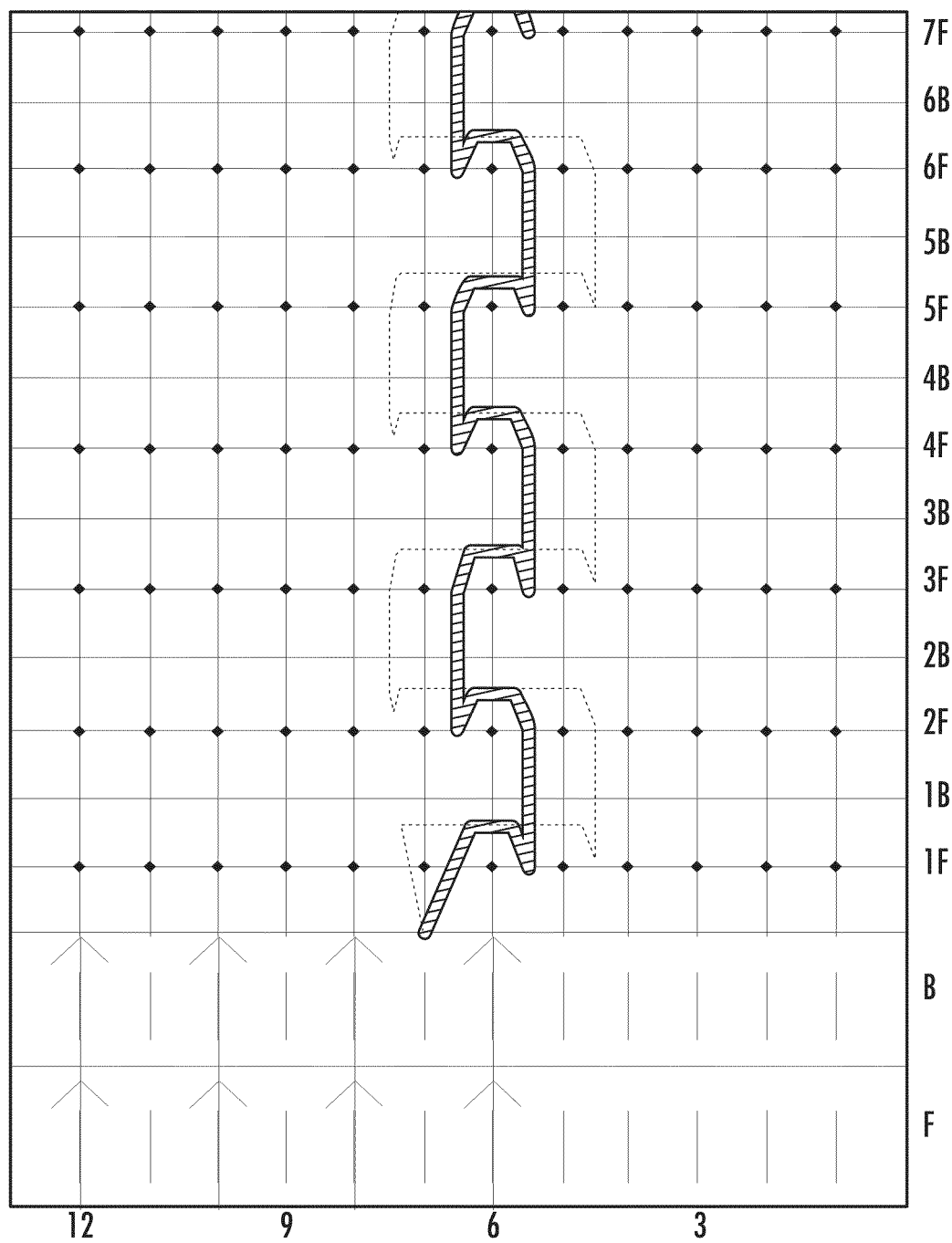
FIGS. 30C and 30D are enlarged views of the example pattern layout and ground bars of FIG. 29B.
Figure 30D:
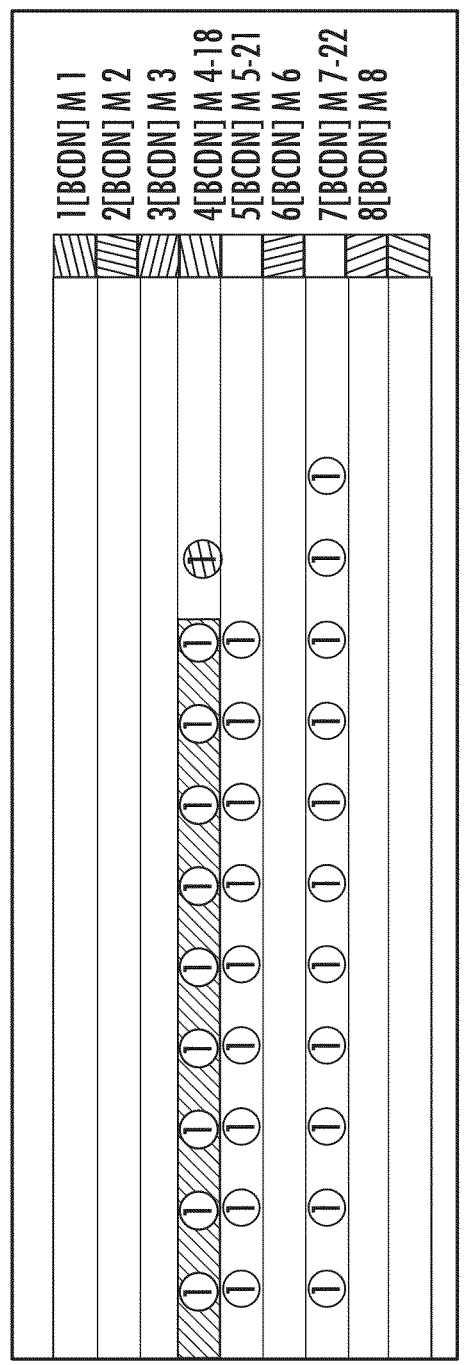
Figure 31A:
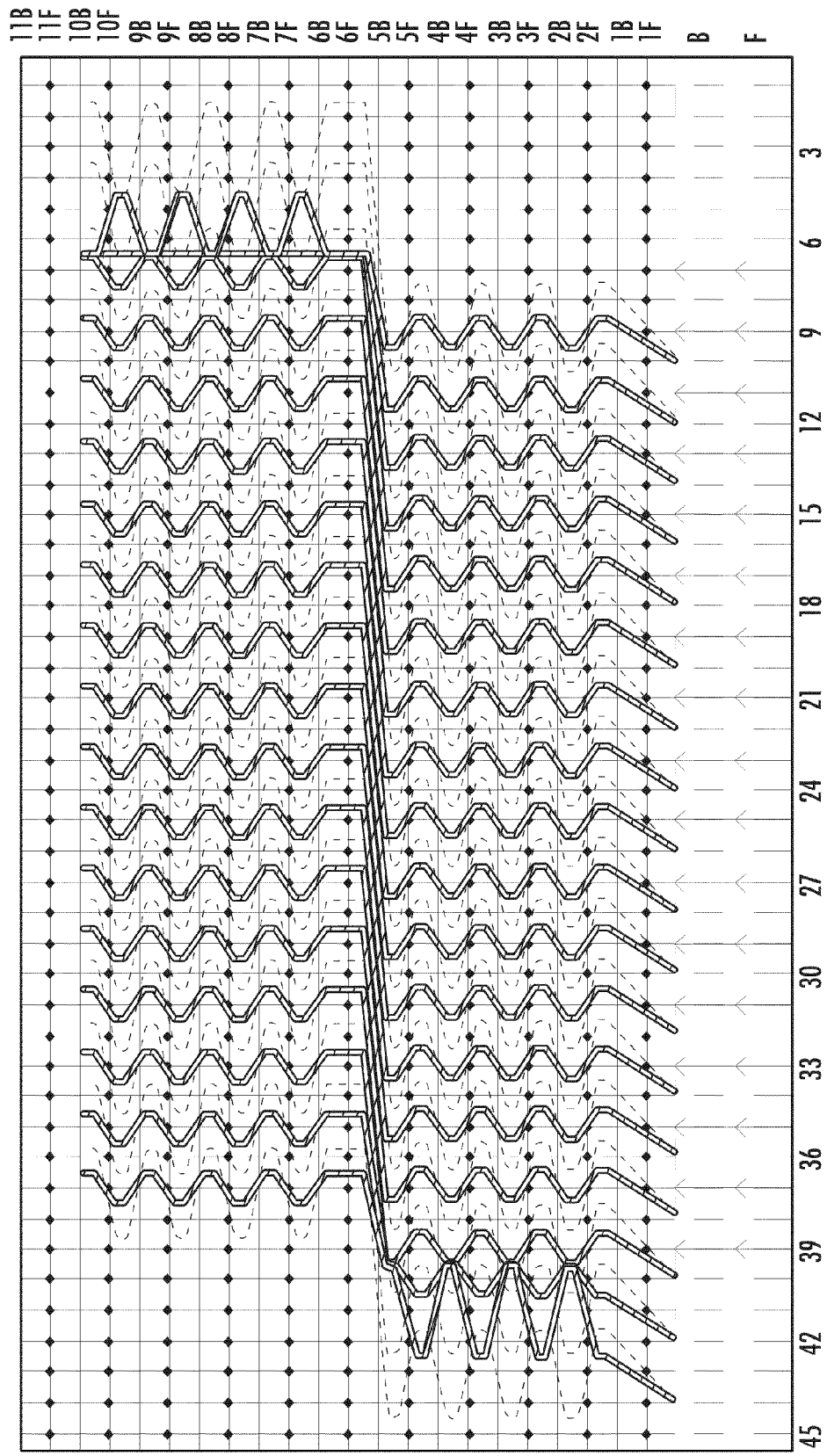
FIGS. 31A and 31B illustrate an example pattern layout for a double needle bed mesh or scaffold according to aspects of the present invention from FIG. 29B for pattern bar #5.
Figure 31B:
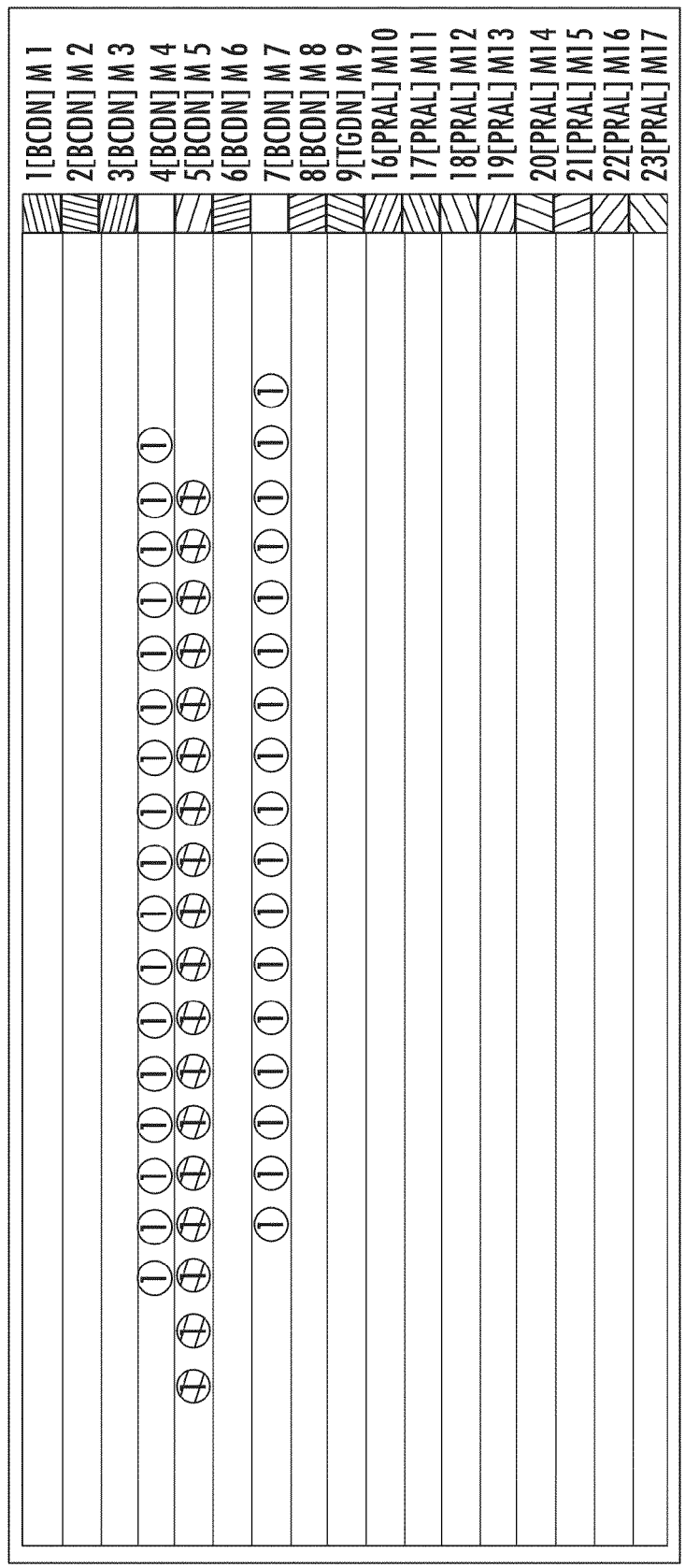
Figure 31C:
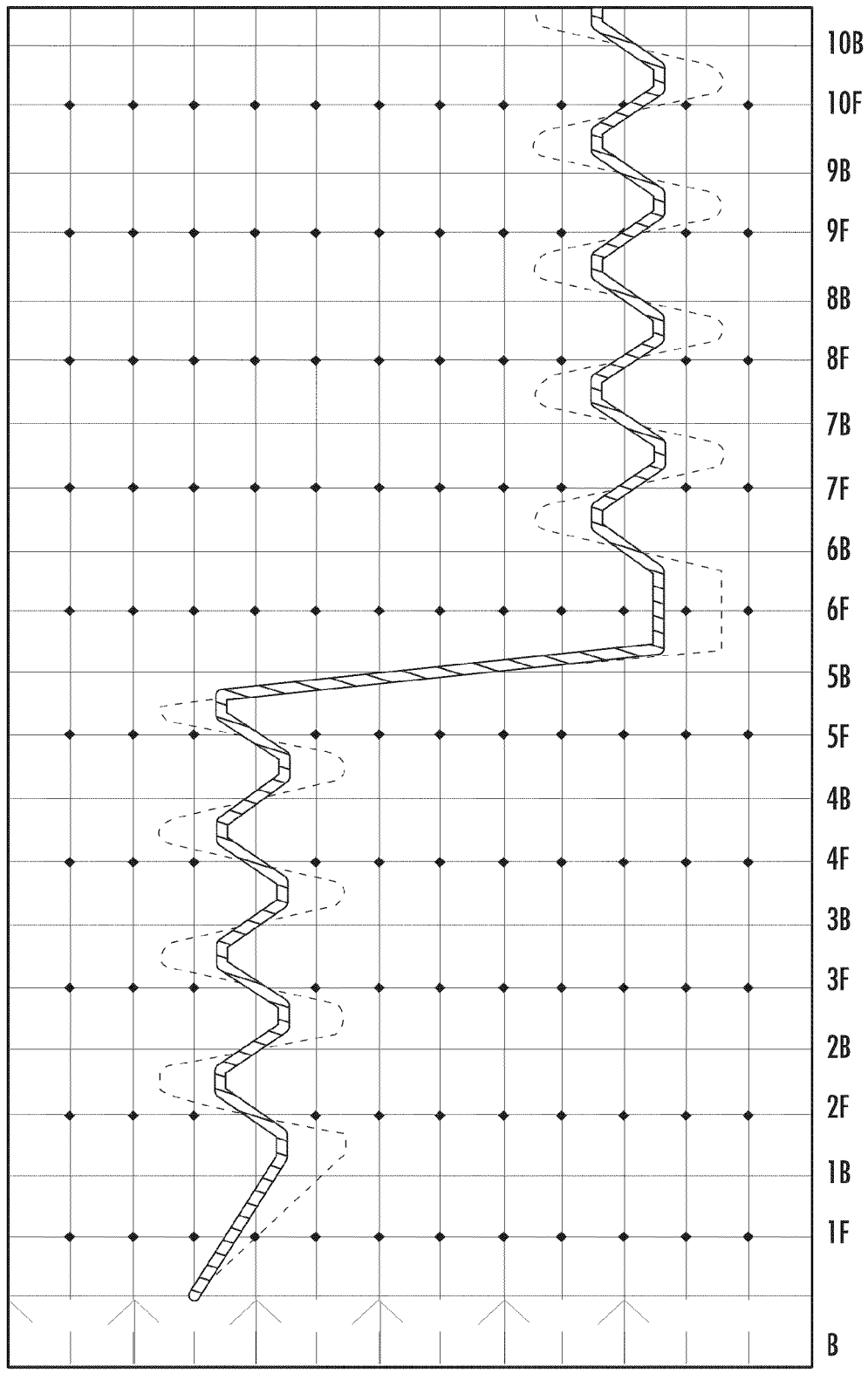
FIGS. 31C and 31D are enlarged views of the example pattern layout and ground bars of FIG. 29B.
Figure 31D:
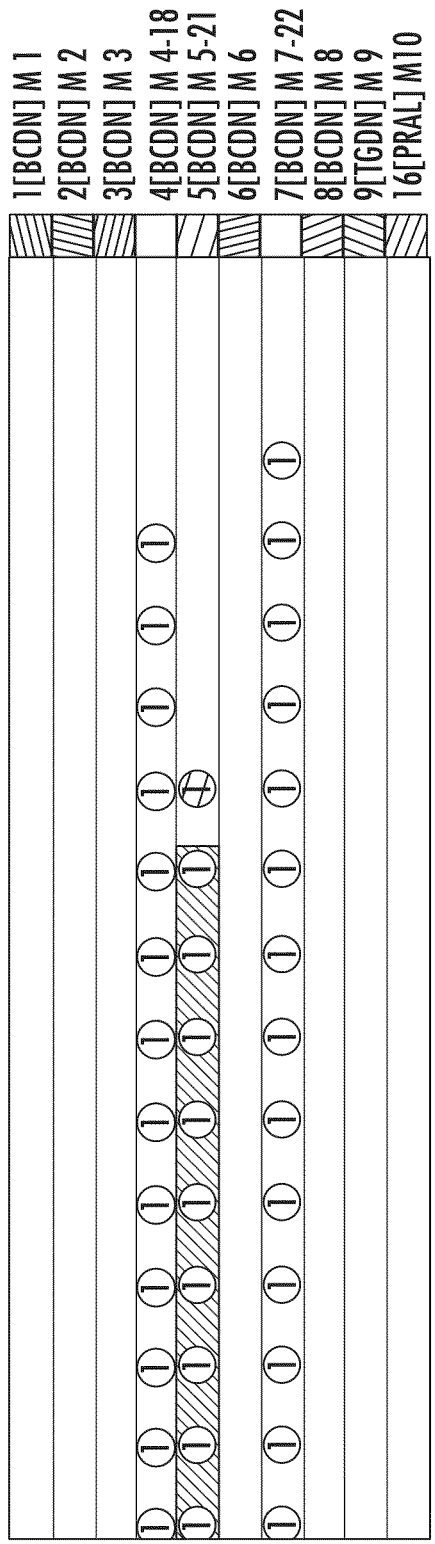
Figure 32A:
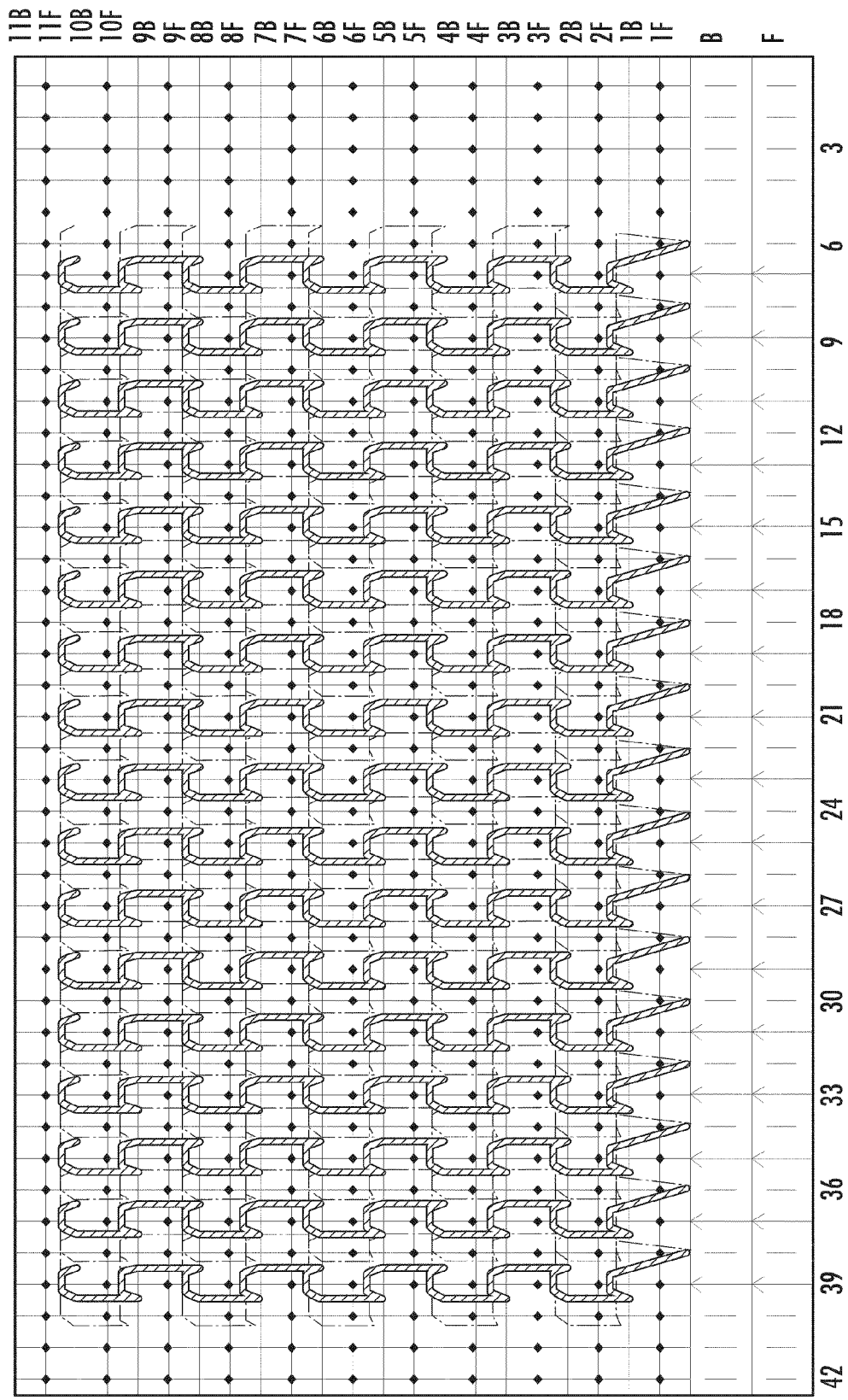
FIGS. 32A and 32B illustrate an example pattern layout for a double needle bed mesh according to aspects of the present invention from FIG. 29B for ground bar #7.
Figure 32B:
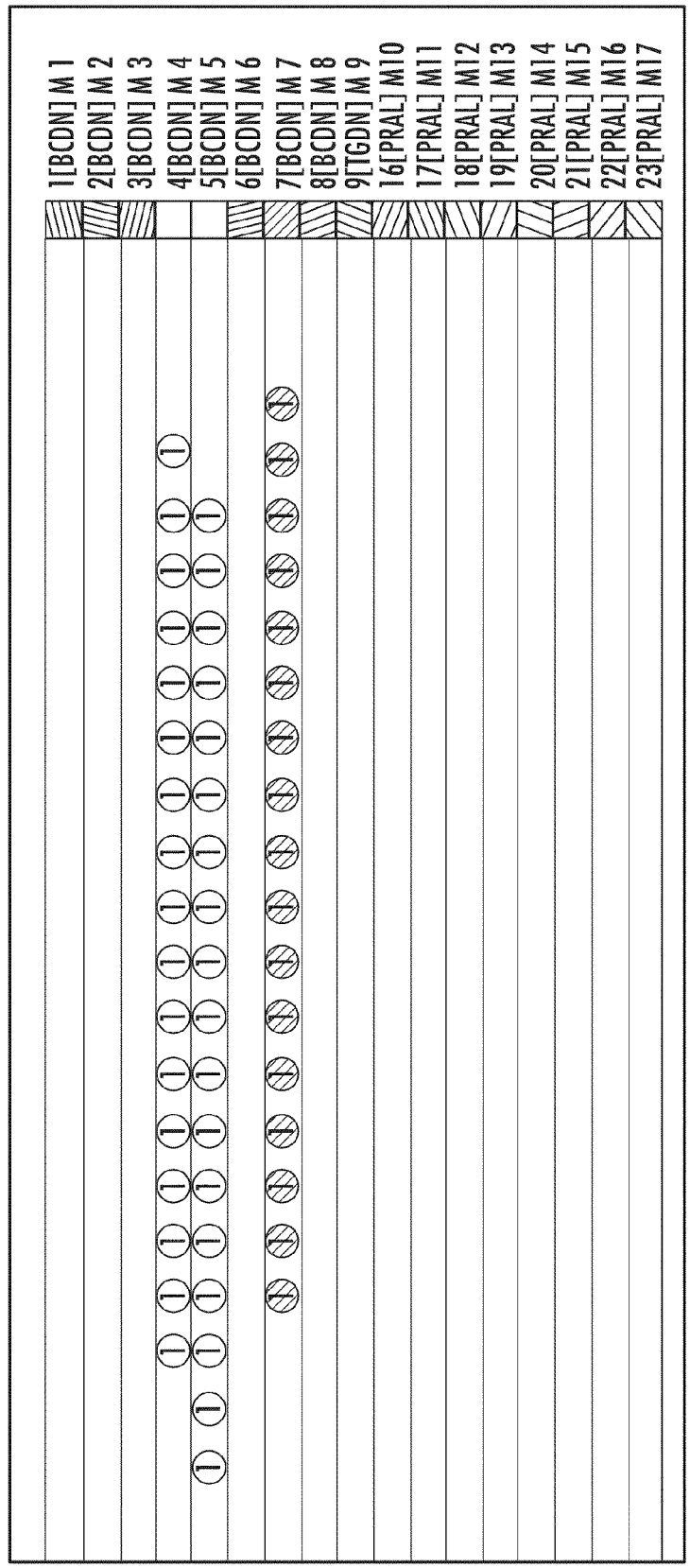
Figure 32C:
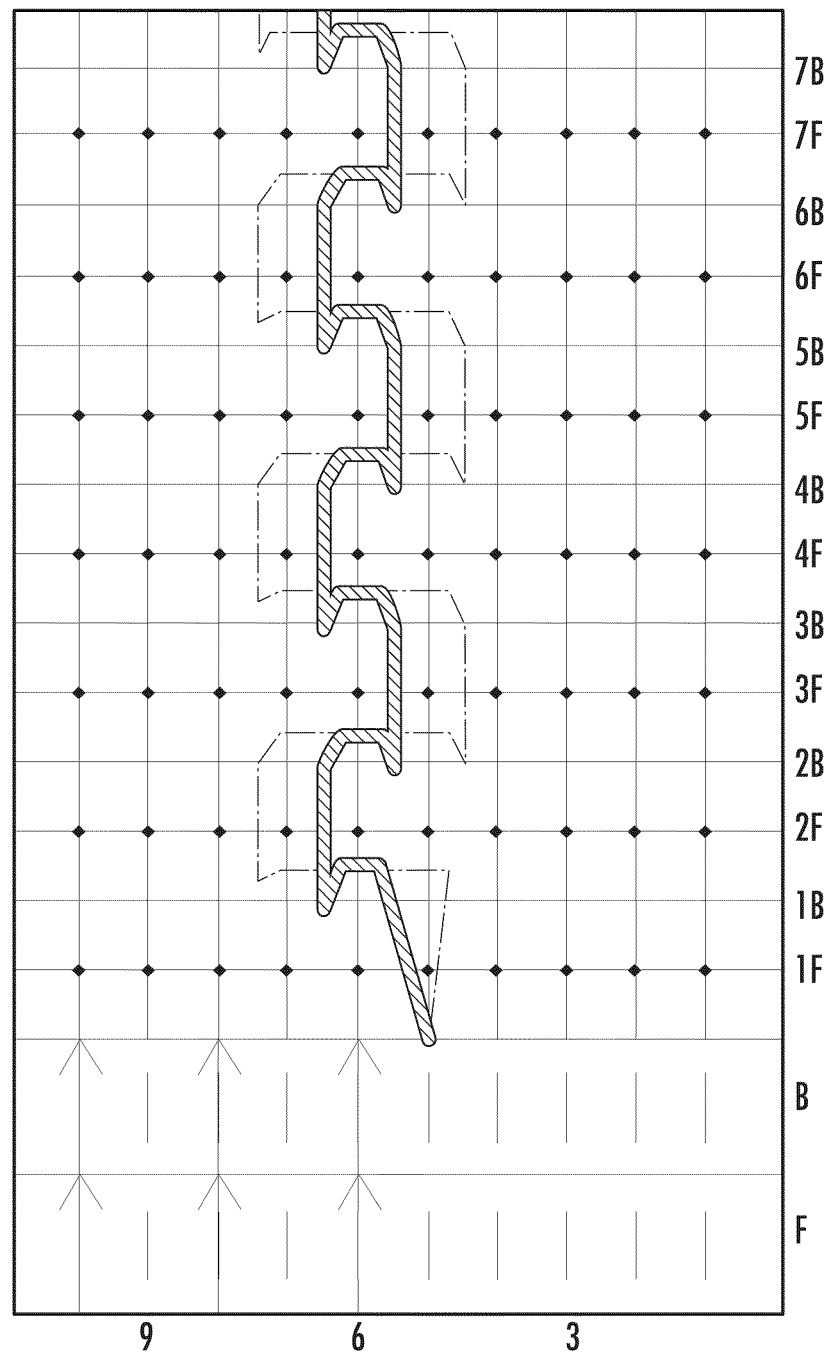
FIGS. 32C and 32D are enlarged views of the example pattern layout and ground bars of FIG. 29B.
Figure 32D:
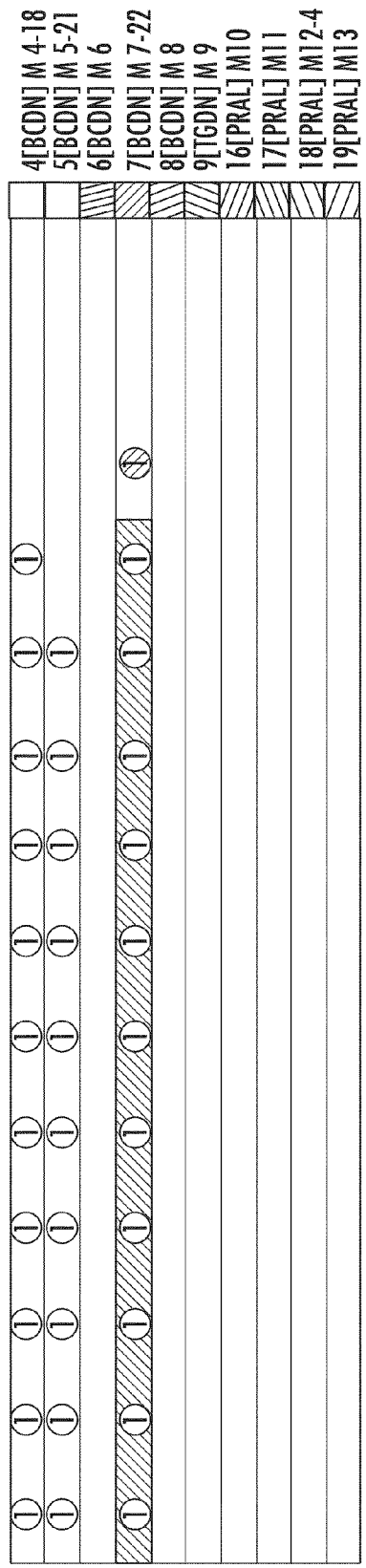
Figure 33:
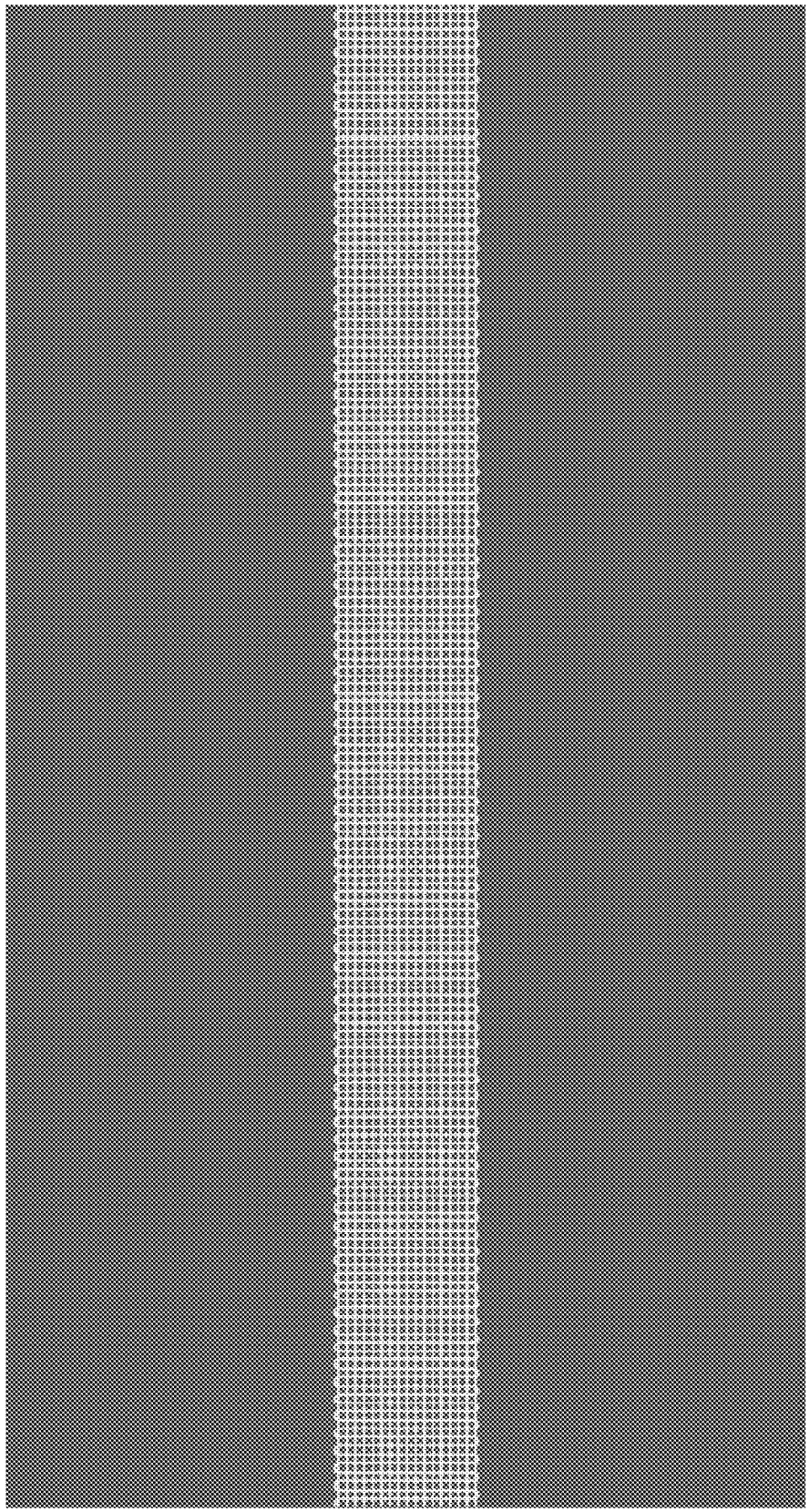
FIG. 33 illustrates an example pattern simulation for a double needle bed mesh demonstrated in FIG. 29B according to aspects of the present invention.

One variation of the mesh in accordance with aspects of the present invention is preferably formed on a raschel knitting machine such as Comez DNB/EL-800-8B set up in 10 gg needle spacing by the use of three movements as shown in pattern layout in FIGS. 29B-E: two movements in the wale direction, the vertical direction within the fabric, and one movement in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3 for one of the wale direction movements (see ground bar #4) as shown in FIGS. 30A and B and FIGS. 30C and D and 1/1-1/3-3/3-3/1 for the other wale direction movement (see ground bar #7) as shown in FIGS. 32A and B, FIGS. 32 C and D. The interlacing of the loops within the fabric allows for one yarn to become under more tension than the other under stress, locking it around the less tensioned yarn; keeping the fabric from unraveling when cut. The other movement in the course direction as shown in FIG. 31 occurs in every few courses creating the porous design of the mesh. These yarns follow a repeat pattern of 9/9-9/9-7/7-9/9-7/7-9/9-7/7-9/9-7/7-9/9/-1/1-1/1-3/3-1/1-3/3-1/1-3/3-1/1-3/3-1/1 (see ground bar #5) for the course direction movement as shown in FIGS. 31A and B and FIGS. 31C and D. The pattern simulation layout of this pattern is rendered with ComezDraw 3 software in FIG. 33 considering a yarn design made with 2 ends of Td (denier count) 20/22 raw silk twisted together in the S direction to form a ply with 6 tpi (turns per inch) and further combining three of the resulting ply with 3 tpi. The same yarn design is used for the movements occurring in the wale and course directions. The stitch density or pick count for the mesh in FIG. 33 is 40 picks per centimeter considering the total picks count for the technical front face and the technical back face of the fabric, or 20 picks per cm considering only on the face of the fabric. The operating parameters are not limited to those described in FIGS. 29B-E, but are merely the optimum values for the specific yarn design used for the pattern simulation layout of FIG. 33.

Figure 34A:
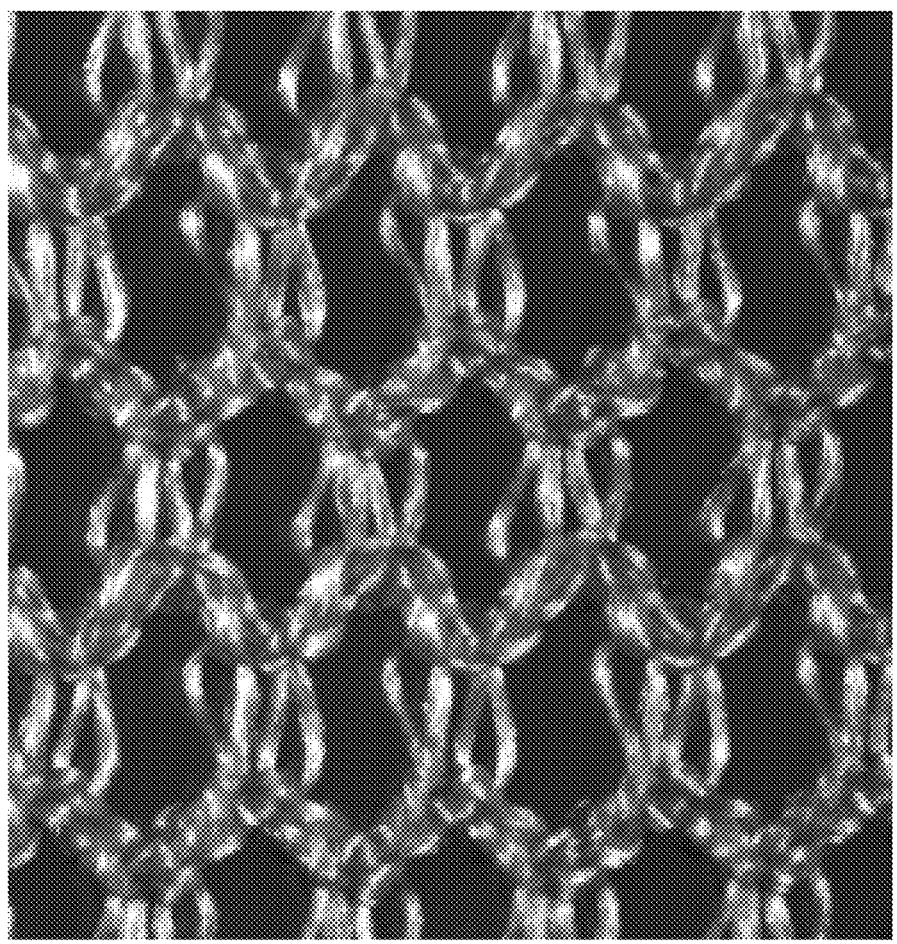
FIG. 34A is a photograph of a pattern layout for a silk-based mesh in accordance with aspects of the present invention.

FIG. 34A is a photograph of a pattern layout for a silk-based mesh in accordance with aspects of the present invention.

Figure 34B:
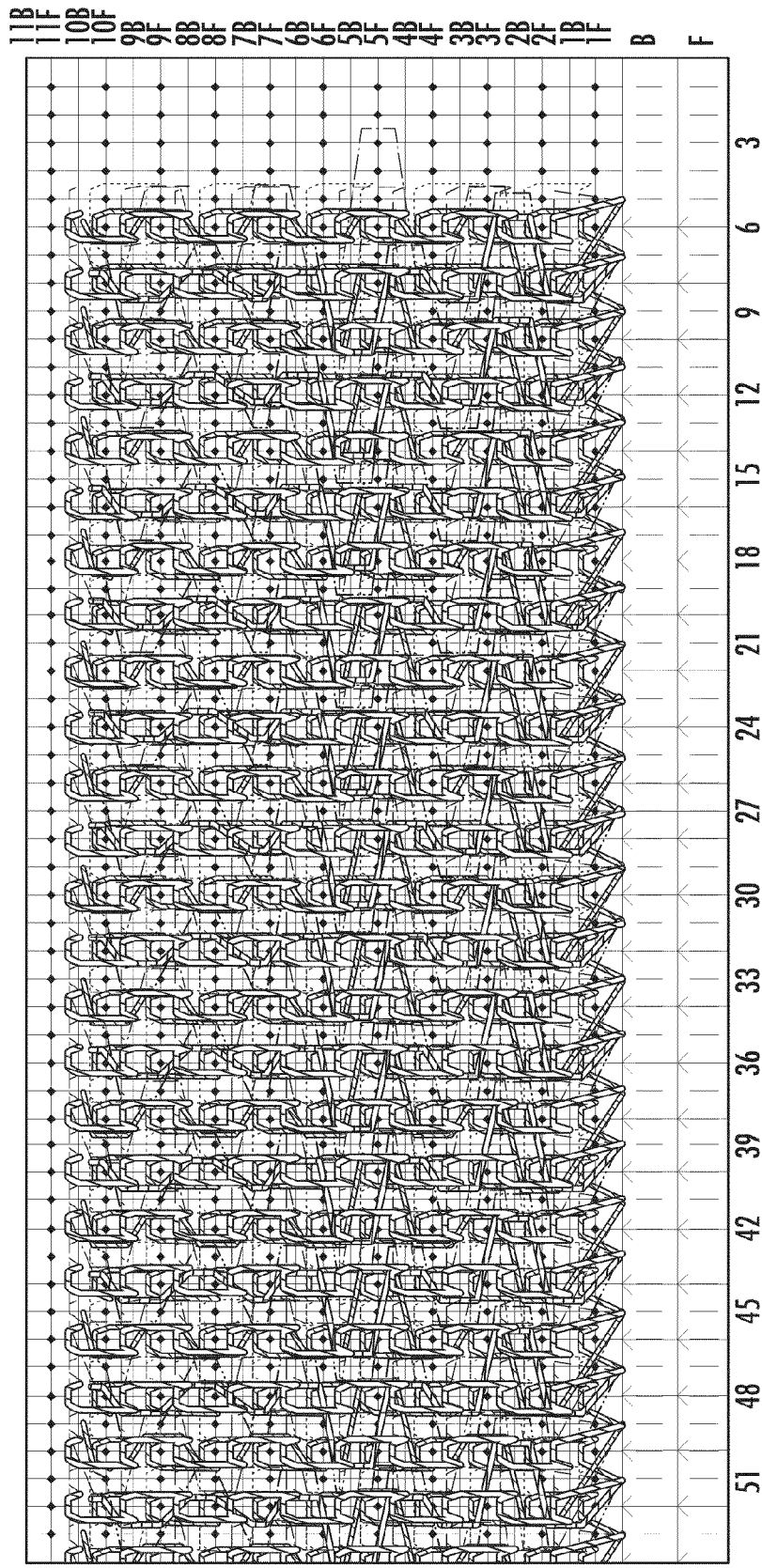
FIGS. 34B and 34C illustrate an example pattern layout for a silk-based mesh design of FIG. 34A for use as a mesh in accordance with aspects of the present invention including all pattern and ground bars according to aspects of the present invention.
Figure 34C:
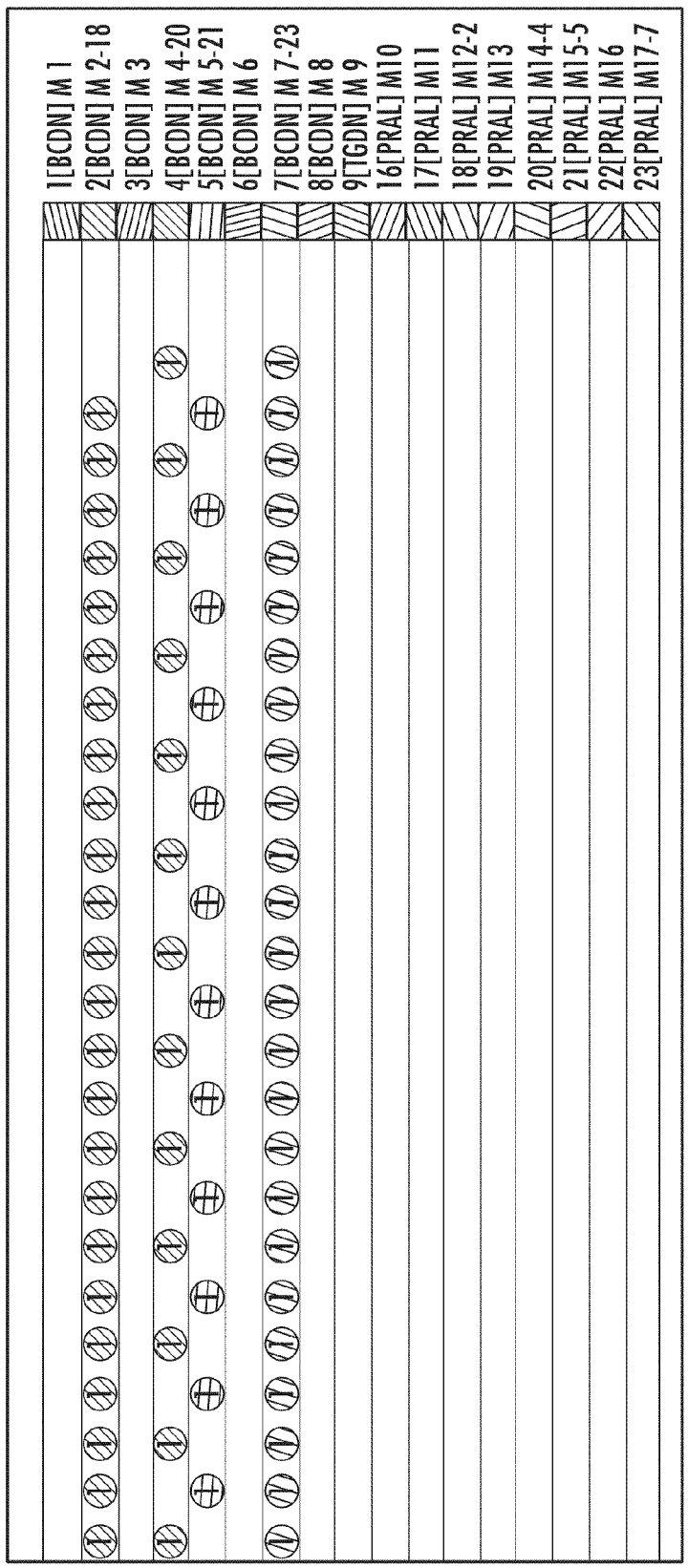
Figure 34D:
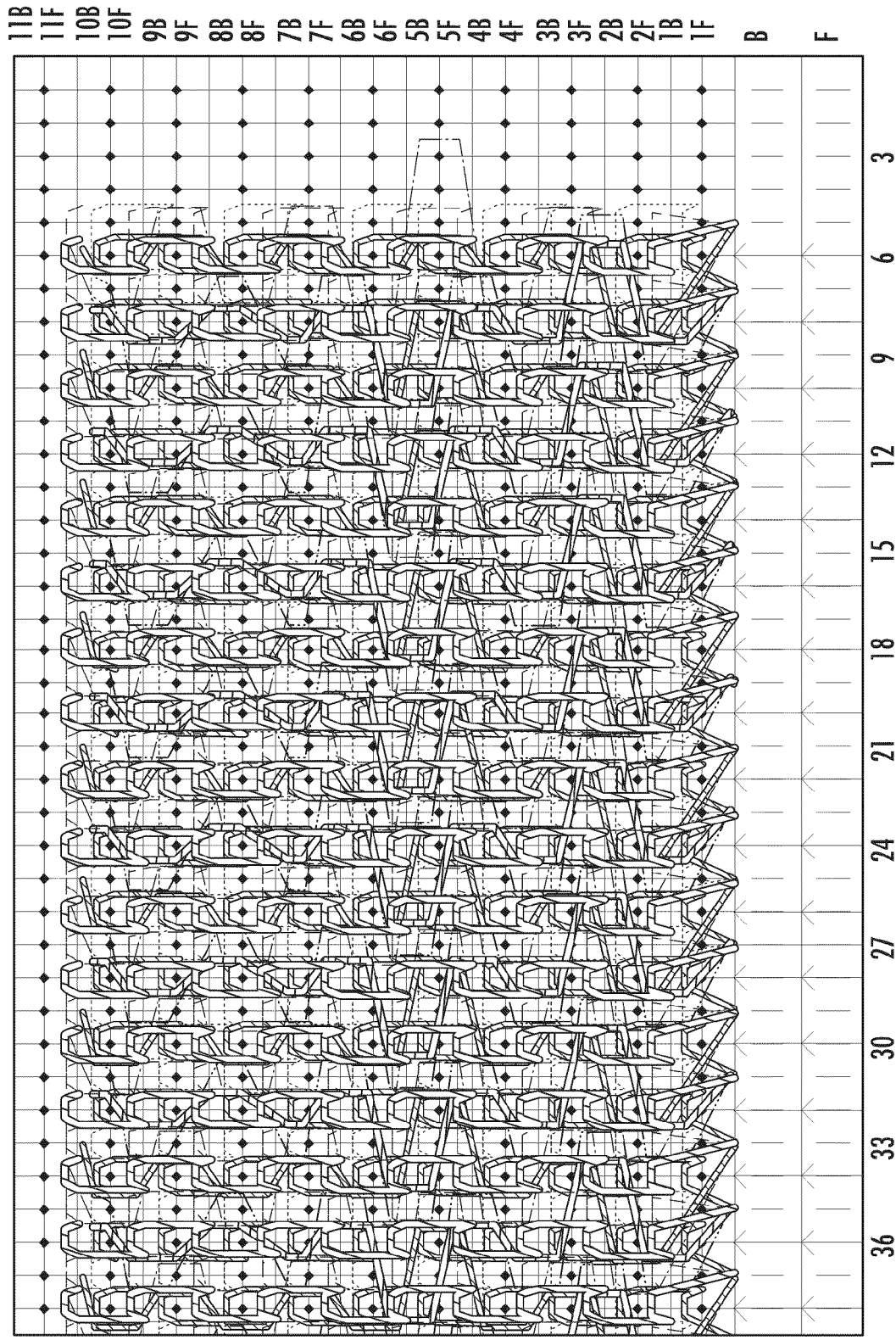
FIGS. 34D and 34E are enlarged views of the example pattern layout and ground bars of FIG. 34B.
Figure 34E:
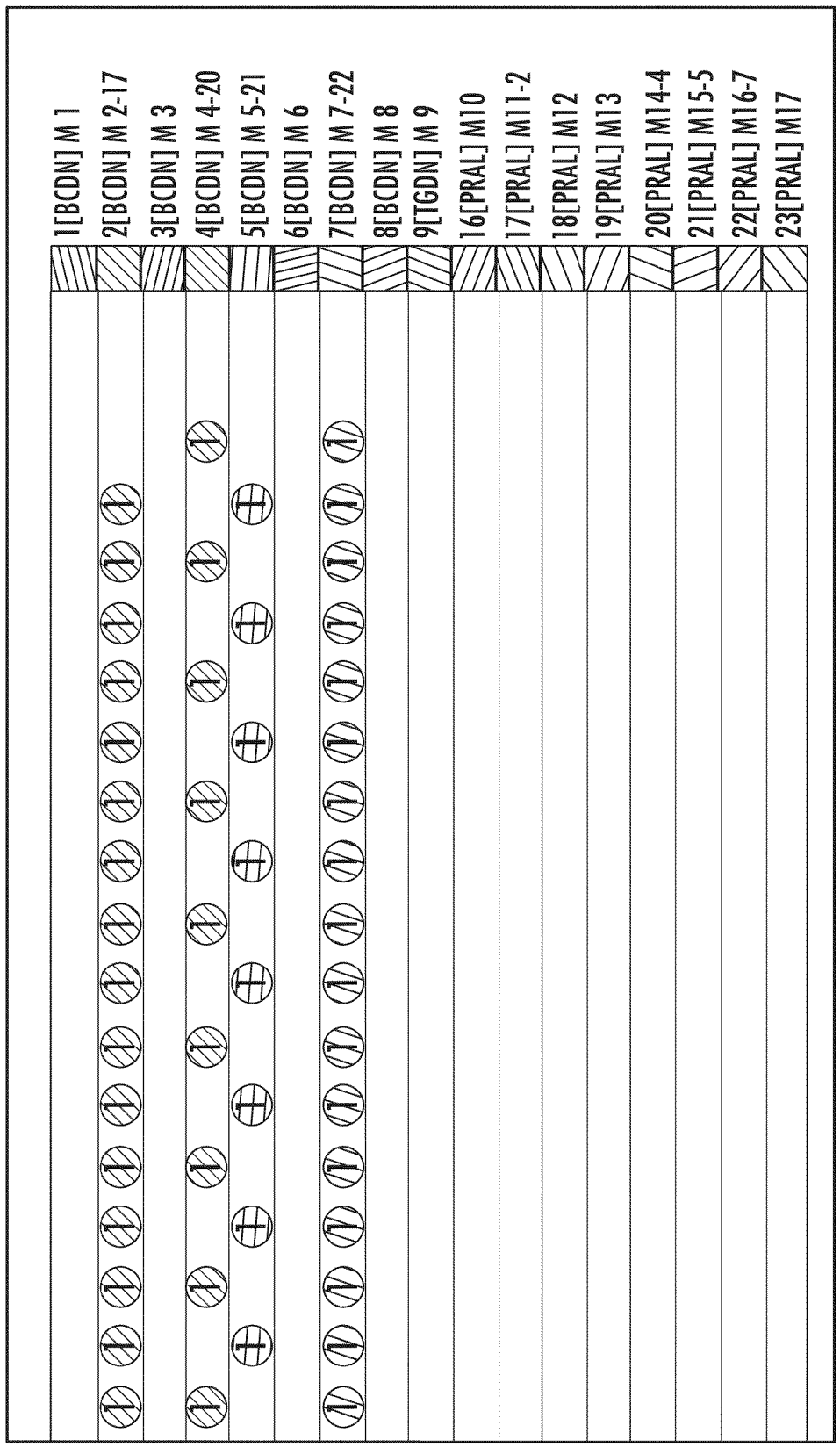
Figure 35A:
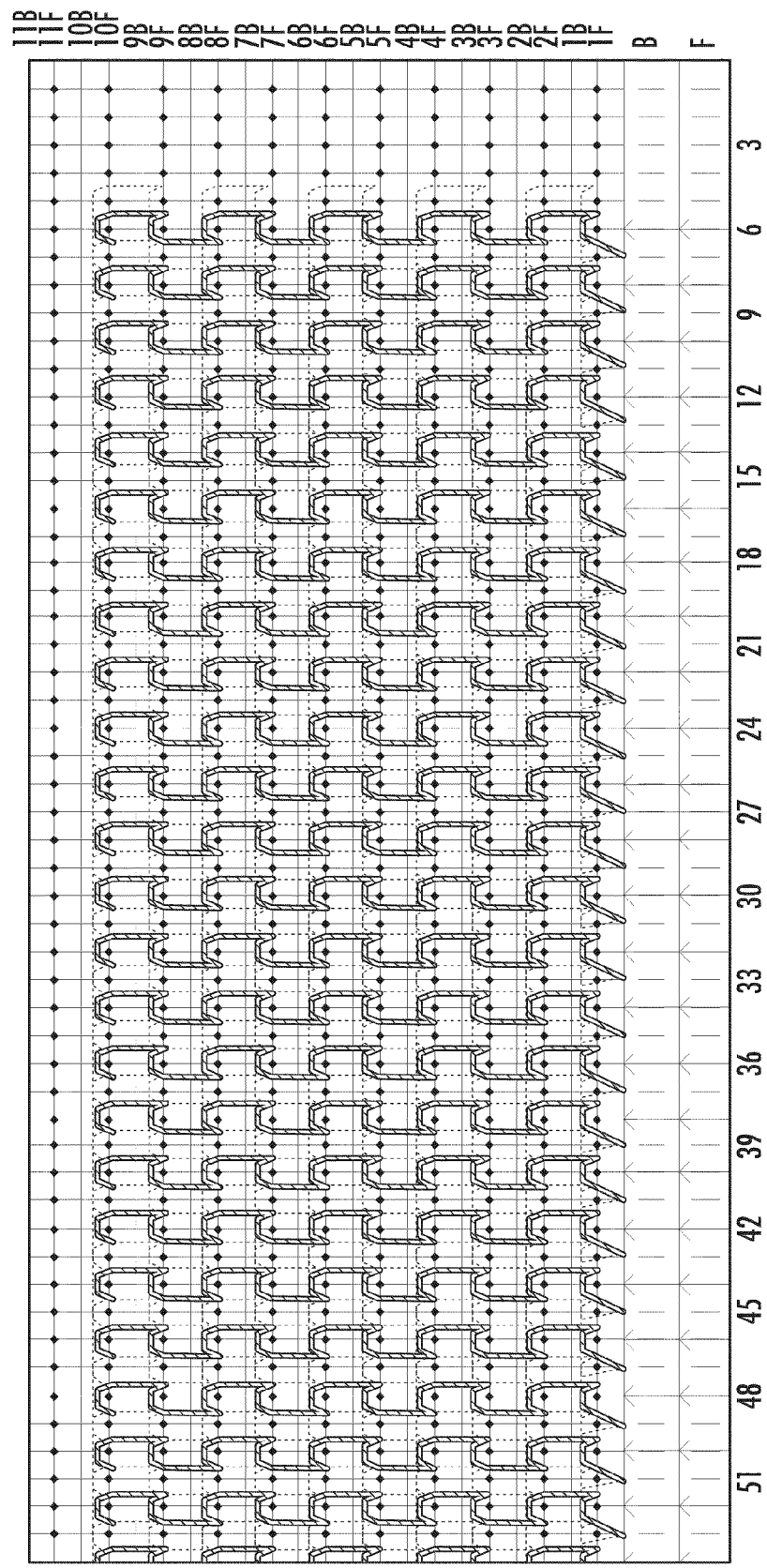
FIGS. 35A and 35B illustrate an example pattern layout for a double needle bed mesh according to aspects of the present invention from FIG. 34B for ground bar #2.
Figure 35B:
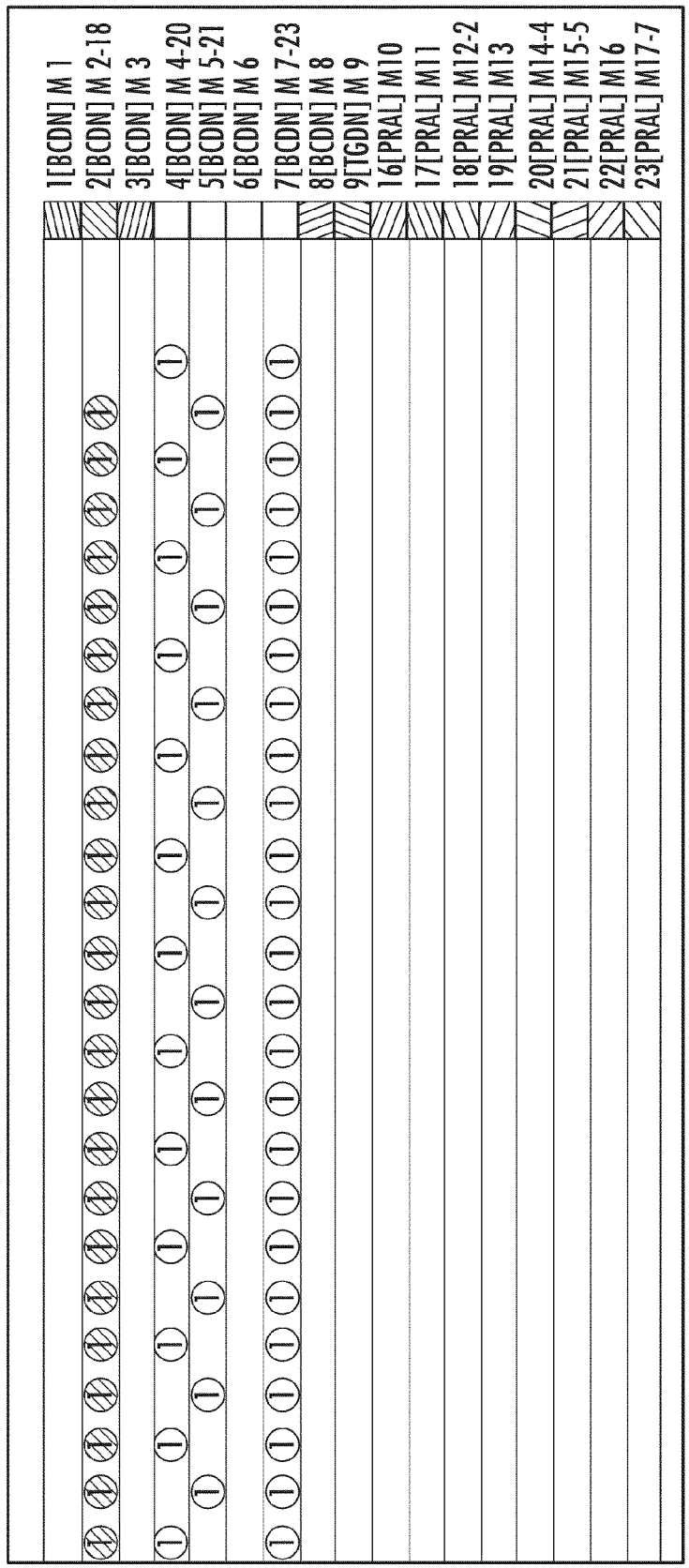
Figure 35C:
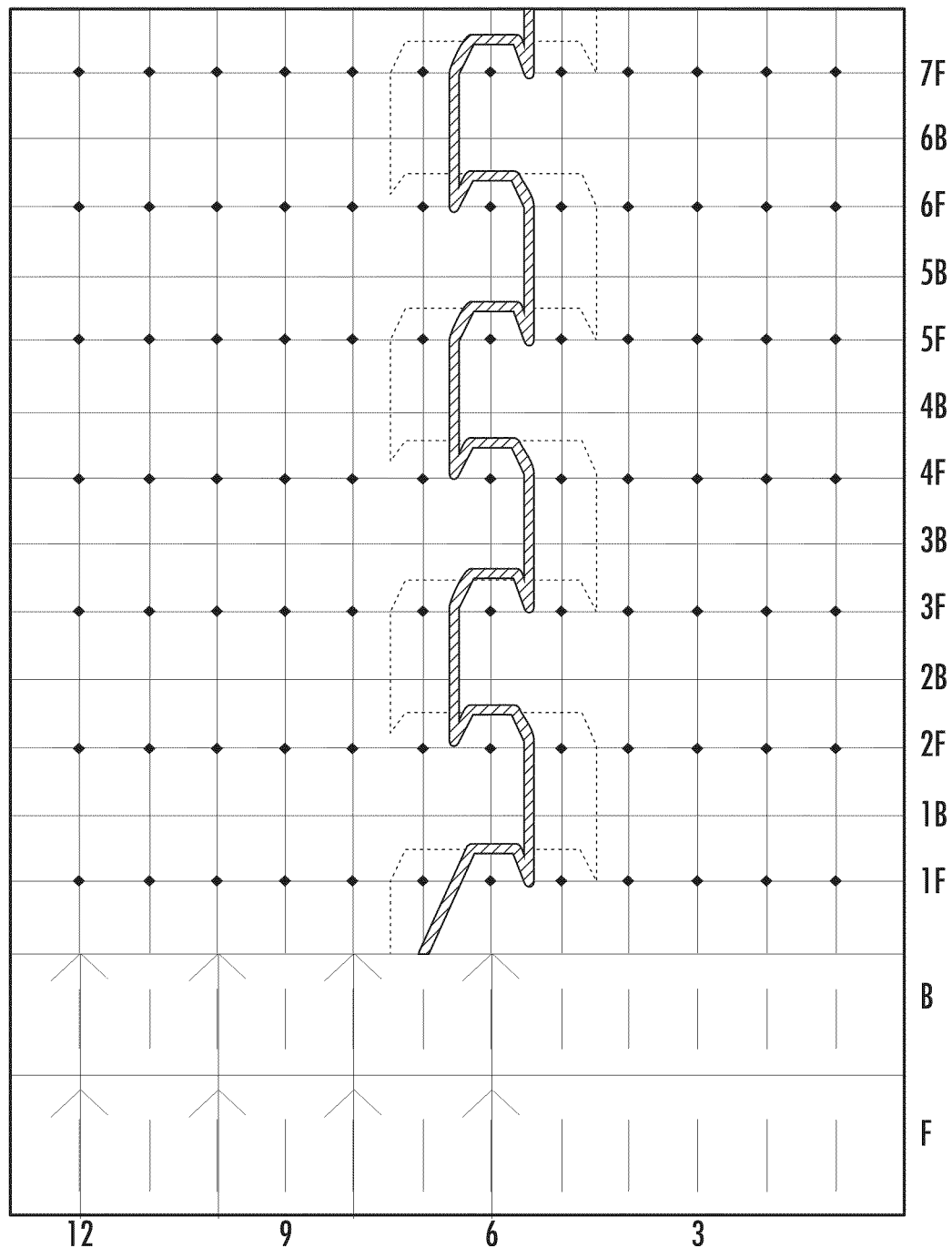
FIGS. 35C and 35D are enlarged views of the example pattern layout and ground bars of FIG. 34B.
Figure 35D:
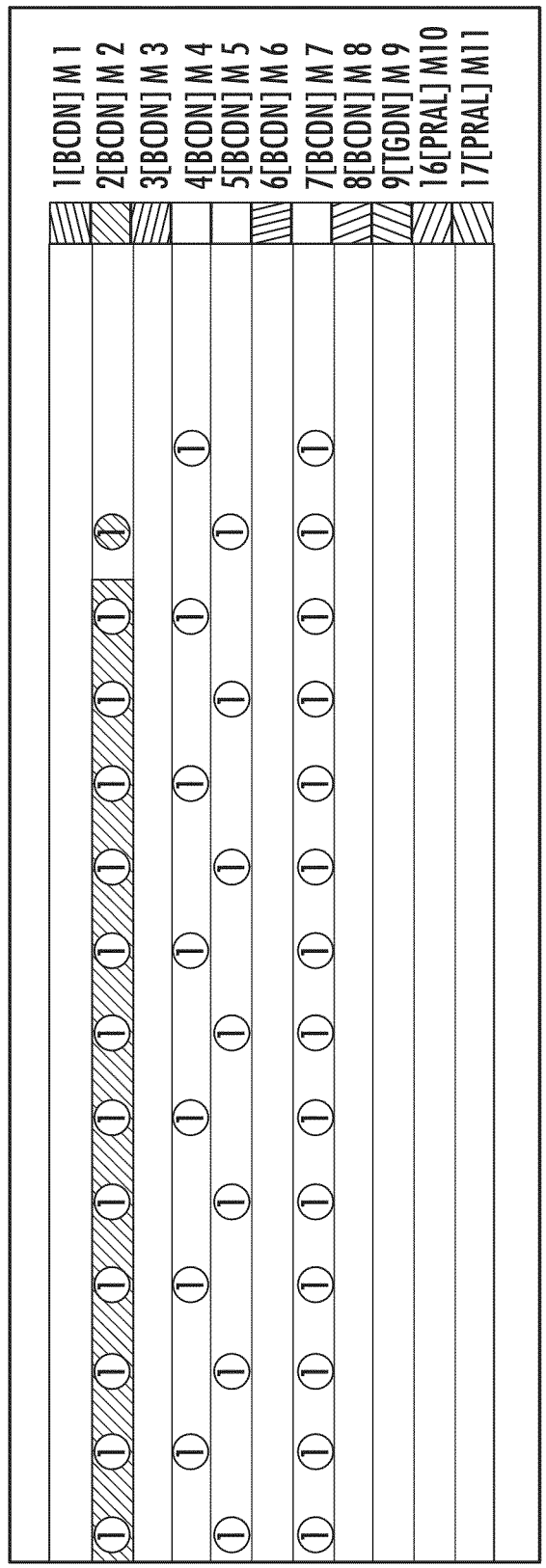
Figure 36A:
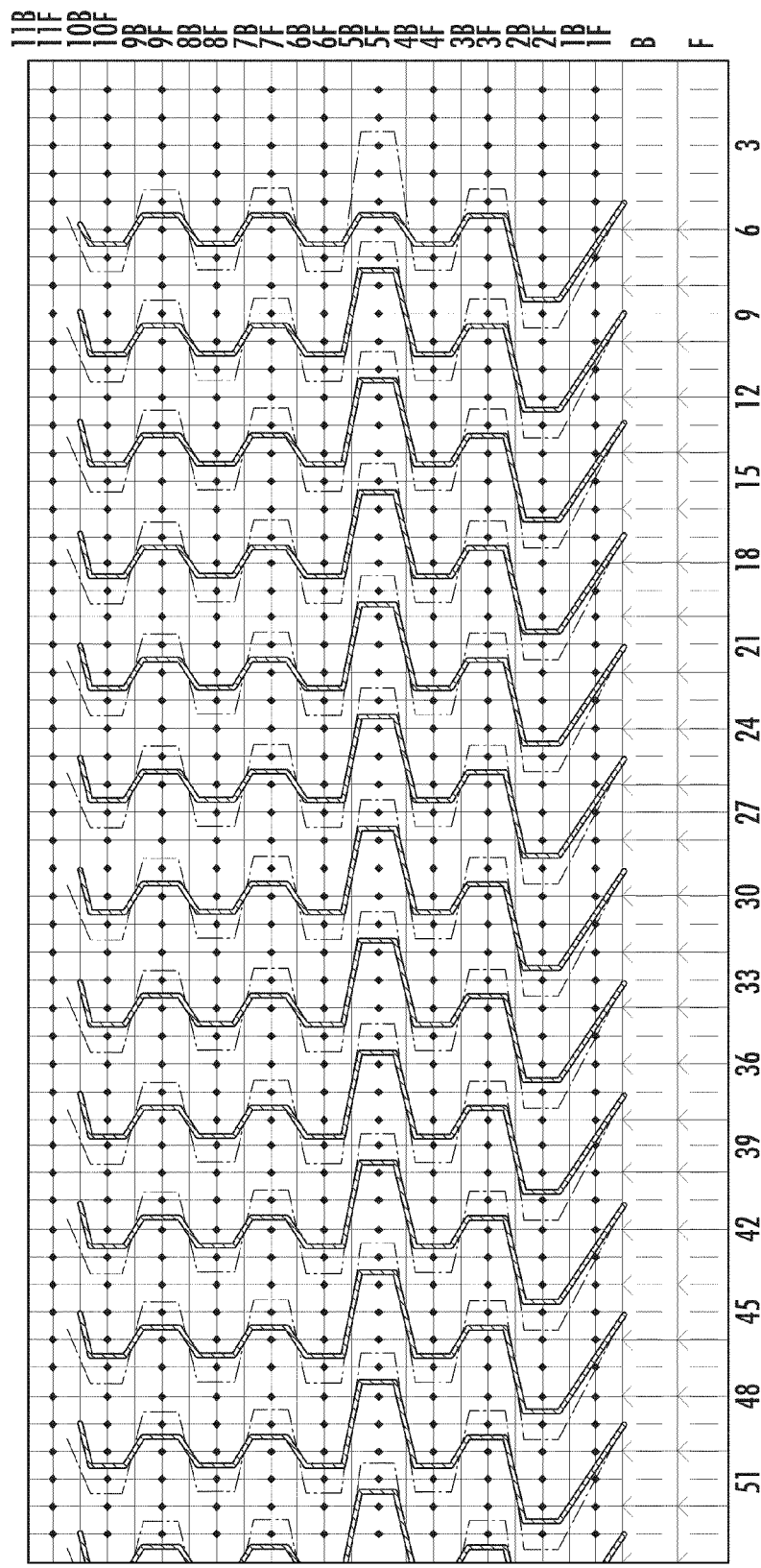
FIGS. 36A and 36B illustrate an example pattern layout for a double needle bed mesh according to aspects of the present invention from FIG. 34B for pattern bar #4.
Figure 36B:
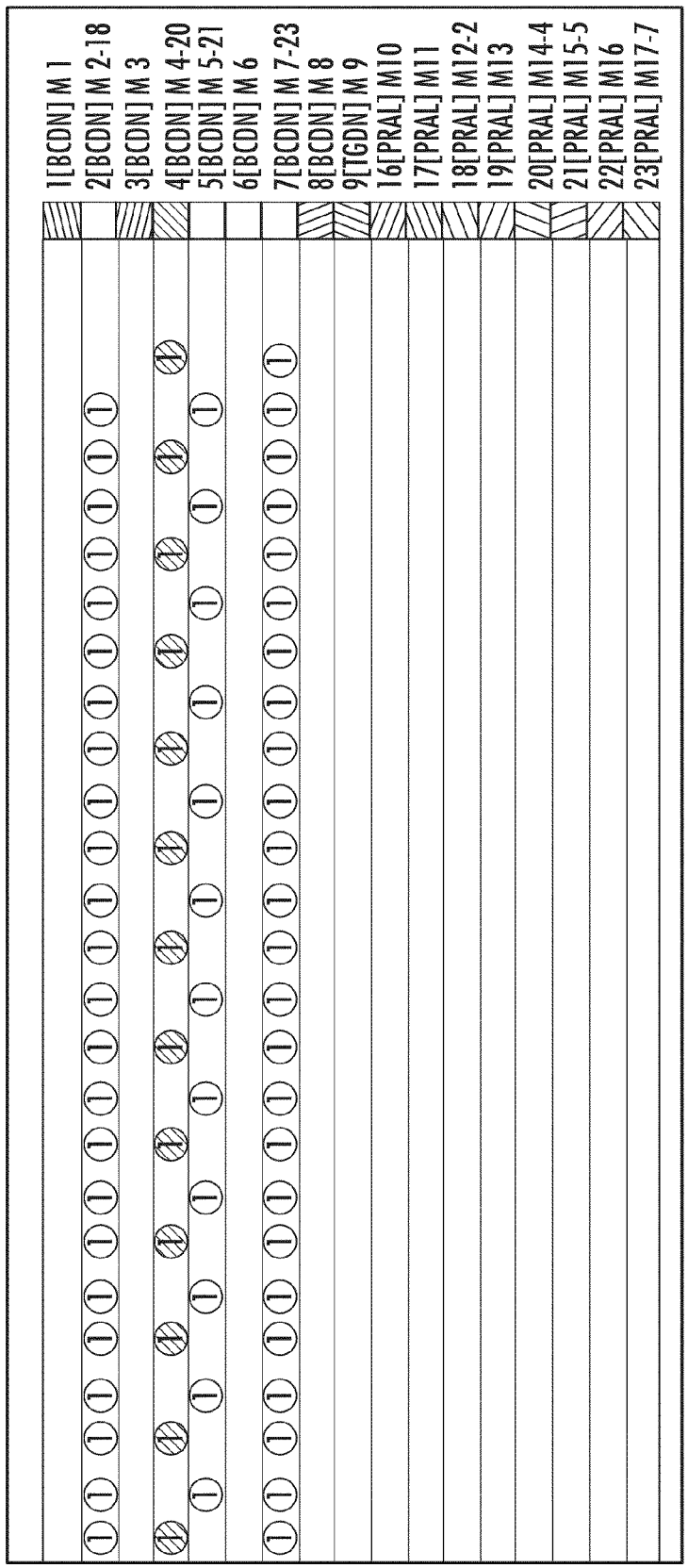
Figure 36C:
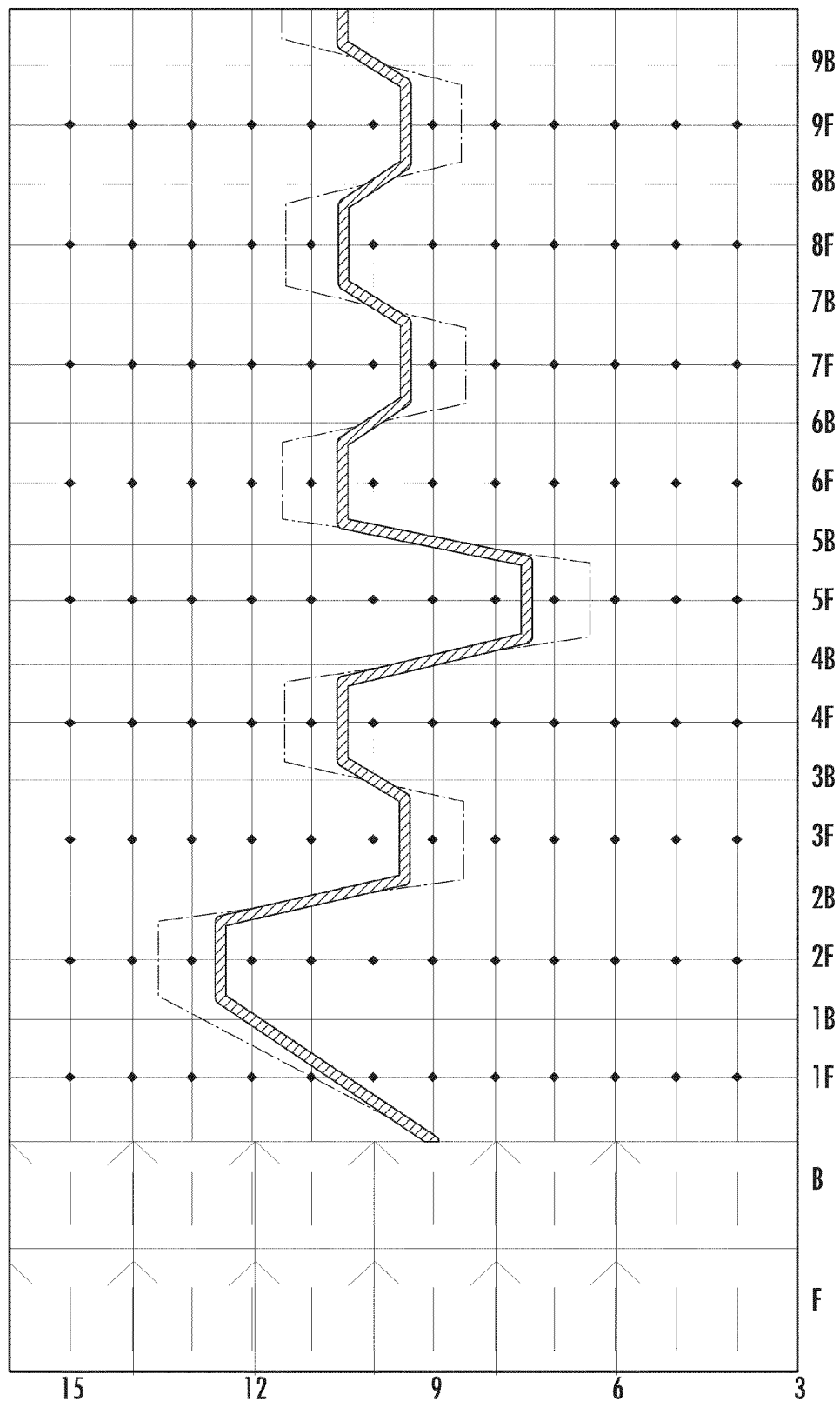
Figure 36D:
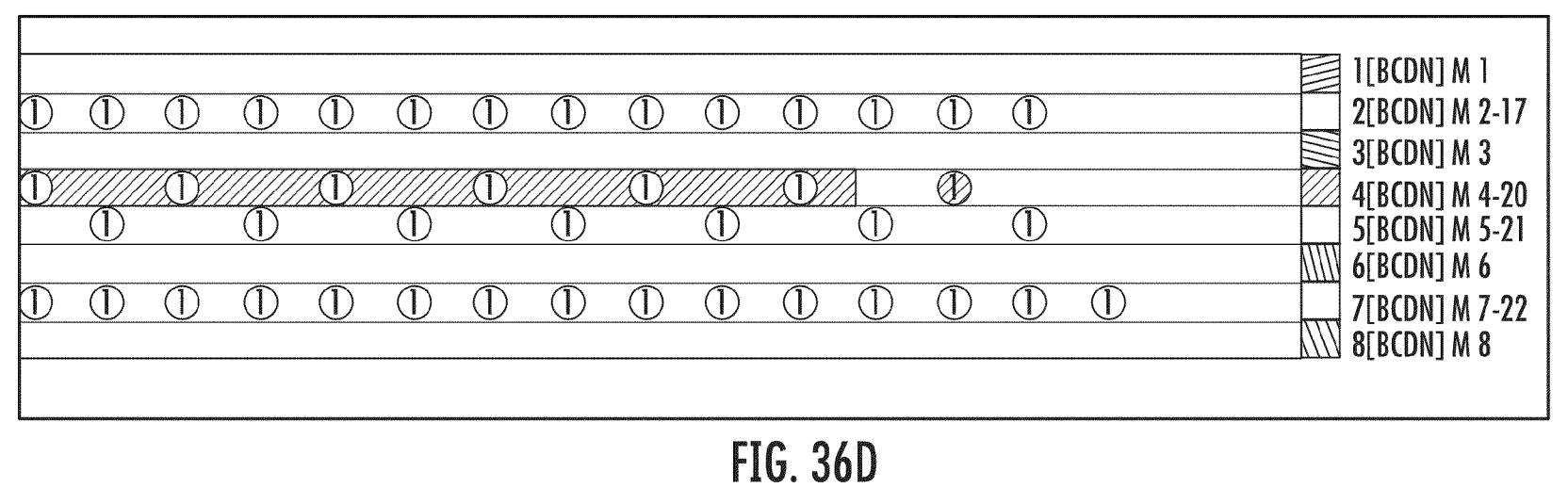
Figure 37A:
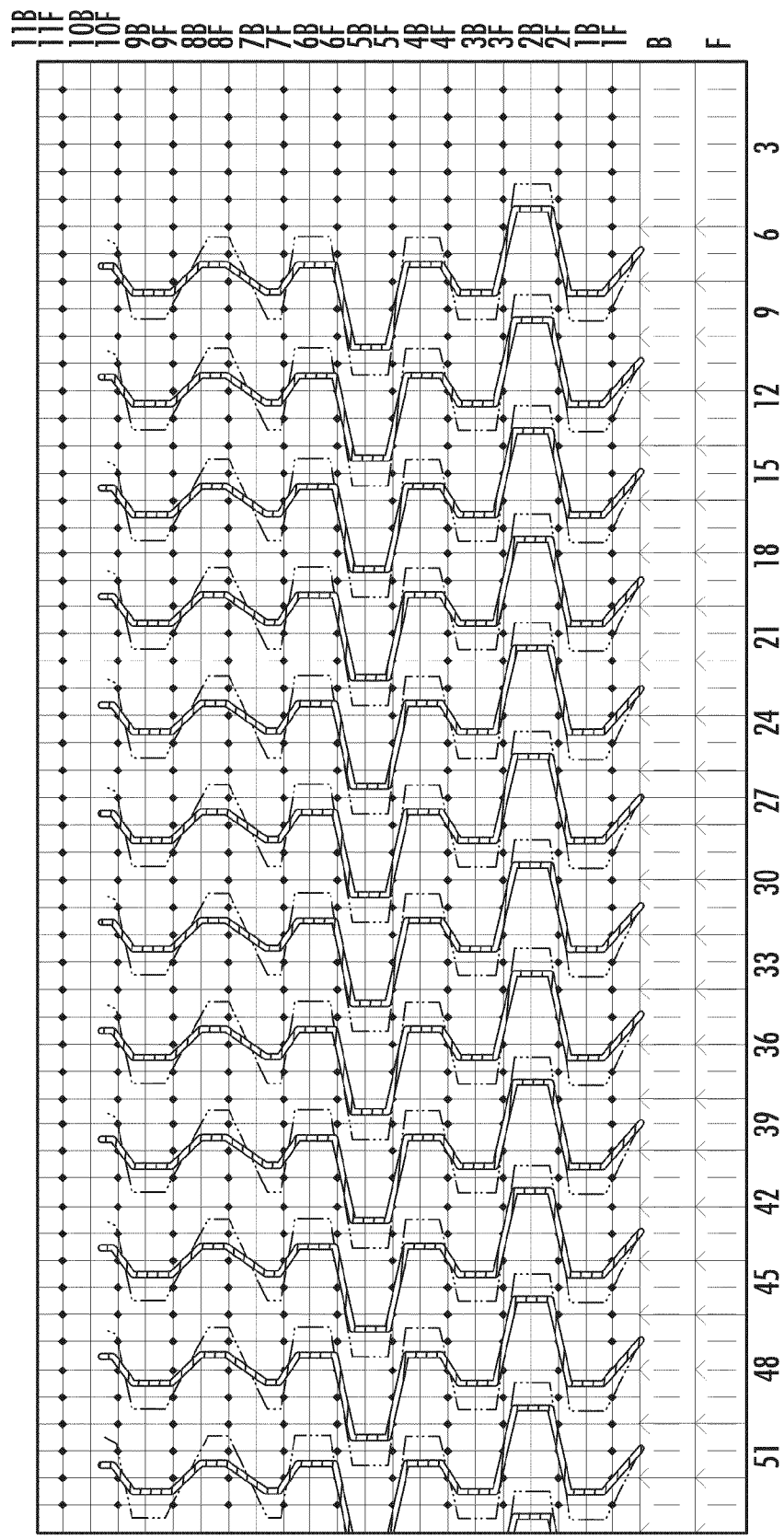
FIGS. 37A and 37B illustrate an example pattern layout for a double needle bed mesh according to aspects of the present invention from FIG. 34B for pattern bar #5.
Figure 37B:
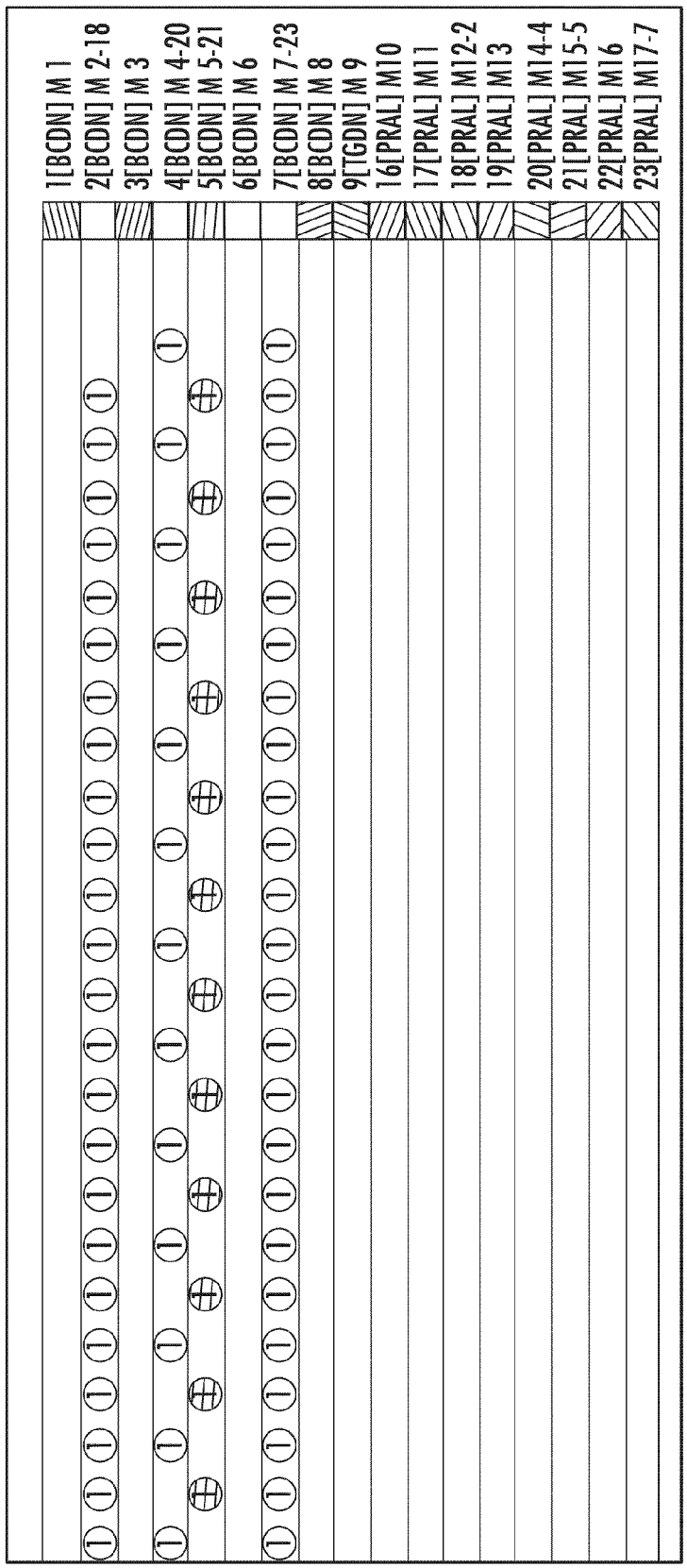
Figure 37C:
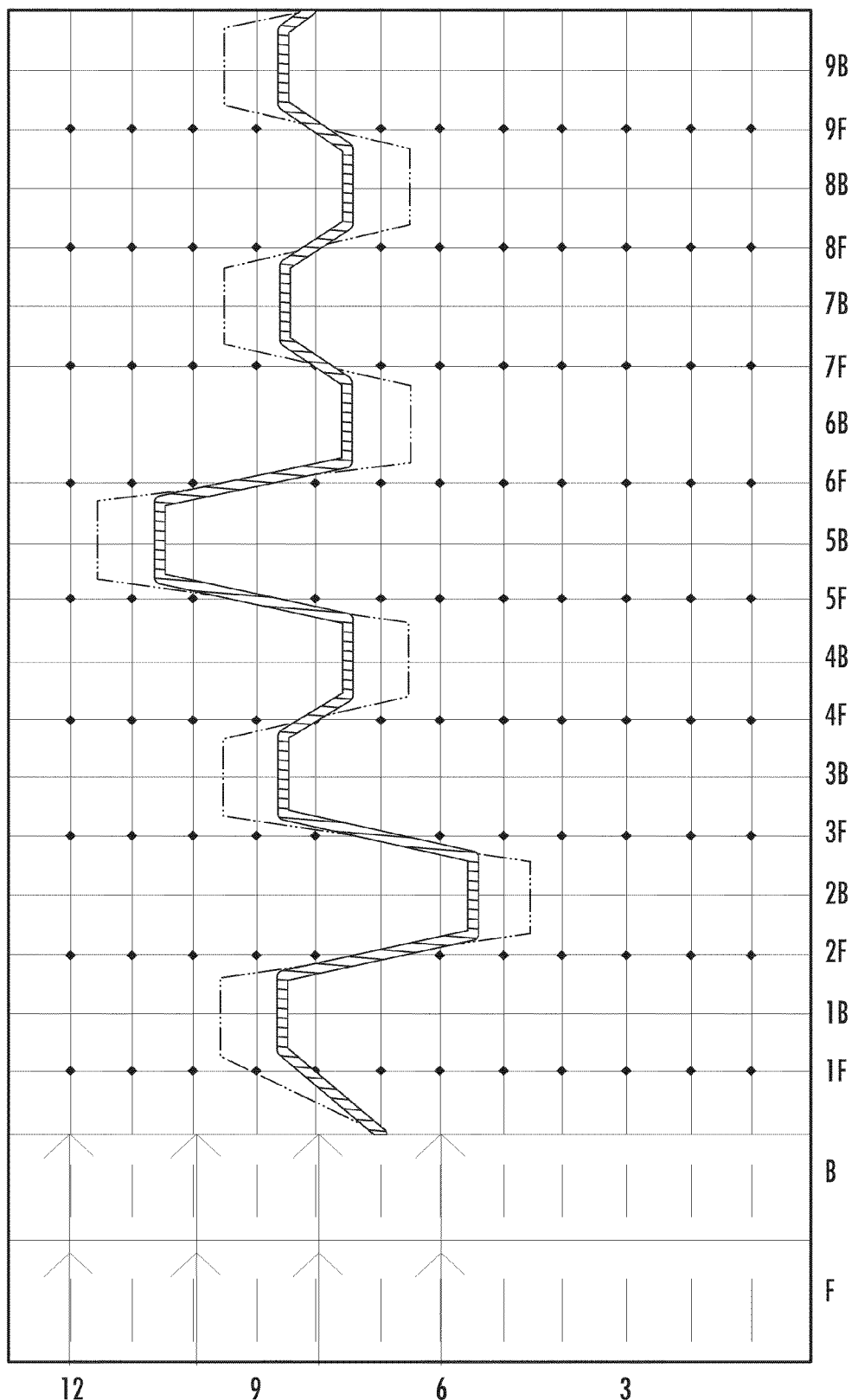
FIGS. 37C and 37D are enlarged views of the example pattern layout and ground bars of FIG. 34B.
Figure 37D:
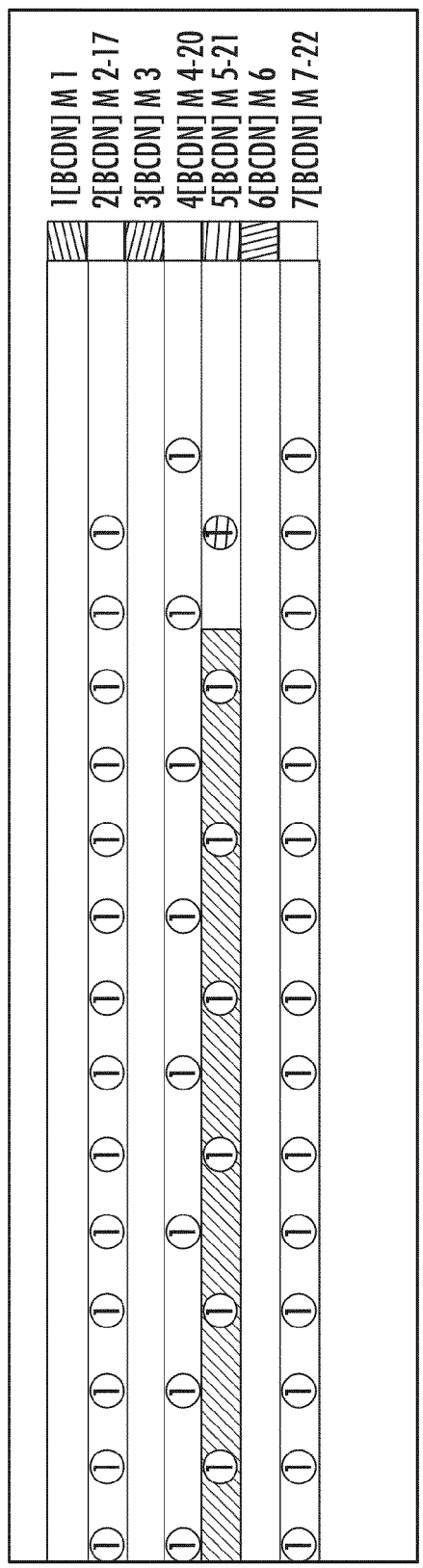
Figure 38A:
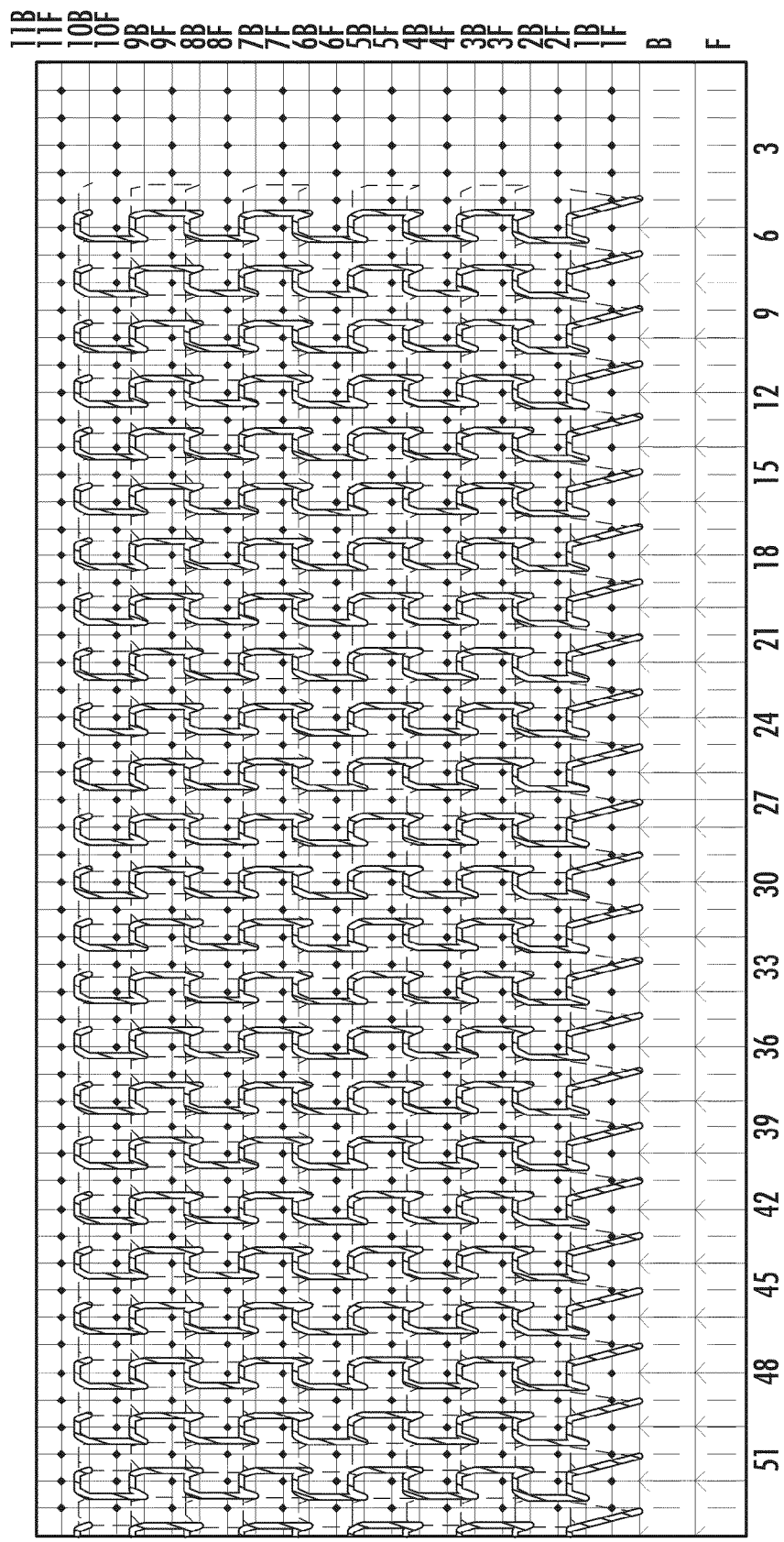
FIGS. 38A and 38B illustrate an example pattern layout for a double needle bed mesh according to aspects of the present invention from FIG. 34B for ground bar #7.
Figure 38B:
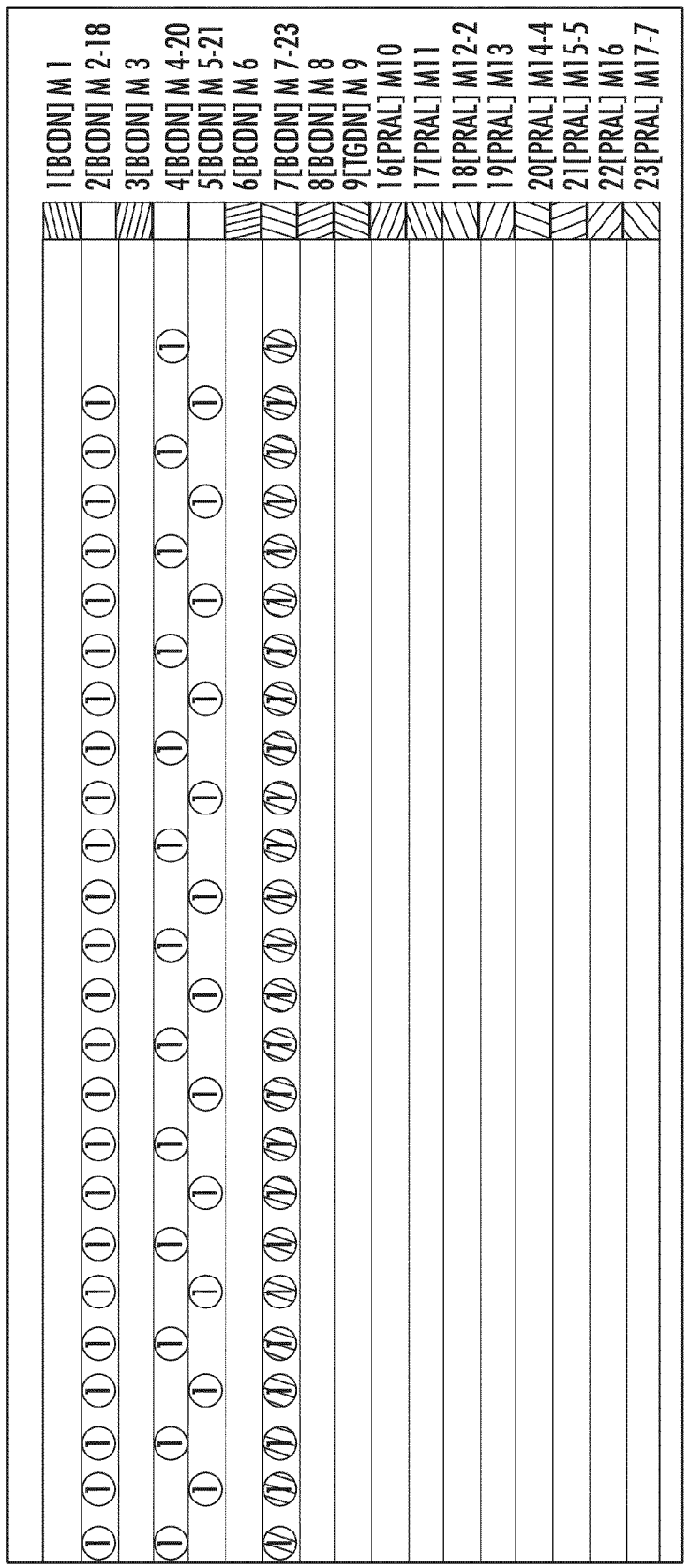
Figure 38C:
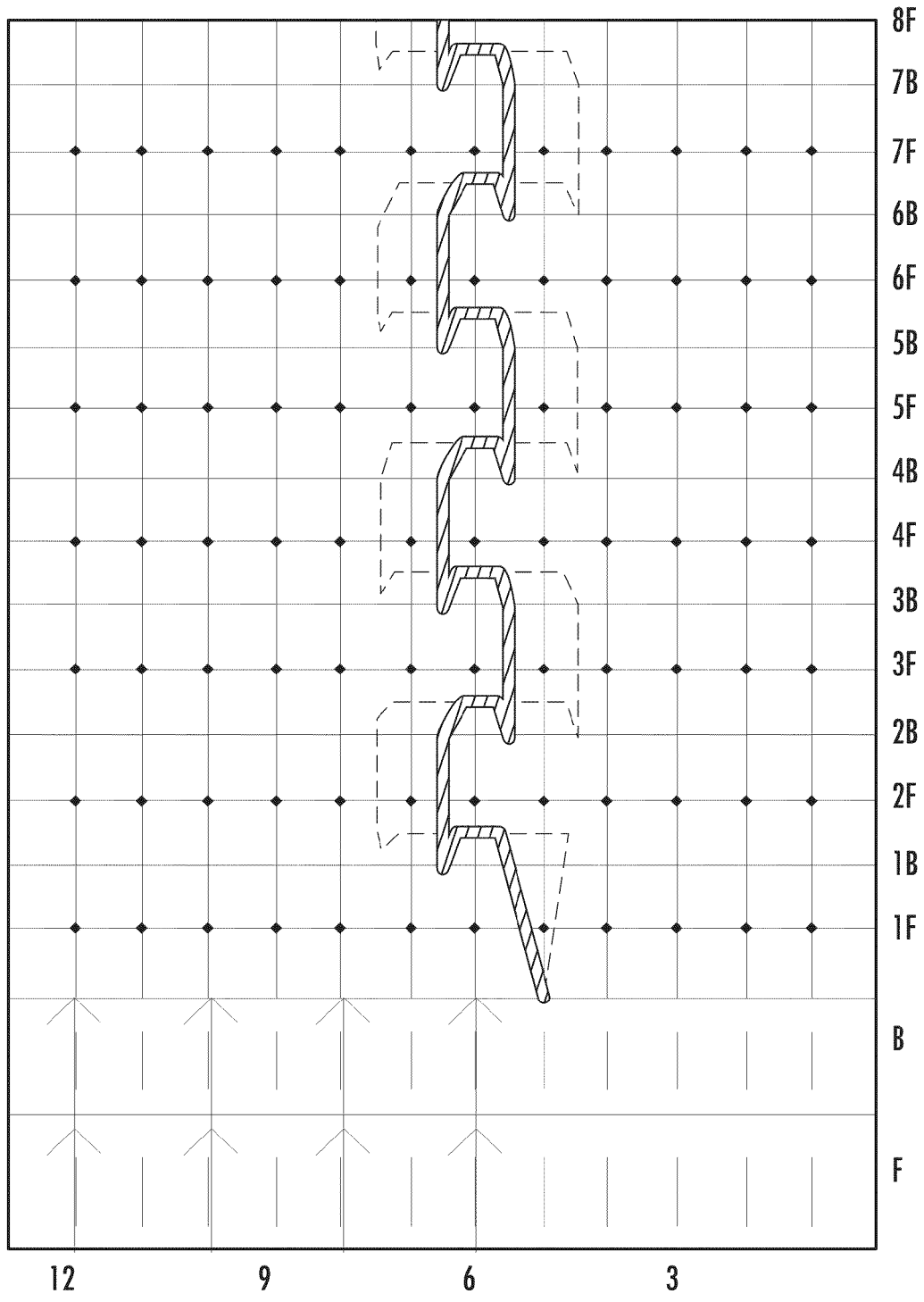
FIGS. 38C and 38D are enlarged views of the example pattern layout and ground bars of FIG. 34B.
Figure 38D:
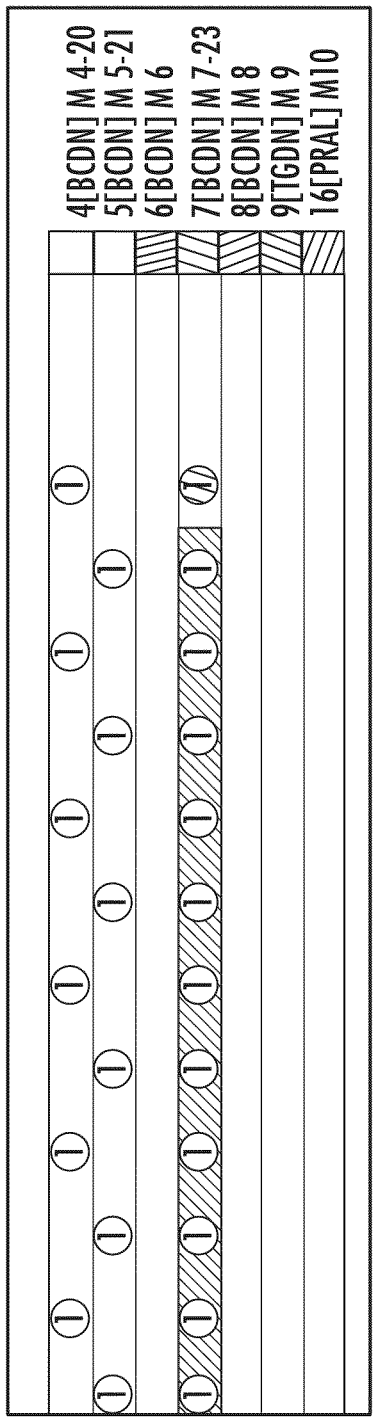
Figure 39:
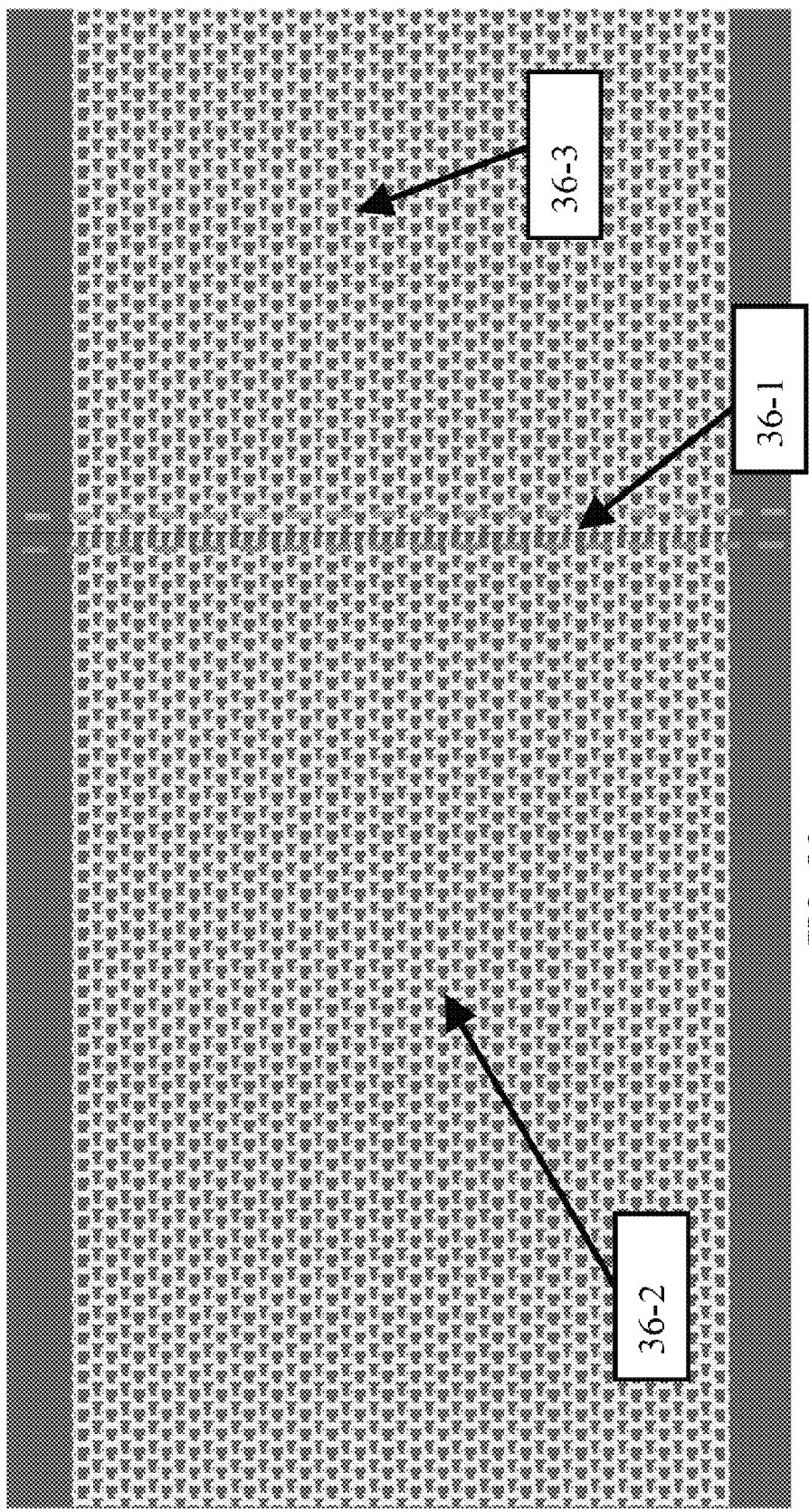
FIG. 39 illustrates an example pattern simulation for a double needle bed mesh demonstrated in FIG. 34B according to aspects of the present invention.

Another variation of the mesh in accordance with aspects of the present invention is preferably created on a raschel knitting machine such as Comez DNB/EL-800-8B set up in 10 gg needle spacing by the use of four movements as shown in pattern layout in FIGS. 34B and C and FIGS. 34D and E: two movements in the wale direction, the vertical direction within the fabric, and two movements in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3 for one of the wale direction movements as shown in FIGS. 35A-D and 1/1-1/3-3/3-3/1 for the other wale direction movement as shown in FIGS. 38A-D. The interlacing of the loops within the fabric allows for one yarn to be under more tension than the other under stress, locking it around the less tensioned yarn; keeping the fabric from unraveling when cut. One of the other two movements in the course direction as shown in FIGS. 36A-D occurs in every few courses creating the porous design of the mesh. These yarns follow a repeat pattern of 3/3-3/3-7/7-7/7-3/3-3/3-5/5-5/5-1/1-1/1-5/5-5/5-3/3-3/3-5/5-5/5-3/3-3/3-5/5-5/5 for the course direction movement. The other movements in the course direction as shown in FIGS. 37A-D occur in every few courses creating the openings in the mesh. These yarns follow a repeat pattern of 3/3-3/3-5/5-5/5-1/1-1/1-5/5-5/5-3/3-3/3-7/7-7/7-3/3-3/3-5/5-5/5-3/3-3/3-5/5-5/5-3/3 for the course direction movement. The pattern simulation layout of this pattern is rendered with ComezDraw 3 software in FIG. 39 considering a yarn design made with 2 ends of Td 20/22 raw silk twisted together in the S direction to form a ply with 6 tpi and further combining three of the resulting ply with 3 tpi. The same yarn design is used for the movements occurring in the wale and course directions. The stitch density or pick count for the surgical mesh design in FIG. 39 is 39 picks per centimeter considering the total picks count for the technical front face and the technical back face of the fabric, or 19.5 picks per cm considering only one face of the fabric. The operating parameters are not limited to those described in FIGS. 34B-E, but just the optimum values for the specific yarn design used for the pattern simulation layout of FIG. 39.

Furthermore, FIG. 39 demonstrates a process improvement for the manufacturing process of the mesh with the pattern layout in FIGS. 34B-E. The improvement consists of a separation area, 36-1, between two individual meshes, 36-2 and 36-3. The advantage of the separation area is to provide guidance for the correct length that the mesh needs to measure and to provide guidance for the tools necessary for separating two individual surgical meshes. For example in order to achieve the mesh length of 5 cm±0.4 cm, the pattern in FIGS. 34B-E requires repeating from pattern line 1 to pattern line 16 for 112 times followed by a repeat of 2 times from pattern line 17 to pattern line 20.

Figure 40A:
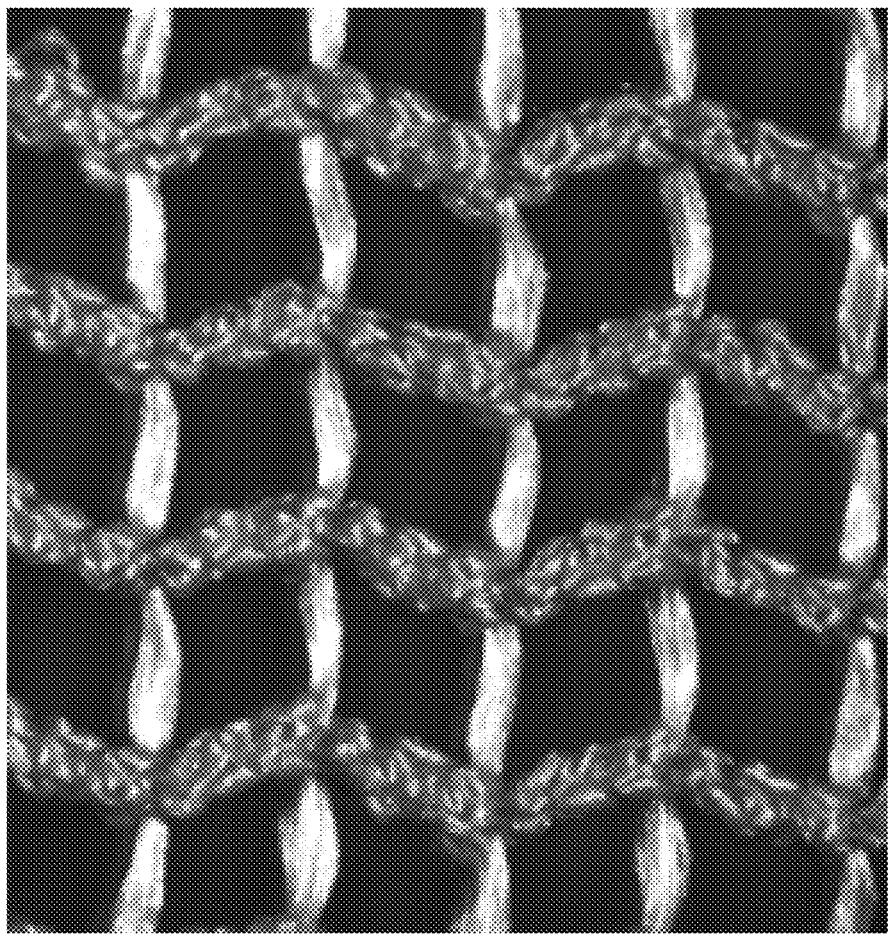
FIG. 40A is a photograph of a pattern layout for a silk-based mesh in accordance with aspects of the present invention.
Figure 40C:
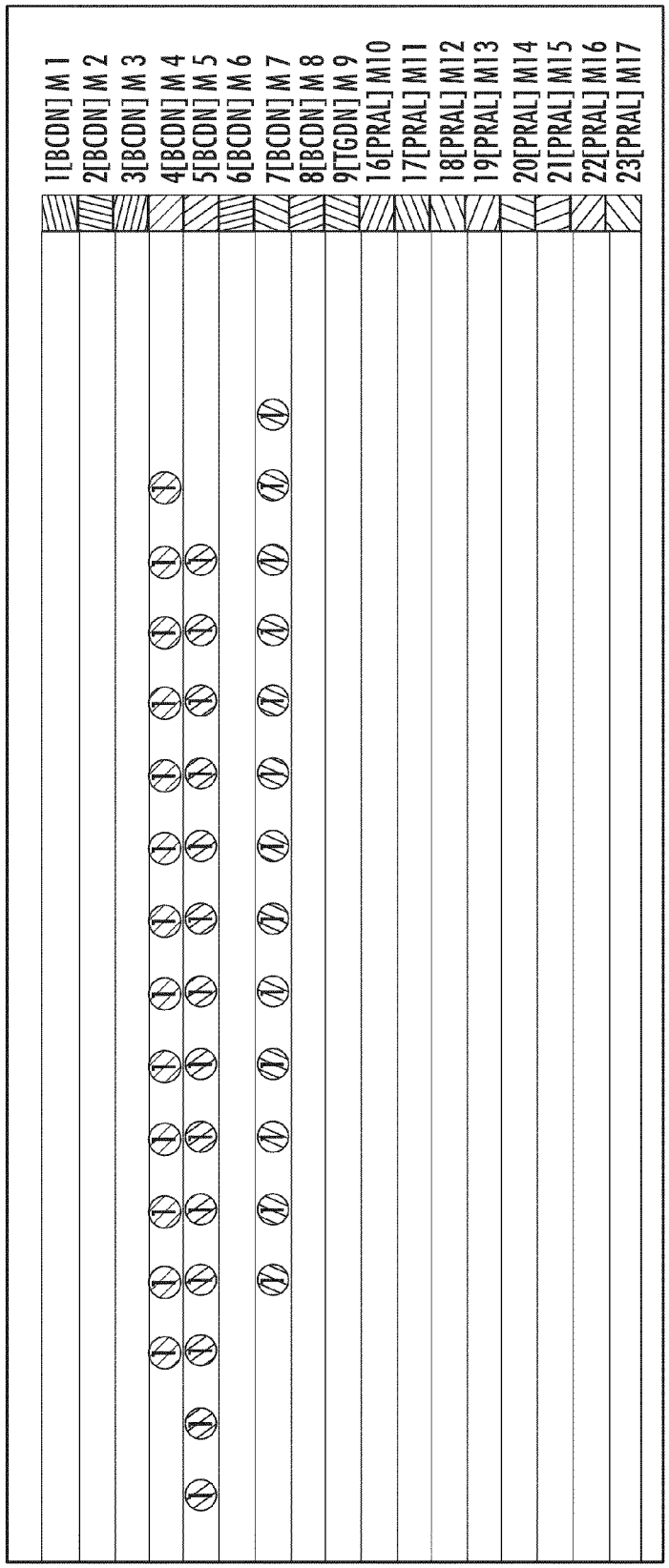
Figure 40E:
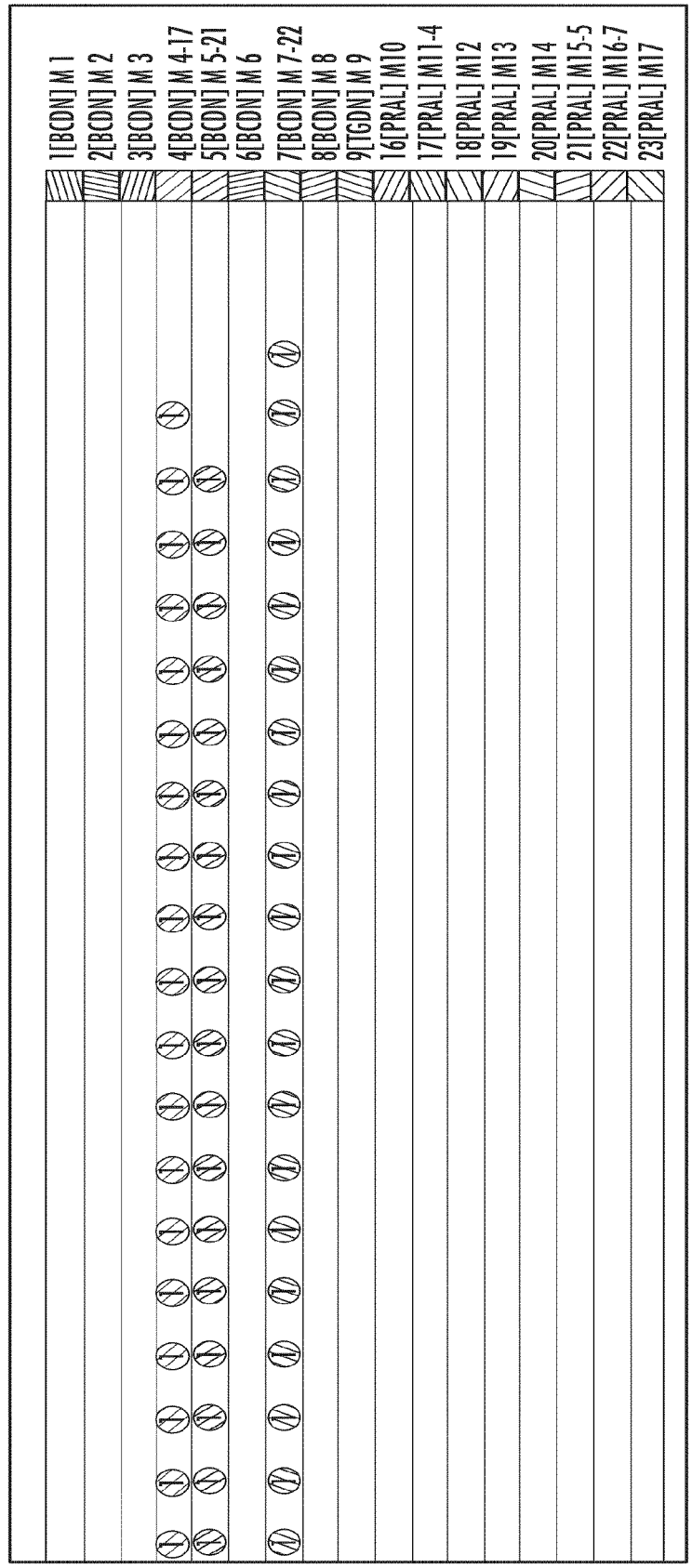
Figure 41A:
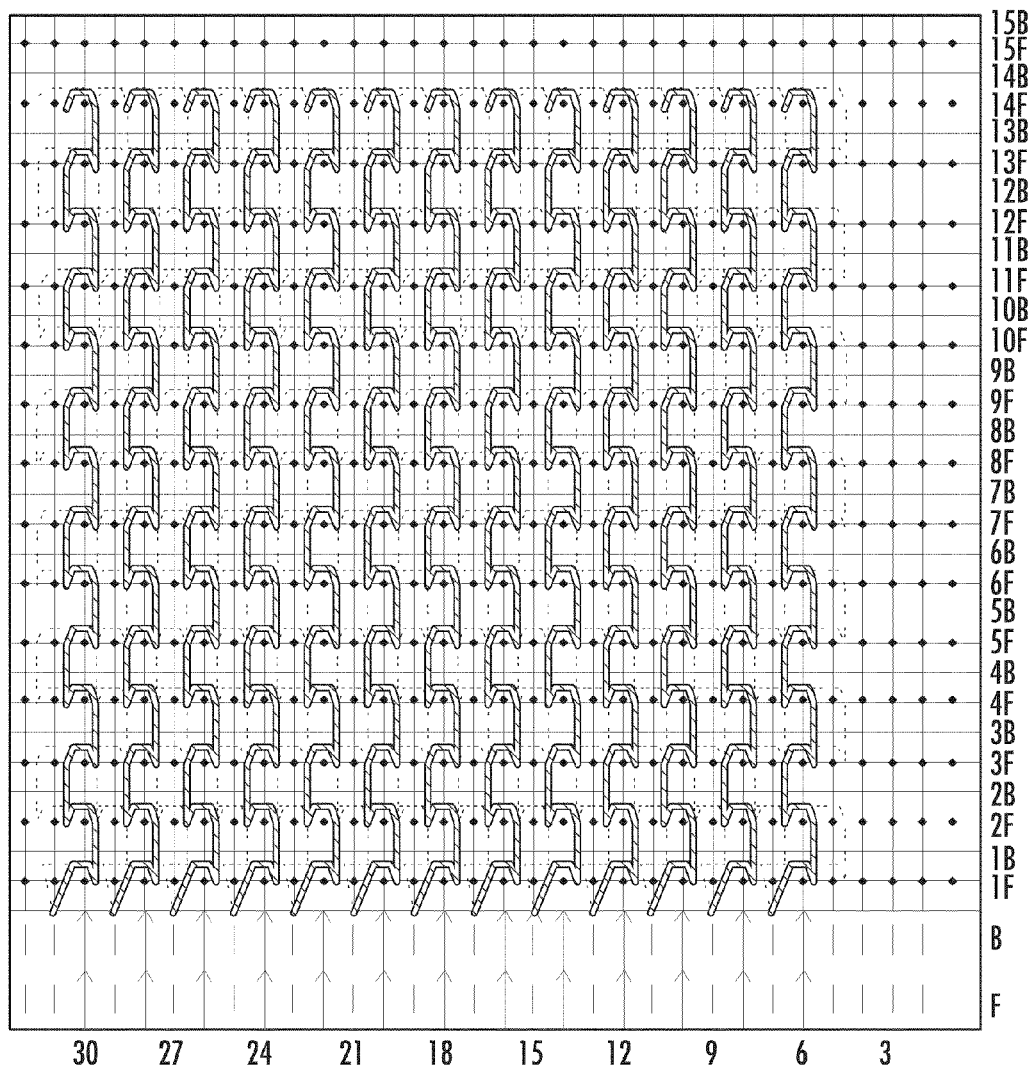
FIG. 41A and FIG. 41B illustrate an example pattern layout for a double needle bed mesh according to aspects of the present invention from FIG. 40B for ground bar #4.
Figure 41B:
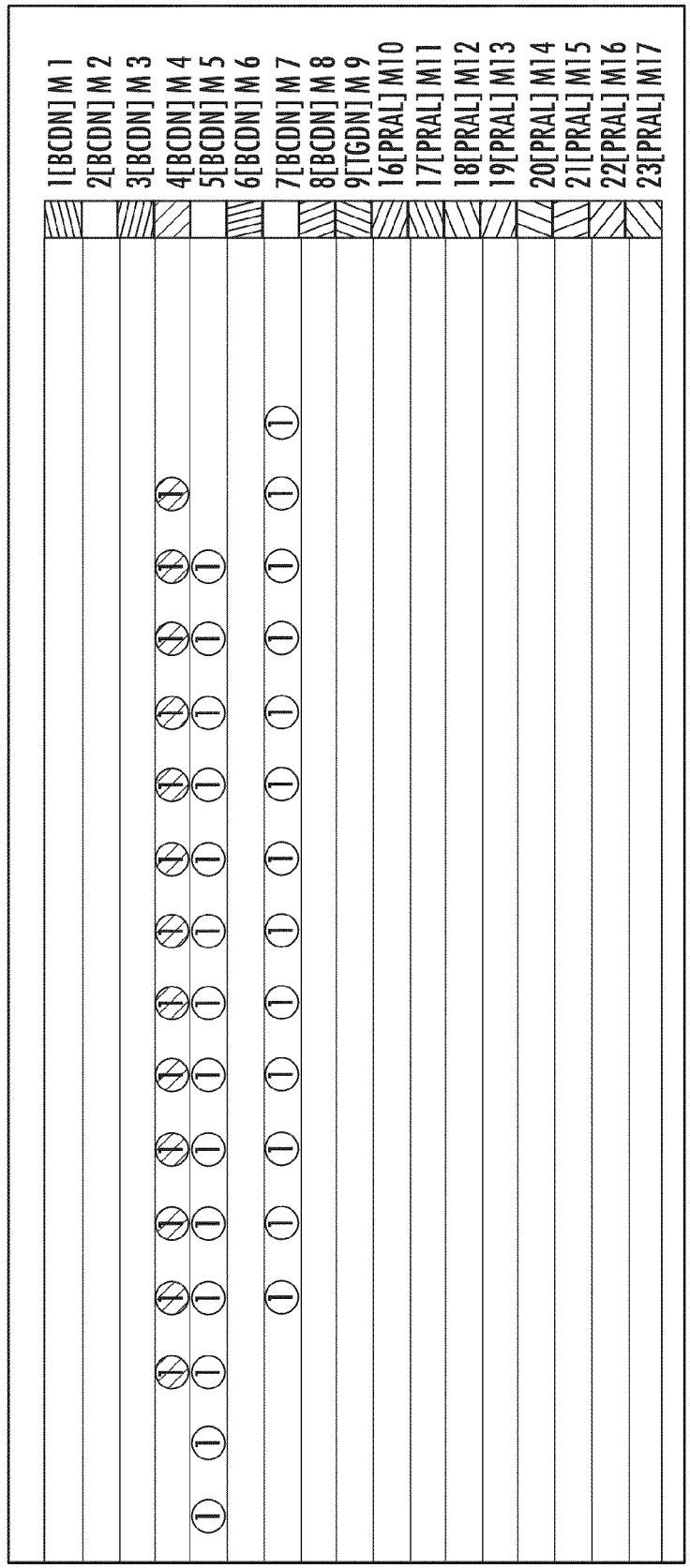
Figure 41C:
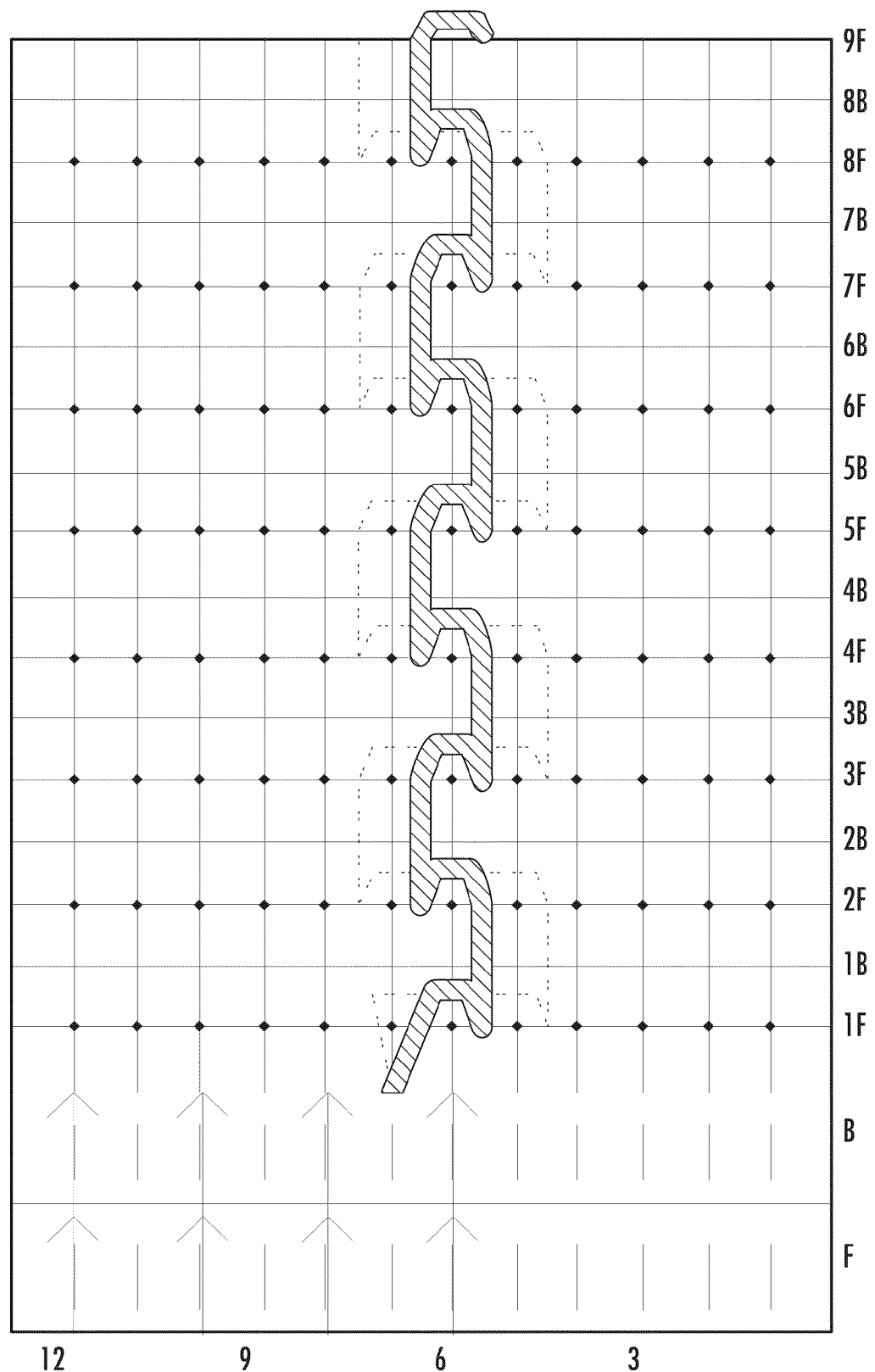
FIGS. 41C and 41D are enlarged views of the example pattern layout and ground bars of FIG. 40B.
Figure 41D:
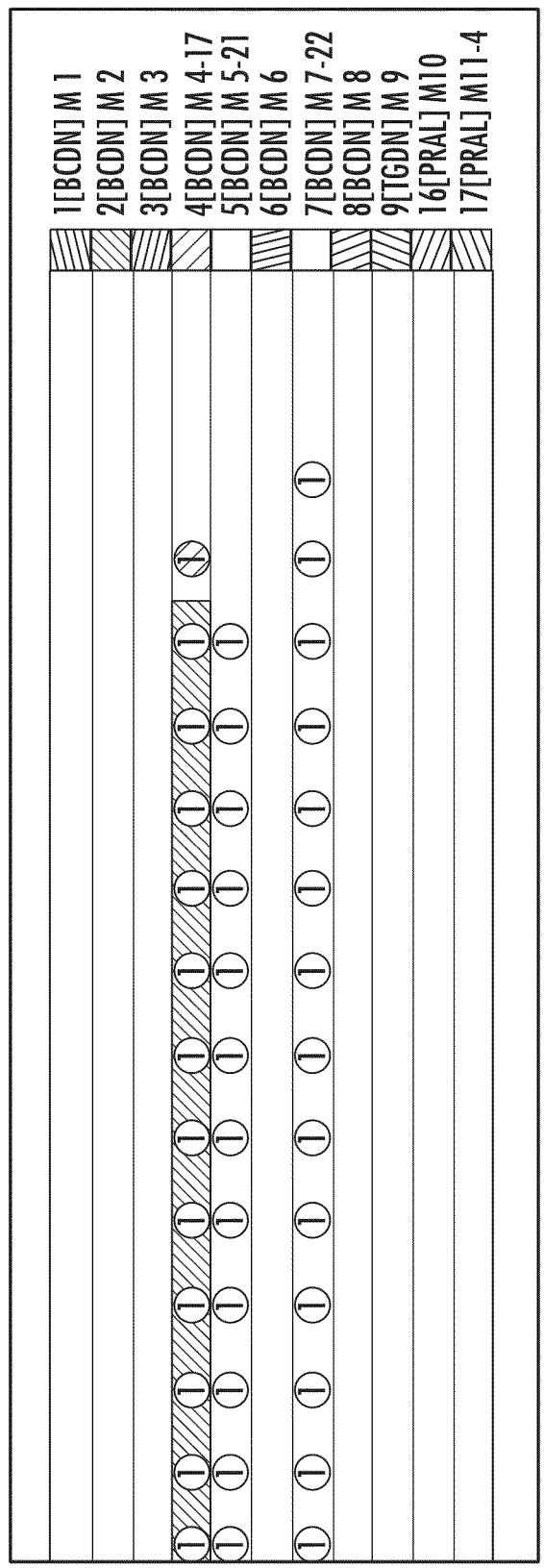
Figure 42A:
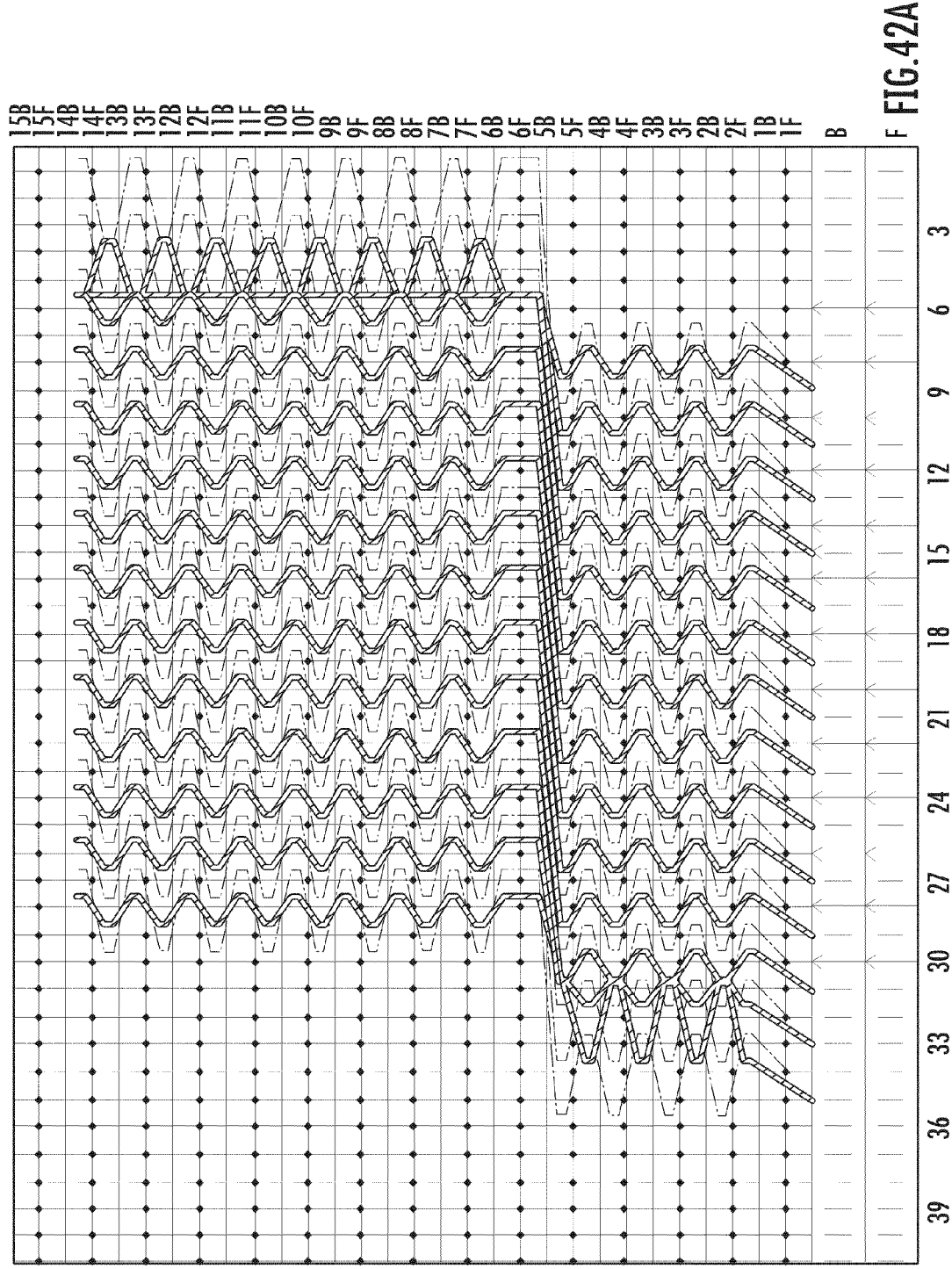
FIGS. 42A and 42B illustrate an example pattern layout for a double needle bed mesh according to aspects of the present invention from FIG. 40B for pattern bar #5.
Figure 42B:
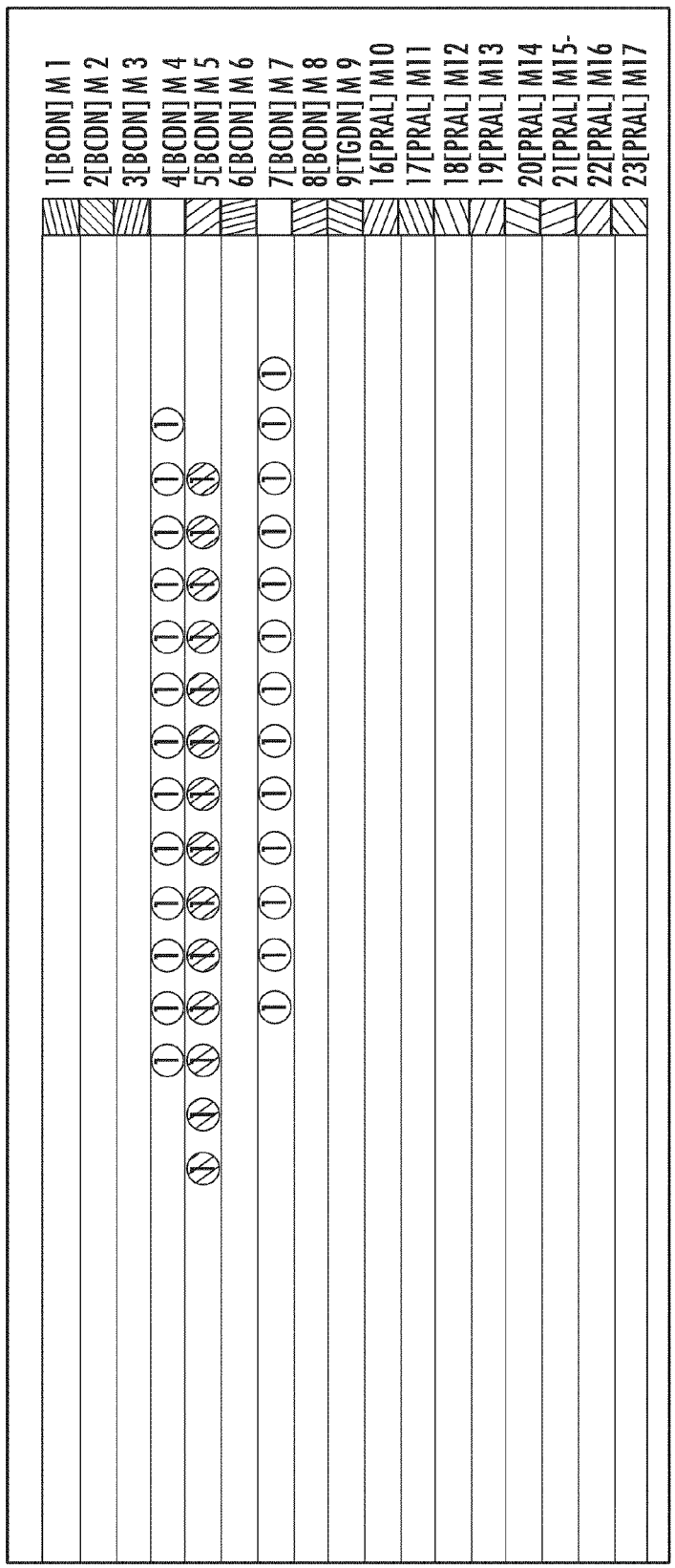
Figure 42C:
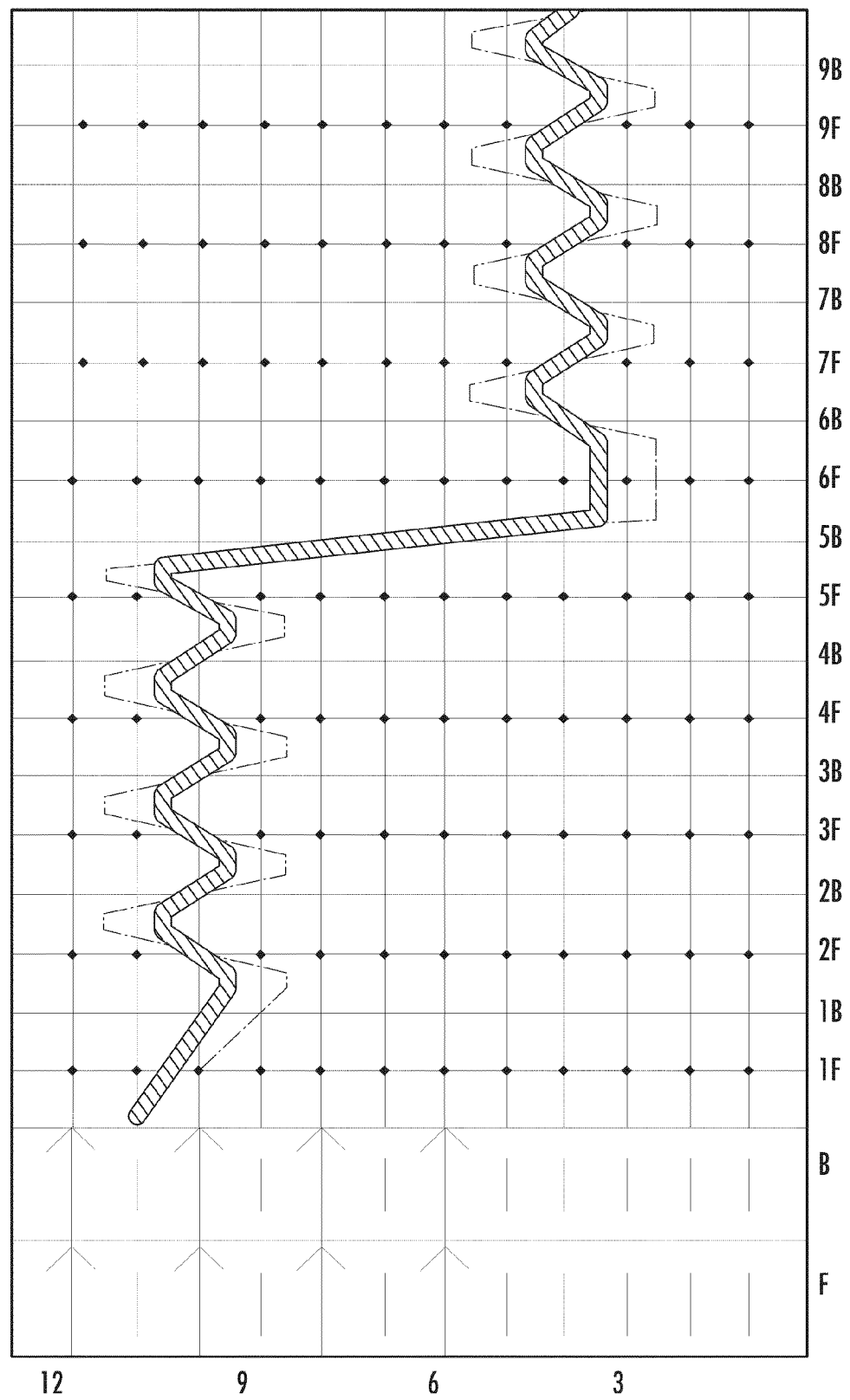
FIGS. 42C and 42D are enlarged views of the example pattern layout and ground bars of FIG. 40B.
Figure 42D:
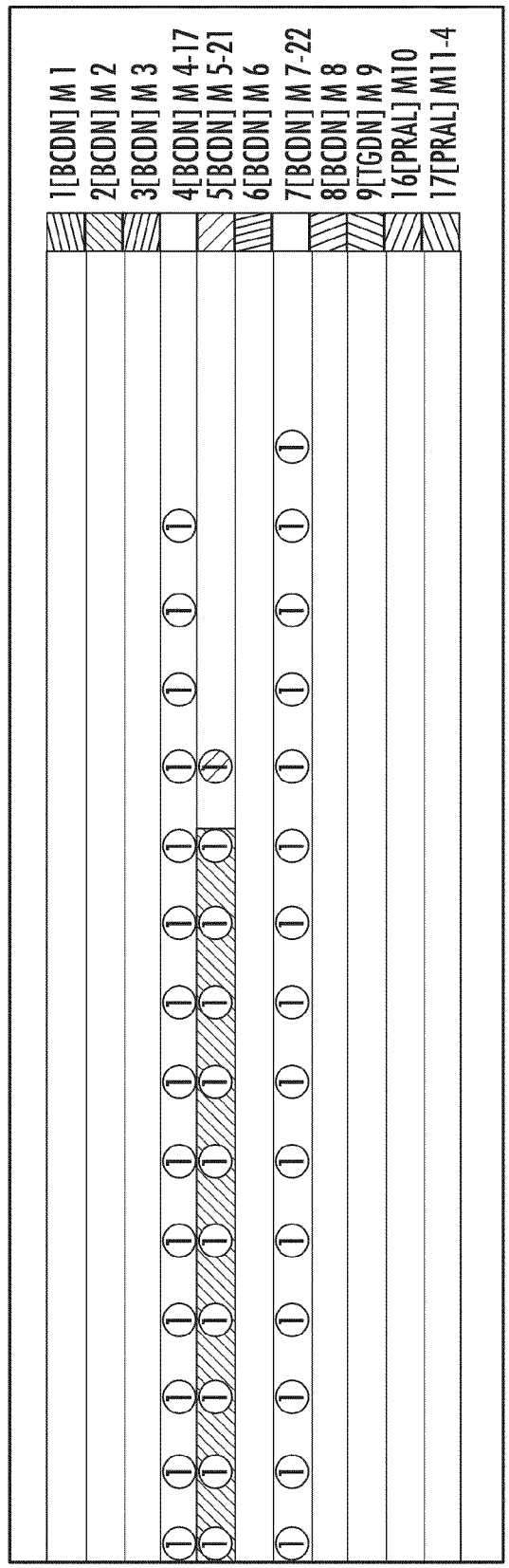
Figure 43A:
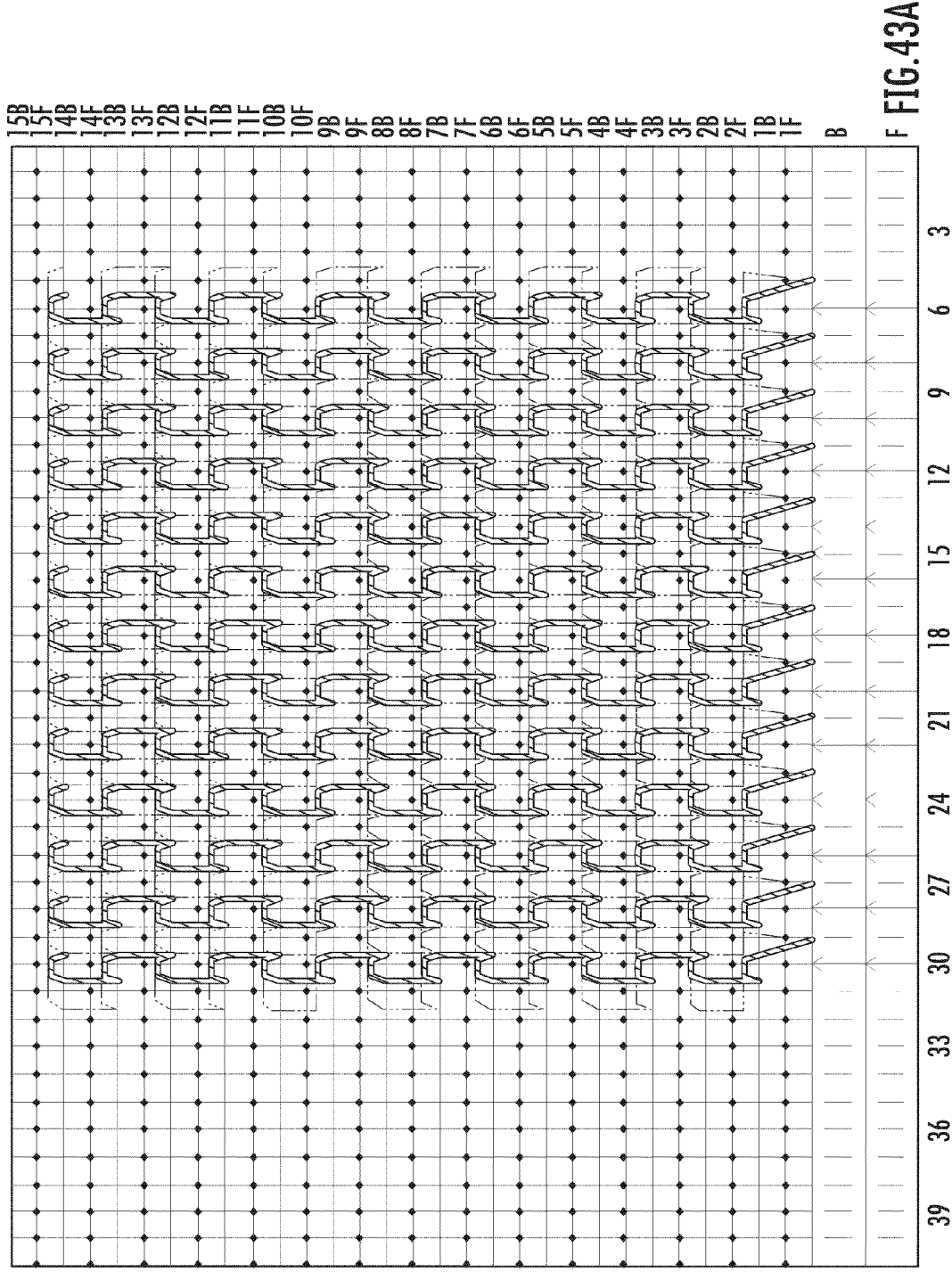
FIGS. 43A and 43B illustrate an example pattern layout for a double needle bed mesh according to aspects of the present invention from FIG. 40B for ground bar #7.
Figure 43B:
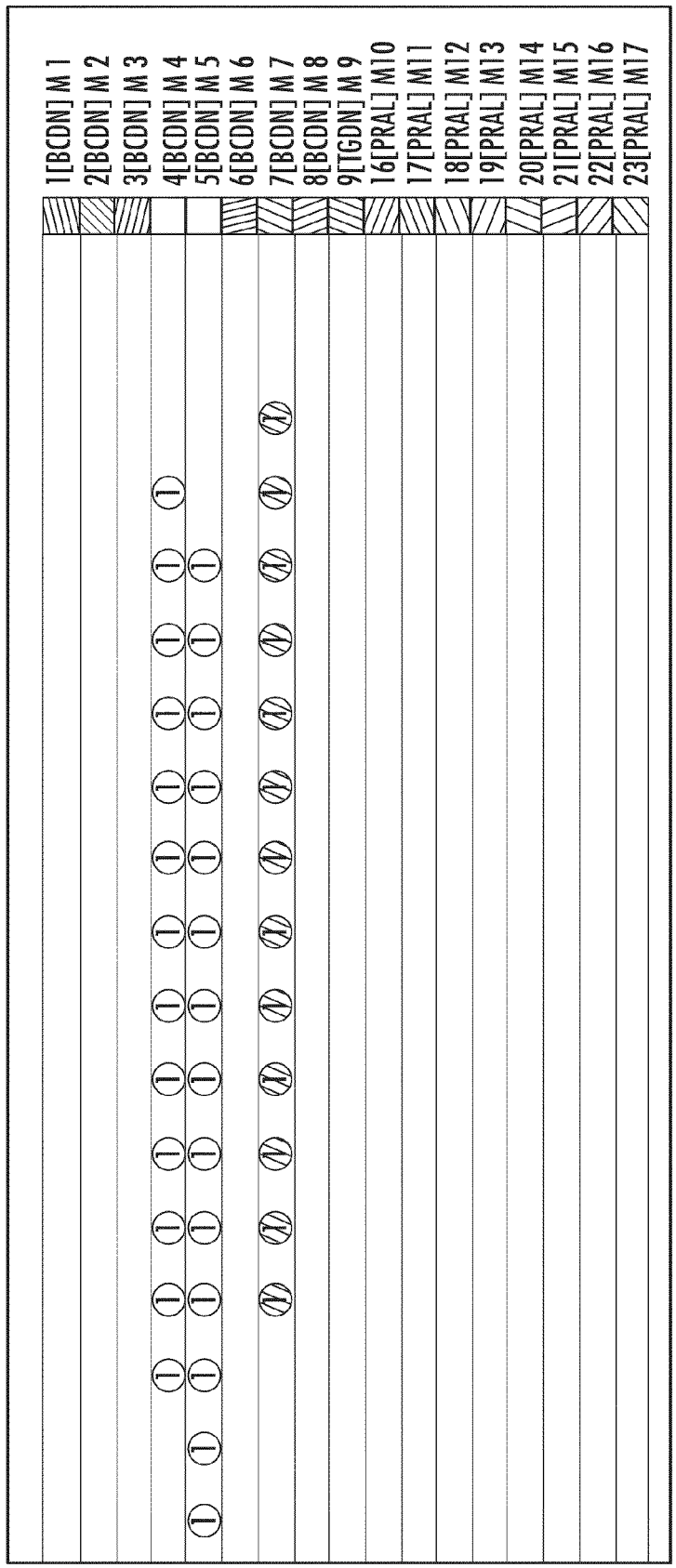
Figure 43C:
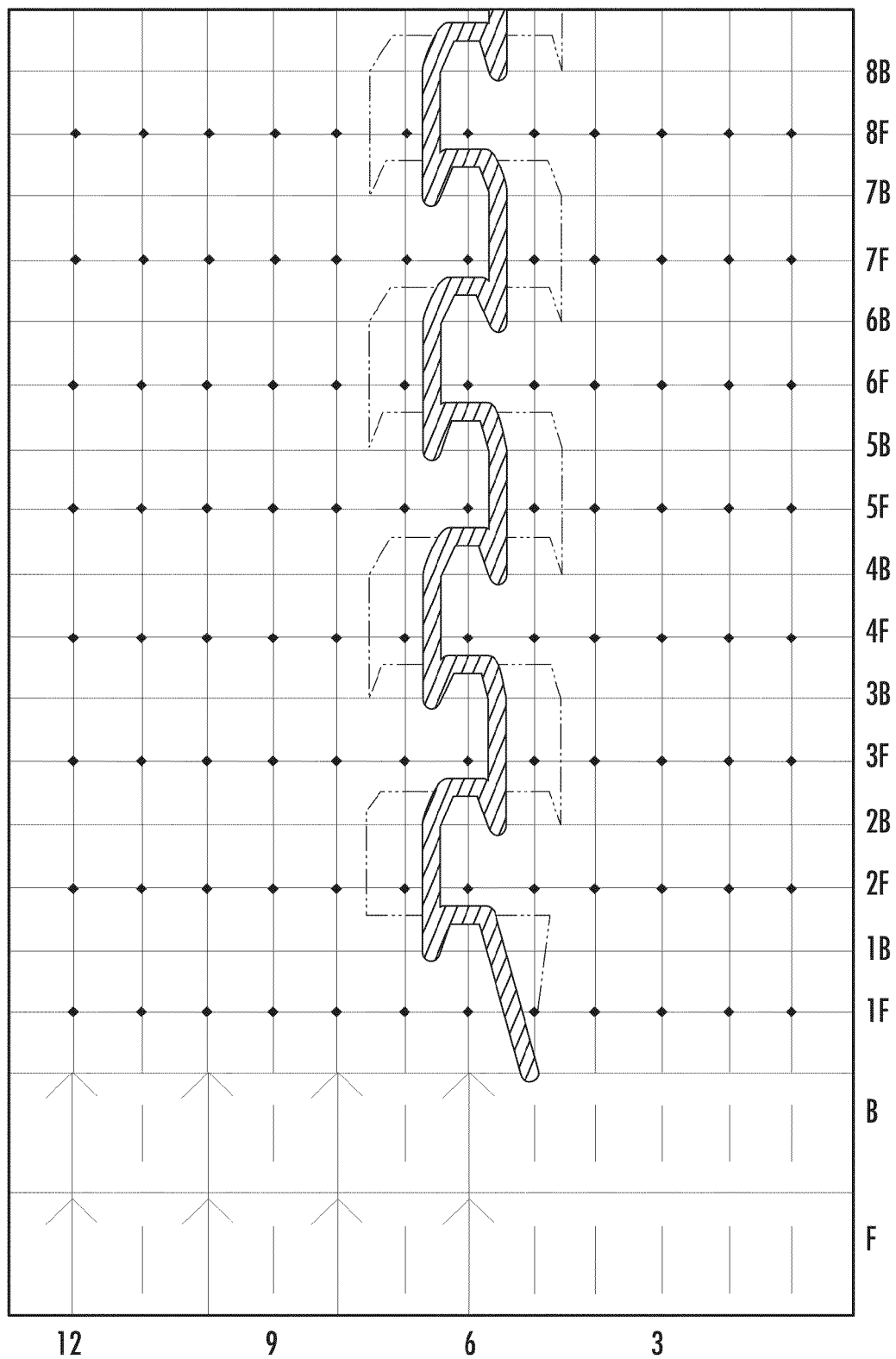
FIGS. 43C and 43D are enlarged views of the example pattern layout and ground bars of FIG. 40B.
Figure 43D:
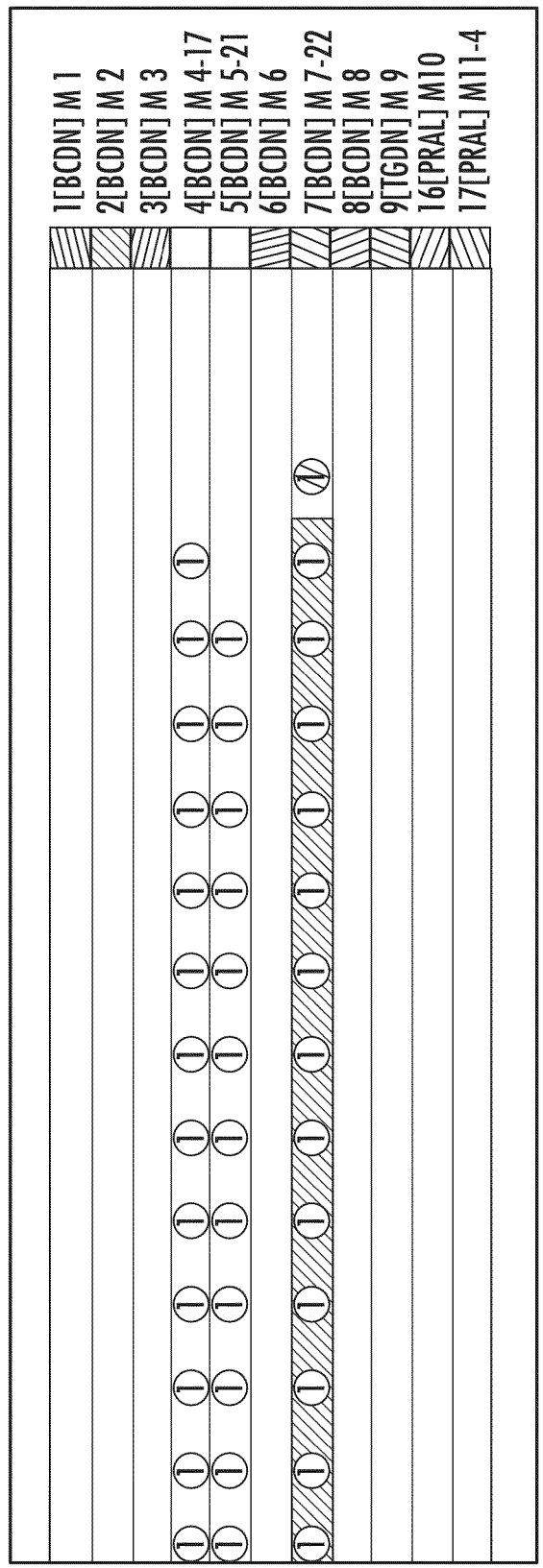

FIG. 40A is a photograph of a pattern layout for a silk-based mesh in accordance with aspects of the present invention.

Figure 44:
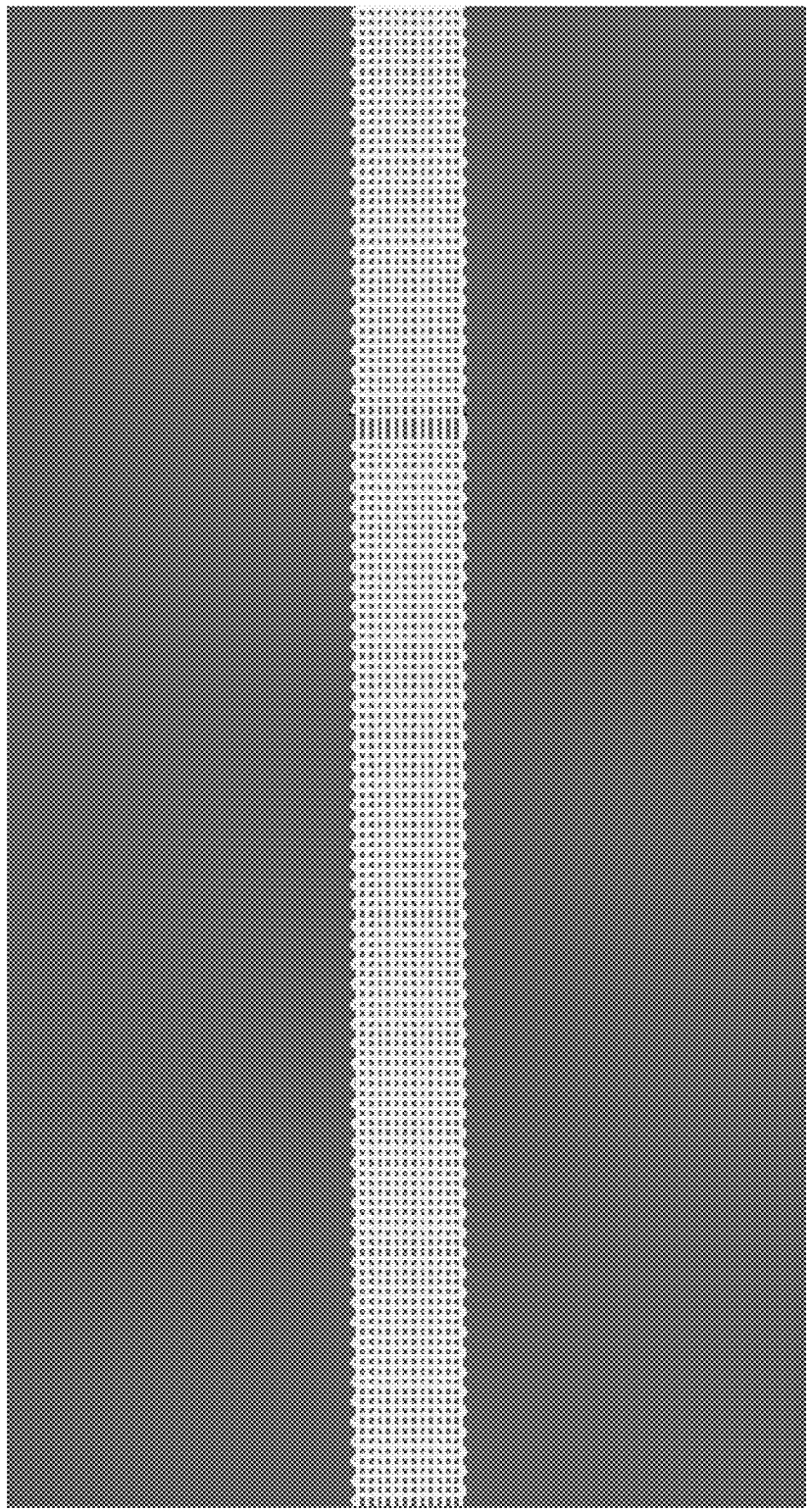
FIG. 44 illustrates an example pattern simulation for a double needle bed mesh demonstrated in FIG. 40B according to aspects of the present invention.

Another variation of the mesh according to an aspect of the present invention is preferably created on a raschel knitting machine such as Comez DNB/EL-800-8B set up in 10 gg needle spacing by the use of three movements as shown in pattern layout in FIGS. 40B-E: two movements in the wale direction, the vertical direction within the fabric, and one movement in the course direction, the horizontal direction of the fabric. The movements in the wale direction occurs on separate needle beds with alternate yarns; loops that occur on every course are staggered within repeat. The yarn follows a repeat pattern of 3/1-1/1-1/3-3/3—for one of the wale direction movements shown in FIGS. 41A-D and 1/1-1/3-3/3-3/1 for the other wale direction movement as shown in FIGS. 43A-D. The interlacing of the loops within the fabric allows for one yarn to be under more tension than the other under stress, locking it around the less tensioned yarn; keeping the fabric from unraveling when cut. The other movement in the course direction which is shown in FIGS. 42A-D occurs in every few courses creating the porous design of the mesh. These yarns follow a repeat pattern of 9/9-9/9-7/7-9/9-7/7-9/9-7/7-9/9-7/7-9/9-1/1-1/1-3/3-1/1-3/3-1/1-3/3-1/1-3/3-1/1 for the course direction movement. The pattern simulation layout of this pattern is rendered with ComezDraw 3 software in FIG. 44 considering a yarn design made with 3 ends of Td 20/22 raw silk twisted together in the S direction to form a ply with 6 tpi and further combining three of the resulting ply with 3 tpi. The same yarn design is used for the movements occurring in the wale and course directions The stitch density or pick count for the mesh in FIG. 44 is 34 picks per centimeter considering the total pick count for the technical front face and the technical back face of the fabric, or 17 picks per cm considering only on the face of the fabric. The operating parameters are not limited to those described in FIGS. 40B-E, but just the optimum values for the specific yarn design used for the pattern simulation layout of FIG. 44.

Figure 45A:
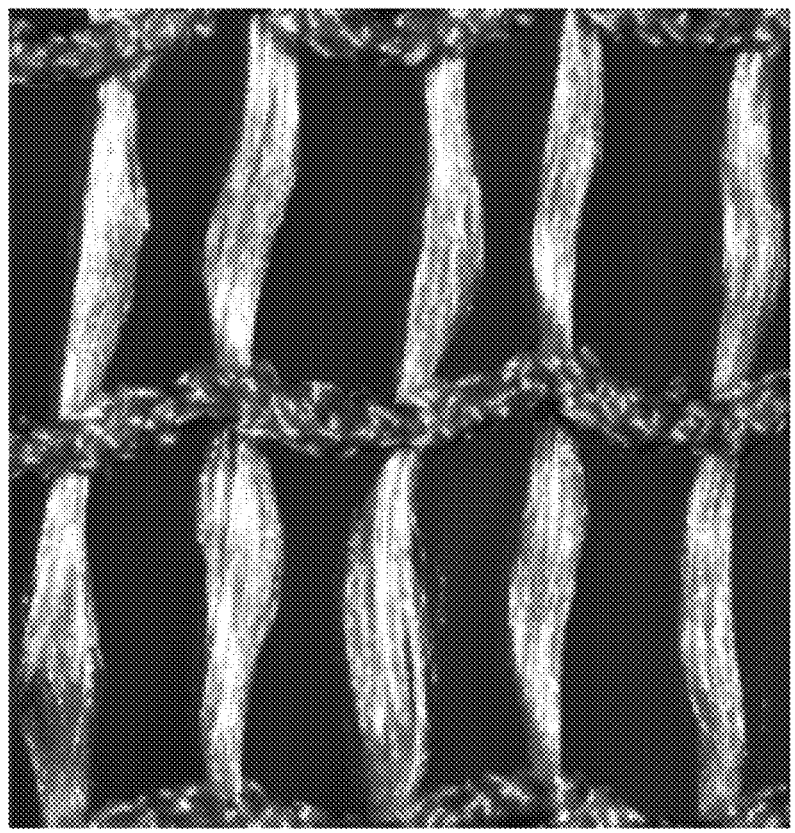
FIG. 45A is a photograph of a pattern layout for a silk-based mesh in accordance with aspects of the present invention.
Figure 45C:
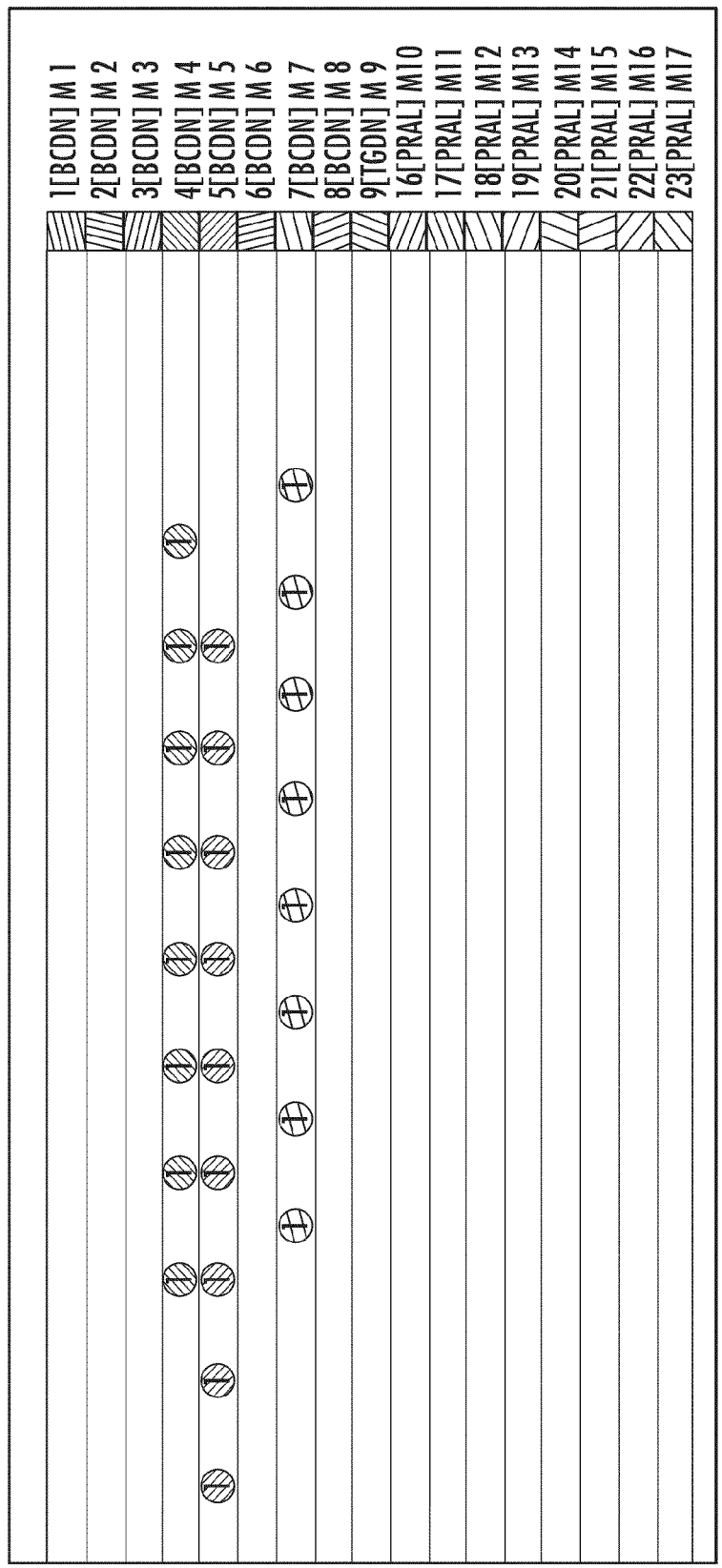
Figure 45D:
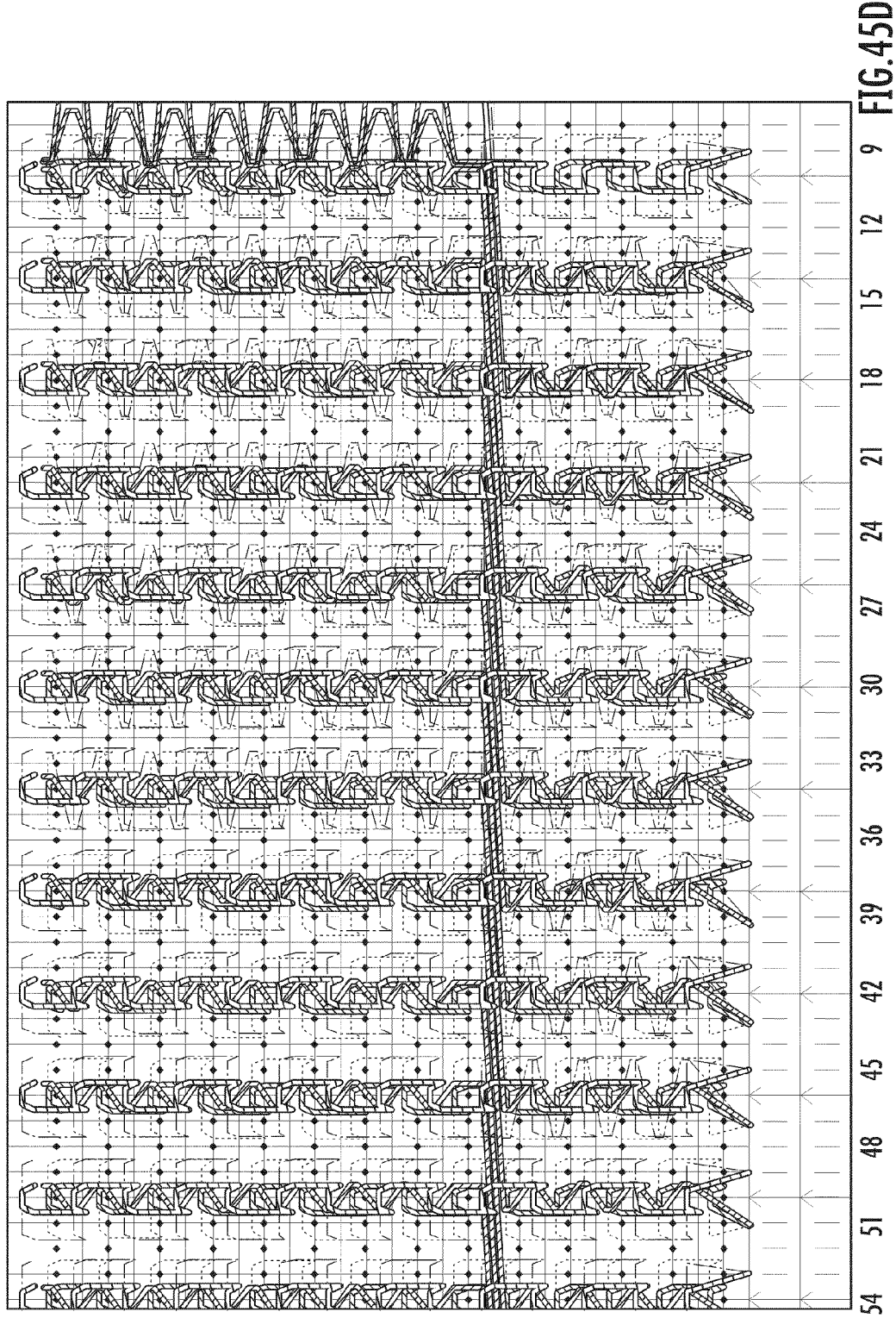
FIGS. 45D and 45E are enlarged views of the example pattern layout and ground bars of FIG. 45B.
Figure 45E:
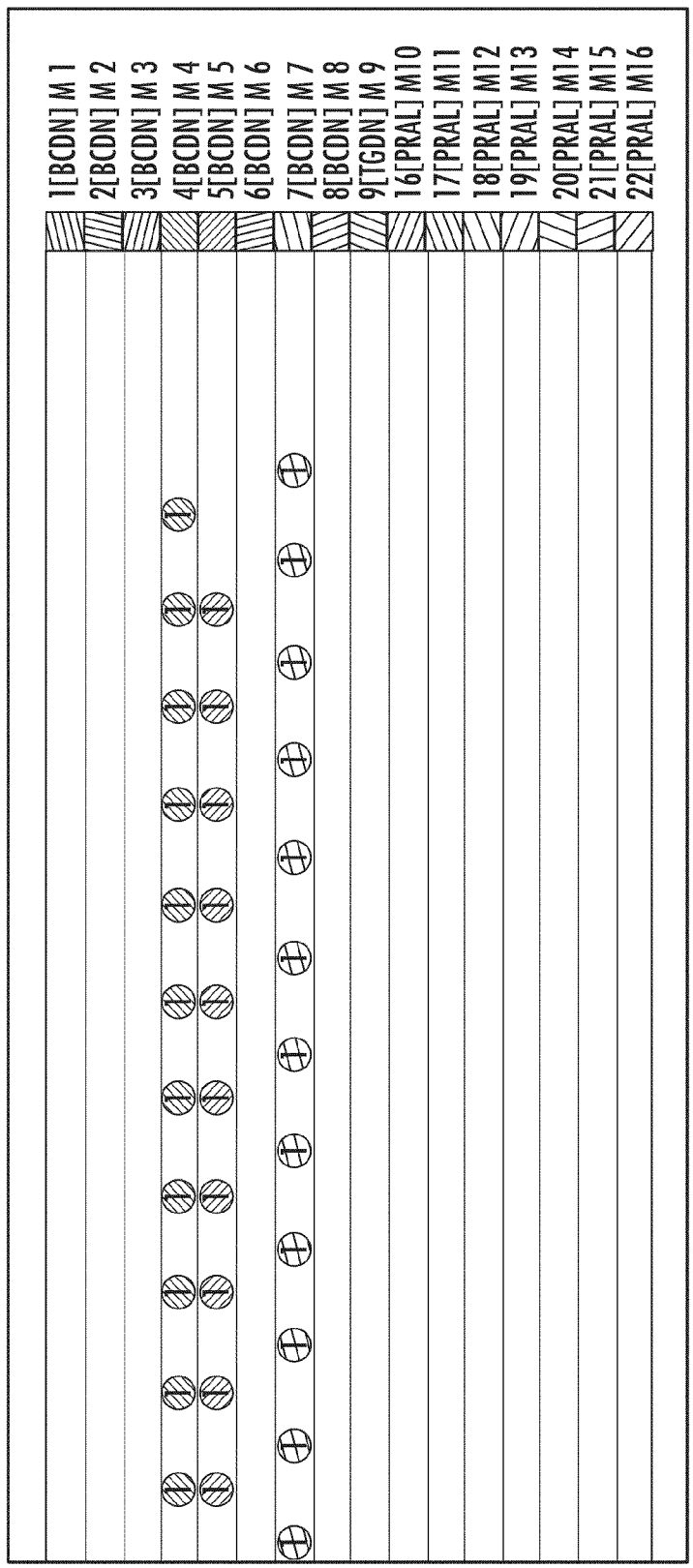
Figure 46B:
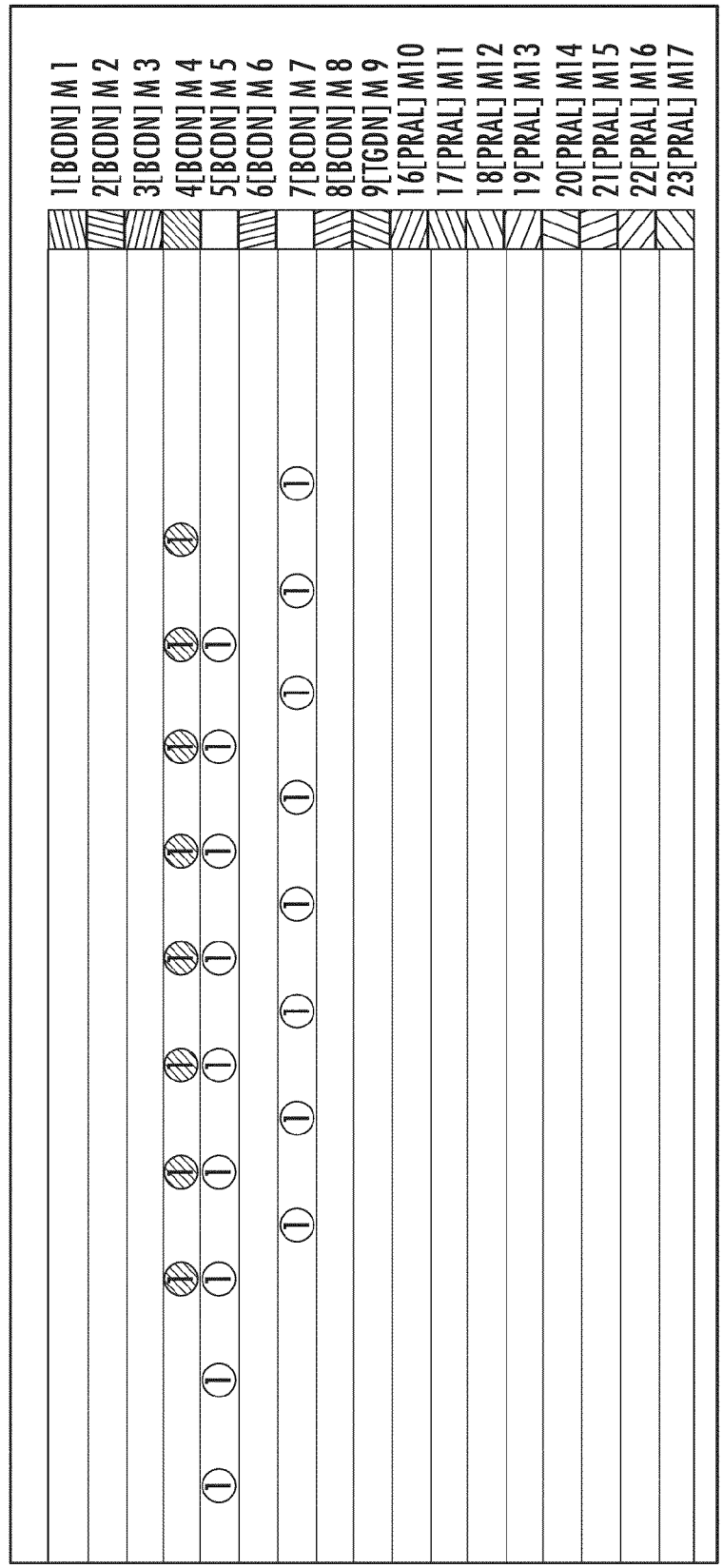
Figure 46C:
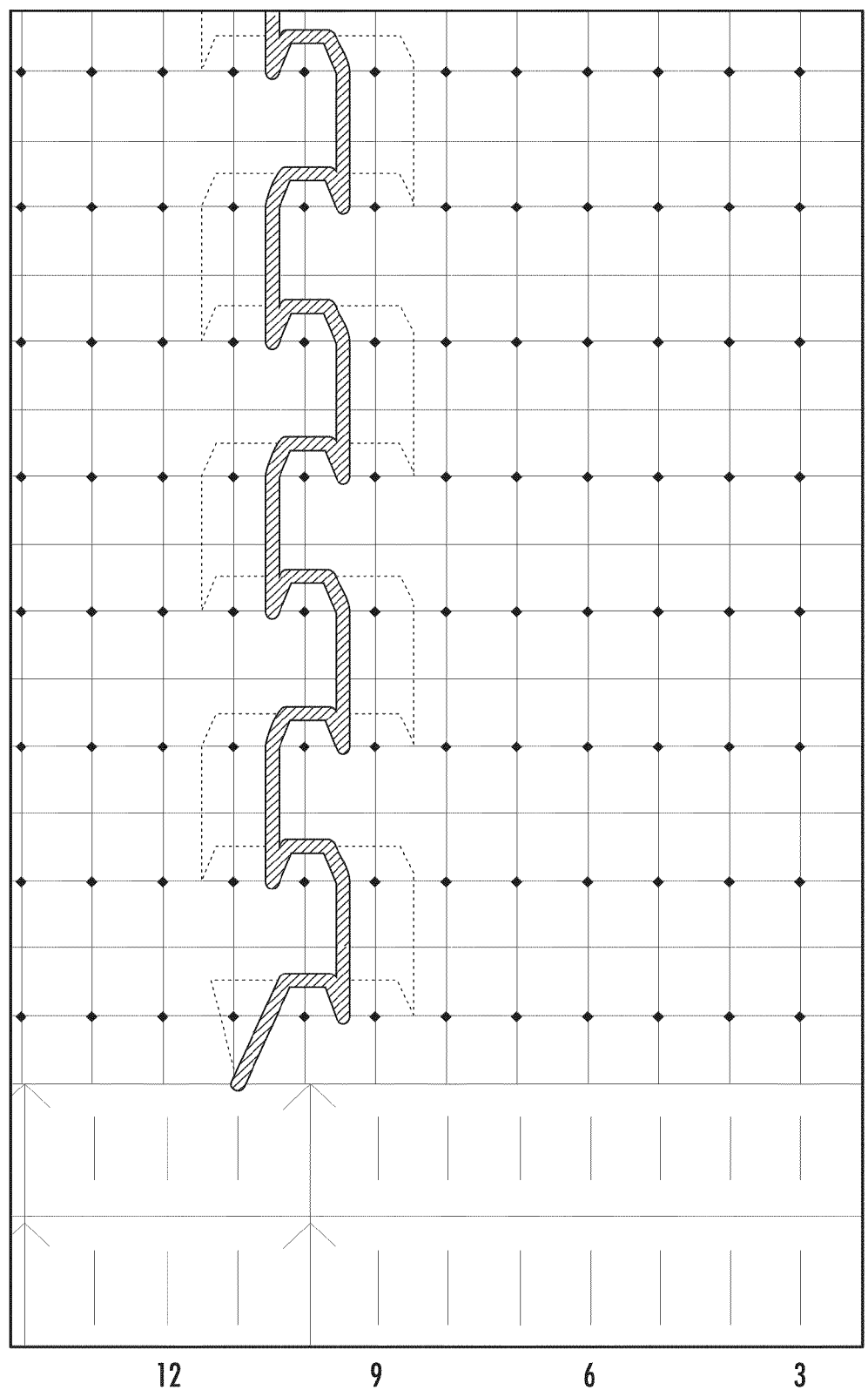
FIGS. 46C and 46D are enlarged views of the example pattern layout and ground bars of FIG. 45B.
Figure 46D:
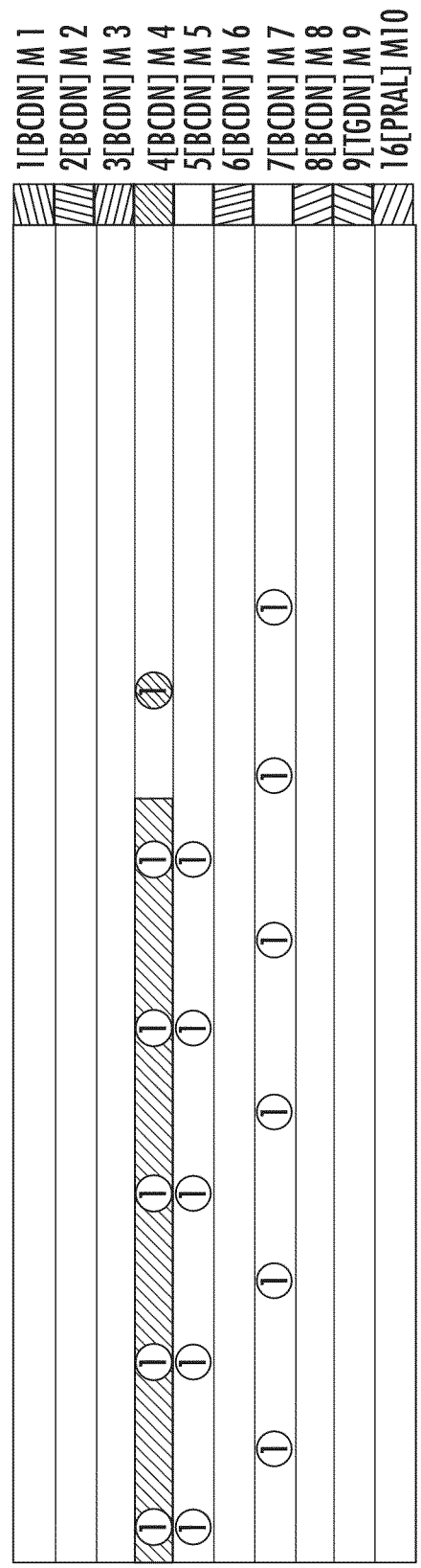
Figure 47B:
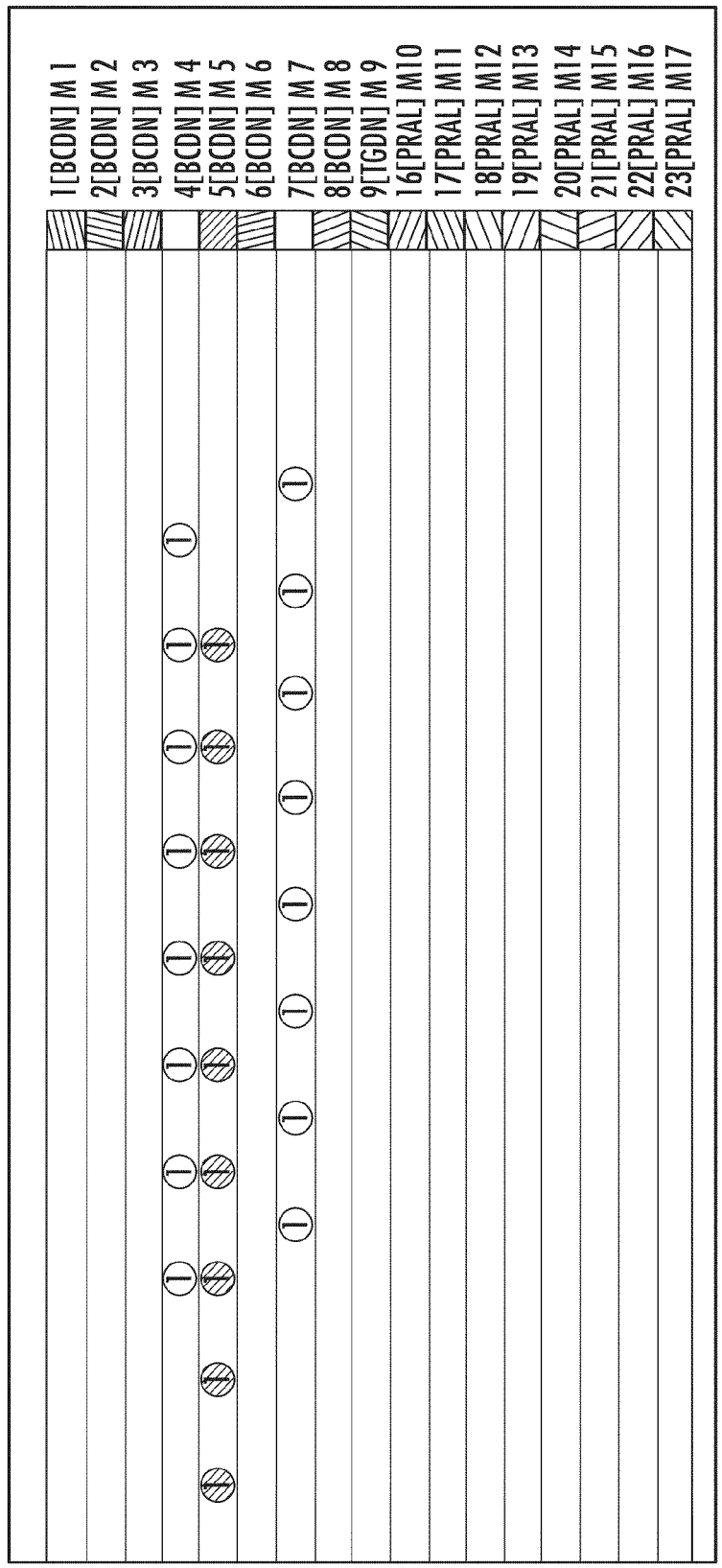
Figure 47C:
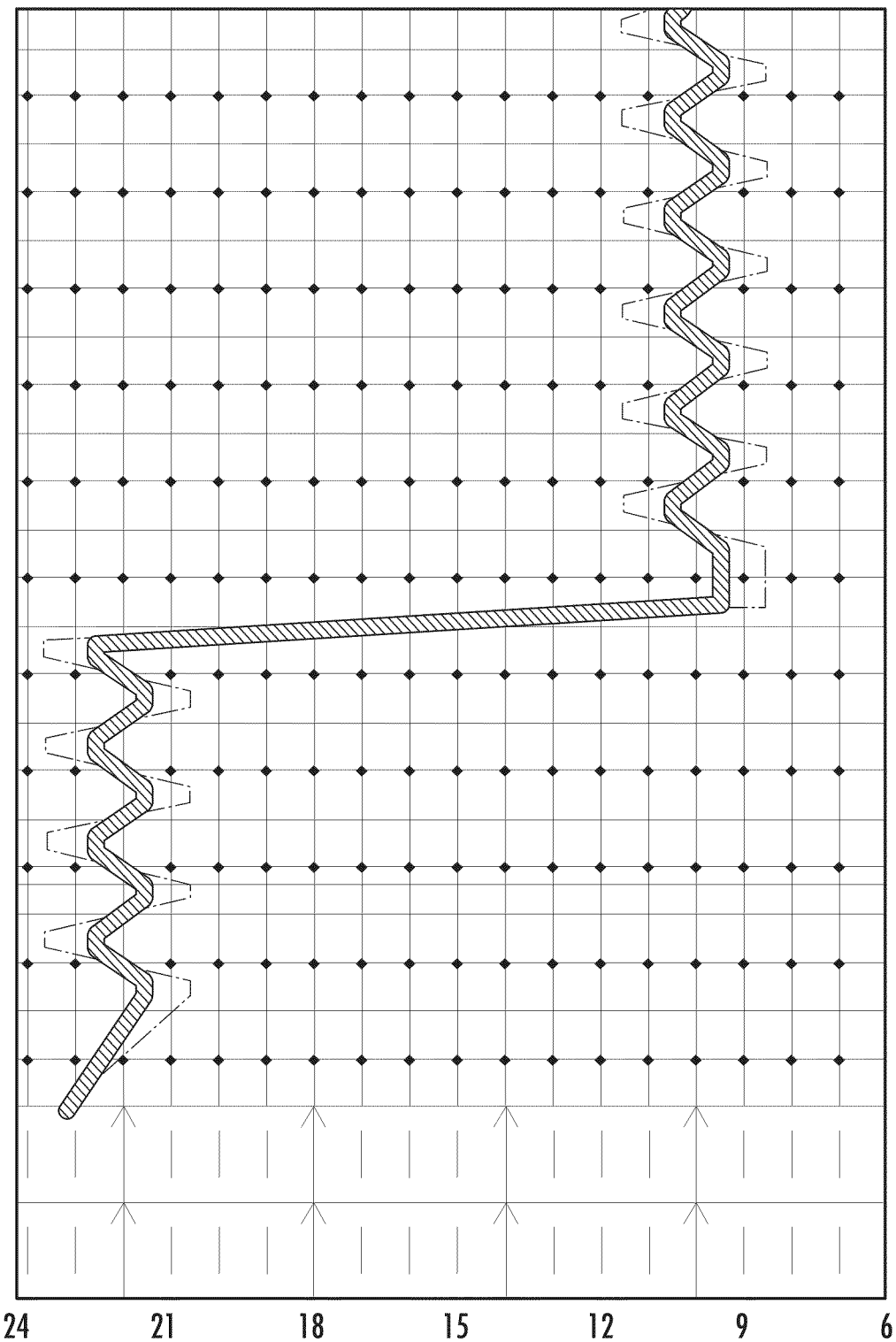
FIGS. 47C and 47D are enlarged views of the example pattern layout and ground bars of FIG. 45B.
Figure 47D:
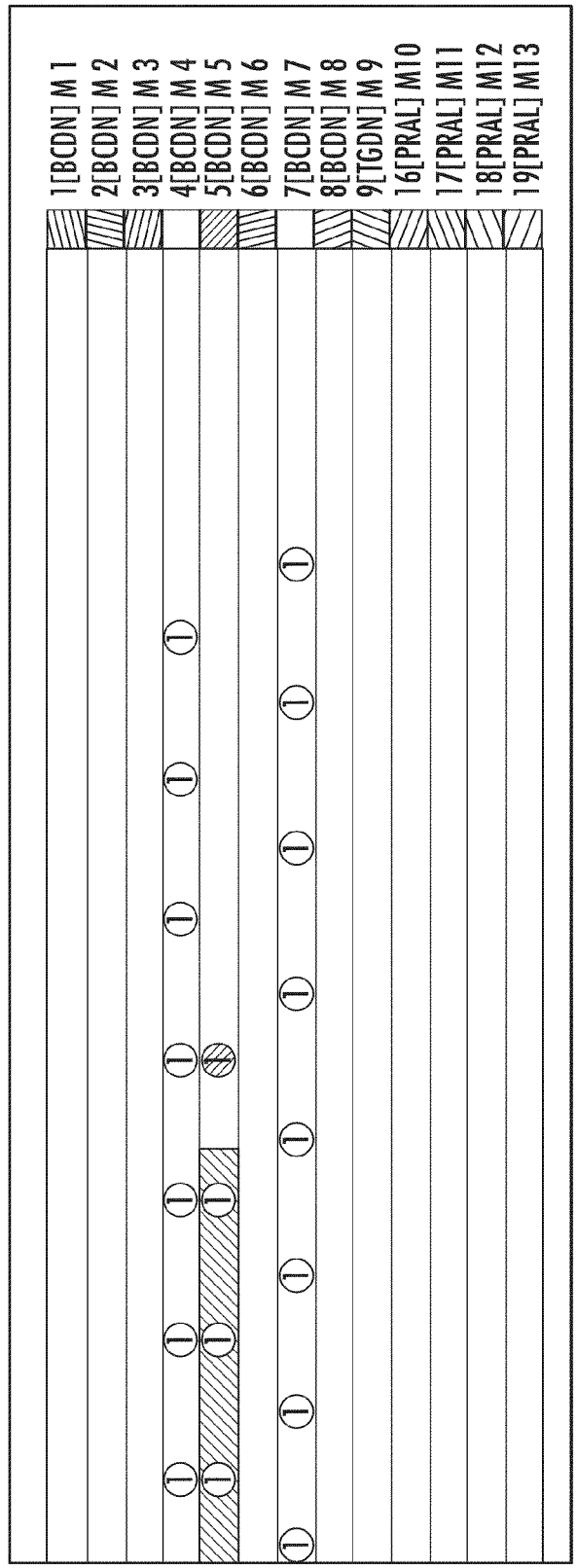
Figure 48B:
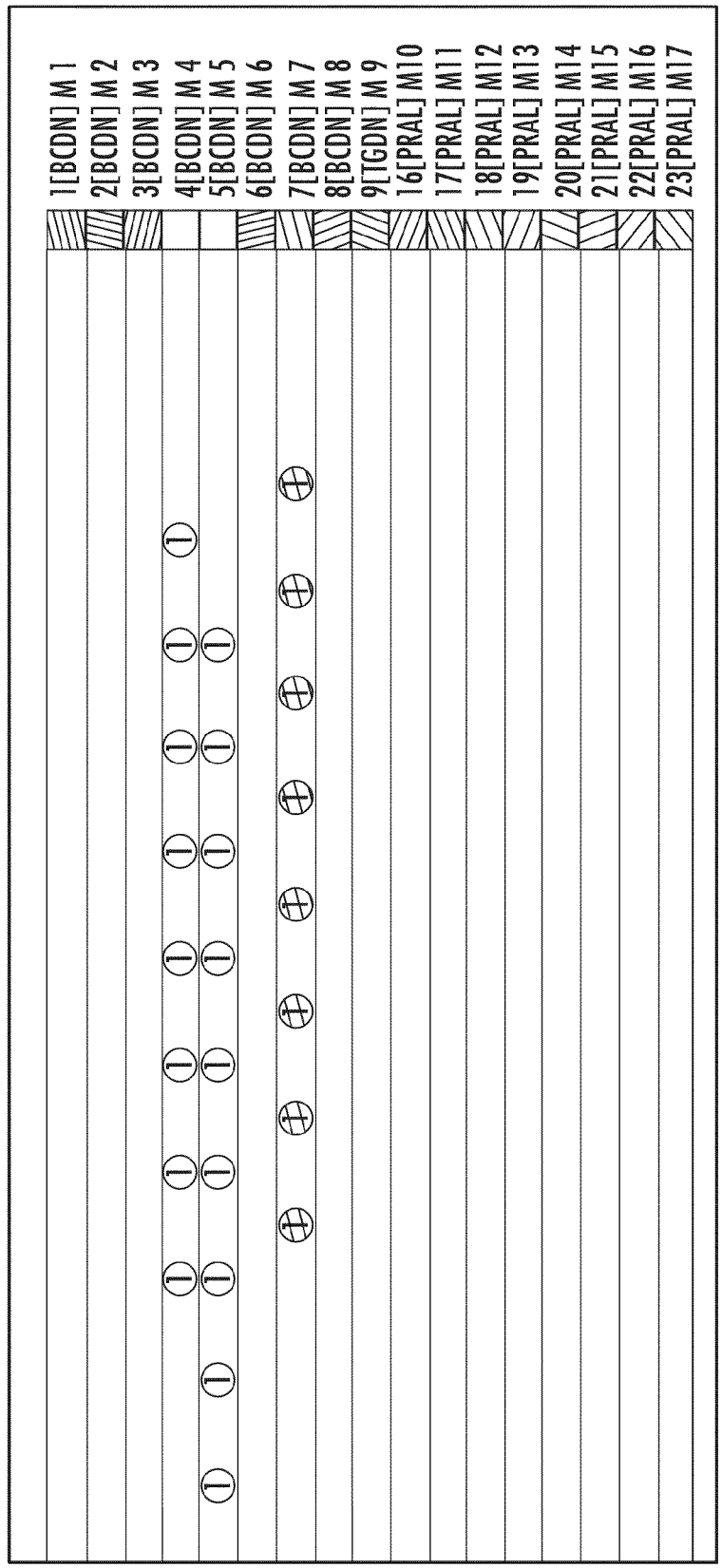
Figure 48C:
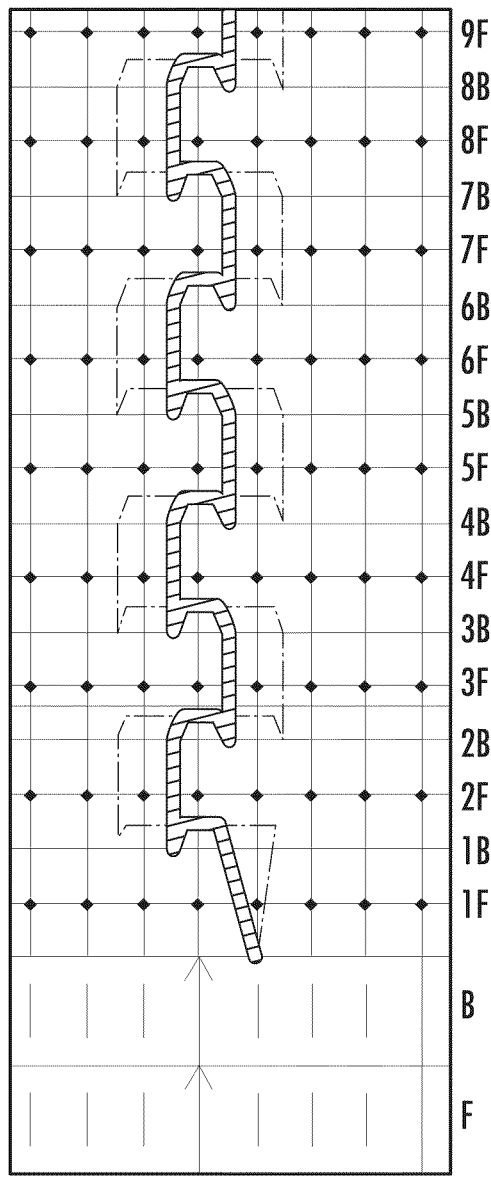
FIGS. 48C and 48D are enlarged views of the example pattern layout and ground bars of FIG. 45B.
Figure 48D:
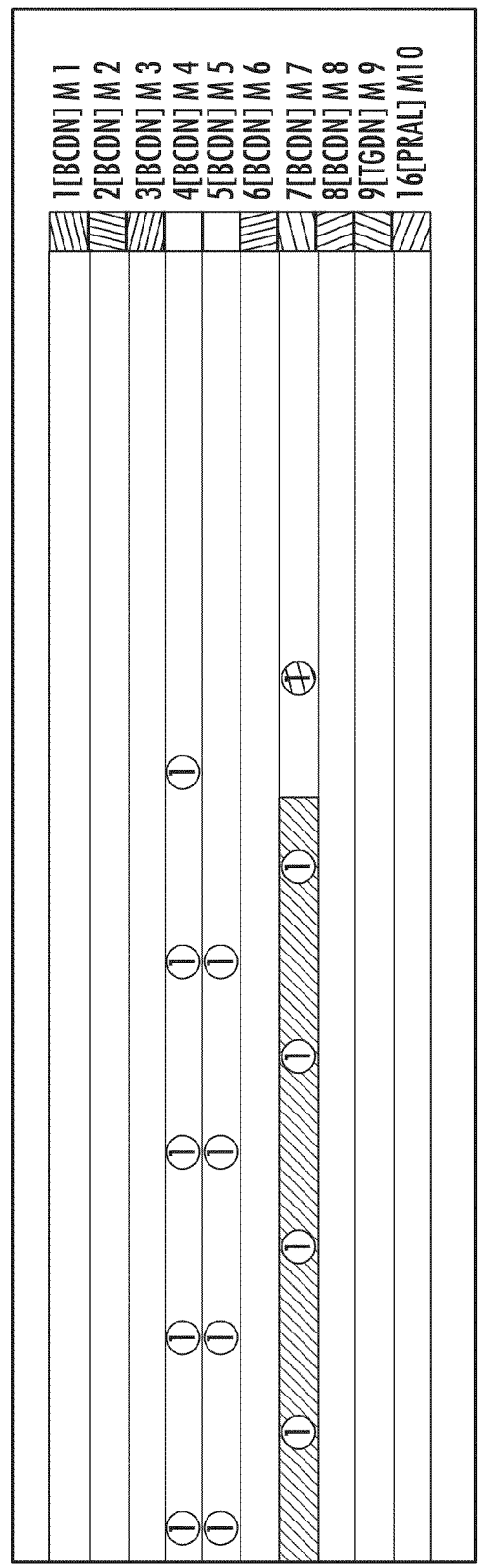

FIG. 45A is a photograph of a pattern layout for a silk-based mesh in accordance with aspects of the present invention.

Figure 49:
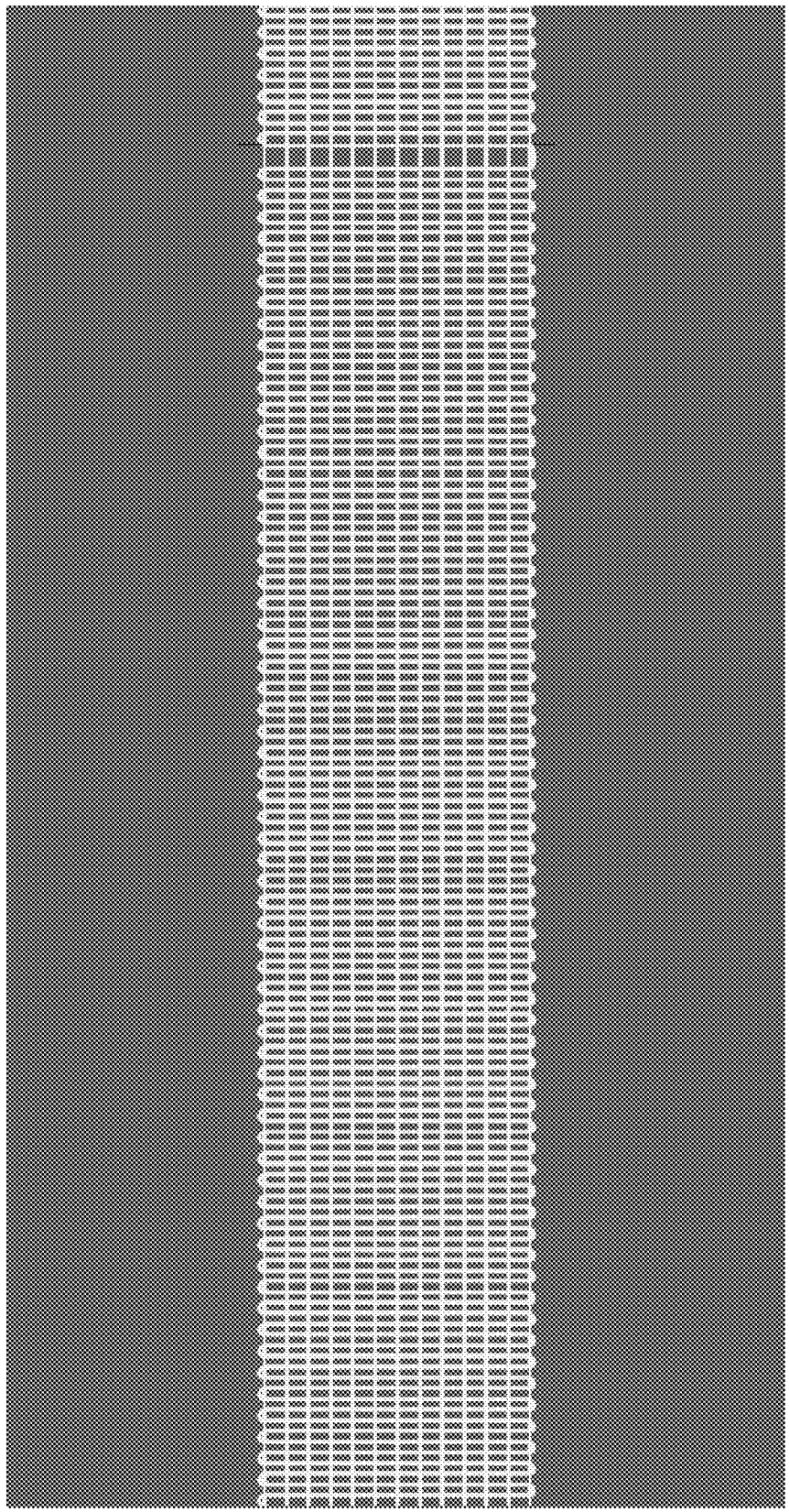
FIG. 49 illustrates an example pattern simulation for a double needle bed mesh demonstrated in FIG. 45B according to aspects of the present invention.

Another variation of the mesh in accordance with another aspect of the present invention is preferably created on a raschel knitting machine such as Comez DNB/EL-800-8B set up in 5 gg needle spacing by the use of three movements as shown in the pattern layout in FIGS. 45B-E: two movements in the wale direction, the vertical direction within the fabric, and one movement in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3—for one of the wale direction movements as shown in FIGS. 46A-D and 1/1-1/3-3/3-3/1 for the other wale direction movement as shown in FIGS. 48A-D. The interlacing of the loops within the fabric allows for one yarn to be under more tension than the other under stress, locking it around the less tensioned yarn; keeping the fabric from unraveling when cut. The other movement in the course direction as shown in FIGS. 47A-D occurs in every few courses creating the porous design of the mesh. These yarns follow a repeat pattern of 15/15-15/15-13/13-15/15-13/13-15/15-13/13-15/15-13/13-15/15-13/13-15/15/-1/1-1/1-3/3-1/1-3/3-1/1-3/3-1/1-3/3-1/1 for the course direction movement. The pattern simulation layout of this pattern is rendered with ComezDraw 3 software in FIG. 49 considering a yarn design made with 2 ends of Td 20/22 raw silk twisted together in the S direction to form a ply with 6 tpi and further combining three of the resulting ply with 3 tpi for the two movements in the wale direction. For the movements in the course direction the yarn design is made with 3 ends of Td 20/22 raw silk twisted together in the S direction to form a ply with 6 tpi and further combining three of the resulting ply with 3 tpi. The stitch density or pick count for the mesh design in FIG. 49 is 40 picks per centimeter considering the total pick count for the technical front face and the technical back face of the fabric, or 20 picks per cm considering only on the face of the fabric. The operating parameters are not limited to these described in FIGS. 45B-E, but just the optimum values for the specific yarn design used for the pattern simulation layout of FIG. 49.

Figure 50A:
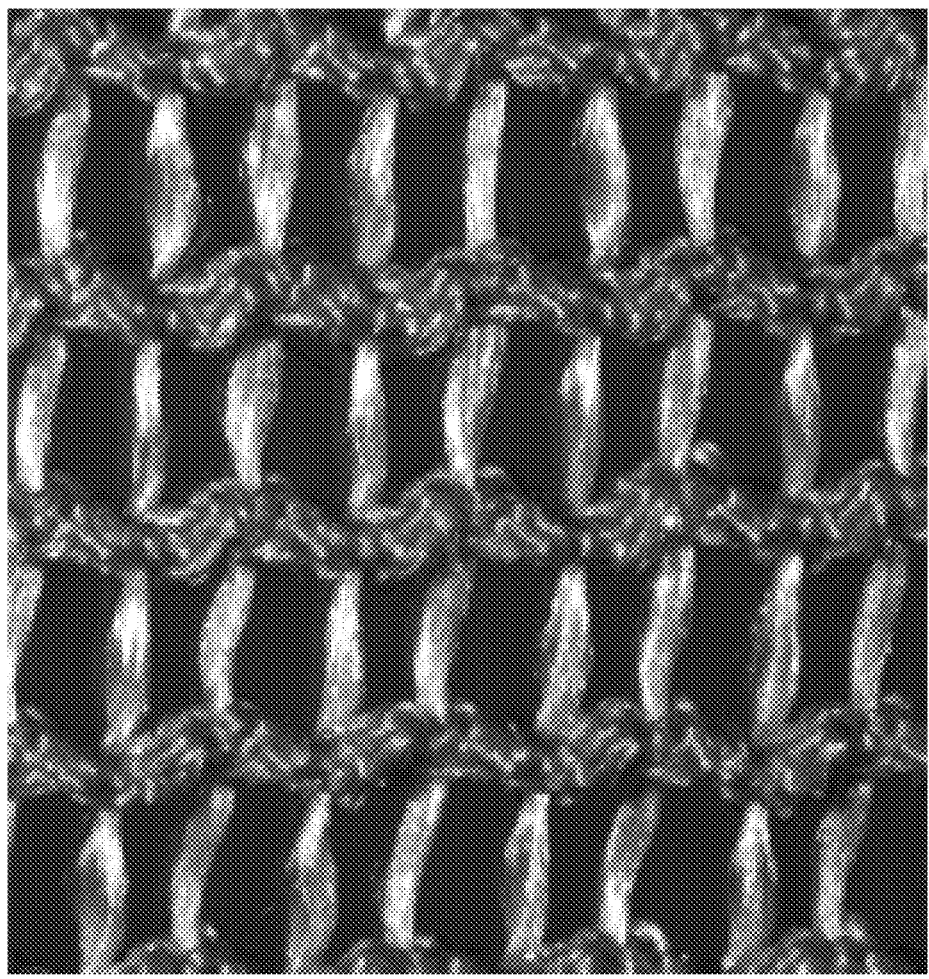
FIG. 50A is a photograph of a pattern layout for a silk-based mesh in accordance with aspects of the present invention.
Figure 50B:
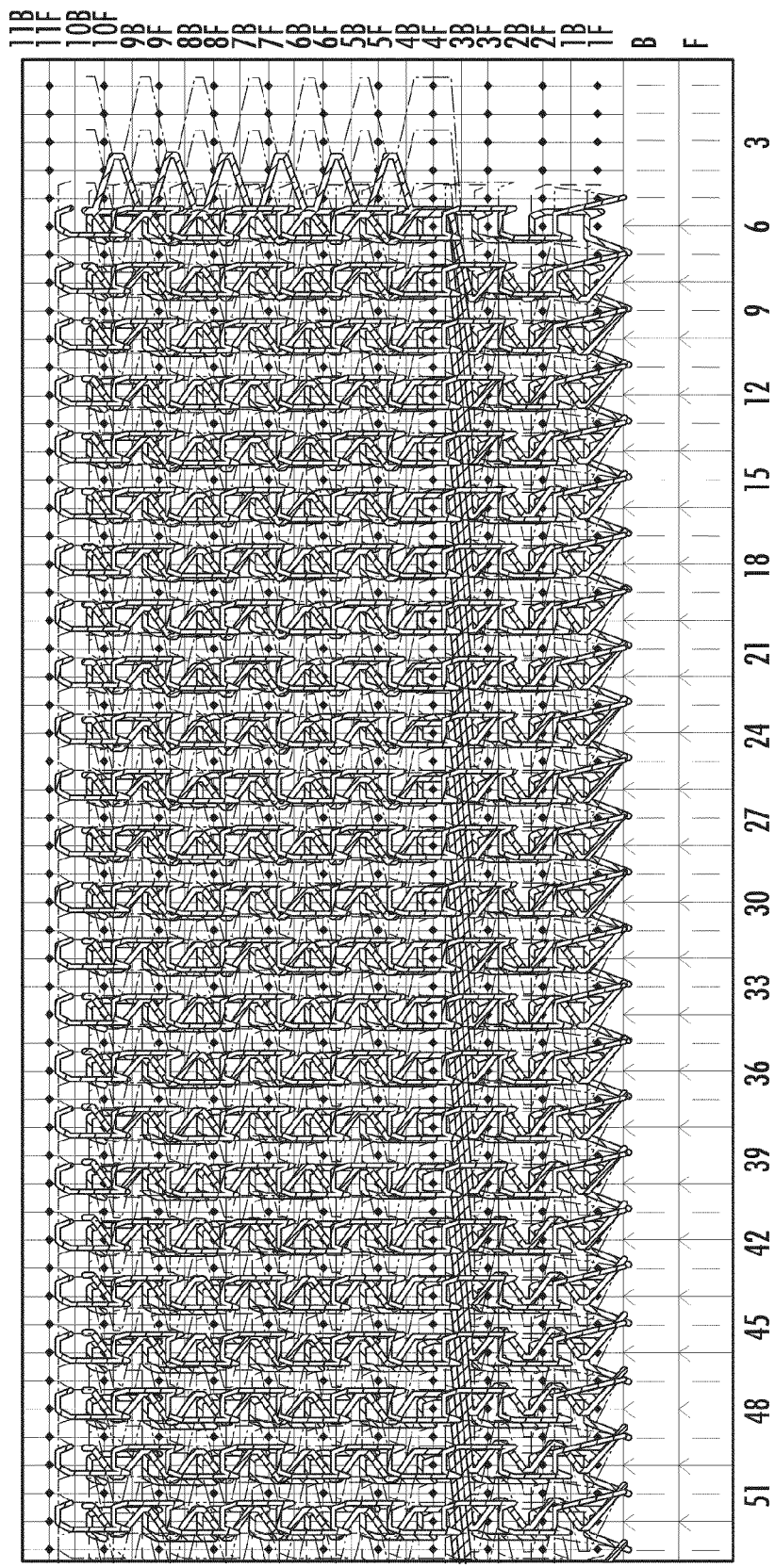
FIGS. 50B and 50C illustrate an example pattern layout for the silk-based mesh design of FIG. 50A in accordance with the present invention including all pattern and ground bars according to aspects of the present invention.
Figure 50C:
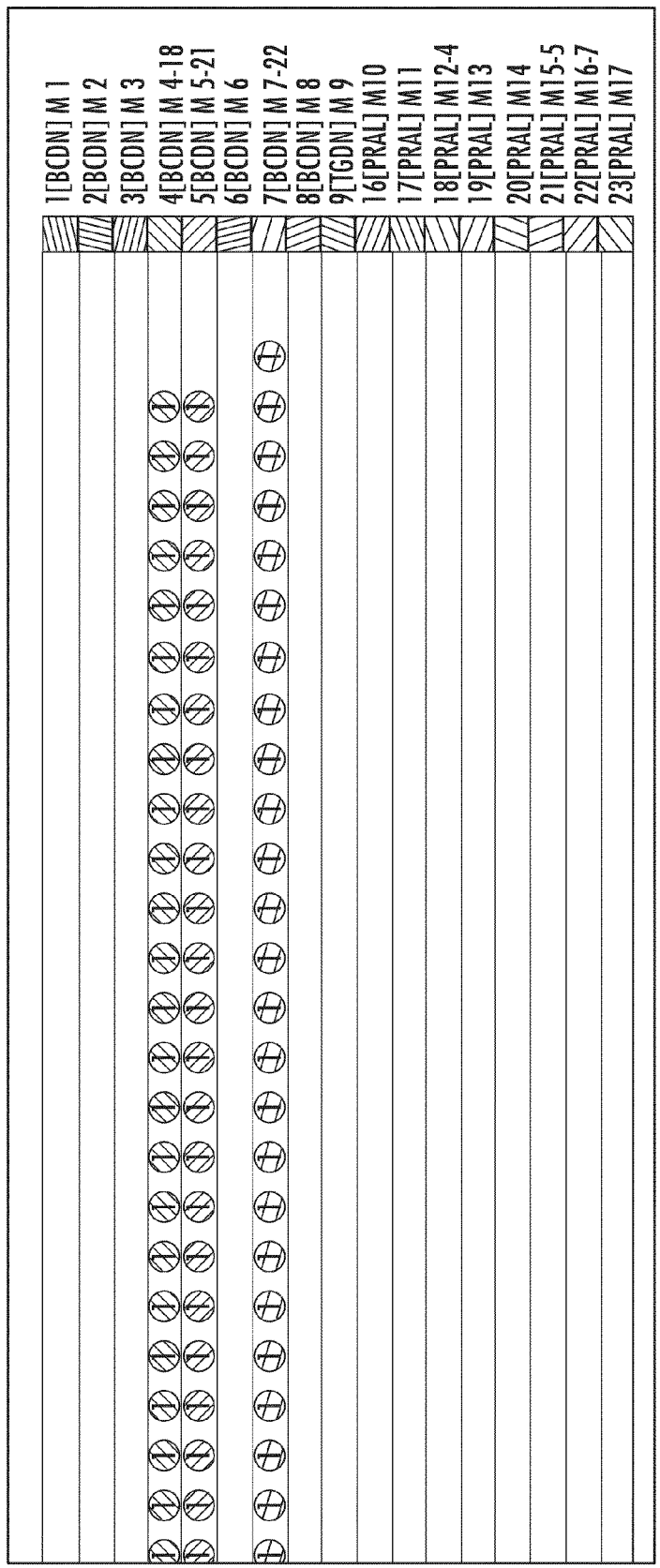
Figure 50D:
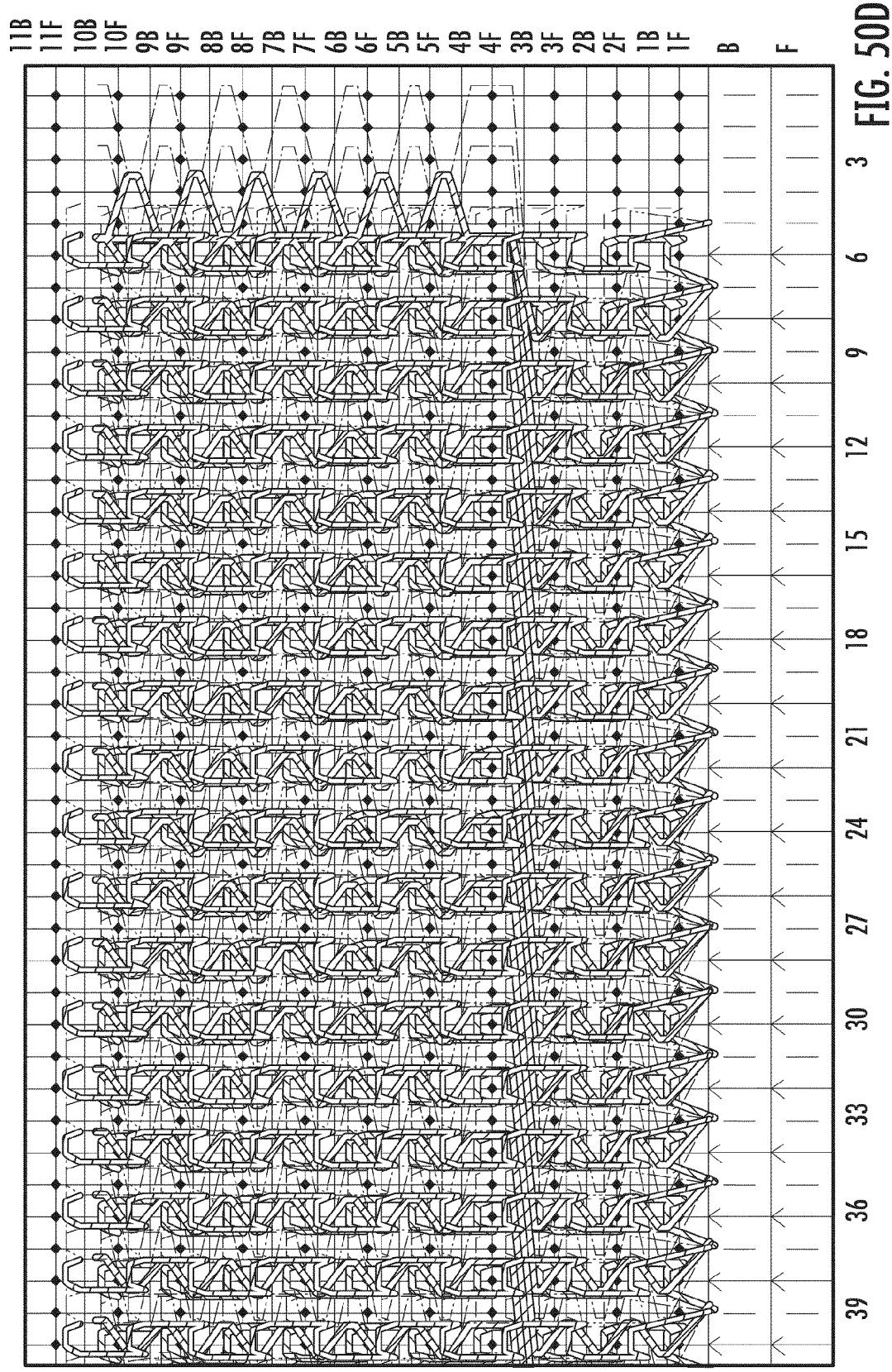
FIGS. 50D and 50E are enlarged views of the example pattern layout and ground bars of FIG. 50B.
Figure 50E:
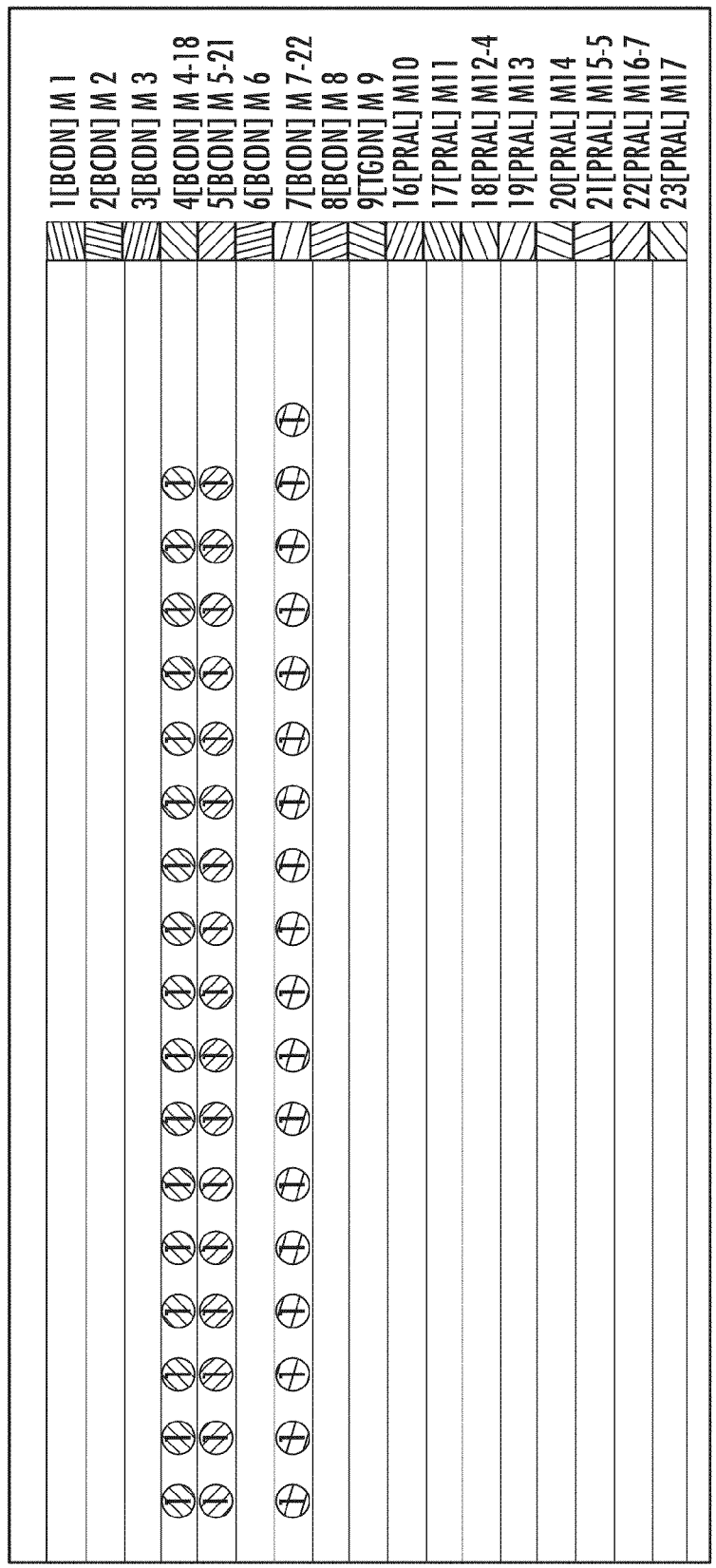
Figure 51A:
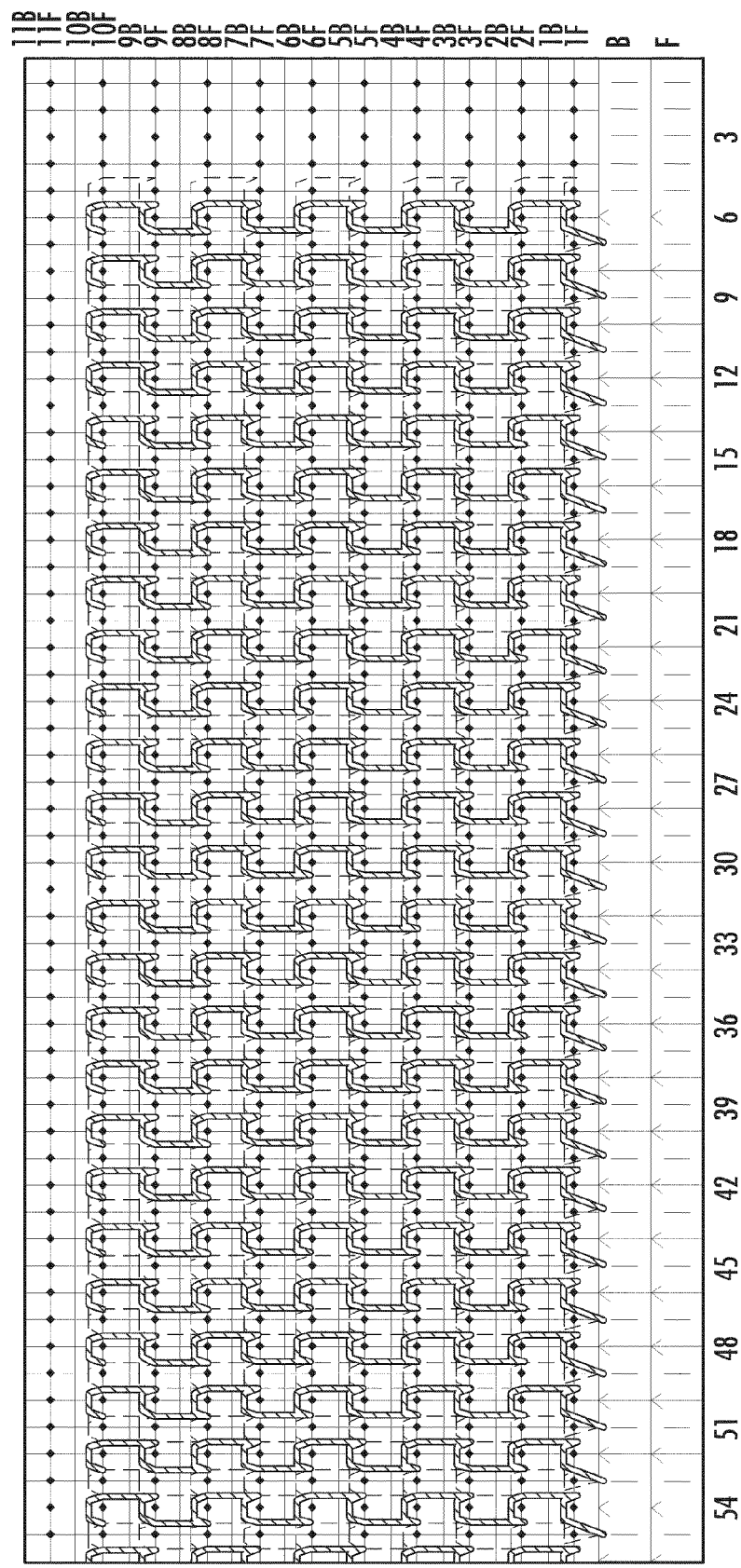
FIGS. 51A and 51B illustrate an example pattern layout for a double needle bed mesh according to aspects of the present invention from FIG. 50B for ground bar #4.
Figure 51B:
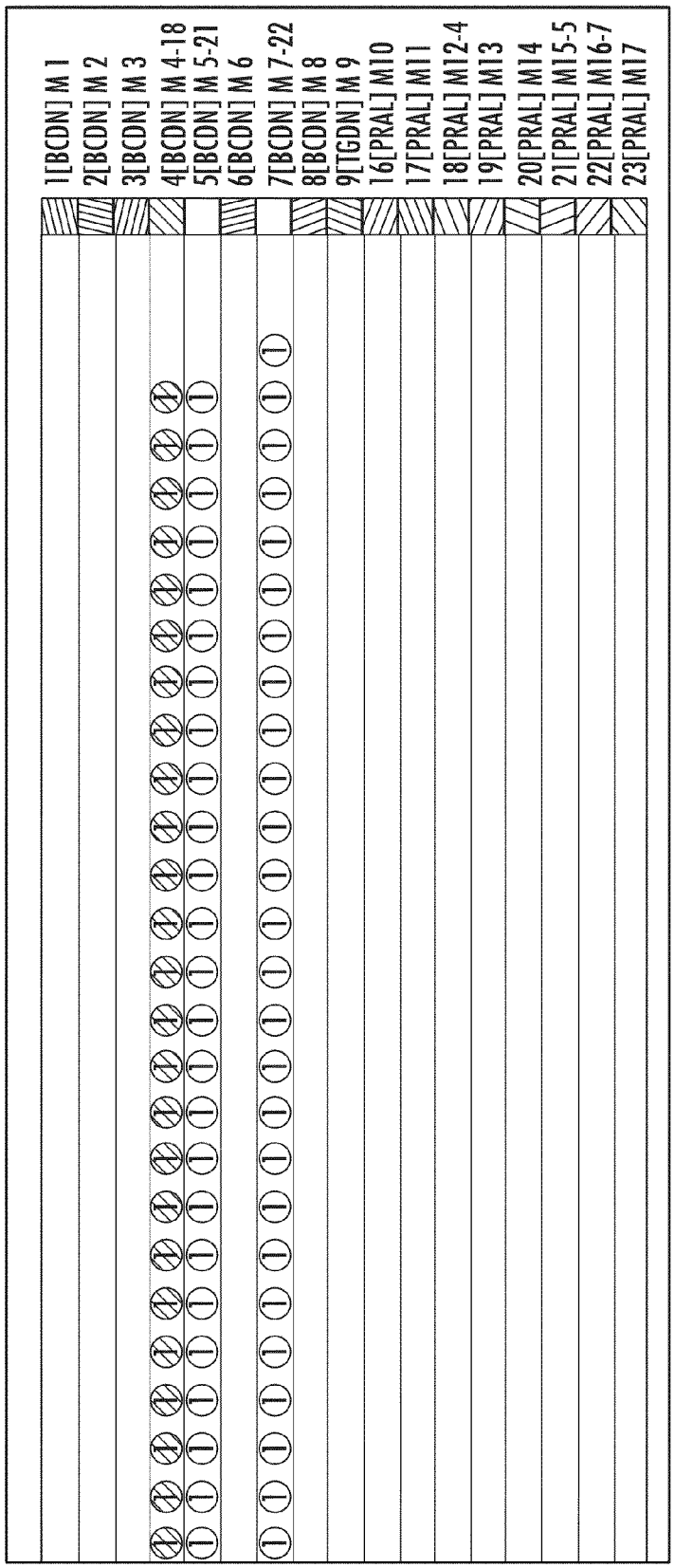
Figure 51C:
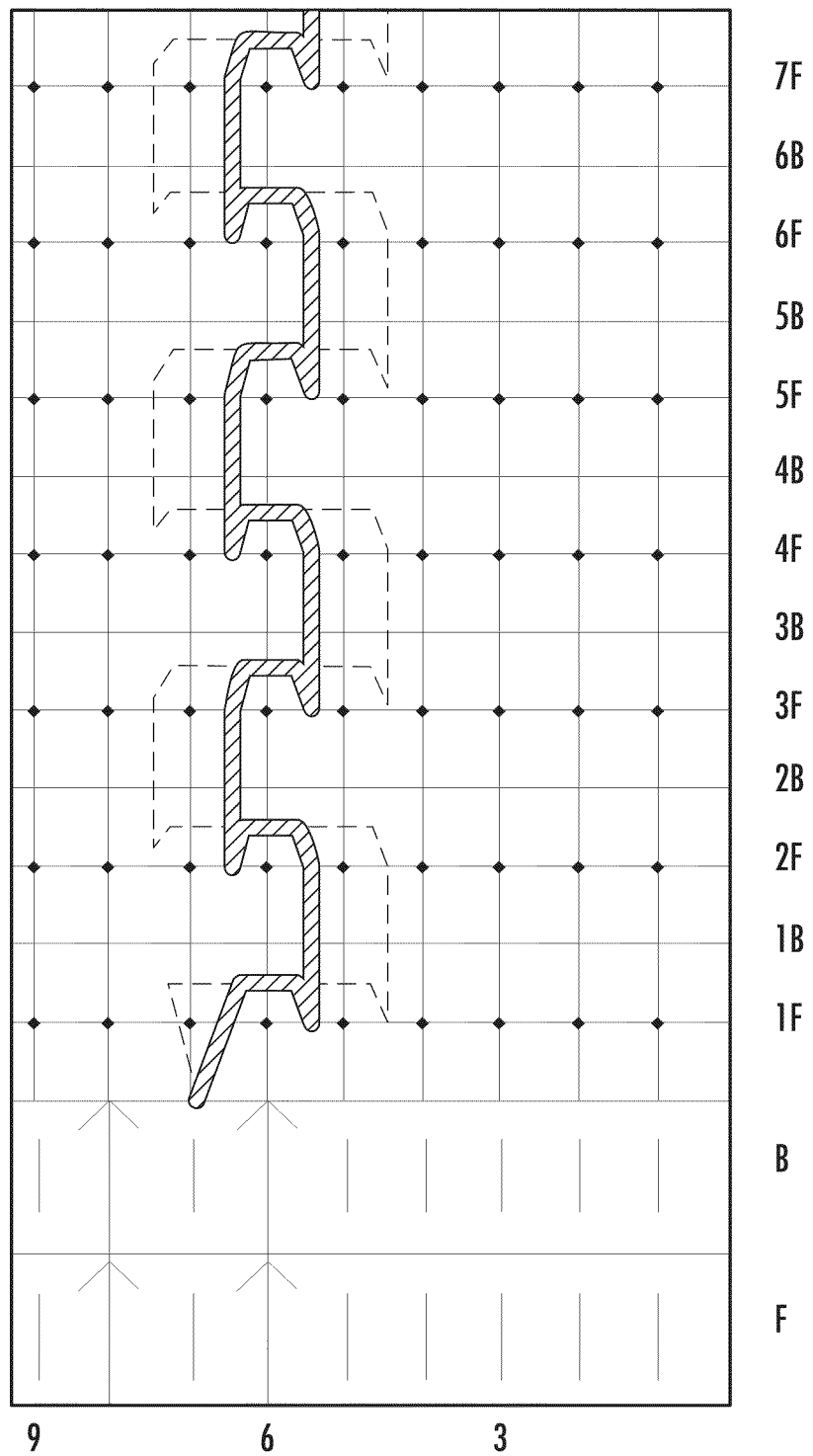
FIGS. 51C and 51D are enlarged views of the example pattern layout and ground bars of FIG. 50B.
Figure 51D:
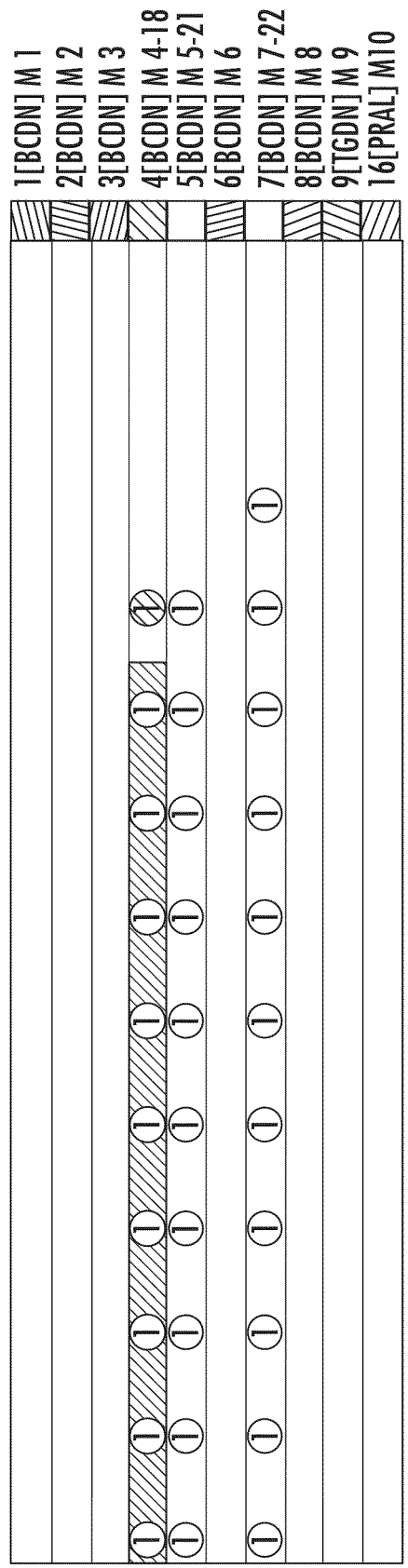
Figure 52A:
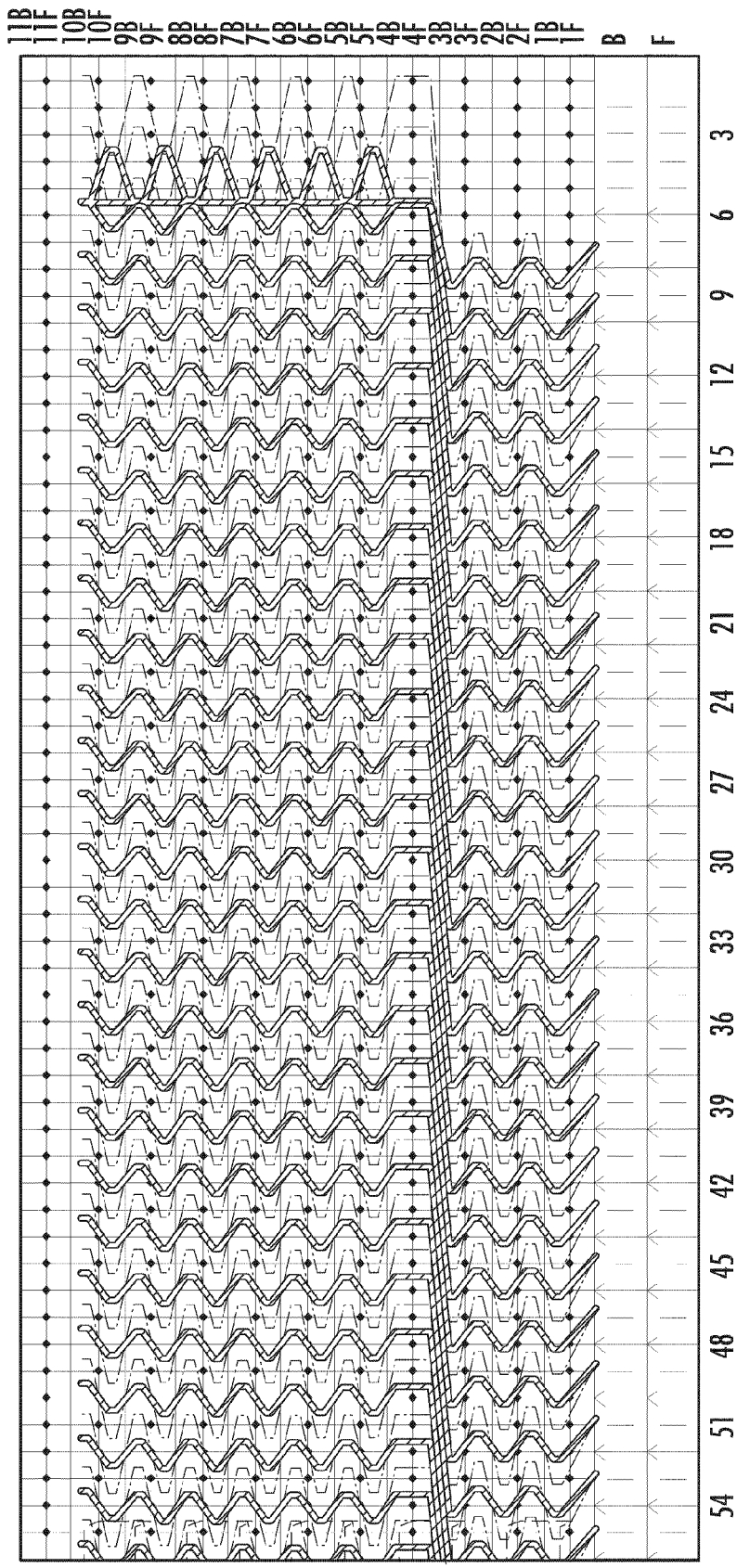
FIGS. 52A and 52B illustrate an example pattern layout for a double needle bed mesh according to aspects of the present invention from FIG. 50B for pattern bar #5.
Figure 52B:
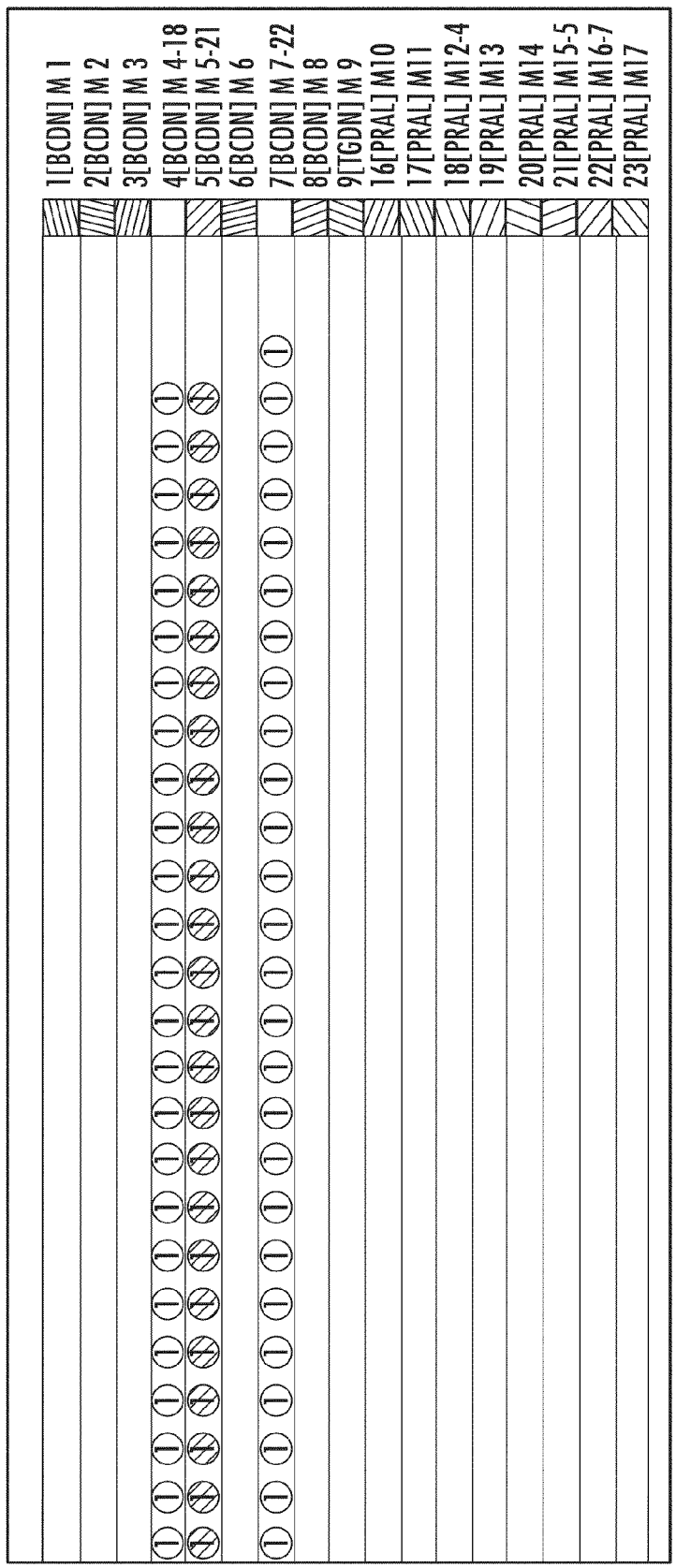
Figure 52C:
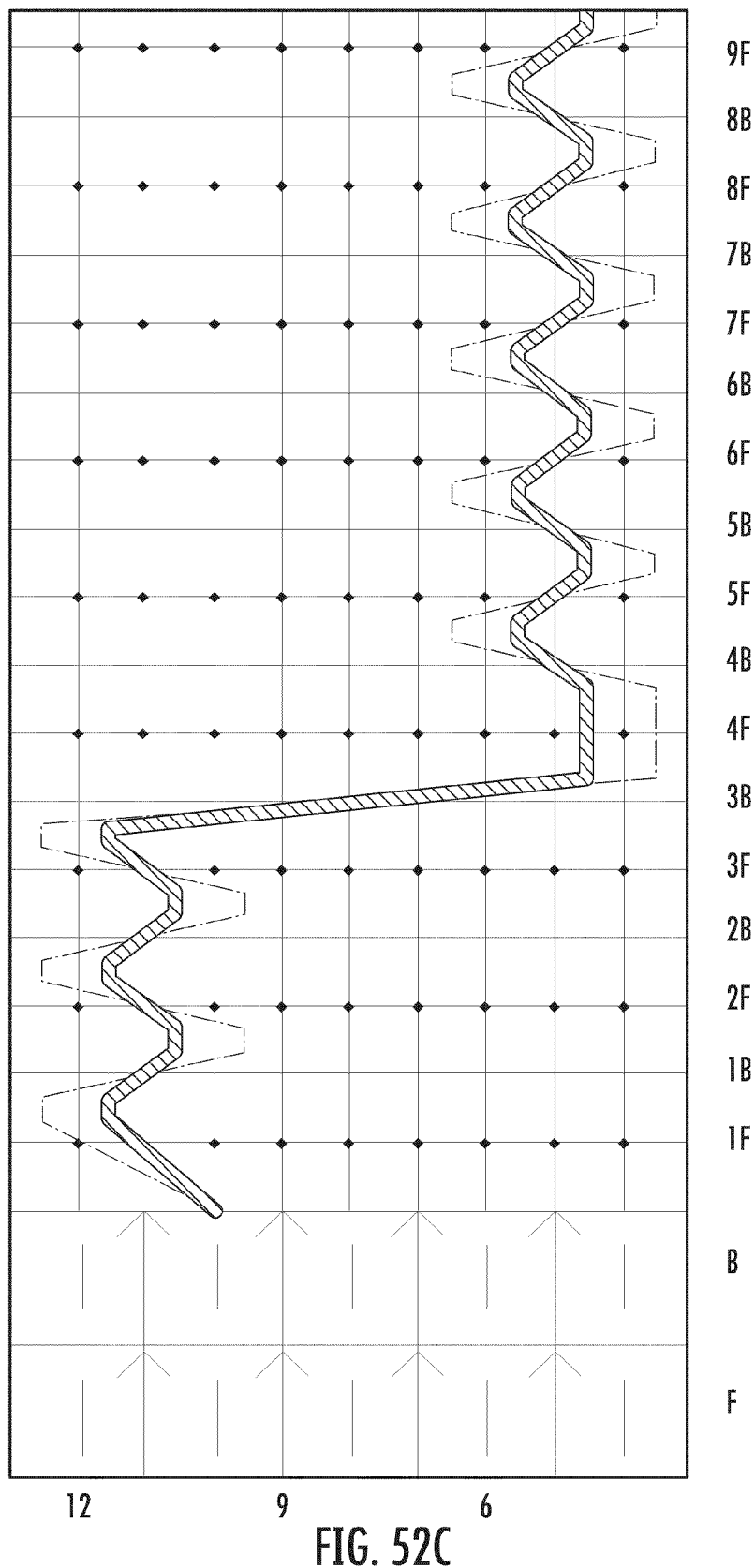
FIGS. 52C and 52D are enlarged views of the example pattern layout and ground bars of FIG. 50B.
Figure 52D:
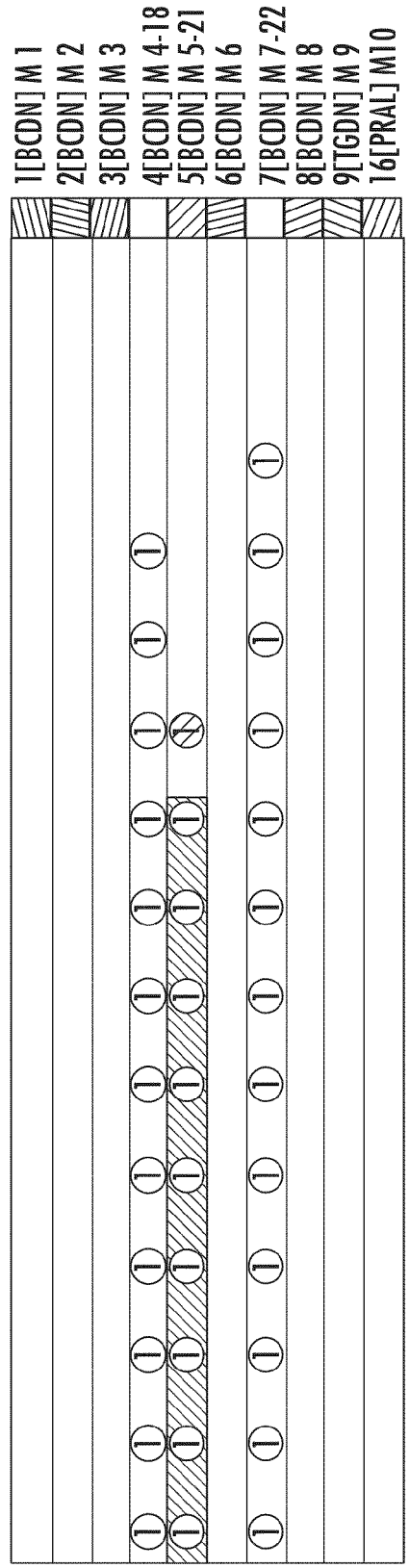
Figure 53A:
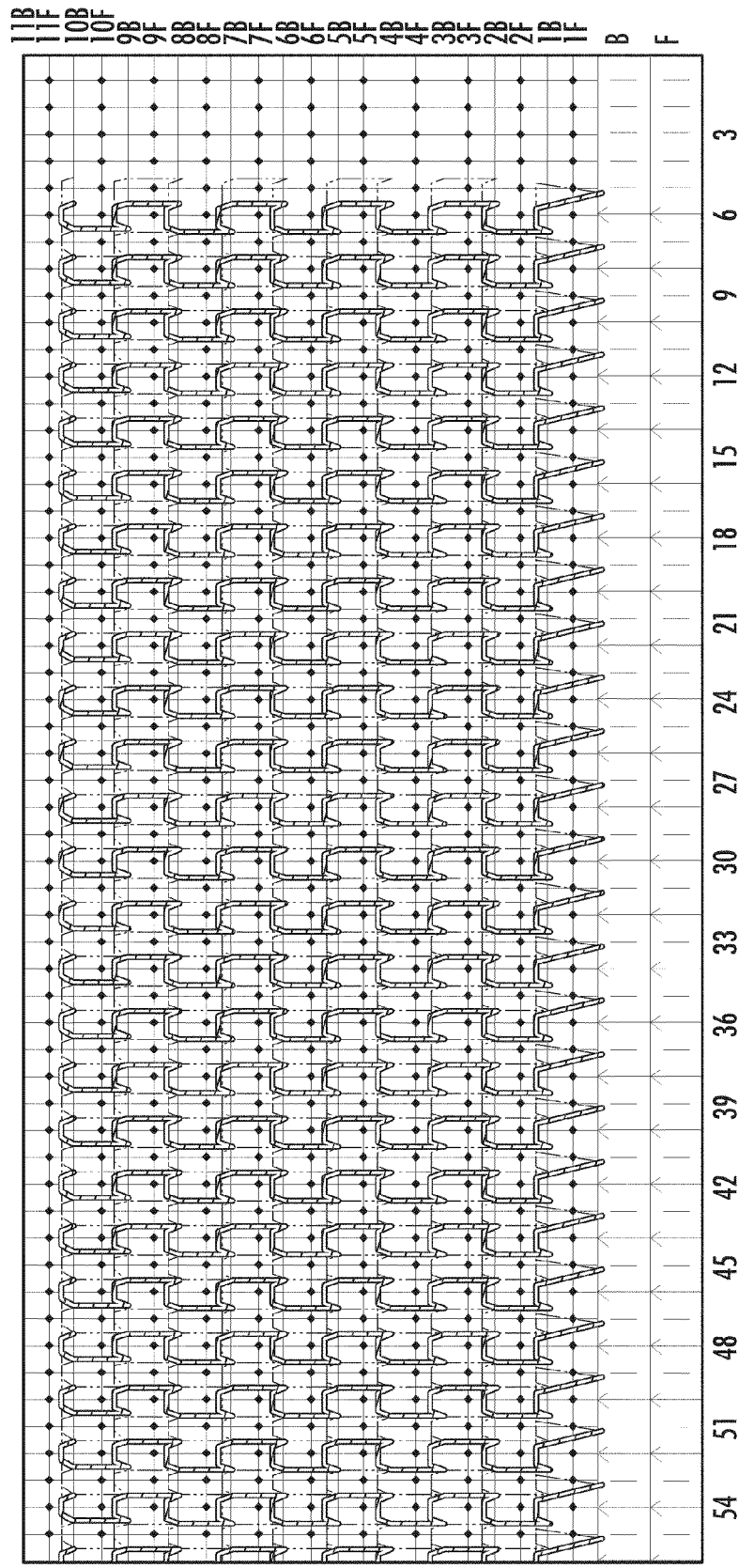
FIGS. 53A and 53B illustrate an example pattern layout for a double needle bed mesh according to aspects of the present invention from FIG. 50B for ground bar #7.
Figure 53B:
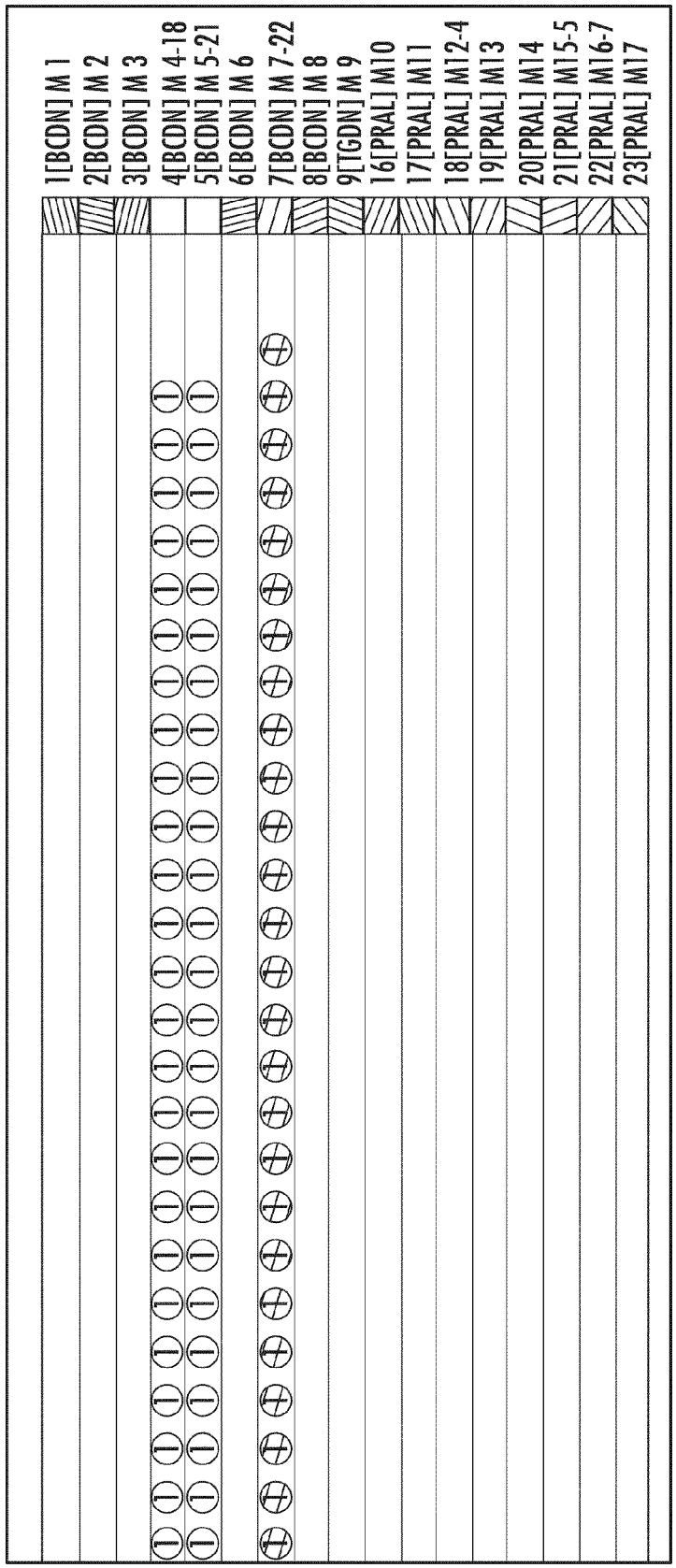
Figure 53C:
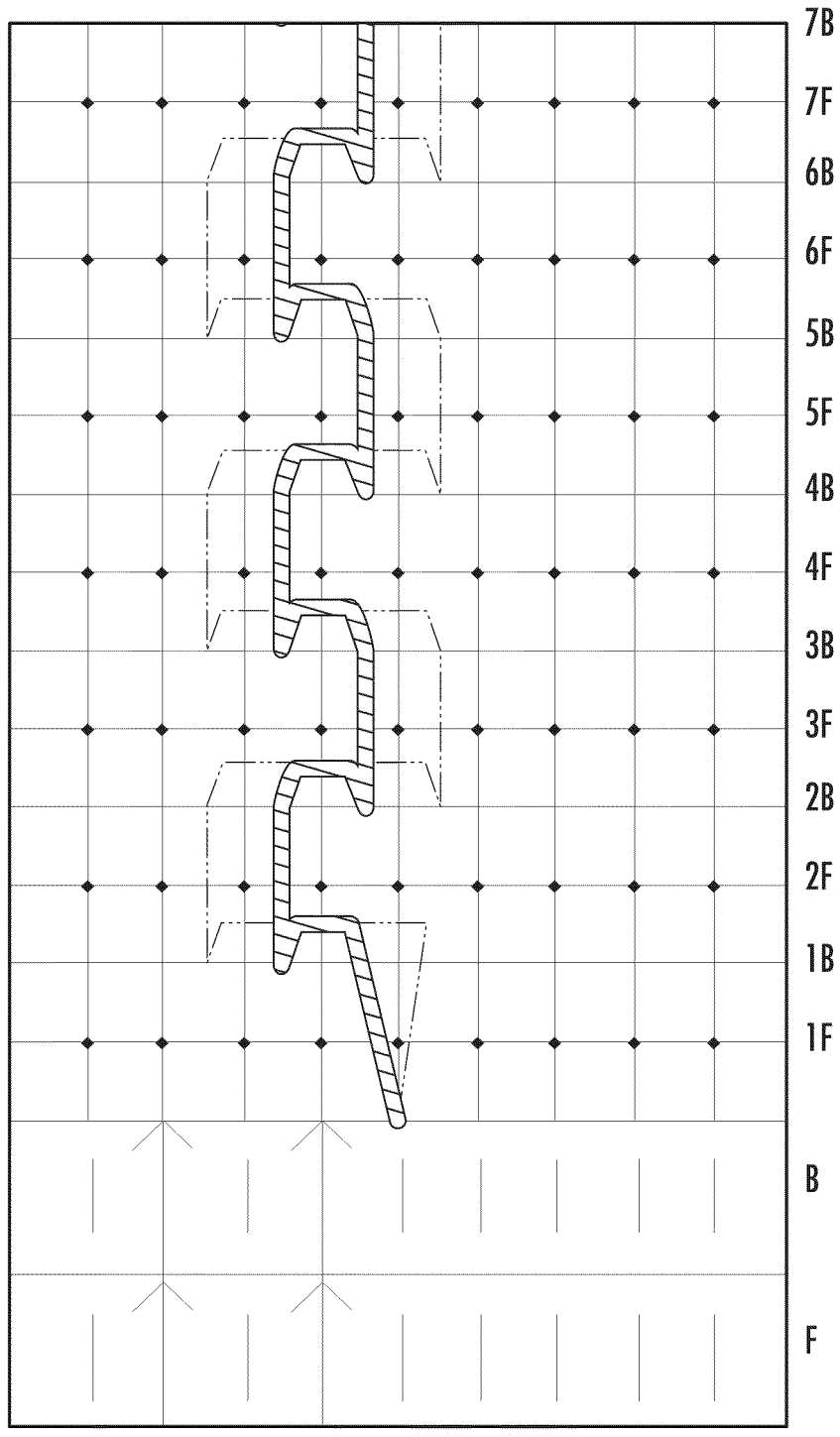
FIGS. 53C and 53D are enlarged views of the example pattern layout and ground bars of FIG. 50B.
Figure 53D:
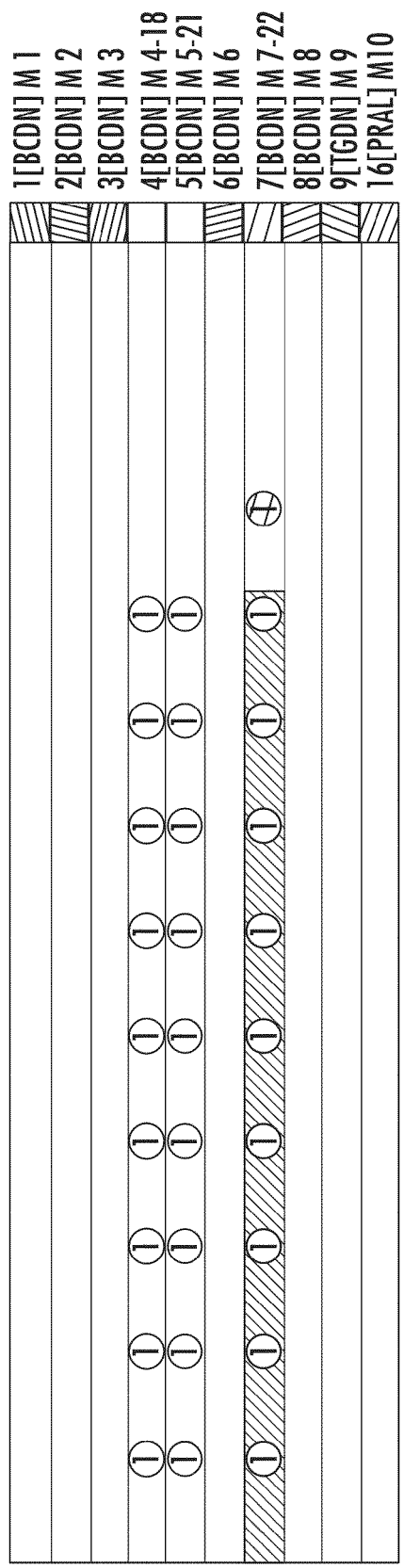

FIG. 50A is a photograph of a pattern layout for a silk-based mesh in accordance with aspects of the present invention.

Figure 54:
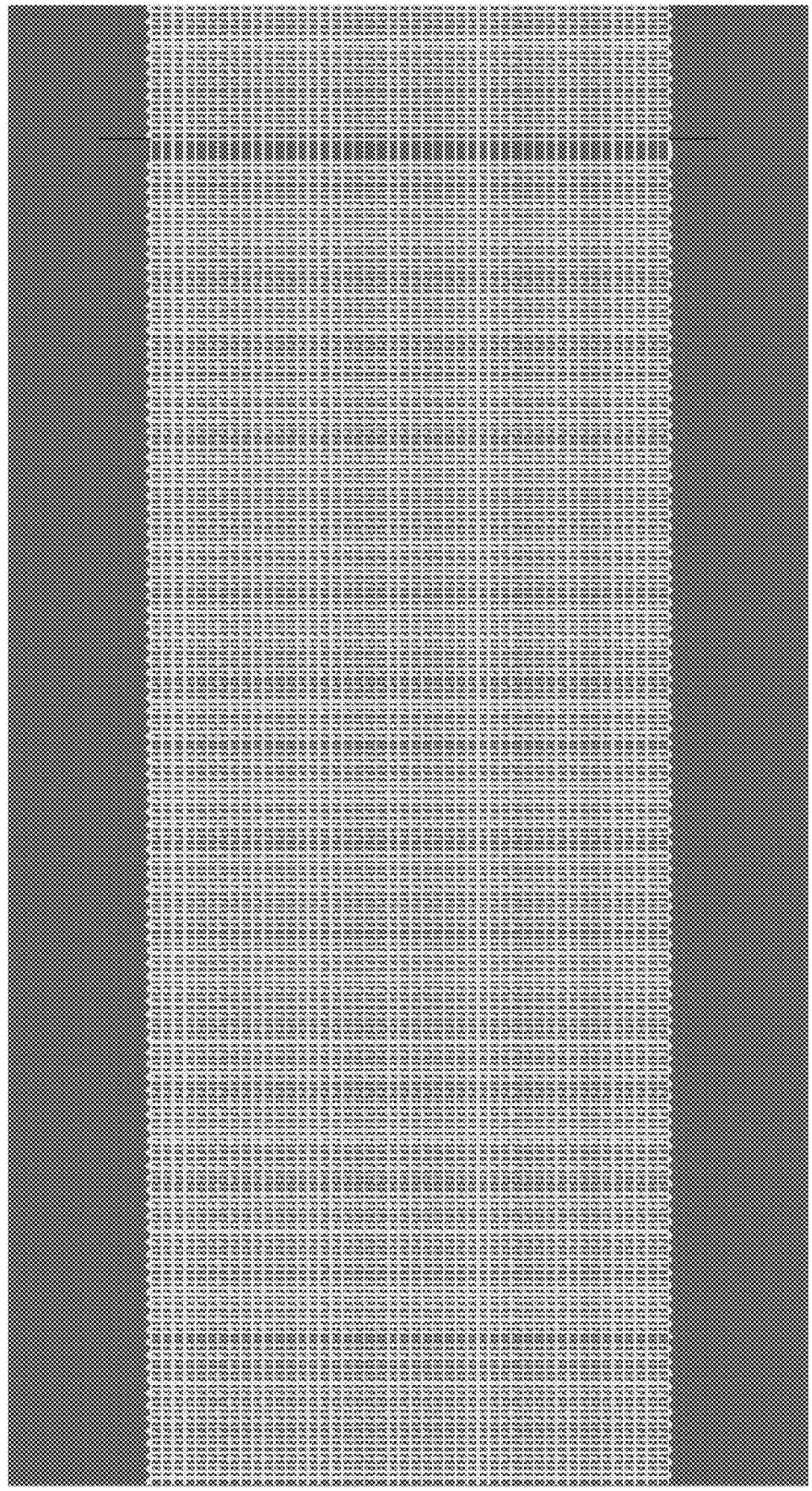
FIG. 54 illustrates an example pattern simulation for a double needle bed mesh demonstrated in FIG. 50B according to aspects of the present invention.

Another variation of the mesh in accordance with an aspect of the present invention may be created on a raschel knitting machine such as Comez DNB/EL-800-8B set up in 10 gg needle spacing by the use of three movements as shown in the pattern layout in FIGS. 50B-E: two movements in the wale direction, the vertical direction within the fabric, and one movement in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3—for one of the wale direction movements shown in FIGS. 51A-D and 1/1-1/3-3/3-3/1 for the other wale direction movement shown in FIGS. 53A-D. The interlacing of the loops within the fabric allows for one yarn to be under more tension than the other under stress, locking it around the less tensioned yarn; keeping the fabric from unraveling when cut. The other movement in the course direction as shown in FIGS. 52A-D occurs in every few courses creating the porous design of the mesh. These yarns follow a repeat pattern of 9/9-9/9-7/7-9/9-7/7-9/9-7/7-9/9-7/7-9/9/-1/1-1/1-3/3-1/1-3/3-1/1-3/3-1/1-3/3-1/1 for the course direction movement. The pattern simulation layout of this pattern is rendered with ComezDraw 3 software in FIG. 54 considering a yarn design made with 2 ends of Td 20/22 raw silk twisted together in the S direction to form a ply with 6 tpi and further combining three of the resulting ply with 3 tpi. The same yarn design is used for the movements occurring in the wale and course directions. The stitch density or pick count for the mesh in FIG. 54 is 40 picks per centimeter considering the total picks count for the technical front and the technical back of the fabric, or 20 picks per cm considering only on the face of the fabric. The operating parameters are not limited to the those described in FIGS. 50B-E, but just the optimum values for the specific yarn design used for the pattern simulation layout of FIG. 54.

In embodiments employing silk yarn, the silk yarn may be twisted from yarn made by 20-22 denier raw silk fibers approximately 40 to 60 μm in diameter. Preferably, raw silk fibers ranging from 10 to 30 deniers may be employed; however any fiber diameters that will allow the device to provide sufficient strength are acceptable. Advantageously, a constant yarn size may maximize the uniformity of the surgical mesh mechanical properties, e.g. stiffness, elongation, etc., physical and/or biological properties within each region. However, the yarn size may be varied in sections of the mesh in order to achieve different mechanical, physical and/or biological characteristics in the preferred mesh locations. Factors that may be influenced by the size of the yarn include, but are not limited to: ultimate tensile strength (UTS); yield strength, i.e. the point at which yarn is permanently deformed; percent elongation; fatigue and dynamic laxity (creep); bioresorption rate; and transfer of cell/nutrients into and out of the mesh.

The knit patterns illustrated in FIGS. 29A, 34A, 40A, 45A and 50A respectively, may be knit to any width depending upon the knitting machine and could be knitted with any of the gauges available with the various crochet machines or warp knitting machines. Table 1B outlines the fabric widths that may be achieved using a different numbers of needles on different gauge machines. It is understood that the dimensions in Table 1B are approximate due to the shrink factor of the knitted fabric which depends on stitch design, stitch density, and yarn size used.

TABLE 1B

| Gauge | Needle Count | | Knitting Width (mm) | |
|---|---|---|---|---|
| | From | To | From | To |
| 48 | 2 | 5656 | 0.53 | 2997.68 |
| 24 | 2 | 2826 | 1.06 | 2995.56 |
| 20 | 2 | 2358 | 1.27 | 2994.66 |
| 18 | 2 | 2123 | 1.41 | 2993.43 |
| 16 | 2 | 1882 | 1.59 | 2992.38 |
| 14 | 2 | 1653 | 1.81 | 2991.93 |
| 12 | 2 | 1411 | 2.12 | 2991.32 |
| 10 | 2 | 1177 | 2.54 | 2989.58 |
| 5 | 2 | 586 | 5.08 | 2976.88 |

Mesh or scaffold designs in accordance with aspects of the present invention may be knitted on a fine gauge crochet knitting machine. Crochet machines capable of manufacturing the mesh in accordance with aspects of the present invention include, but are not limited to, those provided by: Changde Textile Machinery Co., Ltd.; Comez; China Textile Machinery Co., Ltd.; Huibang Machine; Jakob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinery Co., Ltd.; Taiwan Giu Chun Ind. Co., Ltd.; Zhangjiagang Victor Textile; Liba; Lucas; Muller Frick; and Texma.

Mesh or scaffold designs in accordance with aspects of the present invention may be knitted on a fine gauge warp knitting machine. Warp knitting machines capable of manufacturing the mesh in accordance with aspects of the present invention include, but are not limited to, those provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Mesh or scaffold designs in accordance with aspects of the present invention may be knitted on a fine gauge flat bed knitting machine. Flat bed machines capable of manufacturing the mesh in accordance with aspects of the present invention include, but are not limited to, those provided by: Around Star; Boosan; Cixing Textile Machine; Fengshen; Flying Tiger Machinery; Fujian Hongqi; G & P; Gorteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

A test method was developed to check the cutability of the surgical mesh formed according to aspects of the present invention. In the test method, the surgical mesh evaluated according to the number of were needed to cut the mesh with surgical scissors. The mesh was found to cut excellently because it took one scissor stroke to cut through it. The mesh was also cut diagonally and in circular patterns to determine how easily the mesh unraveled and how much it unraveled once cut. The mesh did not unravel more than one mode after being cut in both directions. To determine further if the mesh would unravel, a suture, was passed through the closest pore from the cut edge, and pulled. This manipulation did not unravel the mesh. Thus, the surgical mesh is easy to cut and does not unravel after manipulation.

Embodiments may be processed with a surface treatment, which increases material hydrophilicity, biocompatibility, physical, and mechanical properties such as handling for ease of cutting and graft pull-through, as well as anti-microbial and anti-fungal coatings. Specific examples of surface treatments include, but are not limited to:

plasma modification protein such as but not limited to fibronectin, denatured collagen or gelatin, collagen gels and hydrophobin by covalent link or other chemical or physical method peptides with hydrophilic and a hydrophobic end peptides contain one silk-binding sequence and one biologically active sequence—biodegradable cellulose surface sulfonation ozone gas treatment physically bound and chemically stabilized peptides DNA/RNA aptamers Peptide Nucleic Acids Avimers modified and unmodified polysaccharide coatings carbohydrate coating anti-microbial coatings anti-fungal coatings phosphorylcholine coatings A method to evaluate the ease of delivery through a cannula was done to make sure the surgical mesh could be used laparoscopically. Various lengths were rolled up and pushed through two different standard sized cannulas using surgical graspers. The mesh was then evaluated to determine if there was any damage done to the mesh. The mesh that was put through the cannulas was found to have slight distortion to the corner that was held by the grasper. The 16 cm and 18 cm lengths of mesh that were rolled up and pushed through the 8 mm cannula had minimal fraying and one distorted pore, respectively. It was also found that no damage was done to the cannula or septum in any of the tests. It was found that appropriately sized surgical mesh will successfully pass through a laparoscopic cannula without damage, enabling its effective use during laparoscopic procedures.

A surgical mesh device according to aspects of the present invention has been found to bio-resorb by 50% in approximately 100 days. In a study by Horan et al., Sprague-Dawley rats were used to compare the bio-resorption of embodiments according to the present invention to Mersilene™ mesh (Ethicon, Somerville, N.J.). The histology reports from the article state that after 94 days, 43% of the initial mesh of the embodiments remained compared to 96% of the Mersilene™ mesh. It was also reported that the in growth was more uniform with the mesh of embodiments than the Mersilene™ mesh. The Mersilene™ was found to have less in growth in the defect region than along the abdominal wall.

Physical properties include thickness, density and pore sizes. The thickness was measured utilizing a J100 Kafer Dial Thickness Gauge. A Mitutoyo Digimatic Caliper was used to find the length and width of the samples; used to calculate the density. The density was found by multiplying the length, width and thickness of the mesh then dividing the resulting value by the mass. The pore size was found by photographing the mesh with an Olympus SZX7 Dissection Microscope under 0.8× magnification. The measurements were taken using ImagePro 5.1 software and the values were averaged over several measurements. The physical characteristics of the sample meshes, including embodiments according to the present invention, are provided in TABLE 2.

TABLE 2

| | Physical Characterization | | |
|---|---|---|---|
| Device | Thickness (mm) | Pore Size ($mm^2$) | Density ($g/cm^3$) |
| Mersilene Mesh | 0.31 ± 0.01 | 0.506 ± 0.035 | 0.143 ± 0.003 |
| Bard Mesh | 0.72 ± 0.00 | 0.465 ± 0.029 | 0.130 ± 0.005 |
| Vicryl Knitted Mesh | 0.22 ± 0.01 | 0.064 ± 0.017 | 0.253 ± 0.014 |
| Present Embodiments - Single Needle Bed (SB) | 1.0 ± 0.04 | 0.640 ± 0.409 | 0.176 ± 0.002 |
| Present Embodiments - Double Needle Bed (DB) | 0.80 ± 0.20 | 1.27 | 0.135-0.165 |

All devices were cut to the dimensions specified in TABLE 3, for each type of mechanical analysis. Samples were incubated in phosphate buffered saline (PBS) for 3±1.25 hours at 37±2° C. prior to mechanical analysis to provide characteristics in a wet environment. Samples were removed from solution and immediately tested.

TABLE 3

| Test Modality | Length (mm) | Width (mm) |
|---|---|---|
| Tensile | 60 | 10 |
| Burst | 32 | 32 |
| Suture Pull-Out | 40 | 20 |
| Tear | 60 | 40 |
| Tensile Fatigue | 60 | 40 |

Ball burst test samples were scaled down due to limitations in material dimensions. The test fixture employed was a scaled (1:2.5) version of that recommended by ASTM Standard D3787. The samples were centered within a fixture and burst with a 10 mm diameter ball traveling at a displacement rate of 60 mm/min. Maximum stress and stiffness were determined from the burst test. Results can be seen in TABLE 4.

TABLE 4

| | Burst Strength | |
|---|---|---|
| Device | Stress (MPa) | Stiffness (N/mm) |
| Mersilene Mesh | 0.27 ± 0.01 | 13.36 ± 0.85 |
| Bard Mesh | 0.98 ± 0.04 | 38.28 ± 1.49 |
| Vicryl Knitted Mesh | 0.59 ± 0.05 | 32.27 ± 1.86 |
| Pelvitex Polypropylene Mesh | 0.59 ± 0.04 | 29.78 ± 1.33 |
| Permacol Biologic Implant | 1.27 ± 0.27 | 128.38 ± 22.14 |
| Present Embodiments (SB) | 0.76 ± 0.04 | 46.10 ± 2.16 |
| Present Embodiments (DB) | 0.66 | 40.9 |

Tensile tests were performed along the fabric formation and width axes of each device. A 1 cm length of mesh on each end of the device was sandwiched between pieces of 3.0 mm thick silicone sheet and mounted in pneumatic fabric clamps with a clamping pressure of 70-85 psi. Samples were loaded through displacement controlled testing at a strain rate of 100%/s (2400 mm/min) and/or 67%/s (1600 mm/min) until failure. The ultimate tensile strength (UTS), linear stiffness and percent elongation at break can be seen in the following tables. Results can be found in TABLES 5-8. An entry of "NT" indicates that the data has not yet been tested.

TABLE 5

Tensile SPTF (Fabric Formation Axis-1600 mm/min)

| Device | Strength (N) | Stress (MPa) | Stiffness (N/mm) | % Elong. @ Break |
|---|---|---|---|---|
| Mersilene Mesh | 46.14 ± 3.15 | 10.04 ± 0.71 | 0.90 ± 0.06 | 132.1% ± 9.3% |
| Bard Mesh | 30.90 ± 2.0 | 16.64 ± 1.16 | 3.32 ± 0.26 | 106.5% ± 3.2% |
| Vicryl Knitted Mesh | 35.69 ± 3.30 | 35.89 ± 4.48 | 2.59 ± 0.33 | 89.0% ± 7.3% |
| Present Embodiments (SB) | 76.72 ± 4.36 | 10.06 ± 0.38 | 7.13 ± 0.50 | 41.5% ± 2.3% |
| Present Embodiments Mesh (DB) | NT | NT | NT | NT |

TABLE 6

Tensile SPTF (Fabric Formation Axis-2400 mm/min)

| Device | Strength (N) | Stress (MPa) | Stiffness (N/mm) | % Elong. @ Break |
|---|---|---|---|---|
| Mersilene Mesh | 43.87 ± 5.19 | 14.15 ± 1.68 | 2.18 ± 0.3 | 56.6% ± 3.5% |
| Bard Mesh | 35.29 ± 5.69 | 4.90 ± 0.79 | 0.80 ± 0.23 | 177.3% ± 13.2% |
| Vicryl Knitted Mesh | 30.88 ± 3.30 | 14.04 ± 1.50 | 0.76 ± 0.17 | 191.9% ± 14.2% |
| Pelvite Polypropylene Mesh | 23.05 ± 3.75 | 5.36 ± 0.87 | 0.57 ± 0.07 | 110.0% ± 13.6% |
| Permacol Biologic Implant | 164.52 ± 30.58 | 13.71 ± 2.55 | 23.94 ± 2.7 | 23.5% ± 3.3% |
| Present Embodiments (SB) | 72.31 ± 7.80 | 6.95 ± 0.75 | 4.31 ± 0.3 | 45.5% ± 5.2% |
| Present Embodiments (DB) | 74.62 ± 2.70 | 8.68 ± 0.31 | 4.25 ± 0.13 | 48.3% ± 2.1% |

TABLE 7

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 31.14 ± 2.21 | 10.04 ± 0.71 | 0.90 ± 0.06 | 132.1% ± 9.3% |
| Bard Mesh | 119.80 ± 8.36 | 16.64 ± 1.16 | 3.32 ± 0.26 | 106.5% ± 3.2% |
| Vicryl Knitted Mesh | 78.96 ± 9.86 | 35.89 ± 4.48 | 2.59 ± 0.33 | 89.0% ± 7.3% |
| Present Embodiments (SB) | 104.58 ± 3.96 | 10.06 ± 0.38 | 7.13 ± 0.50 | 41.5% ± 2.3% |
| Present Embodiments (DB) | NT | NT | NT | NT |

TABLE 8

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 28.11 ± 2.93 | 28.11 ± 2.93 | 1.05 ± 0.13 | 128.2% ± 23.6% |
| Bard Mesh | 103.53 ± 8.92 | 14.38 ± 1.24 | 3.43 ± 0.5 | 94.0% ± 8.4% |
| Vicryl Knitted Mesh | 106.65 ± 8.46 | 48.48 ± 3.85 | 5.08 ± 0.1 | 58.6% ± 8.4% |
| Pelvite Polypropylene Mesh | 30.24 ± 5.77 | 7.03 ± 1.34 | 1.48 ± 0.1 | 89.6% ± 9.6% |
| Permacol Biologic Implant | 67.71 ± 13.36 | 5.64 ± 1.11 | 8.56 ± 2.0 | 27.4% ± 4.2% |
| Present Embodiments (SB) | 98.84 ± 4.79 | 9.50 ± 0.46 | 8.48 ± 0.3 | 39.0% ± 4.1% |
| Present Embodiments (DB) | 70.08 ± 2.55 | 8.15 ± 0.30 | 5.87 ± 0.22 | 33.6% ± 2.0% |

Tear Strength was found through a method that entailed cutting a 10 mm "tear" into the edge, perpendicular to the long axis edge and centered along the length of the mesh. The mesh was mounted in pneumatic fabric clamps as previously described in the tensile testing methods. Samples were loaded through displacement controlled testing at a strain rate of 100%/s (2400 mm/min) until failure. The load at failure and the mode of failure are shown in TABLE 9.

TABLE 9

| Device | Tear Strength Strength (N) | Failure Mode |
|---|---|---|
| Mersilene Mesh | 110.30 ± 5.63 | Tear Failure: 6/6 |
| Bard Mesh | 181.70 ± 12.33 | Tear Failure: 6/6 |
| Vicryl Knitted Mesh | 109.35 ± 4.85 | Tear Failure: 6/6 |
| Pelvitex Polypropylene Mesh | 108.14 ± 6.95 | Tear Failure: 4/6 |
| Permacol Biologic Implant | 273.79 ± 65.57 | Tear Failure: 6/6 |
| Embodiments (SB) | 194.81 ± 9.12 | Tear Failure: 6/6 |
| Embodiments (DB) | NT | NT |

Tensile fatigue testing was performed on the surgical mesh device according to aspects of the present invention and representative predicate types including Vicryl Mesh and Bard Mesh. Samples were loaded into the pneumatic fabric clamps as previously described in the tensile testing methods above. Samples were submerged in PBS at room temperature during cycling. Sinusoidal load controlled cycling was performed to 60% of mesh ultimate tensile strength. Number of cycles to failure was determined during the cyclic studies and can be seen in TABLE 10, where failure was indicated by fracture or permanent deformation in excess of 200%.

TABLE 10

| Device | Tensile Fatigue Cycles, 60% UTS |
|---|---|
| Bard Mesh | 6994 ± 2987 |
| Vicryl Knitted Mesh | 91 ± 127 |
| Embodiments (DB) | 1950 ± 1409 |

A method was developed to compare the suture pull out strength of the surgical mesh device according to aspects of the present invention to other surgical mesh on the market. Tested mesh was sutured with three 3.5 mm diameter suture anchors (Arthrex, Naples, Fla.) and secured to 15 pcf solid rigid polyurethane foam. Each device was positioned with the center of the 20 mm width over the center anchor with a 3 mm suture bite distance employed during suturing of the mesh to the 3 anchors. The saw bone was mounted in the lower pneumatic fabric clamp and offset to provide loading along the axis of the device when the device was centered under the load cell. The free end of the mesh was sandwiched between the silicone pieces and placed in the upper fabric clamp with 85±5 psi clamping force. Testing was performed under displacement control with a strain rate of 100%/s (1620 mm/min). Maximum load at break and failure mode can be seen in TABLE 11.

TABLE 11

| Device | Suture-Pull-Out Strength/Suture [N] | Failure Mode |
|---|---|---|
| Mersilene Mesh | 13.50 ± 1.65 | Mesh Failure: 6 of 6 |
| Bard Mesh | 28.80 ± 3.39 | Mesh Failure: 6 of 6 |

TABLE 11-continued

| Device | Suture-Pull-Out Strength/Suture [N] | Failure Mode |
|---|---|---|
| Vicryl Knitted Mesh | 12.90 ± 1.30 | Mesh Failure: 6 of 6 |
| Pelvitex Polyproplene Mesh | 18.29 ± 4.04 | Mesh Failure: 6 of 6 |
| Permacol Biologic Implant | 47.36 ± 7.94 | Mesh Failure: 6 of 6 |
| Embodiments (SB) | 41.00 ± 2.98 | Mesh Failure: 6 of 6 |
| Embodiments (DB) | 32.57 ± 2.30 | Mesh Failure: 6 of 6 |

By utilizing the pattern for the double needle bed mesh and modifying the yarn size, yarn feed rate and/or needle bed width, the surgical mesh device according to aspects of the present invention would meet the physical and mechanical properties necessary for a soft or hard tissue repair depending on the application. Such properties include pore size, thickness, ultimate tensile strength, stiffness, burst strength and suture pull out. The pore size could be modified dependent to the feed rate to create a more open fabric and the thickness could range from 0.40 mm up to as wide as 19.0 mm. With modifications to the pore size and thickness the UTS, stiffness, burst strength and suture pull out would all be modified as well, most likely tailoring the modifications of the pore size and/or thickness to meet certain mechanical needs.

This mesh, created on the flat knitting machine would be made in such a way to increase or decrease pore size and/or thickness by changing the yarn size and/or changing the loop length found within the knitting settings. The loop placements in combination with the node lock design allow changes to the shape and/or to the mechanical properties of the mesh. A biocompatible yarn with elasticity, such as highly twisted silk, could be used for shaping.

Figure 21A:
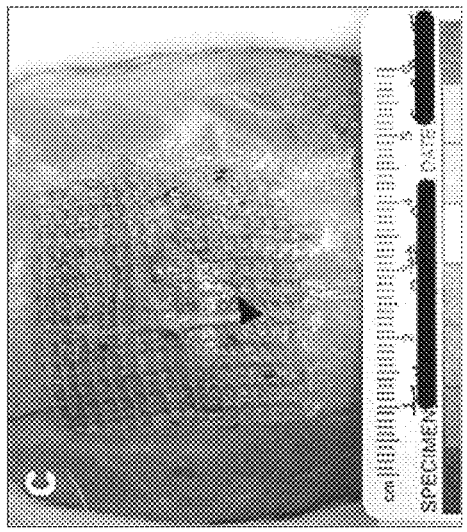
FIG. 21A illustrates a full-thickness rat abdominal defect created using a custom designed 1-cm stainless steel punch, the defect appearing oval in shape due to body wall tension applied.
Figure 21B:
FIG. 21B illustrates a 4 cm×4 cm example implant centered on top of the open defect of FIG. 21A, and held in place with single interrupted polypropylene sutures (arrow) through the implant and muscle.
Figure 21C:
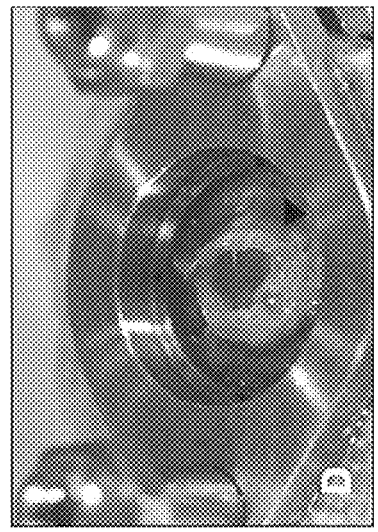
FIG. 21C illustrates an explanted specimen 94 days post implantation as shown in FIG. 21B.
Figure 21D:
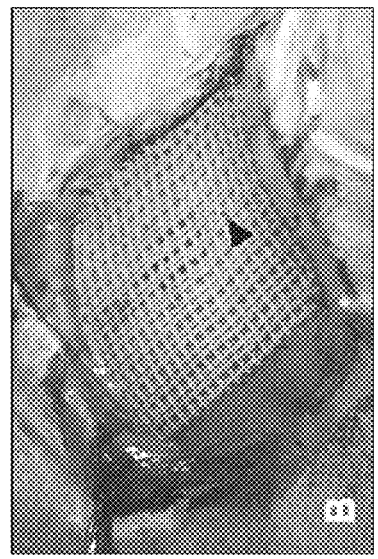
FIG. 21D illustrates ball burst testing performed with a 1-cm diameter ball pushed through the defect site reinforced with the mesh according to aspects of the present invention.

The implantation of a mesh and subsequent testing according to aspects of the present invention is illustrated in FIGS. 21A-D. FIG. 21A illustrates a full-thickness rat abdominal defect created using a custom designed 1-cm stainless steel punch. The defect appears oval in shape due to body wall tension applied. FIG. 21B illustrates a 4 cm×4 cm implant centered on top of the open defect, and held in place with single interrupted polypropylene sutures (arrow) through the implant and muscle. FIG. 21C illustrates an explanted specimen 94 days post implantation. FIG. 21D illustrates ball burst testing performed with a 1-cm diameter ball pushed through the defect site reinforced with the mesh.

While the present invention has been described in connection with a number of exemplary embodiments, and implementations, the present inventions are not so limited, but rather cover various modifications, and equivalent arrangements. For example, a knitted mesh according to aspects of the present invention may be used for a filler material. In one application, the knitted mesh may be cut into 1 mm×1 mm sections to separate one or more nodes, e.g., 3 nodes. The sections may be added to fat tissue or a hydro-gel to form a solution that can be injected into a defective area. Advantageously, the filler material may provide a desired texture, but will not unravel.

What is claimed is:

1. An implantable surgical mesh comprising two sets of yarns differentially engaging each other in a defined pattern to form a plurality of interconnections at each of which the yarns lockingly engage in a manner that substantially deters disengagement of the yarns from each other when tension is applied to the mesh when the mesh is cut;

wherein the two sets of yarns are a first set of yarns and a second set of yarns, the first set of yarns interlacing with the second set of yarns to define nodes, the first set of yarns and the second set of yarns alternately applied in a wale direction to form staggered loops, wherein the alternating application of the first set of yarns and the second set of yarns causes the first set of yarns to have different tensions relative to the second set of yarns at the nodes, and the difference in tension substantially preventing the knitted scaffold from unraveling at the nodes.

2. The mesh according to claim 1, wherein each of the first set of yarns and the second set of yarns consist essentially of a sericin-depleted silk.

3. The mesh according to claim 1, wherein the first set of yarns have different diameters than the second set of yarns.

4. The mesh according to claim 1, wherein first set of yarns have different elastic properties than the second set of yarns.

5. The mesh according to claim 1, wherein at least one of the first set of yarns and the second set of yarns consists essentially of sericin-depleted silk.

6. The mesh according to claim 1, wherein the mesh is a knit fabric.

7. The mesh according to claim 1, wherein said defined pattern forms a plurality of openings to permit tissue ingrowth.

8. An implantable surgical mesh comprising a bioresorbable knitted fabric consisting essentially of sericin-depleted silk, the fabric comprising a first set of yarns and a second set of yarns, the first set of yarns interlacing with the second set of yarns to define nodes, the first set of yarns and the second set of yarns alternately applied in a wale direction to form staggered loops, wherein the alternating application of the first set of yarns and the second set of yarns causes the first set of yarns to have different tensions relative to the second set of yarns at the nodes, and the difference in tension substantially preventing the knitted fabric from unraveling at the nodes.

9. The mesh according to claim 8 wherein the first set of yarns have a different tension than the second set of yarns.

10. The mesh according to claim 8, wherein the first set of yarns have a different diameter than the second set of yarns.

11. The mesh according to claim 8, wherein the first set of yarns have a different elasticity than the second set of yarns.

\* \* \* \* \*